(12) United States Patent
Babul

(10) Patent No.: US 9,125,833 B2
(45) Date of Patent: *Sep. 8, 2015

(54) MULTIMODAL ABUSE RESISTANT AND EXTENDED RELEASE OPIOID FORMULATIONS

(75) Inventor: Najib Babul, Blue Bell, PA (US)

(73) Assignee: Relmada Therapeutics, Inc., Blue Bell, PA (US)

(*) Notice: Subject to any disclaimer, the term of this patent is extended or adjusted under 35 U.S.C. 154(b) by 844 days.

This patent is subject to a terminal disclaimer.

(21) Appl. No.: 12/597,702

(22) PCT Filed: Apr. 26, 2008

(86) PCT No.: PCT/US2008/005541
§ 371 (c)(1),
(2), (4) Date: Jun. 4, 2010

(87) PCT Pub. No.: WO2008/134071
PCT Pub. Date: Nov. 6, 2008

(65) Prior Publication Data
US 2010/0249045 A1    Sep. 30, 2010

Related U.S. Application Data

(63) Continuation-in-part of application No. 12/216,645, filed on Jul. 7, 2008, which is a continuation-in-part of application No. 12/223,987, filed as application No. PCT/US2006/042962 on Nov. 2, 2006, and a (Continued)

(51) Int. Cl.
*A61K 9/42* (2006.01)
*A61K 31/44* (2006.01)
(Continued)

(52) U.S. Cl.
CPC .............. *A61K 9/4866* (2013.01); *A61K 9/485* (2013.01); *A61K 9/4858* (2013.01); *A61K 31/44* (2013.01)

(58) Field of Classification Search
CPC ... A61K 9/2068; A61K 9/4875; A61K 31/00;
A61K 31/13; A61K 31/46; A61K 31/404;
A61K 31/443; A61K 31/444; A61K 31/485;
A61K 31/537; A61K 31/5375
See application file for complete search history.

(56) References Cited

U.S. PATENT DOCUMENTS 2,867,565 A * 1/1959 Wolffe .......................... 514/157
3,493,657 A    2/1970 Lewenstein
(Continued)

FOREIGN PATENT DOCUMENTS

GB      05 06982.8    4/2005
WO    WO 2006/106344    10/2006
(Continued)

OTHER PUBLICATIONS

Banker (Modern Pharmaceutics) Banker, G.S. et al, "Modern Pharmaceutics, 3ed.", Marcel Dekker, New York, 1996, pp. 451 and 596.*

(Continued)

*Primary Examiner* — Lakshmi Channavajjala
(74) *Attorney, Agent, or Firm* — Dilworth Paxson LLP; Gary D. Colby

(57) ABSTRACT

The present invention is in the field of oral, abuse resistant pharmaceutical compositions of opioid agonists, extended release pharmaceutical compositions of opioid agonists and extended release abuse resistant pharmaceutical compositions of opioid agonists and the use thereof. The present invention is also directed to extended release pharmaceutical compositions and the use thereof for preventing or minimizing the risk of abuse and/or toxicity from either intentional or unintentional tampering. The present invention is further directed at a method of preventing or minimizing the risk of abuse and/or toxicity from either intentional or unintentional tampering.

20 Claims, 11 Drawing Sheets

Related U.S. Application Data continuation-in-part of application No. 12/223,327, filed as application No. PCT/US2007/002378 on Jan. 29, 2007.

(60) Provisional application No. 60/907,987, filed on Apr. 26, 2007, provisional application No. 60/732,121, filed on Nov. 2, 2005, provisional application No. 60/929,611, filed on Jul. 5, 2008, provisional application No. 60/762,489, filed on Jan. 27, 2006.

(51) Int. Cl.
*A61K 9/48* (2006.01)
*A61K 9/20* (2006.01)
*A61K 9/26* (2006.01)

(56) References Cited

U.S. PATENT DOCUMENTS

| | | |
|---|---|---|
| 3,773,955 A | 11/1973 | Pachter |
| 3,966,940 A | 6/1976 | Pachter |
| 3,980,766 A | 9/1976 | Shaw |
| 4,070,494 A | 1/1978 | Hoffmeister |
| 4,457,933 A | 7/1984 | Gordon |
| 4,582,835 A | 4/1986 | Lewis |
| 4,713,243 A | 12/1987 | Schiraldi |
| 5,378,474 A | 1/1995 | Morella et al. |
| 5,747,058 A | 5/1998 | Tipton |
| 5,922,341 A | 7/1999 | Smith et al. |
| 5,958,452 A | 9/1999 | Oshlack et al. |
| 5,968,542 A | 10/1999 | Tipton |
| 5,968,551 A | 10/1999 | Oshlack |
| 6,227,384 B1 | 5/2001 | Saylor |
| 6,228,863 B1 | 5/2001 | Palermo |
| 6,261,599 B1 | 7/2001 | Oshlack |
| 6,266,331 B1 | 7/2001 | Baker |
| 6,309,668 B1 | 10/2001 | Bastin |
| 6,326,027 B1 | 12/2001 | Miller |
| 6,335,033 B2 | 1/2002 | Oshlack |
| 6,375,957 B1 | 4/2002 | Kaiko |
| 6,475,494 B2 | 11/2002 | Kaiko |
| 6,559,159 B2 | 5/2003 | Carroll |
| 6,627,635 B2 * | 9/2003 | Palermo et al. .............. 514/282 |
| 6,638,533 B2 | 10/2003 | Krsek |
| 6,692,771 B2 | 2/2004 | Pather |
| 6,696,066 B2 | 2/2004 | Kaiko |
| 6,696,088 B2 | 2/2004 | Oshlack |
| 6,706,281 B2 | 3/2004 | Oshlack |
| 6,743,442 B2 | 6/2004 | Oshlack |
| 7,015,346 B2 | 3/2006 | Jenkins et al. |
| 7,083,808 B2 | 8/2006 | Goldenheim et al. |
| 7,144,587 B2 | 12/2006 | Oshlack et al. |
| 7,169,752 B2 | 1/2007 | Mickle |
| 7,172,767 B2 | 2/2007 | Kaiko |
| 7,201,920 B2 | 4/2007 | Kumar et al. |
| 7,226,619 B1 | 6/2007 | Bear |
| 7,399,488 B2 | 7/2008 | Hirsh |
| 7,419,686 B2 | 9/2008 | Kaiko |
| 7,511,054 B2 | 3/2009 | Stinchcomb et al. |
| 7,731,758 B2 | 6/2010 | Asius et al. |
| 2002/0192287 A1 | 12/2002 | Mooney et al. |
| 2003/0049317 A1 | 3/2003 | Lindsay |
| 2003/0118641 A1 | 6/2003 | Maloney |
| 2003/0124185 A1 | 7/2003 | Oshlack et al. |
| 2003/0129229 A1 | 7/2003 | Krsek |
| 2003/0180352 A1 | 9/2003 | Patel et al. |
| 2004/0042964 A1 | 3/2004 | Joshi et al. |
| 2004/0058946 A1 | 3/2004 | Buchwald et al. |
| 2004/0101557 A1 | 5/2004 | Gibson et al. |
| 2004/0131552 A1 | 7/2004 | Boehm |
| 2004/0131680 A1 | 7/2004 | Goldenheim et al. |
| 2004/0132826 A1 | 7/2004 | Hirsh |
| 2004/0176341 A1 | 9/2004 | Chou et al. |
| 2004/0191323 A1 | 9/2004 | Asius et al. |
| 2004/0202717 A1 | 10/2004 | Mehta |
| 2004/0228802 A1 | 11/2004 | Chang et al. |
| 2005/0020613 A1 | 1/2005 | Boehm et al. |
| 2005/0025832 A1 | 2/2005 | Lam et al. |
| 2005/0031546 A1 | 2/2005 | Bartholomaus et al. |
| 2005/0074493 A1 | 4/2005 | Mehta |
| 2005/0152843 A1 | 7/2005 | Bartholomaus et al. |
| 2005/0208047 A1 | 9/2005 | Anderson |
| 2005/0238709 A1 | 10/2005 | Lam et al. |
| 2005/0281748 A1 | 12/2005 | Hirsh |
| 2006/0002860 A1 | 1/2006 | Bartholomaus et al. |
| 2006/0003006 A1 | 1/2006 | Remon et al. |
| 2006/0034872 A1 | 2/2006 | Woolf |
| 2006/0039864 A1 | 2/2006 | Bartholomaus et al. |
| 2006/0110327 A1 | 5/2006 | Emigh et al. |
| 2006/0188447 A1 | 8/2006 | Arkenau-Maric et al. |
| 2006/0251721 A1 | 11/2006 | Cruz et al. |
| 2007/0020339 A1 | 1/2007 | Bear |
| 2007/0026065 A1 | 2/2007 | Benke et al. |
| 2007/0087977 A1 | 4/2007 | Robbins |
| 2007/0122482 A1 | 5/2007 | Holm et al. |
| 2007/0231268 A1 | 10/2007 | Emigh et al. |
| 2008/0020032 A1 | 1/2008 | Crowley |
| 2008/0069871 A1 | 3/2008 | Vaughn |
| 2008/0075768 A1 | 3/2008 | Vaughn |
| 2008/0075770 A1 | 3/2008 | Vaughn |
| 2008/0075771 A1 | 3/2008 | Vaughn |
| 2008/0076789 A1 | 3/2008 | Stinchcomb et al. |
| 2008/0152595 A1 | 6/2008 | Emigh et al. |
| 2008/0199530 A1 | 8/2008 | Hirsh |
| 2008/0280975 A1 | 11/2008 | Badul |
| 2009/0082466 A1 * | 3/2009 | Babul .............................. 514/646 |
| 2009/0123386 A1 | 5/2009 | Young |

FOREIGN PATENT DOCUMENTS

| | | |
|---|---|---|
| WO | WO 2007/056142 | 5/2007 |
| WO | WO 2007/087452 | 8/2007 |
| WO | WO 2008/033351 | 3/2008 |
| WO | WO 2008/134071 | 11/2008 |

OTHER PUBLICATIONS

West, Anthony R., Solid State Chemistry and its Applications, Wiley, New York, 1988, pp. 358 & 365.*

Wolff, Manfred E. "Burger's Medicinal Chemistry, 5ed, Part I", John Wiley & Sons, 1995, pp. 975-977.*

Lopez, J. "The Neurobiology of Depression" Cyberounds, 2000, 4 pages.

U.S. Appl. No. 12/223,987, Babul.

* cited by examiner

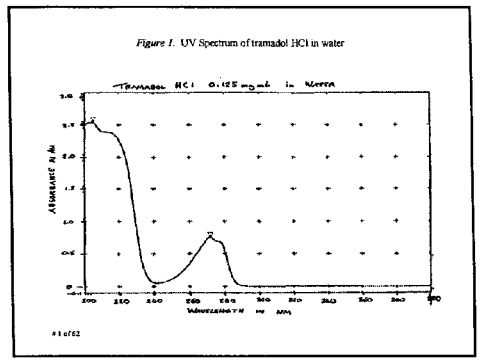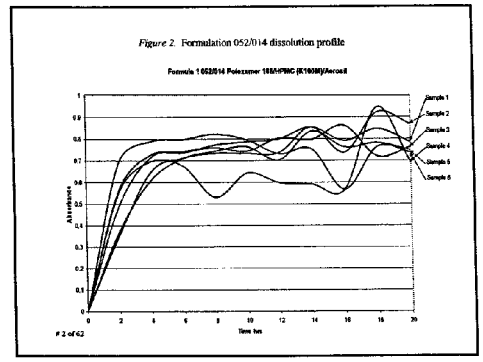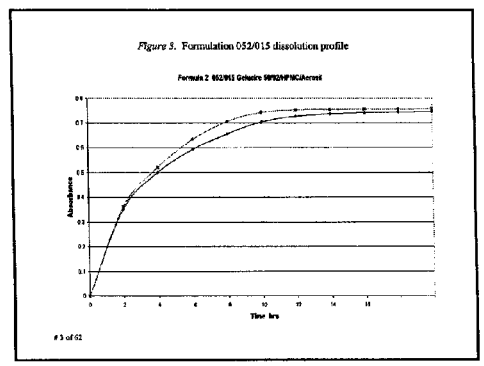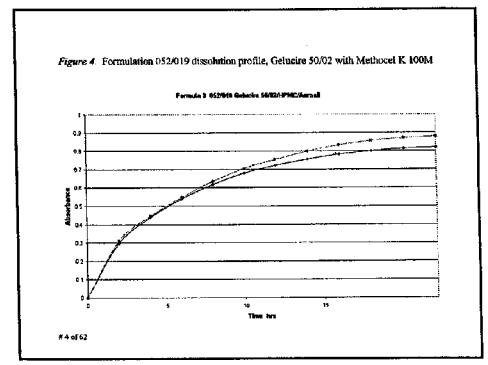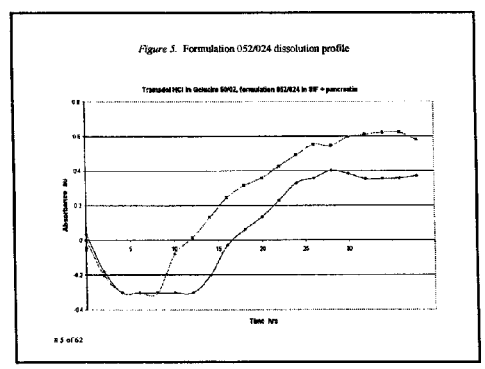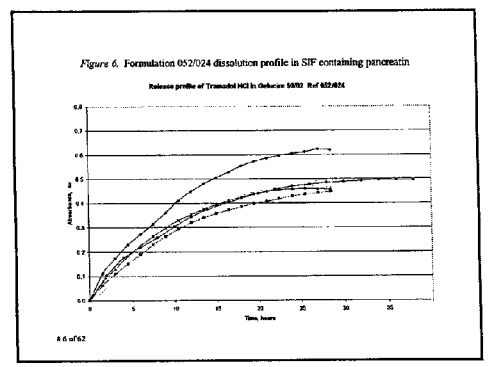

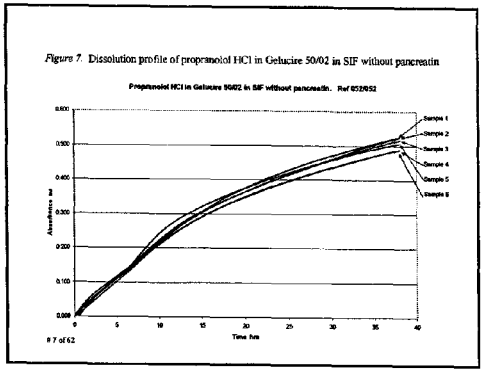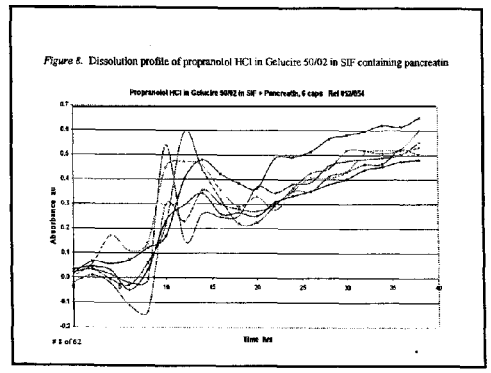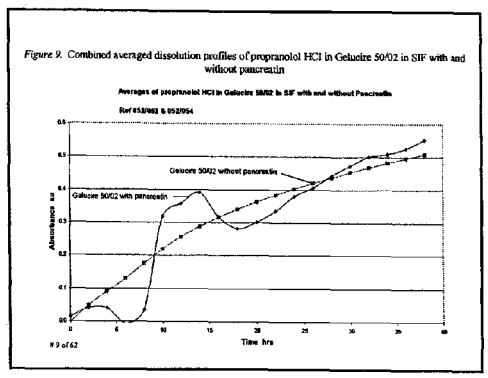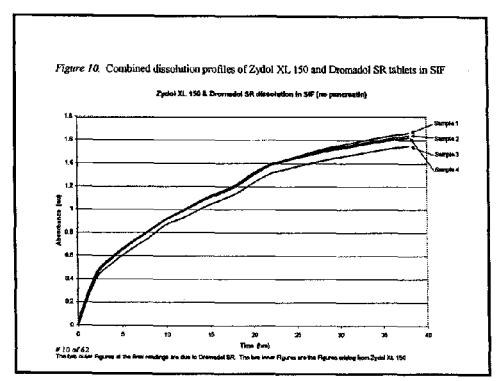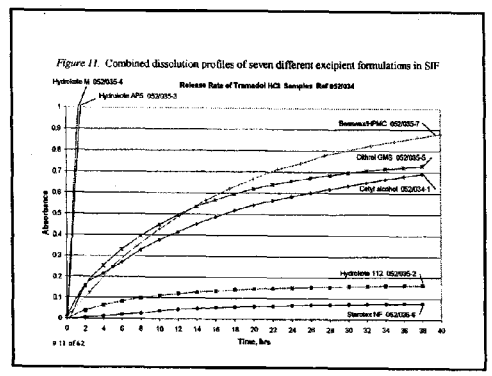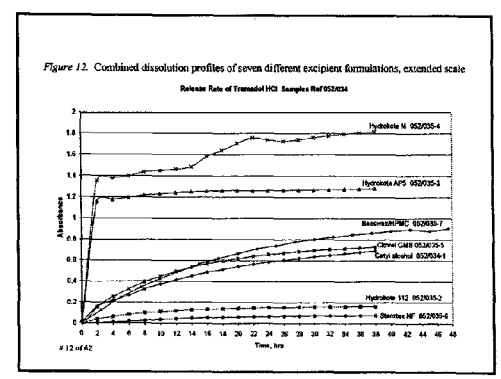

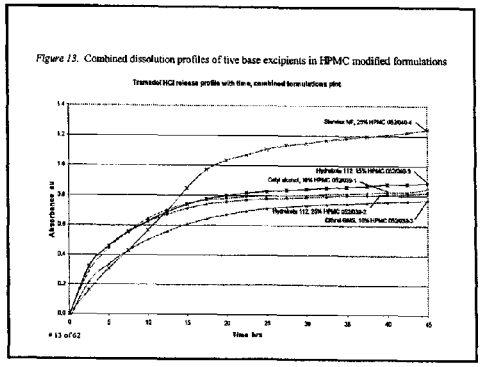
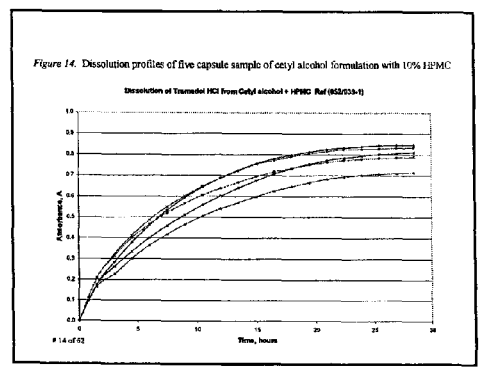
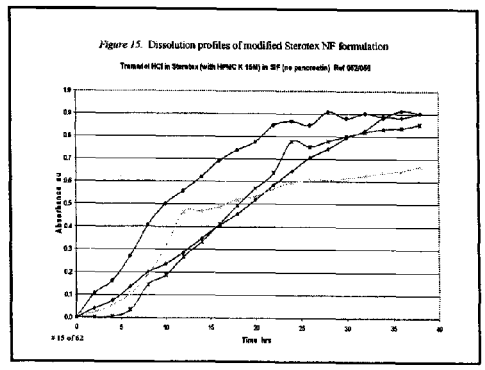
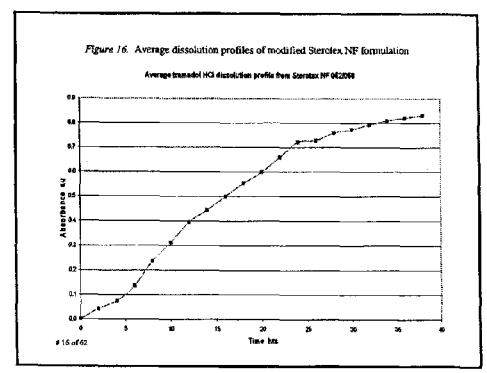
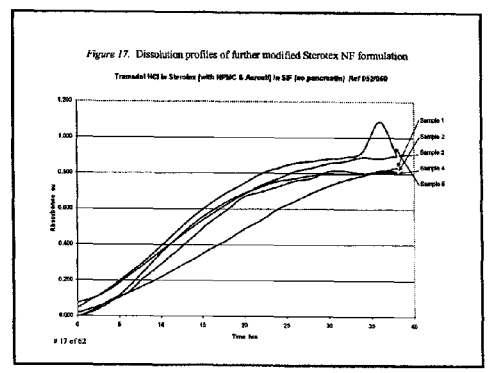
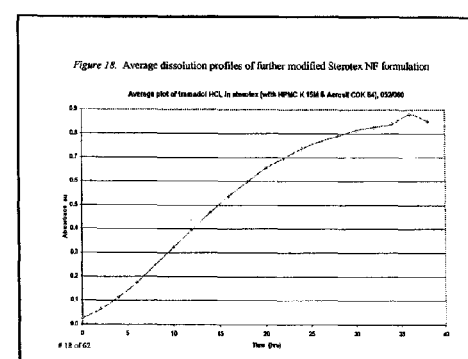

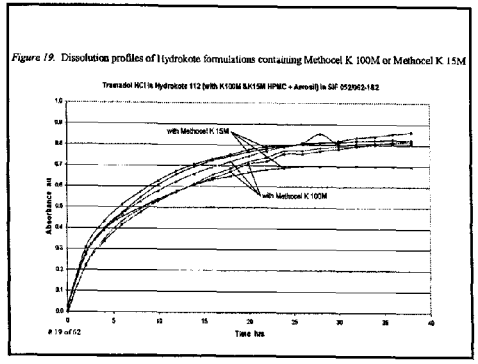

Figure 19. Dissolution profiles of Hydrokote formulations containing Methocel K 100M or Methocel K 15M

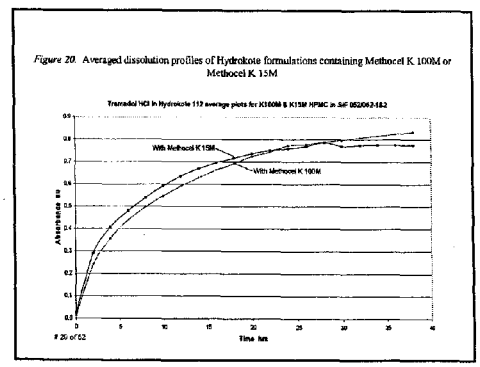

Figure 20. Averaged dissolution profiles of Hydrokote formulations containing Methocel K 100M or Methocel K 15M

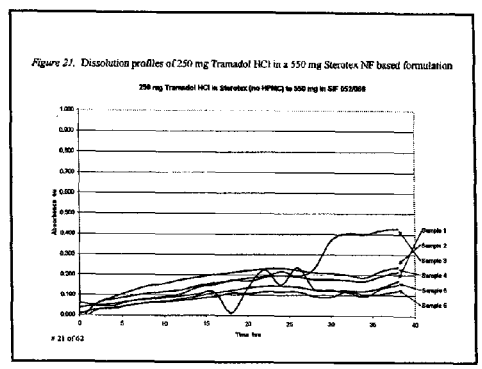

Figure 21. Dissolution profiles of 250 mg Tramadol HCl in a 550 mg Sterotex NF based formulation

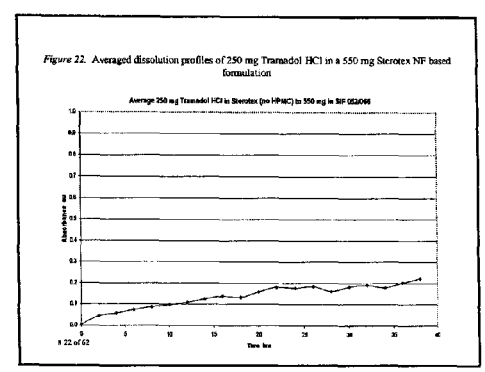

Figure 22. Averaged dissolution profiles of 250 mg Tramadol HCl in a 550 mg Sterotex NF based formulation

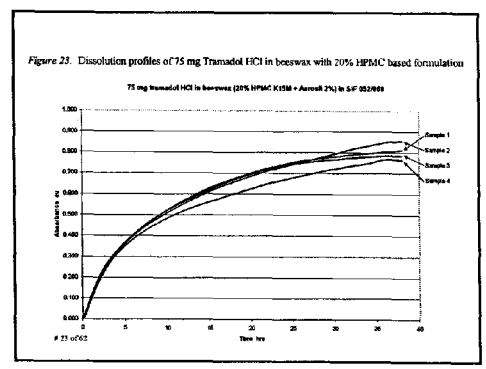

Figure 23. Dissolution profiles of 75 mg Tramadol HCl in beeswax with 20% HPMC based formulation

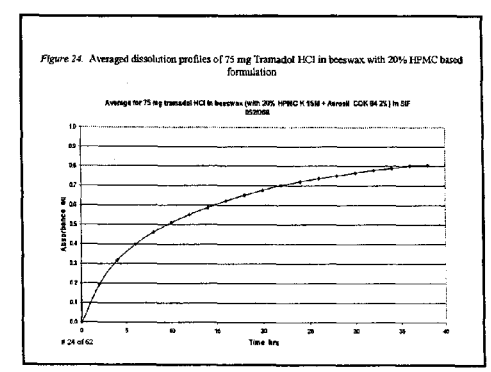

Figure 24. Averaged dissolution profiles of 75 mg Tramadol HCl in beeswax with 20% HPMC based formulation

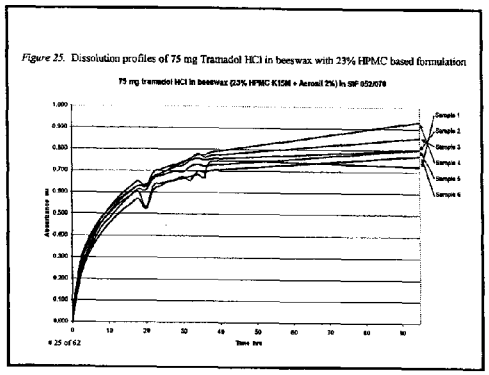
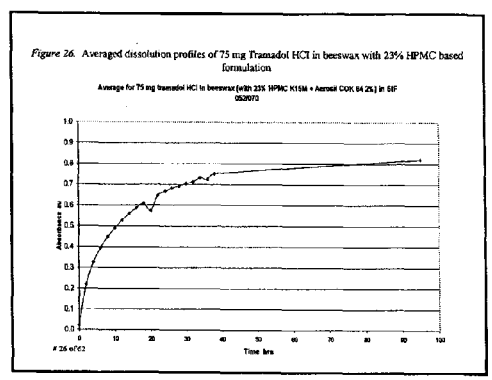
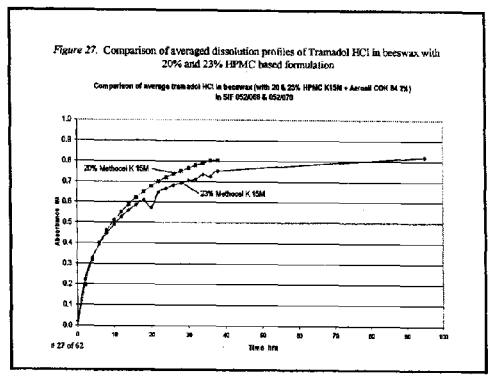
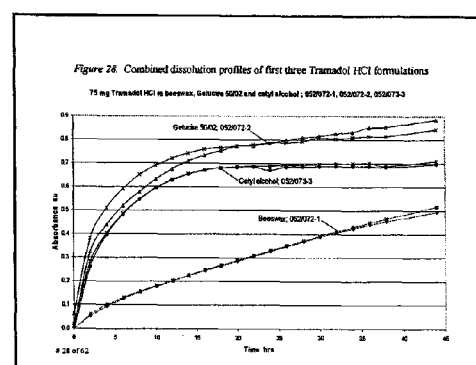
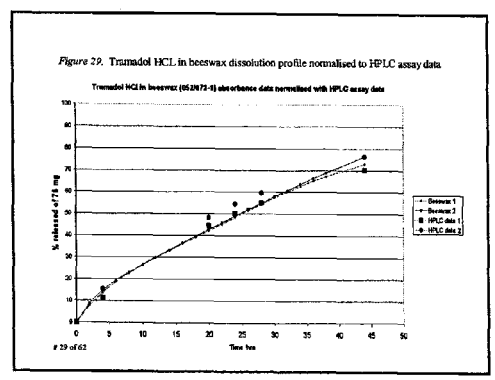
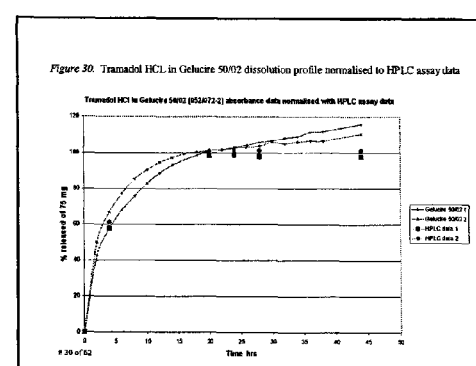

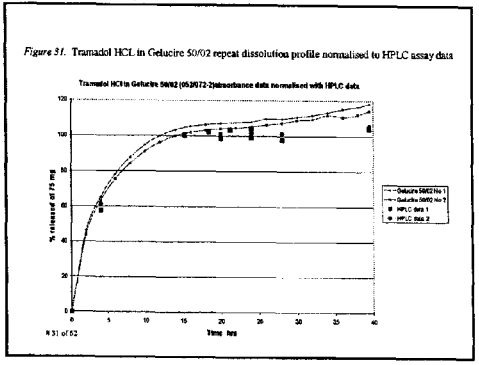
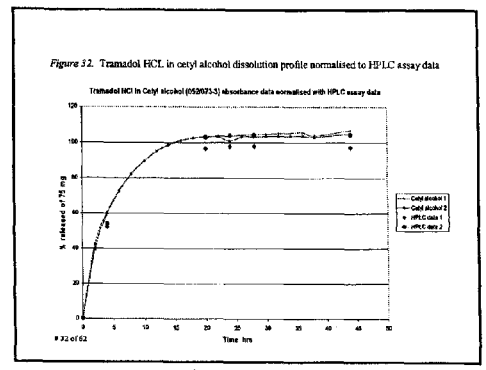
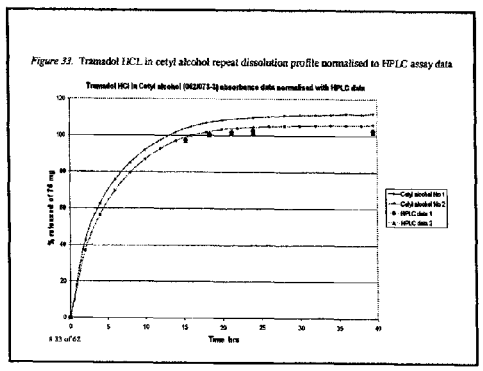
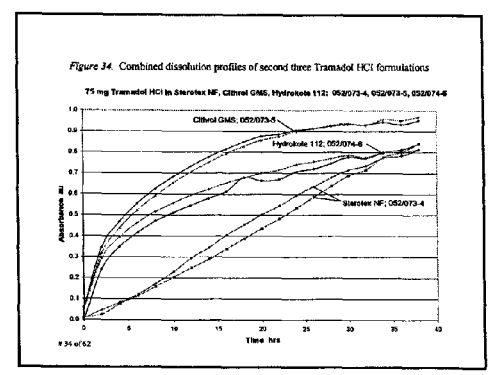
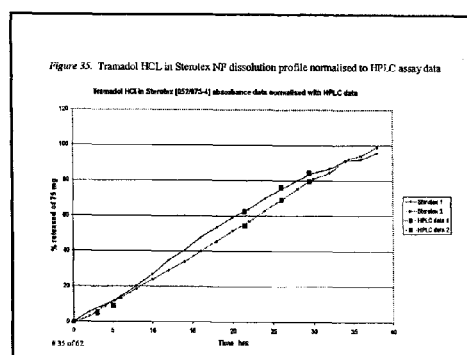
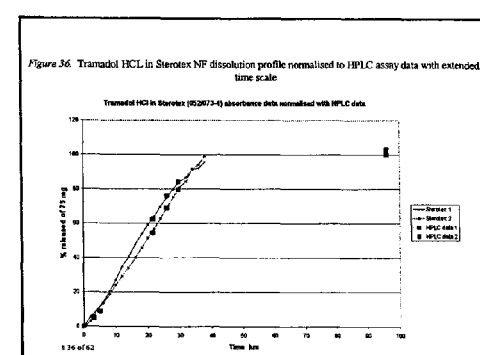

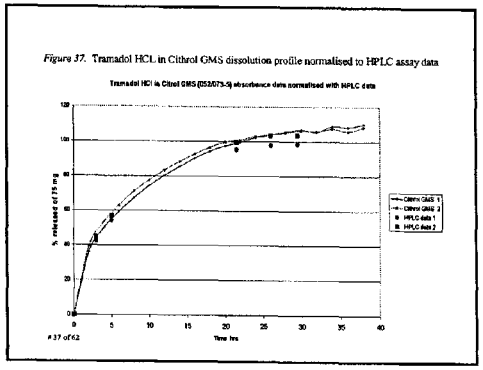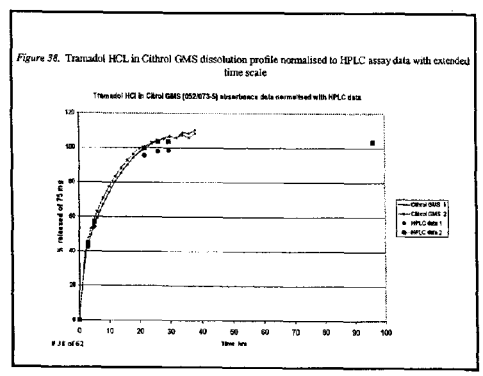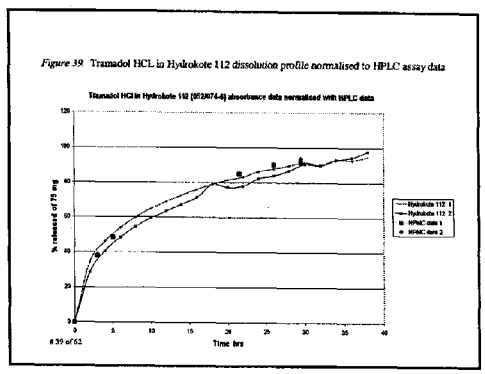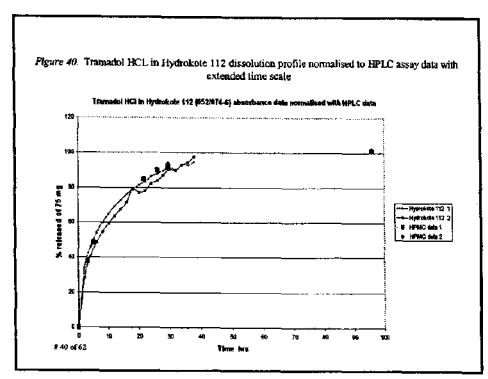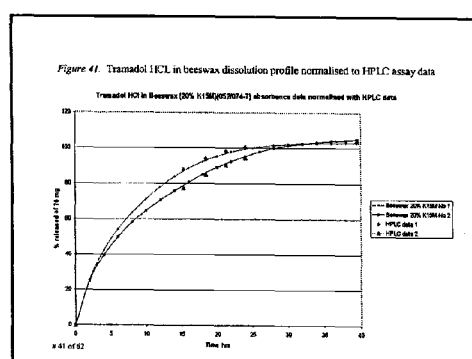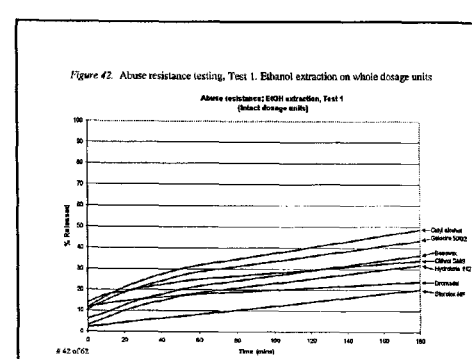

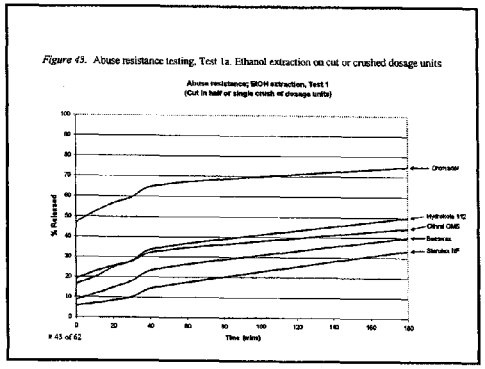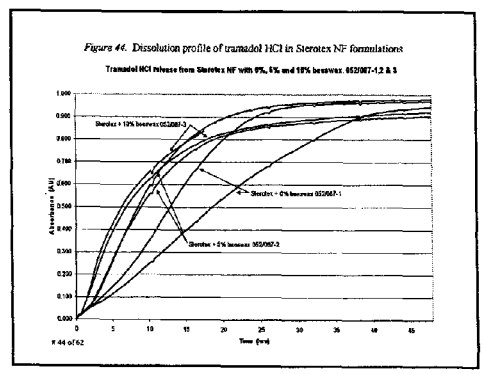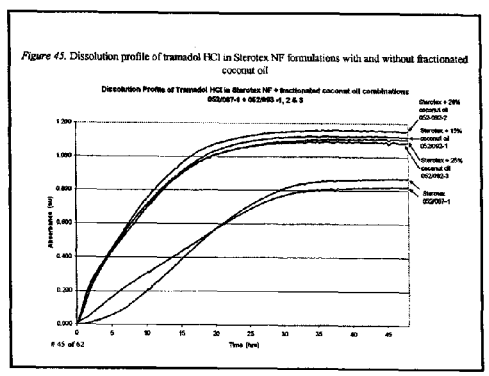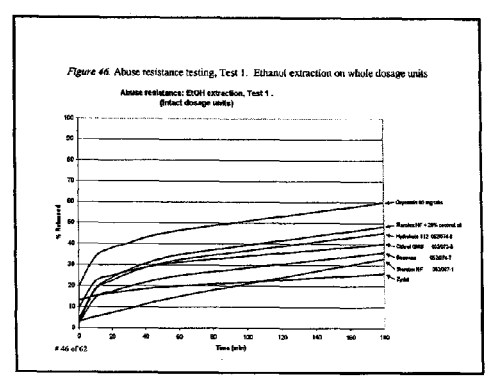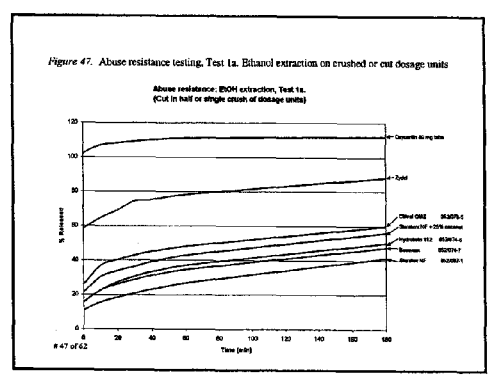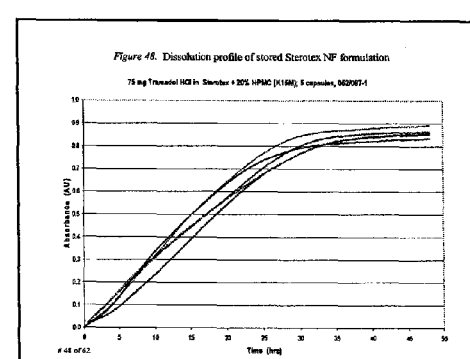

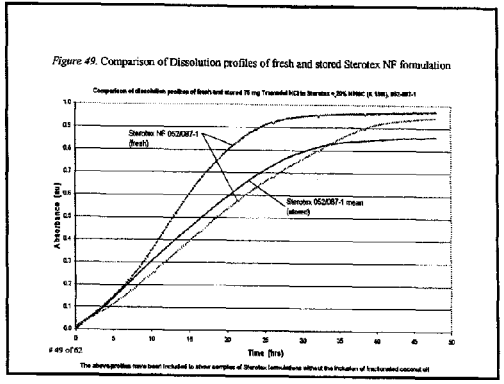
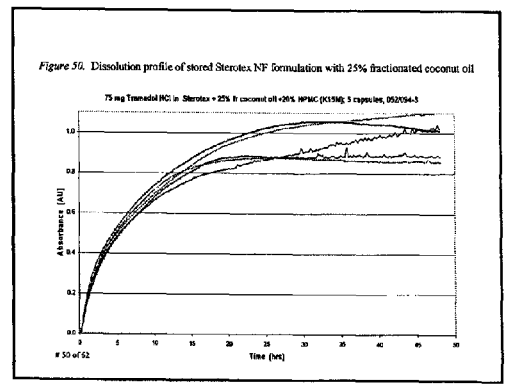
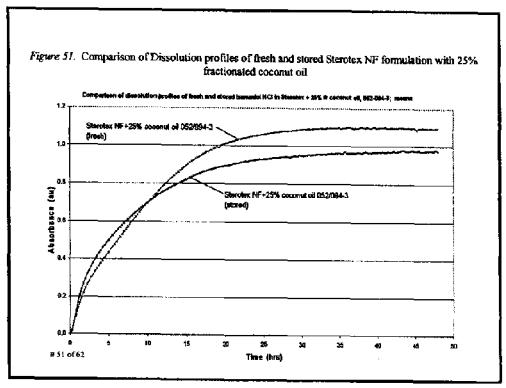
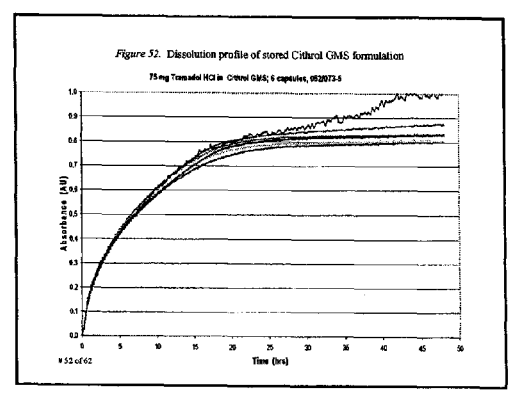
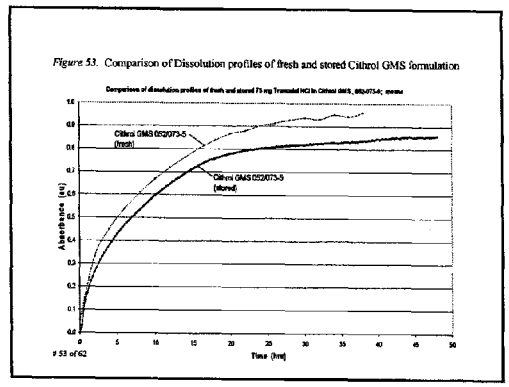
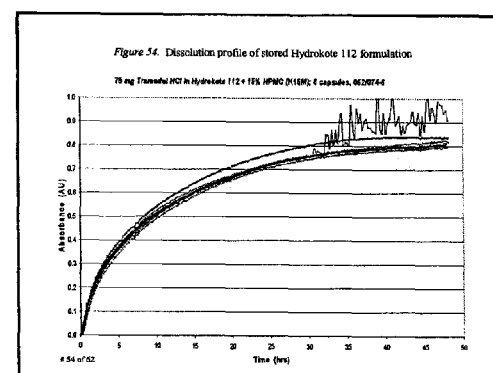

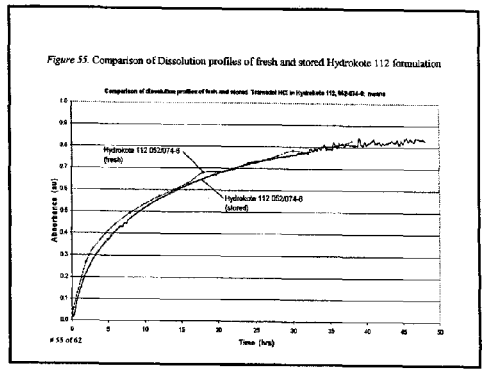
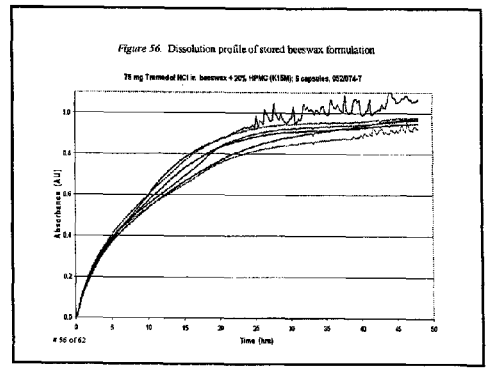
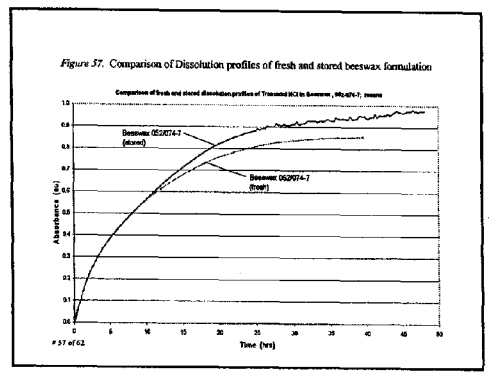
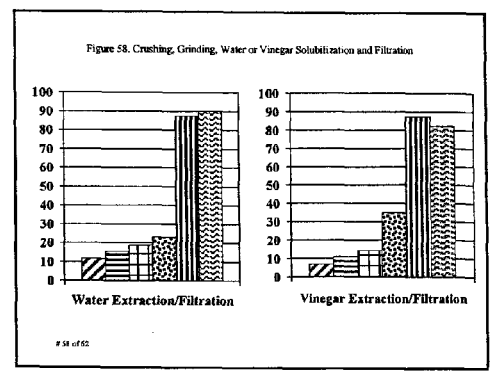
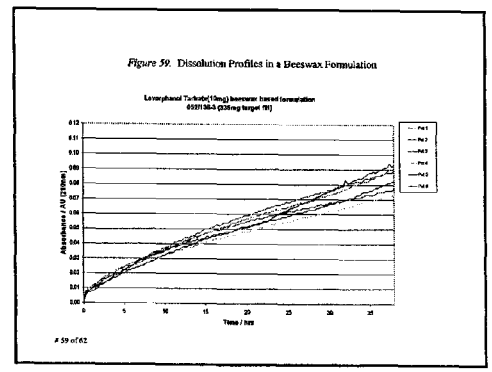
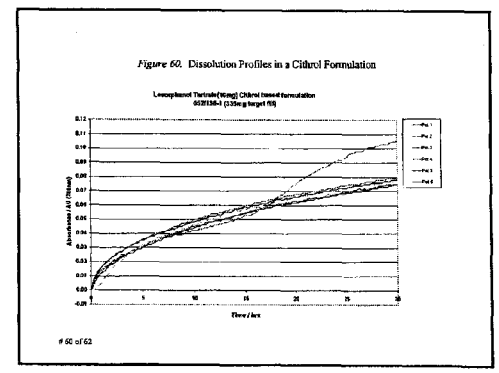

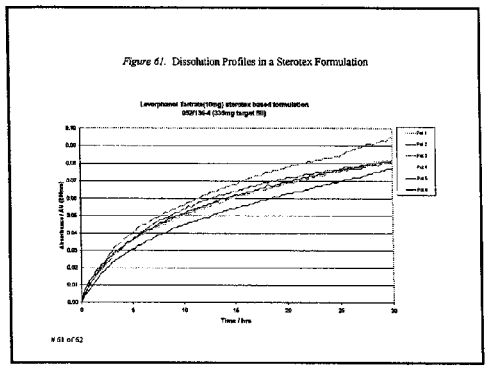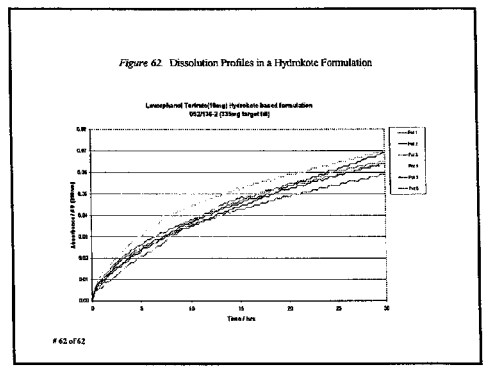

MULTIMODAL ABUSE RESISTANT AND EXTENDED RELEASE OPIOID FORMULATIONS

This application is a section 371 filing corresponding to PCT/US2008/005541, filed 26 Apr. 2008, which is entitled to priority to U.S. provisional application No. 60/907,987, filed 26 Apr. 2007; the present application is also a continuation-in-part of U.S. patent application Ser. No. 12/216,645 (pending), filed 7 Jul. 2008, which is a CIP of U.S. patent application Ser. No. 12/223,987 (pending), filed 2 Nov. 2006, which is a section 371 filing corresponding to PCT/US06/42962 (inactive), filed 2 Nov. 2006, which is entitled to priority to U.S. provisional application No. 60/732,121, filed 2 Nov. 2005; U.S. patent application Ser. No. 12/216,645 is entitled to priority to U.S. provisional application No. 60/929,611, filed 5 Jul. 2008; the present application is also a continuation-in part of U.S. patent application Ser. No. 12/223,327 (pending), which is a section 371 filing corresponding to PCT/US2007/02378 (inactive), filed Jan. 29, 2007, which is entitled to priority to U.S. provisional application no. 60/762,489, filed Jan. 27, 2006; each of the applications identified in this paragraph other than U.S. patent application Ser. No. 12/223,987 is herein incorporated by reference in its entirety.

FIELD OF THE INVENTION

The present invention is in the field of multimodal oral, abuse resistant pharmaceutical compositions of opioid agonists, extended release pharmaceutical compositions of opioid agonists, extended release abuse resistant pharmaceutical compositions of opioid agonists and the use thereof.

BACKGROUND OF THE INVENTION

Although the abuse of opioids has been documented over many centuries, it is largely in the last century that we have been confronted by the abuse of pharmaceutical grade opioids in the form of pharmaceutical dosage forms intended for therapeutic uses. The abuse of opioids is either due to iatrogenic addiction or willful abuse of the products outside their intended use or method of use by drug abusers and recreational drug users.

Currently, medical practitioners may choose from several well-accepted classes of pharmaceutical agents in their attempts to alleviate and prevent pain. Nonlimiting examples of agents used include nonsteroidal anti-inflammatory agents (NSAIDs), e.g., aspirin, ibuprofen, ketoprofen, diclofenac; opioids, e.g., morphine, hydromorphone, hydrocodone, levorphanol, oxycodone, tramadol, and codeine; cyclooxygenase-2 (COX-2) selective NSAIDs, e.g., celecoxib, valdecoxib, etoricoxib, lumiracoxib, and rofecoxib; acetaminophen and nitroparacetamol; tricyclic antidepressants, e.g., amitriptyline, desipramine, nortriptyline; non-tricyclic antidepressants, e.g., doxepin, duloxetine, paroxetine, venlafaxine; antiepileptics, e.g., gabapentin, pregabalin, carbamazepine, oxcarbazepine, lamotrigine; voltage sensitive N-type calcium channel blockers, e.g., ziconotide and alpha adrenergic agonists, e.g., clonidine.

An important goal of analgesic therapy is to achieve continuous relief of pain. Regular administration of an analgesic is generally required to ensure that the next dose is given before the effects of the previous dose have worn off. Continuous suppression of pain through the use of around the clock opioid analgesics is now recommended in treatment guidelines (Principles of Analgesic Use in the Treatment of Acute Pain and Cancer Pain, Fifth Ed., American, Pain Society (2003); Evidence Based Report of the U.S. Agency for Healthcare Research and Quality (AHRQ) on the Management of Cancer Pain, Report No. 35, AHRQ Publication No. 02-E002, October 2001; Can et al. J Nat Cancer Inst Monograph 2004; 32:23-31; Agency for Health Care Policy and Research Clinical Practice Guidelines for Cancer Pain Management, Guideline No. 9, AHCPR Publication No. 94-0592, March 1994; Agency for Health Care Policy and Research Clinical Practice Guideline for Acute Pain Management, Guideline No. 1, AHCPR Publication No. 92-0032, February, 1992; Guideline for the Management of Cancer Pain in Adults, American Pain Society, 2005; Guideline for the Management of Pain in Osteoarthritis, Rheumatoid Arthritis, and Juvenile Chronic Arthritis, $2^{nd}$ Ed., American Pain Society, 2002).

Conventional (so called "immediate-release", "rapid release" or "short acting") opioid analgesics have been demonstrated to provide short-lived plasma levels, thereby requiring dosing every 4-6 hours in chronic pain. In contrast, extended release oral opioids are designed to maintain effective plasma levels throughout a 12 or 24-hour dosing interval. Extended release opioid formulations have now become the standard of care for the management of chronic pain. Use of extended release opioids can result in fewer interruptions in sleep, reduced dependence on caregivers, improved compliance, enhanced quality of life outcomes, and increased control over the management of their pain. In addition, such formulations can provide more constant plasma concentrations and clinical effects, less frequent peak to trough fluctuations and fewer side effects, compared with short acting opioids (Babul et al. Journal of Pain and Symptom Management 2004; 28:59-71; Matsumoto et al., Pain Medicine 2005; 6:357-66; Dhaliwal et al., Journal of Pain Symptom Management 1995; 10:612-23; Hays et al., Cancer 1994; 74:1808-16; Arkinstall et al., Pain 1995; 62:169-78; Hagen et al., Journal of Clinical Pharmacology 1995; 35:38-45; Peloso et al., Journal of Rheumatology 2000; 27:764-71).

Several studies have suggested the benefits of extended release over immediate release opioids. Ferrell et al (Oncol Nur Forum 1989; 4:521-6) compared 12-hourly controlled release morphine and short-acting analgesics in cancer pain and demonstrated that compliance increased as the required dosing frequency decreased, and noncompliance resulted in suboptimal pain control and poor quality-of-life outcomes. Arkinstall et al. (Pain 1995; 62:169-78) demonstrated that around that twice daily administration of controlled release codeine provided superior to pain control than a PRN regimen of acetaminophen plus codeine.

An important drawback with the use of opioids is the risk of drug addiction, drug diversion and drug abuse. Although the use of opioids for non-medical purposes has existed throughout recorded human history, their abuse has increased significantly in the past two decades (Drug Abuse Warning Network, http://dawninfo.samhsa.gov/; Drug Enforcement Administration, http://www.deadiversion.usdoj.gov/; National Survey on Drug Use & Health, http://www.oas.samhsa.gov/nhsda.htm; American Association of Poison Control Centers Toxic Exposure Surveillance System, http://www.aapcc.org/annual.htm).

Our increased understanding of the clinical pharmacology of opioids and data from well controlled clinical trials in chronic non-cancer pain (Peloso et al., Journal of Rheumatology 2000; 27:764-71; Caldwell, et al., Journal of Pain and Symptom Management 2002; 23:278-91; Matsumoto et al., Pain Medicine 2005; 6:357-66; Arkinstall et al., Pain1995; 62:169-78) and neuropathic pain (Watson and Babul, Neurology 1998; 50:1837-41) have resulted in more widespread use in patients with non-malignant pain (for a review, see Sloan and Babul, Expert Opinion on Drug Delivery 2006; 3:489-97). This in turn has led to concerns about the increased non-medical use of opioids through both licit and illicit channels. For instance, unsuspecting clinicians may prescribe opioids for pain to individuals with an addiction disorder or individuals with pain who divert a portion of their prescribed dose to other individuals. There have also been documented cases of inappropriate prescribing or dispensing of opioids by physicians and pharmacists, with its eventual diversion into the non-medical marketplace. Additionally, non-medical supplies of pharmaceutical grade opioids are often obtained through prescription forgeries and break-ins into pharmacies.

Pharmaceutical dosage forms containing opioids may be ingested whole, crushed and ingested, crushed or vaporized and snorted or injected intravenously after attempted extraction of the active pharmaceutical ingredient.

The introduction of extended release morphine (MS Contin®) revolutionized the management of cancer pain. MS Contin® gained widespread acceptance due to its global availability, significant pharmacokinetic and pharmacodynamic data, and the convenience of an extended-release formulation. However, the incidence and severity of side effects limits the use of morphine in some patients (Hagen and Babul, Cancer 1997; 79:1428-37). In patients with renal impairment, morphine's principal metabolites, morphine-3-glucuronide and morphine-6-glucuronide can accumulate. Morphine-3-glucuronide accumulation has been implicated in hyperalgesia, respiratory stimulation, and behavioral excitatory properties through nonopioid receptor mechanisms. Morphine-6-glucuronide accumulation has been implicated in increasing levels of nausea and sedation in patients with renal impairment (Babul and Darke, Clin Pharm Ther, 1993; 54:286-92).

Clinicians treating cancer pain with opioids have reported significant variability among patients in efficacy and side effects with available opioid analgesics. Patients with poor analgesic efficacy or safety outcomes on one opioid frequently tolerate another opioid well. This clinical observation led to the development of oxycodone ER (OxyContin®). Due to the limitations associated with extended release morphine noted above and the "stigma" associated with its use (i.e., association with addiction, advanced cancer, dying and death), extended release oxycodone gained rapid acceptance by patients with chronic non-cancer pain. However, its widespread use for the treatment of chronic non-malignant pain was also associated with its diversion into the non-medical supply for use both by addicts and recreational drug users.

The popularity of extended release oxycodone among addicts and recreational drug users was due to a large amount of drug per tablet (a 12 or 24 hour supply). Commercially available immediate release opioid tablets and capsules are usually administered every 4 to 6 hours and they release their dose into the systemic circulation over one to two hours. New, extended release formulations are designed to gradually release their much larger opioid content over a 12 or 24-hour period. Most recreational drug users and addicts have a unit of use which is one tablet or capsule. The 12 or 24-hour supply of opioid contained in one tablet or capsule, instead of 4 to 6 tablets or capsules means that there is a greater risk that such formulations may be highly sought by drug addicts and recreational drug users alike, for non-medical use. Intentional or inadvertent tampering from extended release formulations will rapidly deliver a massive dose and produce profound a variety of serious and life threatening side effects, including respiratory depression and failure, sedation, cardiovascular collapse, coma and death.

Addicts and recreational drug may user extended release opioids by the parenteral, intranasal or oral route. Opioid abuse can involve physical, mechanical, thermal or chemical tampering of the dosage form (e.g., crushing, melting, solvent extraction and filtration)

Scheduling of opioid drugs has also had the unintentional side-effect of causing physicians, fearful of being accused of permitting "opioid overuse", to prescribe suboptimal doses of opioids to patients in need of them, and to prescribe less effective drugs to patients that are not similarly scheduled. This phenomenon is described in the literature as "opiophobia" or "narcophobia".

There is a growing recognition in the medical community that a large number of patients suffer from the undertreatment of pain. Among the reasons frequently cited as causative of undertreatment are: (1) the failure to prescribe enough drug at the right dosage interval to reach a steady-state threshold commensurate with the pain relief needed; (2) failure of patients to comply with a given dosage regimen; and (3) the reluctance of many physicians to prescribe analgesics categorized as controlled drugs based on often unfounded concerns of future addiction and fear of regulatory sanctions. For example, it has been reported that with respect to cancer pain, a large percentage of cancer patients suffer debilitating pain despite treatment with analgesics (Cleeland et al., New England Journal of Medicine 1994; 330:592-596).

A number of reported cases of opioid toxicity are a result of inadvertent or unintentional medical use of opioids. It is not uncommon for patients who have difficulty swallowing, to crush the contents of tablets or open a capsule, and swallow the contents with liquids or on soft food. In the case of most immediate release formulations, this generally produces no significant harm, with marginally higher peak concentrations ($C_{max}$) and time to peak concentrations ($t_{max}$). However, in the case of extended release opioid formulations, crushing the oral solid dosage form destroys the controlled-release mechanism and results in a rapid surge of drug into the bloodstream, with the entire 12 or 24-hour drug supply released immediately with toxic effects. For this reason, all extended release formulations available for sale in the United States carry a warning to the prescriber and patient not to crush or tamper with the oral solid dosage form (see Prescribing Information for MS Contin®, OxyContin®, Avinza® and Kadian®, Physician's Desk Reference, 2005, Thompson PDR, Montvale, N.J.).

There is therefore a need for a "passive" abuse deterrent system to protect both medical and non-medical users of opioids from intentional or unintentional opioid toxicity, without unnecessary harm to either group from the abuse deterrent technology.

Similarly, abuse deterrent pharmaceutical compositions containing aversive substances can cause serious harm to subjects if injected intravenously and the long terms safety of small amounts of such aversive substances which would be inevitably released in the gastrointestinal tract is unknown.

There is also need, therefore, for novel methods of preventing opioid abuse which do not require the incorporation of aversive and potentially unsafe agents into the formulation.

In 2005, a serious new clinical problem arose with the therapeutic use of extended release opioids, particularly extended release formulations in capsule dosage forms, when co-ingested with alcohol. In this setting, the opioid analgesic was being used for legitimate medical purposes (e.g., to treat pain) and was being ingested as an untampered or intact formulation. Although subjects with chronic pain are discouraged from using opioids with alcohol, the co-ingestion of opioids with alcohol, especially in the setting of intractable pain is widespread. The problem was discovered with a once-a-day extended release formulation of the opioid hydromorphone HCL (Palladone®) capsules). Palladone® capsules were introduced in the United States and Canada in 2004. In 2005, Palladone® capsules were withdrawn from the market in both countries due to dose-dumping when co-ingested with alcohol. In a 24-subject study, patients consuming 240 mL of 40% ethanol had a 6-fold mean increase in peak plasma hydromorphone concentration compared with co-ingestion of Palladone® capsules with water. One subject experienced a 16-fold increase when the drug was ingested with 40% alcohol compared with water. Patients consuming 240 mL of 20% ethanol had a 2-fold mean increase in peak plasma hydromorphone concentration. One subject in this group experienced a 6-fold increase when the drug was ingested with 20% alcohol compared with water. In some subjects, 8 ounces of 4% alcohol (equivalent to ⅔ of a typical serving of beer) resulted in almost twice the peak plasma hydromorphone concentration than when the drug was ingested with water. In requesting the withdrawal of Palladone® capsules, FDA noted that the manufacturer of "Palladone® provided FDA data that showed that drinking alcohol while taking Palladone® capsules may cause rapid release of hydromorphone, leading to high drug levels in the body, with potentially fatal effects. High drug levels of hydromorphone may depress or stop breathing, cause coma, and even cause death. The Agency has concluded that the overall risk versus benefit profile of Palladone® is unfavorable due to a potentially fatal interaction with alcohol. Pharmacokinetic data indicate that the co-ingestion of Palladone® and alcohol results in dangerous increases in the peak plasma concentrations of hydromorphone. These elevated levels may be lethal, even in opioid tolerant patients." (Sloan and Babul, Expert Opinion on Drug Delivery 2006; 3:489-97; http://www.fda.gov/cder/drug/infopage/palladone/default.htm)

FDA has since noted that a number of other capsule formulations of extended release opioids may be similarly vulnerable to dose dumping when co-ingested with alcohol. In vitro studies performed by the FDA have demonstrated that when Avinza® (once-daily extended release morphine) 30 mg was mixed with 900 mL of buffer solutions containing ethanol, the dose of morphine that was released was alcohol concentration-dependent, leading to a more rapid release of morphine. While the relevance of in vitro lab tests regarding Avinza® to the clinical setting remains to be determined, this acceleration of release may correlate with in vivo rapid release of the total morphine dose, which could result in the absorption of a potentially fatal dose of morphine. (http://www.fda.gov/medwatch/SAFETY/2005/AVINZA_DHCP_Letter_Oct2005.pdf; Sloan and Babul, Expert Opinion on Drug Delivery 2006; 3:489-97)

There is therefore also need, therefore, for novel methods of preventing excessive peak concentrations (dose dumping) of opioids when they are co-ingested for medical purposes at prescribed doses with alcohol.

Extended release formulations have become highly preferable and in some cases, the standard of care for the management of a wide variety of conditions, particularly chronic conditions. Additionally, extended release formulations can make otherwise non-viable pharmaceutical agents (e.g., due to an exceedingly short duration of effect) into viable formulations with clinical and commercial potential.

Extended release dosage forms of opioids may result in fewer interruptions in sleep, reduced dependence on caregivers, improved compliance, enhanced quality of life outcomes, and increased control over the management of their medical condition. In addition, such dosage forms may provide more constant plasma concentrations and clinical effects, less frequent peak to trough fluctuations and fewer side effects, compared with short acting or immediate release versions of opioids.

Toxicity from opioids can result from unintentional or intentional tampering of the dosage form. It is not uncommon for patients who have difficulty swallowing, to crush the contents of tablets or open a capsule, and swallow the contents with liquids or on soft food. In the case of most immediate release dosage forms of opioids, this generally produces no significant harm, with marginally higher peak concentrations ($C_{max}$) and time to peak concentrations ($t_{max}$). However, in the case of extended release dosage forms of opioids, crushing the oral solid dosage form destroys the controlled-release mechanism and results in a rapid surge of drug into the bloodstream, with the entire 8, 12 or 24-hour drug supply released immediately with toxic effects, or pleasurable effects in the case of a drug abuser. For this reason, all extended release dosage forms available for sale in the United States carry a warning to the prescriber and patient not to crush or tamper with the oral solid dosage form.

There is a need, therefore, for novel methods and pharmaceutical compositions of extended release formulations of opioids to provide continuous relief of signs and symptoms amenable to treatment with the abusable drug, without having to take frequent doses of opioids. There is a need, therefore, for novel methods and pharmaceutical compositions of extended release formulations of opioids that result in fewer interruptions in sleep, reduced dependence on caregivers, improved compliance, enhanced quality of life outcomes, and increased control over the management of their medical condition. There is a need, therefore, for novel methods and pharmaceutical compositions of extended release formulations of opioids that result in more constant plasma concentrations and clinical effects, less frequent peak to trough fluctuations and fewer side effects, compared with short acting or immediate release versions of opioids. There is a need for novel methods and pharmaceutical compositions of extended release formulations of opioids that achieve the aforementioned benefits without increasing the risk of toxicity, drug diversion and drug abuse. There is a need for novel methods and pharmaceutical compositions of extended release formulations of opioids that achieve the aforementioned benefits and also provide abuse deterrence.

To date, no extended release formulations of opioids with abuse deterrent technology of any kind have been submitted for Marketing Application (New Drug Application) or been commercialized anywhere in the world. Indeed if prior drug development history is any guide, most such strategies are unlikely to be developed or commercialized and the optimal formulation(s) will likely be apparent only through postmarketing surveillance of several formulations with competing technologies. In addition, regional differences in patterns of abuse mean that different abuse deterrence strategies may be useful in different part of the world. Finally, experience with substance abuses indicates that those who are habitual abusers, particularly those who inject drugs intravenously, have a remarkable ability to defeat abuse deterrence strategies through physical and chemical manipulation of opioids and other drugs of abuse. Such addicts are frequently only one step behind strategies to deter abuse. With the ready access to information from their well knit network and more recently, from websites on how to optimally extract the active agent from pharmaceutical dosage forms and maximize euphoriant effects, the development of abuse deterrent formulations has become a major pharmaceutical, clinical, regulatory and law enforcement challenge.

In view of this, it is not surprising that the Food and Drug Administration's Division of Anesthetic, Analgesic and Rheumatology Drug Products and the U.S. Drug Enforcement Administration have encouraged companies to develop wide ranging abuse deterrent strategies for opioids, particularly extended release opioids and as "inducement", offered that such products may include in their prescribing information data about their products abuse deterrent properties (FDA Perspectives on Opioid Risk Management. Opioid Risk Management Meeting, Tufts Healthcare Institute, Boston, Mar. 29, 2005; DEA Perspectives on Opioid Risk Management. Opioid Risk Management Meeting, Tufts Healthcare Institute, Boston, Mar. 29, 2005).

Various attempts have been made and are described in prior art to develop abuse-deterrent dosage forms. Clearly there is a need for a delivery system for commonly used oral dosage formulations of drugs, and in particular analgesics such as opioid analgesics, for patients seeking drug therapy and which deters abuse and minimizes or reduces the potential for psychological dependence. In particular, there is a need for formulations that simultaneously provide robust abuse deterrence properties and an extended release pharmacokinetic profile suitable for every 12 or 24 hour oral administration. There is also a need for extended release formulations of opioids that are stable (i.e., do not dose dump) when used at therapeutic doses for medical purposes in conjunction with alcohol. An ideal formulation will provide a extended release pharmacokinetic profile suitable for every 12 or 24 hour release and will be resistant to crushing at room temperature and upon freezing, melting to allow for filtration and/or aspiration into a syringe and extraction with recreational solvents, all without doing harm to pain patients or patients with a substance abuse disorder, through the use of aversive agents or opioid antagonists.

Pharmaceutical dosage forms containing opioids have been used for non-medical purposes in a variety of settings: i) by patients with a disorder requiring treatment with an abusable drug who have developed an addiction disorder following initiation of therapy; ii) by patients with said disorder who had a pre-existing addiction disorder; iii) by patients with an addiction disorder seeking opioids for their reinforcing, rewarding, euphoriant or other mood altering properties.

Non-medical users of opioids are either recreational drug users who may use such agents episodically, or individuals with an addiction disorder who may require frequent maintenance doses. Opioids may be ingested whole, crushed and ingested, crushed or vaporized and snorted or injected intravenously after attempted extraction of the active pharmaceutical ingredient. The manipulation of pharmaceutical dosage forms of opioids has been documented for many decades. For instance, pentazocine (Talwin®), a synthetic opioid was crushed, extracted and injected intravenously by drug addicts.

Addicts and recreational drug users commonly use extended release versions of opioids by a variety of routes of administration. Commonly used methods include 1) parenteral (e.g., intravenous injection), 2) intranasal (e.g., snorting), and 3) episodic or repeated oral ingestion of intact or crushed tablets or capsules.

One mode of abuse can involve the extraction of the opioid component from the dosage form by first mixing the table or capsule with a suitable solvent (e.g., water or alcohol), and then filtering and/or extracting the opioid component from the mixture for intravenous injection. Another mode of abuse of extended release opioids can involve dissolving the drug in water, alcohol or another "recreational solvent" to hasten its release and to ingest the contents orally, in order to provide high peak concentrations and maximum euphoriant effects.

A number of strategies have been introduced to minimize the abuse of mood altering drugs. Primary among these schemes is a legal infrastructure that controls the manufacture, distribution and sale of such drugs. In the United States, opioids are restricted to dispensing on a prescription-only basis. Most of these drugs are "scheduled" as "controlled drugs", such that distribution of the drug is subject to strict controls and overview. The idea behind scheduling opioids as "controlled" is to ensure that the drugs are dispensed only for the amelioration of legitimate therapeutic maladies, and not for any mood-altering effect "high" or euphoria that may be produced by the drug when used in supra-therapeutic doses or administered by non-approved routes of administration.

While the scheduling of opioids as "controlled drugs" has reduced abuse of the drugs, it has not been entirely successful. For example, some persons who are legitimately prescribed the drugs sometimes divert the drugs to persons seeking their procurement for "recreational uses." These "recreational drug users" are frequently willing to pay significant sums of money for the drugs. In other cases, certain health professionals, unfortunately, have been found to be culprits in the non-approved distribution of opioid drugs.

It is believed that the most widely used diversion techniques at the "street level" are "doctor shopping" and prescription forgeries. In the case of the former, individuals who may or may not have a legitimate ailment requiring a doctor's prescription for controlled substances, visit numerous doctors, sometimes in several states, to acquire large amounts of controlled substances they abuse or sell to others.

There is a growing recognition in the medical community that a large number of patients suffer from the undertreatment of their medical condition when the treatment involves the use of psychoactive drugs, particularly those drugs which tend to diverted and abused. Scheduling of opioids has also had the unintentional side-effect of causing physicians, fearful of being accused of permitting or even promoting drug abuse and drug overuse, to prescribe suboptimal doses of opioids to patients in need of them, and to prescribe less effective drugs to patients that are not similarly scheduled.

An additional issue with extended release forms of drugs, including opioids is the interaction of the drug, even in an untampered form, when consumed with alcohol. Under such conditions, a number of drugs have demonstrated an in vitro and in vivo propensity for significant dose dumping when they are co-ingested for medical purposes at prescribed doses with alcohol, increasing the potential for drug toxicity and further exacerbating the intensity of the (abusable) drug-alcohol pharmacodynamic interaction.

There is therefore also need, therefore, for novel methods of preventing excessive peak concentrations (dose dumping) of opioids when they are co-ingested for medical purposes at prescribed doses with alcohol.

The present invention also involves oral pharmaceutical compositions of opioids and methods of use thereof which provide reduced variability in rate and extent of absorption when taken with food, compared with the fasted state.

The present invention also involves oral extended release pharmaceutical compositions of opioids and methods of use thereof which provide reduced variability in rate and extent of absorption when taken with food, compared with the fasted state.

Most pharmaceutical companies strive to develop oral pharmaceutical products which can be taken without regard to meal intake, i.e., on an empty stomach or with food. Indeed, it is now a requirement of both U.S. and E.U regulatory guidance's to conduct studies of all new chemical entities to determine the influence of concurrent food intake on the bioavailability of products. Concurrent intake of food in so called "fed-fasted" human bioavailability studies may increase, decrease or have no effect on the bioavailability of the pharmaceutical products. Accordingly, the prescribing information guides both the prescriber and the patient on the appropriate use of the pharmaceutical product.

The issue of food effects on oral bioavailability has particular importance with oral extended release products, due to the possibility of "dose dumping" where the is potential that a portion or a substantial portion of the dose intended to be released gradually over time (e.g., over 8, 12 or 24 hours) may be released instantaneously or rapidly, such that the peak plasma concentration of the drug (peak exposure) will be substantially increased, resulting in toxicity and the duration of effect will be significantly reduced, potentially resulting in reduced duration of therapeutic effect. The ability to take the drug without regard to food intake and in the case of extended release pharmaceutical products, the absence of dose dumping has been found to be a significant patient benefit and a competitive marketing advantage. It is not uncommon to see pharmaceutical advertising targeted to medical practitioners which states "no food effect", "may be taken on an empty stomach or with food" and "may be taken without regard to food" and "no change in bioavailability with food".

The U.S. prescribing information for OxyContin™ (oxycodone ER) states "Food has no significant effect on the extent of absorption of oxycodone from OxyContin. However, the peak plasma concentration of oxycodone increased by 25% when a OxyContin 160 mg Tablet was administered with a high-fat meal."

The U.S. prescribing information for Opana™ ER (oxymorphone ER) states "two studies examined the effect of food on the bioavailability of single doses of 20 and 40 mg of OPANA ER in healthy volunteers. In both studies, after the administration of OPANA ER, the Cmax was increased by approximately 50% in fed subjects compared to fasted subjects. A similar increase in Cmax was also observed with oxymorphone solution."

In summary, many opioids in extended release form have a potentially clinically important food effect.

There is therefore a need for oral immediate release pharmaceutical compositions, and particularly extended release pharmaceutical compositions with consistent bioavailability regardless of administration in the fed or fasted state.

There is a need for methods and pharmaceutical compositions of pharmaceuticals and therapeutic agents that provide an extended release profile, preferably suitable for every 8, 12 or 24 hour oral administration. There is a need for methods and pharmaceutical compositions of opioids that provide an extended release profile. There is also a need for methods and pharmaceutical compositions of opioids that provide an abuse deterrent profile. In particular, there is a need for methods and pharmaceutical compositions of opioids that simultaneously provide abuse deterrence properties and extended release profiles, preferably suitable for every 8, 12 or 24 hour oral administration. There is also a need for extended release formulations of pharmaceuticals and therapeutic agents, and opioids that are stable (i.e., do not dose dump) when used at therapeutic doses for medical purposes in conjunction with alcohol. There is also a need for extended release formulations of pharmaceuticals and therapeutic agents, and opioids that provide a extended release pharmacokinetic profile suitable for every 8, 12 or 24 hour release and will be resistant to crushing at room temperature and upon freezing, melting to allow for filtration and/or aspiration into a syringe and extraction with recreational solvents. There is also a need for extended release formulations of pharmaceuticals and therapeutic agents, and opioids that provide a extended release pharmacokinetic profile suitable for every 8, 12 or 24 hour release and will be resistant to crushing at room temperature and upon freezing, melting to allow for filtration and/or aspiration into a syringe and extraction with recreational solvents, all without doing harm to patients or patients with a substance abuse disorder, through the use of aversive agents or antagonists.

BRIEF DESCRIPTION OF THE DRAWINGS

FIG. 1 is a graph which depicts the UV spectrum of tramadol HCl in water.

FIG. 2 is a graph which depicts a dissolution profile for formulation 052/014.

FIG. 3 is a graph which depicts a dissolution profile for formulation 052/015.

FIG. 4 is a graph which depicts a dissolution profile for formulation 052/019.

FIG. 5 is a graph which depicts a dissolution profile for formulation 052/024.

FIG. 6 is a graph which depicts a dissolution profile for formulation 052/024 in SIF containing pancreatin.

FIG. 7 is a graph which depicts a dissolution profile of propanolol HCl in Gelucire 50/02 in SIF without pancreatin.

FIG. 8 is a graph which depicts a dissolution profile of propanolol HCl in Gelucire 50/02 in SIF containing pancreatin.

FIG. 9 is a graph which depicts average dissolution profiles of propanolol HCl in Gelucire 50/02 in SIF with and without pancreatin.

FIG. 10 is a graph which depicts dissolution profiles of Zydol XL 150 and Dromadol SR tablets in SIF.

FIG. 11 is a graph which depicts combined dissolution profiles of seven different excipient formulations in SIF.

FIG. 12 is a graph which depicts combined dissolution profiles of seven different excipient formulations, using an extended scale.

FIG. 13 is a graph which depicts combined dissolution profiles of five base excipients in HPMC modified formulations.

FIG. 14 is a graph which depicts dissolution profiles of five capsule sample of cetyl alcohol formulation with 10% HPMC.

FIG. 15 is a graph which depicts dissolution profiles of modified Sterotex NF formulation.

FIG. 16 is a graph which depicts average dissolution profiles of modified Sterotex NF formulation.

FIG. 17 is a graph which depicts dissolution profiles of further modified Sterotex NF formulation.

FIG. 18 is a graph which depicts average dissolution profiles of further modified Sterotex NF formulation.

FIG. 19 is a graph which depicts dissolution profiles of Hydrokote formulations containing Methocel K 100M or Methocel K 15M.

FIG. 20 is a graph which depicts average dissolution profiles of Hydrokote formulations containing Methocel K 100M or Methocel K 15M.

FIG. 21 is a graph which depicts dissolution profiles of 250 mg Tramadol HCl in a 550 mg Sterotex NF based formulation.

FIG. 22 is a graph which depicts averaged dissolution profiles of 250 mg Tramadol HCL in a 550 mg Sterotex NF based formulation.

FIG. 23 is a graph which depicts dissolution profiles of 75 mg Tramadol HCl in beeswax with 20% HPMC based formulation.

FIG. 24 is a graph which depicts averaged dissolution profiles of 75 mg Tramadol HCL in beeswax with 20% HPMC formulation.

FIG. 25 is a graph which depicts dissolution profiles of 75 mg Tramadol HCl in beeswax with 23% HPMC based formulation.

FIG. 26 is a graph which depicts averaged dissolution profiles of 75 mg Tramadol HCl in beeswax with 23% HPMC based formulation.

FIG. 27 is a graph which depicts a comparison of averaged dissolution profiles of Tramadol HCl in beeswax with 20% and 23% HPMC based formulation.

FIG. 28 is a graph which depicts combined dissolution profiles of first three Tramadol HCl formulations.

FIG. 29 is a graph which depicts Tramadol HCl in beeswax dissolution profile normalized to HPLC assay data.

FIG. 30 is a graph which depicts Tramadol HCL in Gelucire 50/02 dissolution profile normalized to HPLC assay data.

FIG. 31 is a graph which depicts Tramadol HCl in Gelucire 50/02 repeat dissolution profile normalized to HPLC assay data.

FIG. 32 is a graph which depicts Tramadol HCl in cetyl alcohol dissolution profile normalized to HPLC assay data.

FIG. 33 is a graph which depicts Tramadol HCl in cetyl alcohol repeat dissolution profile normalized to HPLC assay data.

FIG. 34 is a graph which depicts combined dissolution profiles of second three Tramadol HCl formulations.

FIG. 35 is a graph which depicts Tramadol HCl in Sterotex NG dissolution profile normalized to HPLC assay data.

FIG. 36 is a graph which depicts Tramadol HCl in Sterotex NG dissolution profile normalized to HPLC assay data with an extended time scale.

FIG. 37 is a graph which depicts Tramadol HCl in Cithrol GMS dissolution profile normalized to HPLC assay data.

FIG. 38 is a graph which depicts Tramadol HCl in Cithrol GMS dissolution profile normalized to HPLC assay data with an extended time scale.

FIG. 39 is a graph which depicts Tramadol HCl in Hydrokote 112 dissolution profile normalized to HPLC assay data.

FIG. 40 is a graph which depicts Tramadol HCl in Hydrokote 112 dissolution profile normalized to HPLC assay data with an extended time scale.

FIG. 41 is a graph which depicts Tramadol HCl in beeswax dissolution profile normalized to HPLC assay data.

FIG. 42 is a graph which depicts abuse resistance testing, specifically ethanol extraction on whole dosage units.

FIG. 43 is a graph which depicts abuse resistance testing, specifically ethanol extraction on cut or crushed dosage units.

FIG. 44 is a graph which depicts dissolution profile of Tramadol HCl in Sterotex NF formulations.

FIG. 45 is a graph which depicts dissolution profile of Tramadol HCl in Sterotex NF formulations with and without fractionated coconut oil.

FIG. 46 is a graph which depicts abuse resistance testing, specifically ethanol extraction on whole dosage units.

FIG. 47 is a graph which depicts abuse resistance testing, specifically ethanol extraction on crushed or cut dosage units.

FIG. 48 is a graph which depicts dissolution profile of stored Sterotex NF formulation.

FIG. 49 is a graph which depicts comparison of dissolution profiles of fresh and stored Sterotex NF formulation.

FIG. 50 is a graph which depicts dissolution profile of stored Sterotex NF formulation with 25% fractionated coconut oil.

FIG. 51 is a graph which depicts comparison of dissolution profiles of fresh and stored Sterotex NF formulations with 25% fractionated coconut oil.

FIG. 52 is a graph which depicts dissolution profile of stored Cithrol GMS formulation.

FIG. 53 is a graph which depicts comparison of dissolution profiles of fresh and stored Cithrol GMS formulations.

FIG. 54 is a graph which depicts dissolution profile of stored Hydrokote 112 formulation.

FIG. 55 is a graph which depicts comparison of dissolution profiles of fresh and stored Hydrokote 112 formulations.

FIG. 56 is a graph which depicts dissolution profile of stored beeswax formulation.

FIG. 57 is a graph which depicts comparison of dissolution profiles of fresh and stored beeswax formulations.

FIG. 58 is a pair of bar graphs which depict the effects of crushing, grinding, water or vinegar solubilization and filtration.

FIG. 59 is a graph which depicts dissolution profiles in a beeswax formulation.

FIG. 60 is a graph which depicts dissolution profiles in a Cithrol formulation.

FIG. 61 is a graph which depicts dissolution profiles in a Sterotex formulation.

FIG. 62 is a graph which depicts dissolution profiles in a Hydrokote formulation.

DETAILED DESCRIPTION OF THE INVENTION

In some preferred embodiments, the present invention is directed at pharmaceutical compositions of abusable drugs to provide abuse deterrence properties.

In some preferred embodiments, the present invention is directed at pharmaceutical compositions of abusable drugs to provide extended release properties.

In some preferred embodiments, the present invention is directed at pharmaceutical compositions of abusable drugs that provide simultaneous abuse deterrence properties and extended release properties.

In some preferred embodiments, the present invention is directed at pharmaceutical compositions of abusable drugs that provide simultaneous abuse deterrence properties and extended release properties using substantially the same ingredients to achieve abuse deterrence properties and extended release.

In some preferred embodiments, the present invention is directed at liquid pharmaceutical compositions of abusable drugs that solidify at room temperature to provide abuse deterrence properties.

In some preferred embodiments, the present invention is directed at liquid pharmaceutical compositions of abusable drugs that solidify at room temperature to provide extended release properties.

In some preferred embodiments, the present invention is directed at oral solid pharmaceutical compositions of abusable drugs that are in the form of a liquid, semisolid, oil or otherwise difficult to granulate.

In some preferred embodiments, the present invention is directed at liquid pharmaceutical compositions of abusable drugs that solidify at room temperature to provide simultaneous abuse deterrence properties and extended release properties.

In some preferred embodiments, the present invention is directed at liquid pharmaceutical compositions of abusable drugs that solidify at room temperature to provide simultaneous abuse deterrence properties and extended release properties using substantially the same ingredients to achieve abuse deterrence properties and extended release.

In some preferred embodiments, the present invention is directed at oral abusable drug pharmaceutical compositions and the use thereof for preventing or minimizing the risk of abusable drug toxicity from either intentional or unintentional tampering.

In some preferred embodiments, the present invention is directed at oral abusable drug pharmaceutical compositions and the use thereof for deterring abuse by drug addicts and/or recreational drug users.

In some preferred embodiments, the present invention is directed at oral abusable drug pharmaceutical compositions that provide extended release delivery of the drug and the use thereof for the treatment of pain and addiction disorders.

For the purposes of the present invention and not withstanding anything to the contrary, the phrase "abusable drugs" are limited to one or more "opioid agonists" or "opioid receptor agonists", as further defined herein.

In some preferred embodiments, abusable drugs of the present invention can be formulated with the substantially the same ingredients to deter abuse and minimize abusable drug toxicity on tampering while simultaneously providing an extended release pharmacokinetic profile suitable for every 4, 6, 8, 12 or 24 hour dosing.

In some preferred embodiments, abusable drugs of the present invention can be formulated with the substantially the same ingredients to deter abuse and minimize abusable drug toxicity on tampering while simultaneously providing an extended release pharmacokinetic profile suitable for every 4, 6, 8, 12 or 24 hour dosing, without the need to include an aversive agent or an antagonist for the abusable drug in the formulation.

In some preferred embodiments, abusable drug pharmaceutical compositions and methods of the present invention provide (i) abuse deterrence; (ii) extended release; and (iii) simultaneous abuse deterrence and extended release, prepared using one or more ADER compounds.

As used herein, the term "ADER". "ADER material" and "ADER agent" refers to one or more compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof. In some preferred embodiments, ADER is a mixture of two or more compounds from the forgoing group [i.e., (a) to (d)]. In some preferred embodiments, to qualify as an "ADER" requires a mixture of two or more compounds from the form the foregoing group [i.e., (a) to (d)]. In some particularly preferred embodiments, to qualify as an "ADER" requires a mixture of two or more compounds selected from at least two categories[i.e., (a) to (d)].

As used herein, the term "ADER". "ADER material" and "ADER agent" also includes glyceryl behenate (e.g., Comptirol™ 888 ATO), glyceryl palmitostearate (e.g., Precirol™ ATO 5), stearoyl macrogolglycerides (Gelucire™ 50/13), lauroyl macrogolglycerides (Labrafil™ M 2130 CS).

In some preferred embodiments, abusable drug pharmaceutical compositions and methods of the present invention provide simultaneous abuse deterrence and extended release, prepared using ADER, using substantially the same ingredients to effect abuse deterrence and extended release.

In some preferred embodiments, abusable drug pharmaceutical compositions and methods of the present invention provide (i) extended release; and (ii) protection against ethanol induced dose dumping, prepared using ADER.

In some preferred embodiments, abusable drug pharmaceutical compositions and methods of the present invention provide (i) extended release; and (ii) protection against ethanol induced dose dumping, prepared using ADER, using substantially the same ingredients to effect extended release and protection against ethanol induced dose dumping.

In some preferred embodiments, abusable drug pharmaceutical compositions and methods of the present invention provide (i) abuse deterrence and extended release; and (ii) protection against ethanol induced dose dumping, prepared using ADER.

In some preferred embodiments, abusable drug pharmaceutical compositions and methods of the present invention provide (i) abuse deterrence and extended release; and (ii) protection against ethanol induced dose dumping, prepared using ADER, using substantially the same ingredients to effect abuse deterrence and extended release, and protection against ethanol induced dose dumping.

In some preferred embodiments, the present invention is directed to a novel method for reducing the peak concentration ($C_{max}$) of the abusable drug, said method comprising administering the abusable drug and a suitable amount of ADER.

In some preferred embodiments, the present invention is directed to a novel method for reducing the early post-dose partial area under the plasma concentration time curve (e.g., $AUC_{0-2}$, $AUC_{0-4}$ and $AUC_{0-6}$) of the abusable drug, said method comprising administering the abusable drug and a suitable amount of ADER.

In some preferred embodiments, the present invention is directed to a novel method for reducing the early post-dose average plasma concentration time (Cave) of the abusable drug, said method comprising administering the abusable drug and a suitable amount of ADER.

In some preferred embodiments, the present invention is directed to a novel method for reducing the incidence of abusable drug toxicity upon tampering of the abusable drug, said method comprising administering the abusable drug and a suitable amount of ADER.

In some preferred embodiments, the present invention is directed to a novel method for reducing the intensity of abusable drug toxicity upon tampering of the abusable drug, said method comprising administering the abusable drug and a suitable amount of ADER.

In some preferred embodiments, the present invention is directed to a novel method for reducing the intensity or frequency of one or more signs and symptoms of abusable drug toxicity, including nausea, vomiting, somnolence, stupor, coma, respiratory depression, apnea, respiratory arrest, circulatory depression, bradycardia, hypotension, shock and skeletal muscle flaccidity, said method comprising administering the abusable drug and a suitable amount of ADER.

In some preferred embodiments, the present invention is directed to a novel method for reducing the intensity or frequency of one or more signs and symptoms of abusable drug toxicity, including tachycardia, mood alteration, euphoria, CNS stimulation, agitation, increased sweating, psychotomimetic effects, hallucinations, perception alterations, cognitive alterations, reinforcing effects and pleasurable effects said method comprising administering the abusable drug and a suitable amount of ADER.

In some preferred embodiments, the present invention is directed to a novel method for reducing the intensity or frequency of one or more signs and symptoms of abusable drug toxicity, including "high", "liking", pleasurable, euphoric, alertness, wakefulness, calming, anxiolytic, auditory and visual perceptual alterations, relaxing, analgesic and rewarding effects.

In some preferred embodiments, the present invention is directed to novel pharmaceutical compositions for use in reducing the peak concentration ($C_{max}$) of the abusable drug, said method comprising administering the abusable drug and a suitable amount of ADER.

In some preferred embodiments, the present invention is directed to novel pharmaceutical compositions for reducing the early post-dose partial area under the plasma concentration time curve (e.g., $AUC_{0-2}$, $AUC_{0-4}$ and $AUC_{0-6}$) of the abusable drug, said method comprising administering the abusable drug and a suitable amount of ADER.

In some preferred embodiments, the present invention is directed to novel pharmaceutical compositions for reducing the early post-dose average plasma concentration time (Cave) of the abusable drug, said method comprising administering the abusable drug and a suitable amount of ADER.

In some preferred embodiments, the present invention is directed to novel pharmaceutical compositions for reducing the incidence of abusable drug toxicity, said method comprising administering the abusable drug and a suitable amount of ADER.

In some preferred embodiments, the present invention is directed to novel pharmaceutical compositions for reducing the intensity of abusable drug toxicity, said method comprising administering the abusable drug and a suitable amount of ADER.

In some embodiments, the invention provides an oral pharmaceutical composition of an abusable oral drug which is: (a) abuse resistant; (b) extended release; (c) resistant to dose dumping due to alcohol; (d) resistant to significant changes in oral bioavailability due to changes in food intake; and (e) resistant to intentional or surreptitious adulteration of beverages; or two or more of the above [(a) to (e)], said composition comprising: (A) an abusable drug or a pharmaceutically acceptable salt thereof or a mixture thereof; and (B) One or more compounds selected from the categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes.

In some embodiments, the invention provides an oral pharmaceutical composition of an abusable oral drug which is: (a) abuse resistant; (b) extended release; (c) resistant to dose dumping due to alcohol; (d) resistant to significant changes in oral bioavailability due to changes in food intake; and (e) resistant to intentional or surreptitious adulteration of beverages; or two or more of the above [(a) to (e)], said composition comprising: (A) an abusable drug or a pharmaceutically acceptable salt thereof or a mixture thereof; and (B) Two or more compounds selected from the categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes.

In some embodiments, the invention provides an oral pharmaceutical composition of an abusable oral drug which is: (a) abuse resistant; (b) extended release; (c) resistant to dose dumping due to alcohol; (d) resistant to significant changes in oral bioavailability due to changes in food intake; and (e) resistant to intentional or surreptitious adulteration of beverages; or two or more of the above [(a) to (e)], said composition comprising: (A) an abusable drug or a pharmaceutically acceptable salt thereof or a mixture thereof; and (B) Two or more compounds selected from at least two categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes.

In some embodiments, the invention provides an oral pharmaceutical composition of an abusable oral drug which is: (a) abuse resistant; (b) extended release; (c) resistant to dose dumping due to alcohol; (d) resistant to significant changes in oral bioavailability due to changes in food intake; and (e) resistant to intentional or surreptitious adulteration of beverages; or two or more of the above [(a) to (e)], said composition comprising: (A) an abusable drug or a pharmaceutically acceptable salt thereof or a mixture thereof; and (B) One or more compounds selected from the categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes; said composition [(a) to (e)] using substantially the same ingredients.

In some embodiments, the invention provides an oral pharmaceutical composition of an abusable oral drug which is: (a) abuse resistant; (b) extended release; (c) resistant to dose dumping due to alcohol; (d) resistant to significant changes in oral bioavailability due to changes in food intake; and (e) resistant to intentional or surreptitious adulteration of beverages; or two or more of the above [(a) to (e)], said composition comprising: (A) an abusable drug or a pharmaceutically acceptable salt thereof or a mixture thereof; and (B) Two or more compounds selected from the categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes; said composition [(a) to (e)] using substantially the same ingredients.

In some embodiments, the invention provides an oral pharmaceutical composition of an abusable oral drug which is: (a) abuse resistant; (b) extended release; (c) resistant to dose dumping due to alcohol; (d) resistant to significant changes in oral bioavailability due to changes in food intake; and (e) resistant to intentional or surreptitious adulteration of beverages; or two or more of the above [(a) to (e)], said composition comprising: (A) an abusable drug or a pharmaceutically acceptable salt thereof or a mixture thereof; and (B) Two or more compounds selected from at least two categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes; said composition [(a) to (e)] using substantially the same ingredients.

In some embodiments, compositions and methods of the present invention include: (i) one or more abusable drugs (i.e., one or more opioid agonists); and (ii) ADER; and (iii) optionally, other therapeutic agents in immediate or extended release form; and (iv) optionally one or more excipients or auxiliary agents (e.g., glidants, lubricants, disintegrants, antistatic agents, solvents, channel forming agents, coating agents, flavorants, preservatives, bulking agents, polymers, etc) and inert carriers; wherein the dosage form provides for abuse deterrence of the abusable drugs.

In some embodiments, compositions and methods of the present invention include: (i) one or more abusable drugs (i.e., one or more opioid agonists); and (ii) ADER; and (iii) optionally, other therapeutic agents in immediate or extended release form; and (iv) optionally one or more excipients or auxiliary agents (e.g., glidants, lubricants, disintegrants, antistatic agents, solvents, channel forming agents, coating agents, flavorants, preservatives, bulking agents, polymers, etc) and inert carriers; wherein the dosage form resists, deters or prevents crushing, shearing, grinding, chewing, dissolving, melting, needle aspiration, inhalation, insufflation or solvent extraction of the abusable drug.

In some embodiments, compositions and methods of the present invention include: (i) one or more abusable drugs (i.e., one or more opioid agonists); and (ii) ADER; and (iii) optionally, other therapeutic agents in immediate or extended release form; and (iv) optionally one or more excipients or auxiliary agents (e.g., glidants, lubricants, disintegrants, antistatic agents, solvents, channel forming agents, coating agents, flavorants, preservatives, bulking agents, polymers, etc) and inert carriers; wherein the dosage form provides extended release of the abusable drug.

In some embodiments, compositions and methods of the present invention include: (i) one or more abusable drugs (i.e., one or more opioid agonists); and (ii) ADER; and (iii) optionally, other therapeutic agents in immediate or extended release form; and (iv) optionally one or more excipients or auxiliary agents (e.g., glidants, lubricants, disintegrants, antistatic agents, solvents, channel forming agents, coating agents, flavorants, preservatives, bulking agents, polymers, etc) and inert carriers; wherein the dosage form provides abuse deterrence and extended release of the abusable drug.

In some embodiments, compositions and methods of the present invention include: (i) one or more abusable drugs (i.e., one or more opioid agonists); and (ii) ADER; and (iii) optionally, other therapeutic agents in immediate or extended release form; and (iv) optionally one or more excipients or auxiliary agents (e.g., glidants, lubricants, disintegrants, antistatic agents, solvents, channel forming agents, coating agents, flavorants, preservatives, bulking agents, polymers, etc) and inert carriers; wherein the dosage form provides simultaneous abuse deterrence and extended release of the abusable drug.

In some embodiments, compositions and methods of the present invention include: (i) one or more abusable drugs (i.e., one or more opioid agonists); and (ii) ADER; and (iii) optionally, other therapeutic agents in immediate or extended release form; and (iv) optionally one or more excipients or auxiliary agents (e.g., glidants, lubricants, disintegrants, antistatic agents, solvents, channel forming agents, coating agents, flavorants, preservatives, bulking agents, polymers, etc) and inert carriers; wherein the dosage form provides simultaneous abuse deterrence and extended release of the abusable drug using substantially the same ingredients.

In some preferred embodiments, the present invention is directed to novel pharmaceutical compositions for reducing the intensity or frequency of one or more symptoms, including nausea, vomiting, somnolence, stupor, coma, respiratory depression, apnea, respiratory arrest, circulatory depression, bradycardia, hypotension, shock and skeletal muscle flaccidity, said method comprising administering the abusable drug and a suitable amount of ADER.

In some preferred embodiments, the present invention is directed to novel pharmaceutical compositions for reducing the intensity or frequency of one or more signs and symptoms of abusable drug toxicity, including tachycardia, mood alteration, euphoria, CNS stimulation, agitation, increased sweating, psychotomimetic effects, hallucinations, perception alterations, cognitive alterations, reinforcing effects and pleasurable effects said method comprising administering the abusable drug and a suitable amount of ADER.

In some preferred embodiments, the present invention is directed to a novel pharmaceutical compositions for reducing the intensity or frequency of one or more signs and symptoms of abusable drug toxicity, including "high"; "liking"; "pleasurable"; "euphoric"; "alertness"; "wakefulness"; "calming"; "anxiolytic"; auditory and visual perceptual alterations; "relaxing" and "rewarding" effects.

In some preferred embodiments, the present invention is directed to a novel method and pharmaceutical compositions for preventing or minimizing excessive peak concentrations (dose dumping) of therapeutic doses of extended release abusable drugs used for medical purposes, when they are co-ingested with alcohol.

In some preferred embodiments, the present invention is directed to a novel method and pharmaceutical compositions for reducing the solvent extraction efficiency of the dosage form upon tampering.

In some preferred embodiments, the present invention is directed to a novel method and pharmaceutical compositions for reducing the filtration efficiency of the dosage form upon tampering.

In some preferred embodiments, the present invention is directed to a novel method and pharmaceutical compositions for preventing the surreptitious adulteration of beverages.

In some preferred embodiments, the present invention is directed pharmaceutical compositions which include one or more abusable drugs alone or in combination with other therapeutic agents, one or more ADER agents specified herein, and optionally one or more excipients (e.g., glidants, lubricants, disintegrants, etc) and inert carriers, said composition resisting, deterring, discouraging or preventing crushing, shearing, grinding, chewing, dissolving, melting, needle aspiration, inhalation, insufflation, solvent extraction and filtration of the abusable drug.

In some preferred embodiments, pharmaceutical compositions of the present invention provide a more extended release pharmacokinetic profile compared with formulations devoid of ADER.

In some preferred embodiments, pharmaceutical compositions and methods of the present invention can form a viscous substance upon contact with a solvent such that the abusable drug cannot be easily drawn into a syringe; crushed and powdered to facilitate or enhance nasal delivery (snorting or nasal insufflation), inhalation or rapid oral delivery of a larger than medically intended delivery of the abusable drug; extracted with solvents and filtered.

In some preferred embodiments, the pharmaceutical composition resists the rapid release of all or substantially all of the abusable drug content of the unit dose upon tampering. In another preferred embodiment of the invention, the pharmaceutical composition resists the rapid release of a portion of the abusable drug content of the unit dose upon tampering. In yet another preferred embodiment of the invention, upon tampering, the abusable drug formulated with ADER resists the release of the abusable drug to a greater extent than when formulated without ADER.

In some preferred embodiments, the pharmaceutical composition resists the rapid release of all or substantially all of the abusable drug content of the unit dose upon co-administering with alcohol. In another preferred embodiment of the invention, the pharmaceutical composition resists the rapid release of a portion of the abusable drug content of the unit dose upon co-administering with alcohol. In yet another preferred embodiment of the invention, upon co-administering with alcohol, the abusable drug formulated with ADER resists the release of the abusable drug to a greater extent than when formulated without ADER.

In some preferred embodiment of the abuse deterrent pharmaceutical composition, the therapeutic pharmaceutical composition can be filled in a hard gelatin capsule without banding. In some preferred embodiment of the abuse deterrent pharmaceutical composition, the therapeutic pharmaceutical composition can be filled in a hard gelatin capsule with security banding. In another preferred embodiment of the abuse deterrent pharmaceutical composition, the therapeutic pharmaceutical composition can be filled in a soft shell capsules. In another preferred embodiment of the abuse deterrent pharmaceutical composition, the therapeutic pharmaceutical composition can be prepared as a solid dispersion for direct compression into tablets, for extrusion and pelletization, followed by compression into a tablet or filling into a capsule. In another preferred embodiment of the abuse deterrent pharmaceutical composition, the therapeutic pharmaceutical composition can be compressed into tablets. In another preferred embodiment of the abuse deterrent pharmaceutical composition, the therapeutic pharmaceutical composition can be prepared into multiparticulate matrices followed by tabletting or capsule filling.

The present invention is directed at oral pharmaceutical compositions of abusable drugs or their pharmaceutically acceptable salts or mixtures thereof.

The present invention also relates to oral abusable drug pharmaceutical compositions and methods for the prevention and treatment of pain, musculoskeletal disorders ands other medical conditions amenable to treatment with the abusable drug.

It is an object of certain preferred embodiments of the present invention to substantially improve the efficiency and quality of disease management for: (i) pain; (ii) musculoskeletal disorders; (iii) addiction disorders; and/or (iv) other medical conditions amenable to treatment with the abusable drug.

It is an object of certain preferred embodiments of the present invention to provide bioavailable oral formulations of abusable drugs suitable for up to once-daily (e.g., Q4H, Q6H, Q8H, Q12H, Q24H) administration which substantially improve the efficiency and quality of disease management for: (i) pain; (ii) musculoskeletal disorders; (iii) addiction disorders; and/or (iv) other medical conditions amenable to treatment with the abusable drug.

It is an object of certain preferred embodiments of the present invention to provide bioavailable oral formulations of abusable drugs which provide a substantially increased duration of effect as compared to immediate release formulations.

It is an object of certain preferred embodiments of the present invention to provide bioavailable oral formulations of abusable drugs which provide a substantially reduced abuse potential compared with immediate release formulations of abusable drugs.

It is an object of certain preferred embodiments of the present invention to provide bioavailable oral formulations of abusable drugs which provide a substantially reduced abuse potential compared with currently available extended release formulations.

It is an object of certain preferred embodiments of the present invention to provide bioavailable oral formulations of abusable drugs which provide a substantially reduced abuse potential compared with commercially available formulations of abusable drugs.

It is an object of certain preferred embodiments of the present invention to provide bioavailable oral immediate release formulations of abusable drugs which provide a substantially reduced abuse potential.

It is an object of certain preferred embodiments of the present invention to provide bioavailable oral immediate release formulations of abusable drugs which provide a substantially reduced variability in rate and extent of absorption when taken with food, compared with the fasted state.

It is an object of certain preferred embodiments of the present invention to provide bioavailable oral immediate release formulations of abusable drugs which provide a substantially reduced variability in rate and extent of absorption when taken with alcohol, compared to an alcohol-free state.

It is an object of certain preferred embodiments of the present invention to provide bioavailable oral extended release formulations of abusable drugs which provide a substantially reduced variability in rate and extent of absorption when taken with food, compared with the fasted state.

It is an object of certain preferred embodiments of the present invention to provide bioavailable oral extended release formulations of abusable drugs which provide a substantially reduced variability in rate and extent of absorption when taken with alcohol, compared to an alcohol-free state.

It is an object of certain preferred embodiments of the present invention to provide bioavailable oral abuse resistant and abuse deterrent extended release formulations of abusable drugs which provide a substantially reduced variability in rate and extent of absorption when taken with food, compared with the fasted state.

It is an object of certain preferred embodiments of the present invention to provide bioavailable oral abuse resistant and abuse deterrent extended release formulations of abusable drugs which provide a substantially reduced variability in rate and extent of absorption when taken with alcohol, compared to an alcohol-free state.

It is an object of certain preferred embodiments of the present invention to provide bioavailable oral extended release formulations of abusable drugs which provide a substantially reduced abuse potential compared with currently available extended release formulations.

It is an object of certain preferred embodiments of the present invention to provide bioavailable formulations for oral administration suitable for up to once-a-day administration (e.g., Q4H, Q6H, Q8H, Q12H, and Q24H).

It is an object of certain preferred embodiments of the present invention to provide bioavailable formulations for oral administration suitable for up to once-a-day administration which provide an early onset and sustained duration of therapeutic effect.

It is an object of certain preferred embodiments of the present invention to provide formulations of abusable drugs which provide a therapeutic effect for up to about 30 minutes. In other preferred embodiments, the formulations of abusable drugs provide a therapeutic effect for up to about 1 hour, or up to about 2 hours, or up to about 4 hours, or up to about 6 hours, or up to about 8 hours, or up to about 10 hours, or up to about 12 hours, or up to about 16 hours, or up to about 18 hours, or up to about 24 hours or up to about 36 hours, or up to about 48 hours.

It is an object of certain preferred embodiments of the invention to provide a method and formulations of oral abusable drugs for the prevention and treatment of: (i) pain; (ii) musculoskeletal disorders; (iii) addiction disorders; and/or (iv) other medical conditions amenable to treatment with the abusable drug.

It is an object of certain preferred embodiments of the invention to provide a method and formulations of oral abusable drugs for the prevention and treatment of (i) pain; (ii) musculoskeletal disorders; (iii) addiction disorders; and/or (iv) other medical conditions amenable to treatment with the abusable drug; said formulations and methods not having a propensity of substantial drug accumulation.

It is an object of certain preferred embodiments of the invention to provide a method and formulations of oral abusable drugs for the prevention and treatment of (i) pain; (ii) musculoskeletal disorders; (iii) addiction disorders; and/or (iv) other medical conditions amenable to treatment with the abusable drug; said formulations having a reduced potential for tampering (e.g., mechanical, thermal, chemical or physical tampering).

It is an object of certain preferred embodiments of the invention to provide a method and formulations of oral abusable drugs for the prevention and treatment of (i) pain; (ii) musculoskeletal disorders; (iii) addiction disorders; and/or (iv) other medical conditions amenable to treatment with the abusable drug; said formulations in some embodiments having a reduced potential for drug abuse (e.g., inhalational, intranasal, intravenous or oral abuse); said formulations in some embodiments having a reduced potential for drug diversion; said formulations in some embodiments having a reduced intrasubject and intrasubject pharmacokinetic variability; said formulations in some embodiments having a reduced intersubject and intrasubject pharmacodynamic variability; said formulations in some embodiments having a reduced peak to trough fluctuation; said formulations in some embodiments having a shorter time to therapeutic concentrations and a shorter time to steady-state; said formulations in some embodiments being in extended release dosage form, and said formulations providing an extended duration of action; said formulations in some embodiments providing more than one of the aforementioned properties.

It is an object of certain preferred embodiments of the invention to provide a method and formulations of oral abusable drugs for the prevention and treatment of pain, said formulations suitable for use in acute pain, including acute postsurgical pain. In other preferred embodiments, the invention provides a method and formulations of oral abusable drugs for the prevention and treatment of chronic pain, cancer pain, neuropathic pain, somatic pain, visceral pain, idiopathic pain and breakthrough pain of various etiologies, including cancer, chronic pain and neuropathic pain.

It is an object of certain embodiments of the present invention to provide oral formulations of abusable drugs with both immediate release and controlled release forms.

It is an object of certain embodiments of the present invention to provide oral formulations of abusable drugs in pulsatile release form.

It is an object of certain embodiments of the present invention to provide abusable drugs for oral administration wherein the abusable drugs are dispersed within a matrix.

In certain preferred embodiments the oral dosage form of the present invention comprises a matrix which includes ADER and an abusable drug or a pharmaceutically acceptable salt thereof. In certain preferred embodiments, the matrix is compressed into a tablet and may be optionally overcoated with a coating that in addition to the sustained release material of the matrix may control the release of the abusable drug or pharmaceutically acceptable salt thereof from the formulation, such that blood levels of active ingredient are maintained within the therapeutic range over an extended period of time. In certain alternate embodiments, the matrix is encapsulated.

In certain preferred embodiments, the sustained release oral dosage form of the present invention comprises ADER and a plurality of pharmaceutically acceptable sustained release matrices comprising an abusable drug or a pharmaceutically acceptable salt thereof, the dosage form maintaining the plasma levels of abusable drug within the therapeutic range over an extended period of time when administered to patients.

In some preferred embodiments of the invention, the abusable drugs are in a matrix that is in the form of pellets or beads.

In some preferred embodiments, the dosage form of the invention comprises a compressed tablet, compressed capsule or uncompressed capsule. In other embodiments, the dosage form comprises a liquid fill capsule.

In some preferred embodiments, the dosage form of the invention comprises an oral formulation (e.g., tablet or capsule) which is coated to prevent substantial direct contact of abusable drug with oral cavity (e.g. tongue, oral mucosa), oropharyngeal mucosal surface, esophagus or stomach. In some preferred embodiments, the dosage form of the invention comprises an oral formulation which is coated with a film or polymer. In some preferred embodiments, the dosage form of the invention comprises abusable drugs in an enteric coating. In some preferred embodiments, the dosage form of the invention comprises abusable drugs formulated with pharmaceutical excipients and auxiliary agents known in the art, such that the abusable drug is released after a approximately specific amount of time, or at an approximately specific anatomic location in the gastrointestinal tract, or when the dosage form is in contact with specific gastrointestinal conditions (e.g., pH range, osmolality, electrolyte content, food content.).

In some preferred embodiments, the in vivo pharmacokinetic parameters of the specifications and claims are derived or determined under fed conditions. In other preferred embodiments, the in vivo pharmacokinetic parameters are derived or determined under fasted conditions.

Some or all of the above objects and other objects herein are achieved by embodiments of the present invention, which is directed in part to a dosage form of oral abusable drugs in abuse deterrent form.

Some or all of the above objects and other objects herein are achieved by embodiments of the present invention, which is directed in part to a dosage form of oral abusable drugs in extended release form.

Some or all of the above objects and other objects herein are achieved by embodiments of the present invention, which is directed in part to a dosage form of oral abusable drugs in an abuse deterrent and extended release form.

Some or all of the above objects and other objects herein are achieved by embodiments of the present invention, which is directed in part to a dosage form of oral abusable drugs and ADER.

Some or all of the above objects and other objects herein are achieved by embodiments of the present invention, which is directed in part to a dosage form of oral extended release abusable drugs and ADER.

Some or all of the above objects and other objects herein are achieved by embodiments of the present invention, which is directed in part to a dosage form of abuse deterrent abusable drugs and ADER.

Some or all of the above objects and other objects herein are achieved by embodiments of the present invention, which is directed in part to a dosage form which provides simultaneous abuse deterrence and extended release through the inclusion of ADER.

In some preferred embodiments, compositions and methods of the present invention involve abusable drugs, wherein the abusable drugs are limited to opioid agonists which are scheduled drugs under the United States Controlled Substances Act of 1970, as amended.

In some preferred embodiments, compositions and methods of the present invention involve abusable drugs, wherein the abusable drugs are limited to prodrugs of abusable drugs.

In some preferred embodiments, the dosage form is a capsule, said capsule rendered tamper-resistant with a security banding seal between the capsule parts.

In some preferred embodiments, the dosage form is a capsule, said capsule rendered liquid tight or leak resistant with a banding seal between the capsule parts.

In another aspect, the invention relates to a method and pharmaceutical compositions for prevention or treatment of (i) pain; (ii) musculoskeletal disorders; (iii) addiction disorders; or (iv) other medical conditions amenable to treatment with the abusable drug; comprising oral administration of a dosage form containing an abusable drug or a pharmaceutically acceptable salt of abusable drug or a mixture thereof and ADER.

In some preferred embodiments, the dosage form provides an oral pharmaceutical composition for the prevention and treatment of (i) pain; (ii) musculoskeletal disorders; (iii) addiction disorders; or (iv) other medical conditions amenable to treatment with the abusable drug; comprising a therapeutically effective amount of abusable drug or a pharmaceutically acceptable salt of abusable drug or a mixture thereof and ADER material to render said dosage form: (a) abuse deterrent; and/or (b) extended release; and/or (c) resistant to significant alcohol dose-dumping; and/or (d) resistant to significant variations in rate and/or extent of absorption based on a fed or fasted state; and/or (e) resistant to intentional or unintentional tampering; and/or (f) resistant to abusable drug toxicity due to intentional or unintentional tampering; and/or (g) resistant to significant variations in clinical effects when ingested after attempted tampering; and/or (h) resistant to intentional or surreptitious adulteration of beverage; and/or (i) resistant to significant drug-food interaction (i.e., large changes in rate or extent of absorption when taken with food); said rendering by said ADER material achieved in some embodiments using substantially the same ADER material; said dosage form in some embodiments suitable for administration up to about every 2 hours, or up to about every 4 hours, or up to about every 6 hours, or up to about every 8 hours, or up to about every 12 hours, or up to about every 24 hours to a human patient; said dosage form in some embodiments having a therapeutic effect of up to about every 1 hour, or up to about every 4 hours, or up to about every 6 hours, or up to about every 8 hours, or up to about every 12 hours, or up to about every 24 hours upon administration to a human patient.

In some preferred embodiments, the dosage form provides an oral pharmaceutical composition comprising a therapeutically effective amount of abusable drug or a pharmaceutically acceptable salt of abusable drug or a mixture thereof and ADER material to render said dosage form abuse deterrent, said dosage form suitable for up to every 24 hour (once-a-day) administration to a human patient; said dosage form providing at least 60% of the steady state concentration of abusable drug after administration of one dose at its intended dosing frequency. In other preferred embodiments, the dosage form provides at least about 62.5%, or at least about 65%, or at least about 67.5%, or at least about 70%, or at least about 72.5%, or at least about 75%, or at least about 77.5%, or at least about 80%, or at least about 82.5%, or at least about 85%, or at least about 87.5%, or at least about 90%, or at least about 92.5%, or at least about 95% or at least 98% of the steady state therapeutic concentration of abusable drug after administration of one dose at its intended dosing frequency.

In some preferred embodiments, the dosage form provides an oral pharmaceutical composition comprising a therapeutically effective amount of abusable drug or a pharmaceutically acceptable salt of abusable drug or a mixture thereof and ADER material to render said dosage form extended release; said dosage form providing at least 60% of the steady state concentration of abusable drug after administration of one dose at its intended dosing frequency. In other preferred embodiments, the dosage form provides at least about 62.5%, or at least about 65%, or at least about 67.5%, or at least about 70%, or at least about 72.5%, or at least about 75%, or at least about 77.5%, or at least about 80%, or at least about 82.5%, or at least about 85%, or at least about 87.5%, or at least about 90%, or at least about 92.5%, or at least about 95% or at least 98% of the steady state therapeutic concentration of abusable drug after administration of one dose at its intended dosing frequency.

In some preferred embodiments, the dosage form provides an oral pharmaceutical composition comprising a therapeutically effective amount of abusable drug or a pharmaceutically acceptable salt of abusable drug or a mixture thereof and ADER material to render said dosage form abuse deterrent and extended release, said dosage form suitable for up to every 24 hour (once-a-day) administration to a human patient; said dosage form providing at least 60% of the steady state concentration of abusable drug after administration of one dose at its intended dosing frequency. In other preferred embodiments, the dosage form provides at least about 62.5%, or at least about 65%, or at least about 67.5%, or at least about 70%, or at least about 72.5%, or at least about 75%, or at least about 77.5%, or at least about 80%, or at least about 82.5%, or at least about 85%, or at least about 87.5%, or at least about 90%, or at least about 92.5%, or at least about 95% or at least 98% of the steady state therapeutic concentration of abusable drug after administration of one dose at its intended dosing frequency.

In some preferred embodiments, the dosage form provides an oral pharmaceutical composition comprising a therapeutically effective amount of abusable drug or a pharmaceutically acceptable salt of abusable drug or a mixture thereof and ADER material to render said dosage form resistant to alcohol dose dumping, said dosage form suitable for up to every 24 hour (once-a-day) administration to a human patient; said dosage form providing at least 60% of the steady state concentration of abusable drug after administration of one dose at its intended dosing frequency. In other preferred embodiments, the dosage form provides at least about 62.5%, or at least about 65%, or at least about 67.5%, or at least about 70%, or at least about 72.5%, or at least about 75%, or at least about 77.5%, or at least about 80%, or at least about 82.5%, or at least about 85%, or at least about 87.5%, or at least about 90%, or at least about 92.5%, or at least about 95% or at least 98% of the steady state therapeutic concentration of abusable drug after administration of one dose at its intended dosing frequency.

In some preferred embodiments, the dosage form provides an oral pharmaceutical composition comprising a therapeutically effective amount of abusable drug or a pharmaceutically acceptable salt of abusable drug or a mixture thereof and ADER material to render said dosage form resistant to significant fluctuations in bioavailability when given under fed and fasted conditions, said dosage form suitable for up to every 24 hour (once-a-day) administration to a human patient; said dosage form providing at least 60% of the steady state concentration of abusable drug after administration of one dose at its intended dosing frequency. In other preferred embodiments, the dosage form provides at least about 62.5%, or at least about 65%, or at least about 67.5%, or at least about 70%, or at least about 72.5%, or at least about 75%, or at least about 77.5%, or at least about 80%, or at least about 82.5%, or at least about 85%, or at least about 87.5%, or at least about 90%, or at least about 92.5%, or at least about 95% or at least 98% of the steady state therapeutic concentration of abusable drug after administration of one dose at its intended dosing frequency.

In some preferred embodiments, the invention comprises an oral pharmaceutical composition comprising a therapeutically effective amount of abusable drug or a pharmaceutically acceptable salt of abusable drug, or a mixture thereof and ADER to render said dosage form suitable for three times a day administration (TID) or about every eight hours administration (Q8H).

In some preferred embodiments, the TID or Q8H oral pharmaceutical composition of an abusable drug provides a therapeutic effect for about 8 hours.

In some preferred embodiments, the TID or Q8H oral pharmaceutical composition of an abusable drug provides a $C_{max}$ of abusable drugs at about 1 to about 6 hours.

In some preferred embodiments, the TID or Q8H oral pharmaceutical composition of abusable drugs provide a $C_{min}$ of abusable drugs at about 6 to 10 hours.

In some preferred embodiments, the TID or Q8H oral pharmaceutical composition of abusable drugs provide a mean abusable drugs $C_8/C_{max}$ ratio of 0.25 to about 0.95.

In some preferred embodiments, the TID or Q8H oral pharmaceutical composition of abusable drugs provide a percent fluctuation of less than 400%.

In some preferred embodiments, the TID or Q8H oral pharmaceutical composition of an abusable drug provides a $W_{50}$ of 1.5 to about 6.5 hours.

In some preferred embodiments, the TID or Q8H oral pharmaceutical composition of an abusable drug provides an HVD of 2 to about 7 hours.

In some preferred embodiments, the TID or Q8H oral pharmaceutical composition of an abusable drug provides an HVD of about 2 to about 7 hours.

In some preferred embodiments, the TID or Q8H oral pharmaceutical composition of an abusable drug an AI of not more that 4.0.

In some preferred embodiments, the invention comprises an oral pharmaceutical composition comprising therapeutically effective amounts of abusable drug or pharmaceutically acceptable salts thereof, or mixtures thereof and ADER; said dosage from providing a $C_{max}$ of abusable drug occurring from a mean of about 0.25 to about 30 hours. In other preferred embodiments, the dosage form provides a $C_{max}$ of abusable drug occurring from a mean of about 0.5 to about 30 hours, or from a mean of about 1 to about 30 hours, or about 1 to about 26 hours, or about 1 to about 24 hours, or about 1 to about 20 hours, or about 1 to about 18 hours, or about 1 to about 16 hours, or about 1 to about 14 hours, or about 1 to about 12 hours, or about 1 to about 10 hours, or about 1 to about 8 hours, or about 1 to about 6 hours, or about 1 to about 4 hours, or about 1 to about 3 hours, or about 2 to about 30 hours, or about 4 to about 30 hours, or about 4 to about 24 hours, or about 6 to about 24 hours, or about 8 to about 24 hours, or about 10 to about 20 hours, or about 12 to about 24 hours, or about 18 to about 24 hours, or about 2 to about 12 hours, or about 3 to about 12 hours, or about 3 to about 8 hours, or about 4 to about 10 hours, or about 4 to about 12 hours, or about 4 to about 9 hours, or about 5 to about 8 hours.

In some preferred embodiments, the invention comprises an oral pharmaceutical composition comprising therapeutically effective amounts of abusable drug or pharmaceutically acceptable salts thereof, or mixtures thereof and ADER; said dosage from providing a $C_{min}$ of abusable drug occurring from a mean of about 0.5 to about 28 hours, or about 1 to about 28 hours, or about 1 to 24 hours, or about 1 to about 20 hours, or about 1 to about 18 hours, or about 1 to about 16 hours, or about 1 to about 12 hours, or about 1 to 10 hours, or about 1 to about 8 hours, or about 1 to about 6 hours, or about 1 to about 4 hours, about 2 to about 24 hours, or about 3 to 24 hours, or about 4 to about 24 hours, or about 6 to about 24 hours, or about 8 to about 24 hours, about 2 to about 12 hours, or about 3 to 10 hours, or about 3 to about 8 hours, or about 4 to about 8 hours, or about 6 to about 10 hours.

In some preferred embodiments, the invention comprises an oral pharmaceutical composition comprising therapeutically effective amounts of abusable drug or pharmaceutically acceptable salts thereof, or mixtures thereof and ADER; said dosage form providing a systemic exposure as assessed by the mean abusable drug area under the plasma concentration time curve ($AUC_{0-t}$) after first administration which is at least about 40% of the area under the plasma drug concentration-time curve from time zero to infinity ($AUC_{0-\infty}$). In other preferred embodiments, the dosage from provides an $AUC_{0-t}$ which is at least about 45%, or which is at least about 50%, or which is at least about 55%, or at least about 60%, or which is at least about 65%, or at least about 70%, or which is at least about 75%, or at least about 80%, or at least about 85%, or at least about 88%, or at least about 90%, or at least about 92%, or at least about 94%, or at least about 96% or at least about 98% of the $AUC_{0-\infty}$.

In some preferred embodiments, the dosage form provides an oral pharmaceutical composition comprising a therapeutically effective amount of an abusable drug or pharmaceutically acceptable salts thereof or mixtures thereof and ADER; said dosage form providing at least 80% of the steady state therapeutic concentration of abusable drug after administration of ≤three doses at their intended dosing frequency. In other preferred embodiments, said dosage form provides at least about 60%, or at least about 65%, or at least about 70%, or at least about 75%, or at least about 85%, or at least about 90%, or at least about 92%, or at least about 95%, or at least about 97%, or at least about 99% of the steady state therapeutic concentration of abusable drug after administration of ≤three doses at their intended dosing frequency.

In some preferred embodiments, the dosage form provides an oral pharmaceutical composition comprising a therapeutically effective amount of abusable drug or pharmaceutically acceptable salts thereof or mixtures thereof and ADER; said dosage form providing at least 80% of the steady state therapeutic concentration of abusable drug after administration of ≤two doses at their intended dosing frequency. In other preferred embodiments, said dosage form provides at least about 60%, or at least about 65%, or at least about 70%, or at least about 75%, or at least about 85%, or at least about 90%, or at least about 92%, or at least about 95%, or at least about 97%, or at least about 99% of the steady state therapeutic concentration of abusable drug after administration of ≤two doses at their intended dosing frequency.

In some preferred embodiments, the dosage form provides an oral pharmaceutical composition comprising a therapeutically effective amount of abusable drug or pharmaceutically acceptable salts thereof or mixtures thereof and ADER; said dosage form providing at least 80% of the steady state therapeutic concentration of abusable drug after administration of one dose at their intended dosing frequency. In other preferred embodiments, said dosage form provides at least about 60%, or at least about 65%, or at least about 70%, or at least about 75%, or at least about 85%, or at least about 90%, or at least about 92%, or at least about 95%, or at least about 97%, or at least about 99% of the steady state therapeutic concentration of abusable drug after administration of one dose at their intended dosing frequency.

In some preferred embodiments, the dosage form provides an oral pharmaceutical composition comprising a therapeutically effective amount of abusable drug or pharmaceutically acceptable salts thereof or mixtures thereof and ADER; said dosage form after administration to a human patient providing a $C_{min}/C_{max}$ ratio of abusable drug of 0.1 to about 1.0. In other preferred embodiments, the dosage form provides a $C_{min}/C_{max}$ ratio of abusable drug of about 0.1 to about 0.9, or about 0.1 to about 0.8, or about 0.1 to about 0.7, or about 0.1 to about 0.6, or about 0.1 to about 0.5, or about 0.1 to about 0.4, or about 0.1 to about 0.3, or about 0.2 to about 1.0, or about 0.25 to about 1.0, or about 0.4 to about 1.0, or about 0.5 to about 0.9, or about 0.5 to about 0.85, or about 0.5 to about 0.8, or about 0.5 to about 0.75, or about 0.5 to about 1.0, or about 0.65 to about 1.0, or about 0.75 to about 1.0, or about 0.2 to about 0.9, or about 0.3 to about 0.95, or about 0.3 to about 0.85, or about 0.3 to about 0.8, or about 03 to about 0.75, or about 0.3 to about 0.7, or about 0.3 to about 0.6, or about 0.4 to about 0.9, or about 0.4 to about 0.8, or about 0.4 to about 0.7, or about 0.4 to about 0.6, or about 0.8 to about 1, or about 0.8 to about 1.1.

In some preferred embodiments, the dosage form provides an oral pharmaceutical composition comprising a therapeutically effective amount of abusable drug or pharmaceutically acceptable salts thereof or mixtures thereof and ADER; said dosage form after administration to a human patient providing a percent fluctuation of abusable drug of less than 400%. In other preferred embodiments, the dosage form provides a percent fluctuation of abusable drug of less than 350%, or less than 300%, or less than 250%, or less than 200%, or less than 150%, or less than 100%, or less than 75%, or less than 50%, or less than 25%.

In some preferred embodiments, the dosage form provides an oral pharmaceutical composition comprising a therapeutically effective amount of abusable drug or pharmaceutically acceptable salts thereof or mixtures thereof and ADER; said dosage form after administration to a human patient providing a $W_{50}$ of abusable drug of about 1 to about 6 hours for each 6 hour time period of intended dosing frequency and intended duration of action. In other preferred embodiments, the dosage form provides a $W_{50}$ of abusable drug for each 6 hour time period of intended dosing frequency and intended duration of action of about 1 to about 5 hours, or about 1 to about 4 hours, or about 1 to about 3 hours, or about 1 to about 2 hours, or 2 to about 6 hours, or about 3 to about 6 hours, or about 4 to about 6 hours, or about 2 to about 4 hours.

In some preferred embodiments, the dosage form provides an oral pharmaceutical composition comprising a therapeutically effective amount of abusable drug or pharmaceutically acceptable salts thereof or mixtures thereof and ADER; said dosage form after administration to a human patient providing an HVD of abusable drug of about 1.5 to about 6 hours for each 6 hour time period of intended dosing frequency and intended duration of action. In other preferred embodiments, the dosage form provides a HVD of abusable drug for each 6 hour time period of intended dosing frequency and intended duration of action of about 1.5 to about 5 hours, or about 1.5 to about 4 hours, or about 1.5 to about 3 hours, or about 1.5 to about 2 hours, or 2 to about 6 hours, or about 3 to about 6 hours, or about 4 to about 6 hours, or about 2 to about 4 hours.

In some preferred embodiments, the dosage form provides an oral pharmaceutical composition comprising a therapeutically effective amount of abusable drug or pharmaceutically acceptable salts thereof or mixtures thereof and ADER; said dosage form after administration to a human patient providing an AI of abusable drug of not more than 3.0. In other preferred embodiments, the dosage form provides an AI of abusable drug of not more than about 2.5, or not more than about 2, or not more than about 1.75, or not more than about 1.5, or not more than about 1.25, or not more than about 1, or not more than about 0.75, or not more than about 0.5, or not more than about 0.25.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for twice-a-day administration to a human patient, said dosage form providing a $C_{max}$ of abusable drug at 2 to about 10 hours; and said dosage form providing a therapeutic effect for at least about 12 hours. In other preferred embodiments, the dosage form provides a $C_{max}$ of abusable drug at about 2 to about 8 hour or about 2 to about 6 hours, or about 2 to about 5 hours, or about 2 to about 7 hours, or about 2 to about 4.5 hours, or about 2 to about 4 hours, or 2 to about 3.5 hours, or about 2 to about 3 hours, or about 3 to about 10 hours, or about 3.5 to about 10 hours, or about 4 to about 10 hours, or about 4.5 to about 10 hours, or about 5 to about 10 hours, or 5 to about 10 hours, or about 6 to about 10 hours, or about 3 to about 8 hours, or about 3 to about 7 hours, or about 3 to about 6 hours, or about 4 to about 8 hours, or about 4 to about 6.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for twice-a-day administration to a human patient, said dosage form providing a $C_{12}/C_{max}$ ratio of abusable drug of 0.1 to about 1; and said dosage form providing a therapeutic effect for at least about 12 hours. In other preferred embodiments, the dosage form provides a $C_{12}/C_{max}$ ratio of abusable drug of about 0.25 to about 0.9, or about 0.25 to about 0.8, or about 0.25 to about 0.75, or about 0.25 to about 0.6, or 0.25 to about 0.5, or about 0.25 to about 0.4, or about 0.25 to about 0.35, or about 0.3 to about 0.95, or about 0.4 to about 0.95, or about 0.5 to about 0.95, or about 0.65 to about 0.95, or about 0.75 to about 0.95, or about 0.3 to about 0.8, or about 0.4 to about 0.75, or about 0.5 to about 0.75, or about 0.1 to about 0.9, or about 0.1 to about 0.8, or about 0.1 to about 0.7, or about 0.1 to about 0.6, or about 0.1 to about 0.5, or about 0.1 to about 0.4, or about 0.1 to about 0.3, or about 0.2 to about 1.0, or about 0.25 to about 1.0, or about 0.4 to about 1.0, or about 0.5 to about 0.9, or about 0.5 to about 0.85, or about 0.5 to about 0.8, or about 0.5 to about 0.75, or about 0.5 to about 1.0, or about 0.65 to about 1.0, or about 0.75 to about 1.0, or about 0.2 to about 0.9, or about 0.3 to about 0.95, or about 0.3 to about 0.85, or about 0.3 to about 0.8, or about 03 to about 0.75, or about 0.3 to about 0.7, or about 0.3 to about 0.6, or about 0.4 to about 0.9, or about 0.4 to about 0.8, or about 0.4 to about 0.7, or about 0.4 to about 0.6, or about 0.8 to about 1, or about 0.8 to about 1.1.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for twice-a-day administration to a human patient, said dosage form providing a percent fluctuation of abusable drug of less than 400%; and said dosage form providing a therapeutic effect for at least about 12 hours. In other preferred embodiments, the dosage form provides a percent fluctuation of abusable drug of less than about 375%, or less than about 350%, or less than about 325%, or less than about 300%, or less than about 275%, or less than about 250%, or less than about 225%, or less than about 200%, or less than about 175%, or less than about 150%, or less than about 125%, or less than about 100%, or less than about 75%, or less than about 50%, or less than about 25%.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for twice-a-day administration to a human patient, said dosage form after administration to a human patient, providing a $W_{50}$ of abusable drug of 2 to about 11 hours; and said dosage form providing a therapeutic effect for at least about 12 hours. In other preferred embodiments, the dosage form provides a $W_{50}$ of abusable drug of about 2 to about 10 hours, or about 2 to about 9 hours, or about 2 to about 9 hours, or about 2 to about 8 hours, or 2 to about 7 hours, or about 2 to about 6 hours, or about 2 to about 5 hours, or about 2 to about 4 hours, or about 3 to about 10 hours, or about 4 to about 10 hours, or about 5 to about 10 hours, or about 6 to about 10 hours, or 7 to about 10 hours, or about 3 to about 8 hours, or about 4 to about 8 hours, or about 4 to about 7 hours, or about 3 to about 6 hours.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for twice-a-day administration to a human patient, said dosage form after administration to a human patient, providing a HVD of abusable drug of 1.5 to about 10 hours; and said dosage form providing a therapeutic effect for at least about 12 hours. In other preferred embodiments, the dosage form provides an HVD of abusable drug of about 1.5 to about 9 hours, or about 1.5 to 8 hours, or about 1.5 to about 7 hours, or about 1.5 to 6 hours, or about 1.5 to about 5 hours, or about 1.5 to about 4 hours, or about 2 to about 10 hours, or about 3 to 10 hours, or about 4 to about 10 hours, or about 5 to 10 hours, or about 6 to about 10 hours, or about 8 to 10 hours, about 3 to about 8 hours, or about 4 to 8 hours, or about 5 to about 7 hours, or about 3 to 6 hours, or about 3 to about 8 hours, or about 5 to about 8 hours.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for twice-a-day administration to a human patient, said dosage form after administration to a human patient, providing an AI of abusable drug of not more that 4.0; and said dosage form providing a therapeutic effect for at least about 12 hours. In other preferred embodiments, the dosage form provides an AI of abusable drug of not more than about 3.75, or not more than about 3.5, or not more than about 3.25, or not more than about 3, or not more than about 2.75, or not more than about 2.5, or not more than about 2, or not more than about 1.5, not more than about 1.25, or not more than about 1, or not more than about 0.75.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for twice-a-day administration to a human patient; said dosage form providing an in-vitro release rate by weight of abusable drug, when measured by the USP Basket and Paddle Methods at 100 rpm in 900 mL aqueous buffer at a pH of between 1.6 and 7.2 at 37° C. of from 0% to about 47.5% at 1 hour, from about 10% to about 65% at 2 hours, from about 15% to about 70% at 4 hours, from about 25% to about 77.5% at 6 hours, from about 35% to about 87.5% at 9 hours, and greater than about 65% at 12 hours. In other preferred embodiments, the dosage form provides said an in-vitro release rate of from 0% to about 40% at 1 hour, from about 5% to about 55% at 2 hours, from about 10% to about 60% at 4 hours, from about 15% to about 70% at 6 hours, from about 25% to about 80% at 9 hours, and greater than about 50% at 12 hours.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for twice-a-day administration to a human patient; said dosage form providing an in-vitro release rate by weight of abusable drug, when measured by the USP Basket and Paddle Methods at 100 rpm in 900 mL aqueous buffer at a pH of between 1.6 and 7.2 at 37° C. of from 0% to about 47.5% at 1 hour, from about 10% to about 65% at 2 hours, from about 15% to about 70% at 4 hours, from about 25% to about 77.5% at 6 hours, from about 35% to about 87.5% at 9 hours, and greater than about 65% at 12 hours; said dosage form providing a $C_{max}$ from a mean of about 2 to about 10 hours after first administration or at steady state.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for twice-a-day administration to a human patient; said dosage form providing an in-vitro release rate by weight of abusable drug, when measured by the USP Basket and Paddle Methods at 100 rpm in 900 mL aqueous buffer at a pH of between 1.6 and 7.2 at 37° C. of from 0% to about 47.5% at 1 hour, from about 10% to about 65% at 2 hours, from about 15% to about 70% at 4 hours, from about 25% to about 77.5% at 6 hours, from about 35% to about 87.5% at 9 hours, and greater than about 65% at 12 hours; said dosage form providing a $C_{min}$ occurring from a mean of about 10 to about 14 hours after first administration or at steady state.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for twice-a-day administration to a human patient; said dosage form providing an in-vitro release rate by weight of abusable drug, when measured by the USP Basket and Paddle Methods at 100 rpm in 900 mL aqueous buffer at a pH of between 1.6 and 7.2 at 37° C. of from 0% to about 47.5% at 1 hour, from about 10% to about 65% at 2 hours, from about 15% to about 70% at 4 hours, from about 25% to about 77.5% at 6 hours, from about 35% to about 87.5% at 9 hours, and greater than about 65% at 12 hours; said dosage form providing a mean abusable drug $AUC_{0-t}/AUC_{0-\infty}$ ratio after first administration of about 0.4, or about 0.5, or about 0.6, or about 0.7, or about 0.75, or about 0.8, or about 0.85, or about 0.88, or about 0.90, or about 0.92, or about 0.95, or about 0.97 or about 0.99.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for twice-a-day administration to a human patient; said dosage form providing an in-vitro release rate by weight of abusable drug, when measured by the USP Basket and Paddle Methods at 100 rpm in 900 mL aqueous buffer at a pH of between 1.6 and 7.2 at 37° C. of from 0% to about 47.5% at 1 hour, from about 10% to about 65% at 2 hours, from about 15% to about 70% at 4 hours, from about 25% to about 77.5% at 6 hours, from about 35% to about 87.5% at 9 hours, and greater than about 65% at 12 hours; said in-vitro release rate being substantially independent of pH in that a difference, at any given time, between an amount of abusable drug released at one pH and an amount released at any other pH, when measured in-vitro using the USP Basket and Paddle Methods of USP Drug Release test of U.S. Pharmacopeia (2003) at 100 rpm in 900 ml aqueous buffer, is no greater than 30%.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for once-a-day administration to a human patient, said dosage form providing a $C_{max}$ of abusable drug at about 3 to about 20 hours; and said dosage form providing a therapeutic effect for at least about 24 hours. In some preferred embodiments, the abusable drugs dosage forms provide a $C_{max}$ of abusable drug at about 3 to about 18 hours, or about 3 to about 15 hours, or about 3 to about 12 hours, or at about 3 to about 10 hours, or at about 3 to about 8 hours, or at about 3 to about 7 hours, or at about 3 to about 7 hours, or 4 to about 20 hours, or about 5 to about 20 hours, or about 6 to about 20 hours, or at about 8 to about 20 hours, or about 10 to about 20 hours, or at about 12 to about 20 hours, or at about 14 to about 20 hours, or about 18 to about 20 hours, or about 4 to about 18 hours, or about 4 to about 16 hours, or about 4 to about 12 hours, or at about 4 to about 8 hours, or at about 4 to about 10 hours, or at about 3 to about 6 hours.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for once-a-day administration to a human patient, said dosage form providing a $C_{max}$ of abusable drug at about 20 to about 28 hours; and said abusable drugs dosage forms providing a therapeutic effect for at least about 24 hours. In some preferred embodiments, the abusable drugs dosage forms provide a $C_{min}$ of abusable drug at about 20 to about 26 hours, or about 20 to about 27 hours, or about 20 to about 25 hours, or about 20 to about 24 hours, or about 20 to about 23 hours, or about 21 to about 28 hours, or about 22 to about 28 hours, or about 23 to about 28 hours, or about 23.5 to about 28 hours, or about 22 to 26 hours.

In some preferred embodiments, the dosage form provides an oral pharmaceutical composition comprising a therapeutically effective amount of abusable drug or pharmaceutically acceptable salts thereof or mixtures thereof and ADER; said dosage from providing a $C_{max}$ of abusable drug from about 0.25 hours to about 30 hours.

In some preferred embodiments, the dosage form provides an oral pharmaceutical composition comprising a therapeutically effective amount of abusable drug or pharmaceutically acceptable salts thereof or mixtures thereof and ADER; said dosage from providing a $C_{min}$ of abusable drug from about 0.5 hour to about 30 hours.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for once-a-day administration to a human patient, said dosage form providing a $C_{24}/C_{max}$ ratio of abusable drug of 0.1 to about 1; and said dosage form providing a therapeutic effect for at least about 24 hours. In other preferred embodiments, the dosage form provides a $C_{24}/C_{max}$ ratio of abusable drug of about 0.25 to about 0.9, or about 0.25 to about 0.8, or about 0.25 to about 0.75, or about 0.25 to about 0.6, or 0.25 to about 0.5, or about 0.25 to about 0.4, or about 0.25 to about 0.35, or about 0.3 to about 0.95, or about 0.4 to about 0.95, or about 0.5 to about 0.95, or about 0.65 to about 0.95, or about 0.75 to about 0.95, or about 0.3 to about 0.8, or about 0.4 to about 0.75, or about 0.5 to about 0.75, or about 0.1 to about 0.9, or about 0.1 to about 0.8, or about 0.1 to about 0.7, or about 0.1 to about 0.6, or about 0.1 to about 0.5, or about 0.1 to about 0.4, or about 0.1 to about 0.3, or about 0.2 to about 1.0, or about 0.25 to about 1.0, or about 0.4 to about 1.0, or about 0.5 to about 0.9, or about 0.5 to about 0.85, or about 0.5 to about 0.8, or about 0.5 to about 0.75, or about 0.5 to about 1.0, or about 0.65 to about 1.0, or about 0.75 to about 1.0, or about 0.2 to about 0.9, or about 0.3 to about 0.95, or about 0.3 to about 0.85, or about 0.3 to about 0.8, or about 03 to about 0.75, or about 0.3 to about 0.7, or about 0.3 to about 0.6, or about 0.4 to about 0.9, or about 0.4 to about 0.8, or about 0.4 to about 0.7, or about 0.4 to about 0.6, or about 0.8 to about 1, or about 0.8 to about 1.1.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for once-a-day administration to a human patient, said dosage form providing a percent fluctuation of abusable drug of less than 400%; and said dosage form providing a therapeutic effect for at least about 24 hours. In other preferred embodiments, the dosage form provides a percent fluctuation of abusable drug of less than about 375%, or less than about 350%, or less than about 325%, or less than about 300%, or less than about 275%, or less than about 250%, or less than about 225%, or less than about 200%, or less than about 175%, or less than about 150%, or less than about 125%, or less than about 100%, or less than about 75%, or less than about 50%, or less than about 25%.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for once-a-day administration to a human patient, said abusable drugs dosage form after administration to a human patient, providing a $W_{50}$ of abusable drug of 4 to about 22 hours; and said dosage form providing a therapeutic effect for at least about 24 hours. In other preferred embodiments, the abusable drugs dosage from provides a $W_{50}$ of abusable drug of about 4 to about 20 hours, or about 4 to about 19 hours, or about 4 to about 18 hours, or 4 to about 16 hours, or 4 to about 14 hours, or about 4 to about 12 hours, or about 4 to about 10 hours, or about 4 to about 8 hours, or about 6 to about 20 hours, or about 8 to about 20 hours, or about 10 to about 20 hours, or about 12 to about 20 hours, or 14 to about 20 hours, or about 6 to about 16 hours, or about 8 to about 16 hours, or about 8 to about 14 hours, or about 6 to about 12 hours.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for once-a-day administration to a human patient, said abusable drugs dosage form after administration to a human patient, providing a HVD of abusable drug of 3 to about 20 hours; and said dosage form providing a therapeutic effect for at least about 24 hours. In other preferred embodiments, the abusable drugs dosage from provides an HVD of abusable drug of about 3 to about 18 hours, or about 3 to 16 hours, or about 3 to about 14 hours, or about 3 to 12 hours, or about 3 to about 10 hours, or about 3 to about 8 hours, or about 4 to about 20 hours, or about 6 to 20 hours, or about 8 to about 20 hours, or about 10 to 20 hours, or about 12 to about 20 hours, or about 16 to 20 hours, about 6 to about 16 hours, or about 8 to 16 hours, or about 10 to about 14 hours, or about 6 to 12 hours, or about 6 to about 16 hours, or about 10 to about 16 hours.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for once-a-day administration to a human patient, said dosage form after administration to a human patient, providing an AI of abusable drug of not more that 4.0; and said abusable drugs dosage form providing a therapeutic effect for at least about 24 hours. In other preferred embodiments, the abusable drugs dosage from provides an AI of abusable drug of not more than about 3.75, or not more than about 3.5, or not more than about 3.25, or not more than about 3, or not more than about 2.75, or not more than about 2.5, or not more than about 2, or not more than about 1.5, not more than about 1.25, or not more than about 1, or not more than about 0.75.

In some preferred embodiments, the dosage form provides an oral pharmaceutical composition comprising a therapeutically effective amount of abusable drug or pharmaceutically acceptable salts thereof or mixtures thereof and ADER to render said abusable drug dosage form abuse deterrent and/or suitable for once-a-day administration to a human patient; said abusable drugs dosage form providing an in-vitro release rate by weight of abusable drug, when measured by the USP Basket and Paddle Methods at 100 rpm in 900 mL aqueous buffer at a pH of between 1.6 and 7.2 at 37° C. of from 0% to about 30% at 1 hour, from about 10% to about 65% at 4 hours, from about 20% to about 70% at 8 hours, from about 25% to about 80% at 12 hours, from about 35% to about 95% at 18 hours, and greater than about 65% at 24 hours.

In some preferred embodiments, the dosage form provides an oral pharmaceutical composition comprising a therapeutically effective amount of abusable drug or pharmaceutically acceptable salts thereof or mixtures thereof and ADER to render said abusable drug dosage form abuse deterrent and/or suitable for once-a-day administration to a human patient; said abusable drugs dosage form providing an in-vitro release rate by weight of abusable drug, when measured by the USP Basket and Paddle Methods at 100 rpm in 900 mL aqueous buffer at a pH of between 1.6 and 7.2 at 37° C. of from 0% to about 30% at 1 hour, from about 10% to about 65% at 4 hours, from about 20% to about 70% at 8 hours, from about 25% to about 80% at 12 hours, from about 35% to about 95% at 18 hours, and greater than about 65% at 24 hours; said dosage form providing a $C_{max}$ from a mean of about 3 to about 20 hours after first administration or at steady state.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for once-a-day administration to a human patient; said dosage form providing an in-vitro release rate by weight of abusable drug, when measured by the USP Basket and Paddle Methods at 100 rpm in 900 mL aqueous buffer at a pH of between 1.6 and 7.2 at 37° C. of from 0% to about 30% at 1 hour, from about 10% to about 65% at 4 hours, from about 20% to about 70% at 8 hours, from about 25% to about 80% at 12 hours, from about 35% to about 95% at 18 hours, and greater than about 65% at 24 hours; said dosage form providing a $C_{min}$ of abusable drug occurring from a mean of about 20 to about 28 hours after first administration or at steady state.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for once-a-day administration to a human patient; said dosage form providing an in-vitro release rate by weight of abusable drug, when measured by the USP Basket and Paddle Methods at 100 rpm in 900 mL aqueous buffer at a pH of between 1.6 and 7.2 at 37° C. of from 0% to about 30% at 1 hour, from about 10% to about 65% at 4 hours, from about 20% to about 70% at 8 hours, from about 25% to about 80% at 12 hours, from about 35% to about 95% at 18 hours, and greater than about 65% at 24 hours; said dosage form providing a mean abusable drug $AUC_{0-t}/AUC_{0-\infty}$ ratio after first administration of about 0.4, or about 0.5, or about 0.6, or about 0.7, or about 0.75, or about 0.8, or about 0.85, or about 0.88, or about 0.90, or about 0.92, or about 0.95, or about 0.97 or about 0.99.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for once-a-day administration to a human patient; said dosage form providing an in-vitro release rate by weight of abusable drug, when measured by the USP Basket and Paddle Methods at 100 rpm in 900 mL aqueous buffer at a pH of between 1.6 and 7.2 at 37° C. of from 0% to about 30% at 1 hour, from about 10% to about 65% at 4 hours, from about 20% to about 70% at 8 hours, from about 25% to about 80% at 12 hours, from about 35% to about 95% at 18 hours, and greater than about 65% at 24 hours; said in-vitro release rate being substantially independent of pH in that a difference, at any given time, between an amount of abusable drug released at one pH and an amount released at any other pH, when measured in-vitro using the USP Basket and Paddle Methods of USP Drug Release test of U.S. Pharmacopeia (2003) at 100 rpm in 900 ml aqueous buffer, is no greater than 30%.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for extended release administration to a human patient; said dosage form after administration to a human patient providing a mean abusable drug $C_{max}$ occurring from a mean of about 0.25 to about 22 hours; said dosage form providing a mean abusable drug $C_{min}$ occurring from a mean of about 0.5 to about 28 hours; said dosage form providing a mean abusable drug HVD of about 1 to about 5 hours for each 6 hour time period of intended dosing frequency and intended duration of action; said dosage form providing a mean abusable drug $W_{50}$ of about 1 to about 5.5 hours for each 6 hour time period of intended dosing frequency and intended duration of action; said dosage form providing a mean abusable drug AI of not more than 3.0; said dosage form providing a mean abusable drug percent fluctuation of less than 400%; said dosage form providing a mean abusable drug $C_{min}/C_{max}$ ratio of 0.1 to about 1.0; said dosage form providing at least 80% of the steady state abusable drug therapeutic concentration after administration of ≤three doses at their intended dosing frequency; said dosage form providing a mean abusable drug $AUC_{0-t}$ to $AUC_{0-\infty}$ ratio of greater than 0.4; and said dosage form providing a mean time to 75% abusable drug $C_{max}$ of about 100% to about 2000% of the time to 75% mean $C_{max}$ of an oral immediate release abusable drug solution or suspension.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for extended release administration to a human patient; said dosage form after administration to a human patient providing a mean abusable drug $C_{max}$ which is less than 65% of the $C_{max}$ of an equivalent dose of an oral immediate release abusable drug solution or suspension; and said dosage form maintaining a mean abusable drug plasma concentration within 50% of $C_{max}$ for about 1 to about 5.5 hours for each 6 hour time period of intended dosing frequency and intended duration of action.

In some preferred embodiments, the dosage form provides an oral pharmaceutical composition comprising a therapeutically effective amount of abusable drug or pharmaceutically acceptable salts thereof or mixtures thereof and ADER to render said dosage form abuse deterrent and/or suitable for extended release administration to a human patient; said dosage form after administration to a human patient providing a mean abusable drug $C_{max}$ occurring from a mean of about 0.25 to about 22 hours; said dosage form providing a mean abusable drug $C_{min}$ occurring from a mean of about 0.5 to about 28 hours; said dosage form providing a mean abusable drug HVD of about 1 to about 5 hours for each 6 hour time period of intended dosing frequency and intended duration of action; said dosage form providing a mean abusable drug $W_{50}$ of about 1 to about 5.5 hours for each 6 hour time period of intended dosing frequency and intended duration of action; said dosage form providing a mean abusable drug AI of not more than 3.0; said dosage form providing a mean abusable drug percent fluctuation of less than 400%; said dosage form providing a mean abusable drug $C_{min}/C_{max}$ ratio of 0.1 to about 1.0; said dosage form providing at least 80% of the steady state abusable drug therapeutic concentration after administration of ≤three doses at their intended dosing frequency; said dosage form providing a mean abusable drug $AUC_{0-t}$ to $AUC_{0-\infty}$ ratio of greater than 0.4; said dosage form providing a mean time to 75% abusable drug $C_{max}$ of about 100% to about 2000% of the time to 75% mean $C_{max}$ of an oral immediate release abusable drug solution or suspension; said dosage form after administration to a human patient providing a mean abusable drug $C_{max}$ which is less than 65% of the $C_{max}$ of an equivalent dose of an oral immediate release abusable drug solution or suspension; and said dosage form maintaining a mean abusable drug plasma concentration within 50% of $C_{max}$ for about 1 to about 5.5 hours for each 6 hour time period of intended dosing frequency and intended duration of action.

In some preferred embodiments, the abusable drugs dosage forms provide an in-vitro release of from 0% to about 50% by weight of the abusable drug or a pharmaceutically acceptable salt thereof from the dosage form at one hour when measured by the USP Basket and Paddle Methods at 100 rpm in 700 ml of Simulated Gastric Fluid (SGF) at 37° C. In other preferred embodiments, said in-vitro release rate by weight of the abusable drug or a pharmaceutically acceptable salt thereof from said dosage form is from about 5% to about 45%, or about 10% to about 50%, or about 5% to about 60%, or about 5% to about 70%, or about 5% to about 80%, or about 5% to about 90%, or about 5% to about 100%, or about 10% to about 20%, or about 10% to about 35%, or about 10% to about 50%, or about 10% to about 60%, or about 10% to about 70%, or about 10% to about 80%, or about 10% to about 90%, or about 10% to about 100%, or about 20% to about 40%, or about 20% to about 50%, or about 20% to about 60%, or about 20% to about 70%, or about 20% to about 80%, or about 20% to about 90%, or about 20% to about 100%, or about 30% to about 50%, or about 30% to about 60%, or about 30% to about 70%, or about 30% to about 80%, or about 30% to about 90%, or about 40% to about 80%, or about 40% to about 90%, or about 60% to about 100%, or greater than about 5%, or greater than about 10%, or greater than about 15%, or greater than about 20%, or greater than about 30%, or greater than about 40%, or greater than about 50%, or greater than about 60%, or greater than about 80%, or greater than about 90%, or greater than about 95%, at one hour, when measured by the USP Basket and Paddle Methods at 100 rpm in 700 ml of Simulated Gastric Fluid (SGF) at 37° C.

In some preferred embodiments, the abusable drugs dosage form provides a $C_{max}$ of abusable drug which is less than 65% of the $C_{max}$ of an equivalent dose of an oral immediate release abusable drug solution or suspension. In other preferred embodiments, said dosage form provides a $C_{max}$ which is less than about 85%, or less than about 75%, or less than about 60%, or less than about 55%, or less than about 50%, or less than about 45%, or less than about 40%, or less than about 30%, or less than about 20% of the $C_{max}$ of an equivalent dose of an oral immediate release abusable drug solution or suspension.

In some preferred embodiments, the dosage form provides a time to 75% mean $C_{max}$ of abusable drug which is about 100% to about 2000% of the time to 75% mean $C_{max}$ of an oral immediate release abusable drug solution or suspension.

In some preferred embodiments, the dosage form provides a time to 30% mean $C_{max}$ of abusable drug which is about 100% to about 2000% of the time to 30% mean $C_{max}$ of an oral immediate release abusable drug solution or suspension.

In some preferred embodiments, the dosage from maintains a plasma abusable drug concentration within 50% of $C_{max}$ for about 1 to about 9 hours during a 12 hour dosing interval. In other preferred embodiments, said dosage form maintains plasma abusable drug concentration within 50% of $C_{max}$ for about 2 to about 9 hours, or about 3 to about 9 hours, or about 4 to about 9 hours, or about 5 to about 9 hours, or about 6 to about 9 hours, or about 1 to about 11 hours, or about 2 to about 11 hours, or about 3 to about 11 hours or about 4 to about 11 hours, or about 5 to about 11 hours, or about 6 to about 11 hours, or about 7 to about 11 hours, or about 8 to about 11 hours, or about 1 to about 10 hours, or about 2 to about 10 hours, or about 3 to about 10 hours or about 4 to about 10 hours, or about 5 to about 10 hours, or about 6 to about 10 hours, or about 7 to about 10 hours, or about 8 to about 10 hours, or about 1 to about 7 hours, or about 2 to about 7 hours, or about 3 to about 7 hours or about 4 to about 7 hours, or about 5 to about 7 hours, or about 6 to about 7 hours, or about 1 to about 4 hours, or about 1 to about 5 hours, during a 12 hour dosing interval.

In some preferred embodiments, the dosage from maintains a plasma abusable drug concentration within 30% of $C_{max}$ for about 1.5 to about 9 hours during a 12 hour dosing interval. In other preferred embodiments, said dosage form maintains plasma abusable drug concentration within 30% of $C_{max}$ for about 2 to about 9 hours, or about 3 to about 9 hours, or about 4 to about 9 hours, or about 5 to about 9 hours, or about 6 to about 9 hours, or about 1 to about 11 hours, or about 2 to about 11 hours, or about 3 to about 11 hours or about 4 to about 11 hours, or about 5 to about 11 hours, or about 6 to about 11 hours, or about 7 to about 11 hours, or about 8 to about 11 hours, or about 1 to about 10 hours, or about 2 to about 10 hours, or about 3 to about 10 hours or about 4 to about 10 hours, or about 5 to about 10 hours, or about 6 to about 10 hours, or about 7 to about 10 hours, or about 8 to about 10 hours, or about 1 to about 7 hours, or about 2 to about 7 hours, or about 3 to about 7 hours or about 4 to about 7 hours, or about 5 to about 7 hours, or about 6 to about 7 hours, or about 1 to about 4 hours, or about 1 to about 5 hours, during a 12 hour dosing interval.

In some preferred embodiments, the dosage from maintains a plasma abusable drug concentration within 65% of $C_{max}$ for about 1 to about 9 hours during a 12 hour dosing interval. In other preferred embodiments, said dosage form maintains plasma abusable drug concentration within 65% of $C_{max}$ for about 2 to about 9 hours, or about 3 to about 9 hours, or about 4 to about 9 hours, or about 5 to about 9 hours, or about 6 to about 9 hours, or about 1 to about 11 hours, or about 2 to about 11 hours, or about 3 to about 11 hours or about 4 to about 11 hours, or about 5 to about 11 hours, or about 6 to about 11 hours, or about 7 to about 11 hours, or about 8 to about 11 hours, or about 1 to about 10 hours, or about 2 to about 10 hours, or about 3 to about 10 hours or about 4 to about 10 hours, or about 5 to about 10 hours, or about 6 to about 10 hours, or about 7 to about 10 hours, or about 8 to about 10 hours, or about 1 to about 7 hours, or about 2 to about 7 hours, or about 3 to about 7 hours or about 4 to about 7 hours, or about 5 to about 7 hours, or about 6 to about 7 hours, or about 1 to about 4 hours, or about 1 to about 5 hours, during a 12 hour dosing interval.

In some preferred embodiments, the dosage from maintains a plasma abusable drug concentration within 55% of $C_{max}$ for about 3 to about 22 hours during a 24 hour dosing interval. In other preferred embodiments, said dosage form maintains plasma abusable drug concentration within 50% of $C_{max}$ for about 1 to about 9 hours, or about 4 to about 9 hours, or about 6 to about 9 hours, or about 1 to about 20 hours, or about 2 to about 20 hours, or about 3 to about 20 hours, or about 1 to about 18 hours, or about 1 to about 16 hours or about 2 to about 18 hours, or about 2 to about 16 hours, or about 1 to about 14 hours, or about 1 to about 12 hours, or about 4 to about 16 hours, or about 4 to about 18 hours, or about 4 to about 20 hours, or about 3 to about 15 hours or about 6 to about 15 hours, or about 6 to about 12 hours, or about 6 to about 18 hours, or about 6 to about 20 hours, or about 5 to about 12 hours, or about 5 to about 14 hours, or about 3 to about 22 hours, or about 3 to about 9 hours or about 3 to about 12 hours, or about 1 to about 6 hours, or about 2 to about 8 hours, or about 2 to about 10 hours, or about 3 to about 16 hours, during a 24 hour dosing interval.

In some preferred embodiments, the dosage from maintains a plasma abusable drug concentration within 30% of $C_{max}$ for about 2 to about 22 hours during a 24 hour dosing interval. In other preferred embodiments, said dosage form maintains plasma abusable drug concentration within 30% of $C_{max}$ for about 1 to about 9 hours, or about 4 to about 9 hours, or about 6 to about 9 hours, or about 1 to about 20 hours, or about 2 to about 20 hours, or about 3 to about 20 hours, or about 1 to about 18 hours, or about 1 to about 16 hours or about 2 to about 18 hours, or about 2 to about 16 hours, or about 1 to about 14 hours, or about 1 to about 12 hours, or about 4 to about 16 hours, or about 4 to about 18 hours, or about 4 to about 20 hours, or about 3 to about 15 hours or about 6 to about 15 hours, or about 6 to about 12 hours, or about 6 to about 18 hours, or about 6 to about 20 hours, or about 5 to about 12 hours, or about 5 to about 14 hours, or about 3 to about 22 hours, or about 3 to about 9 hours or about 3 to about 12 hours, or about 1 to about 6 hours, or about 2 to about 8 hours, or about 2 to about 10 hours, or about 3 to about 16 hours, during a 24 hour dosing interval.

In some preferred embodiments, the dosage from maintains a plasma abusable drug concentration within 65% of $C_{max}$ for about 2 to about 22 hours during a 24 hour dosing interval. In other preferred embodiments, said dosage form maintains plasma abusable drug concentration within 65% of $C_{max}$ for about 1 to about 9 hours, or about 4 to about 9 hours, or about 6 to about 9 hours, or about 1 to about 20 hours, or about 2 to about 20 hours, or about 3 to about 20 hours, or about 1 to about 18 hours, or about 1 to about 16 hours or about 2 to about 18 hours, or about 2 to about 16 hours, or about 1 to about 14 hours, or about 1 to about 12 hours, or about 4 to about 16 hours, or about 4 to about 18 hours, or about 4 to about 20 hours, or about 3 to about 15 hours or about 6 to about 15 hours, or about 6 to about 12 hours, or about 6 to about 18 hours, or about 6 to about 20 hours, or about 5 to about 12 hours, or about 5 to about 14 hours, or about 3 to about 22 hours, or about 3 to about 9 hours or about 3 to about 12 hours, or about 1 to about 6 hours, or about 2 to about 8 hours, or about 2 to about 10 hours, or about 3 to about 16 hours, during a 24 hour dosing interval.

In some preferred embodiments, the dosage form provides a $T_{max}$ of abusable drug at a time point 1 to 18 times later than the $T_{max}$ provided by an equivalent dose of an oral immediate release abusable drug solution or suspension. In the dosage form provides a $T_{max}$ at a time point about 1 to 15 times late, or about of 1 to 10 times later, or about of 1 to 7 times later, or about of 1 to 4 times later, or about of 3 to 20 times later, or about of 3 to 10 times later, or about of 3 to 5 times later, or about 1.5 to 15 times later, or about of 1.5 to 10 times later, or about of 1.5 to 7 times later, or about of 1.5 to 3 times later, or about of 2 to 20 times later, or about of 2 to 10 times later, or about of 2 to 5 times later, or about of 2 to 3 times later, or about of 2.5 to 20 times later, or about of 2.5 to 8 times later, or about of 2.5 to 5 times later, or about of 2.5 to 4 times later, or about of 3 to 20 times later, or about of 3 to 10 times later, or about of 3 to 5 times later.

In some preferred embodiments, the dosage form provides a mean in vivo extent of absorption of abusable drug from 0 to 4 hours which is at least 20% of the mean in vivo extent of absorption from to 0 to 12 hours, wherein the mean in vivo extent of absorption is the area under the plasma or serum abusable drug concentration time curve from the time of drug administration to the specified time point. In other preferred embodiments, said in vivo extent of absorption from 0 to 4 hours is at least about 5%, or at least about 10%, or at least about 15%, or at least about 25%, or at least about 30%, or at least about 40%, or at least about 50%, or at least about 60%, or at least about 70%, or at least about 80%, at least about 90%, or about 100% of the mean in vivo extent of absorption from to 0 to 12 hours.

In some preferred embodiments, the dosage form provides a mean in vivo extent of absorption of abusable drug from 0 to 8 hours which is at least 20% of the mean in vivo extent of absorption from to 0 to 24 hours, wherein the mean in vivo extent of absorption is the area under the plasma or serum abusable drug concentration time curve from the time of drug administration to the specified time point. In other preferred embodiments, said in vivo extent of absorption from 0 to 8 hours is at least about 5%, or at least about 10%, or at least about 15%, or at least about 25%, or at least about 30%, or at least about 40%, or at least about 50%, or at least about 60%, or at least about 70%, or at least about 80%, at least about 90%, or about 100% of the mean in vivo extent of absorption from 0 to 24 hours.

In some preferred embodiments, the dosage form provides a mean in vivo extent of absorption of abusable drug from 0 to 12 hours which is at least 20% of the mean in vivo extent of absorption from to 0 to 24 hours, wherein the mean in vivo extent of absorption is the area under the plasma or serum abusable drug concentration time curve from the time of drug administration to the specified time point. In other preferred embodiments, said in vivo extent of absorption from 0 to 12 hours is at least about 5%, or at least about 10%, or at least about 15%, or at least about 25%, or at least about 30%, or at least about 40%, or at least about 50%, or at least about 60%, or at least about 70%, or at least about 80%, at least about 90%, or about 100% of the mean in vivo extent of absorption from to 0 to 24 hours.

In some preferred embodiments, the dosage form provides a mean in vivo extent of absorption of abusable drug over the dosing interval, $AUC_{0-t}$ (e.g., from 0 to 8 hours, or from 0 to 12 hours or from 0 to 24 hours) which is at least 40% of the mean in vivo extent of absorption from to 0 to infinity ($AUC_{0-\infty}$). In other preferred embodiments, said $AUC_{0-t}$ is at least about 50%, or at least about 60%, or at least about 70%, or at least about 80%, or at least about 90% of the mean in vivo extent of absorption from to 0 to infinity ($AUC_{0-\infty}$).

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of abusable drug, when measured by the USP Basket and Paddle Methods at 100 rpm in 900 mL aqueous buffer at a pH of between 1.6 and 7.2 at 37° C. of between 0% to about 100% at 0.5 hours, and greater than about 60% at 1 hour.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of abusable drug, when measured by the USP Basket and Paddle Methods at 100 rpm in 900 mL aqueous buffer at a pH of between 1.6 and 7.2 at 37° C. of between 0% to about 40% at 1 hour, from about 5% to about 60% at 2 hours, from about 10% to about 75% at 4 hours, from about 20% to about 75% at 6 hours, from about 30% to about 80% at 9 hours, and greater than about 70% at 12 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of abusable drug, when measured by the USP Basket and Paddle Methods at 100 rpm in 900 mL aqueous buffer at a pH of between 1.6 and 7.2 at 37° C. of between 1% and about 45% at 1 hour, between about 5% and about 70% at 2 hours, between about 10% and about 90% at 4 hours, between about 20% and about 90% at 8 hours, greater than about 60% at 12 hours, greater than about 80% at 18 hours, and greater than about 85% at 24 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of abusable drug, when measured by the USP Basket and Paddle Methods at 100 rpm in 900 mL aqueous buffer at a pH of between 1.6 and 7.2 at 37° C. of between 5% and about 60% at 1 hour, between about 12.5% and about 80% at 2 hours, between about 25% and about 95% at 4 hours, between about 45% and about 100% at 8 hours, greater than about 55% at 12 hours, greater than about 65% at 18 hours, and greater than about 70% at 24 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of abusable drug, when measured by the USP Basket and Paddle Methods at 100 rpm in 900 mL aqueous buffer at a pH of between 1.6 and 7.2 at 37° C. of between 0% and about 40% at 1 hour, between about 0% and about 70% at 2 hours, between about 5% and about 95% at 4 hours, between about 12.5% and about 100% at 8 hours, between about 20% and about 100% at 12 hours, between about 35% and about 100% at 16 hours, between about 55% and about 100% at 24 hours, and greater than about 75% at 36 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of abusable drug, when measured by the USP Basket and Paddle Methods at 100 rpm in 900 mL aqueous buffer at a pH of between 1.6 and 7.2 at 37° C. of between 0% and about 60% at 1 hour, between about 0% and about 75% at 2 hours, between about 5% and about 95% at 4 hours, between about 12.5% and about 100% at 8 hours, between about 15% and about 100% at 12 hours, between about 25% to about 100% at 16 hours, between about 30% and about 100% hours at 24 hours and greater than 60% at 36 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release from the dosage form at one hour when measured by the USP Basket and Paddle Methods at 100 rpm in 700 ml of Simulated Gastric Fluid (SGF) at 37° C. of between 0% to about 50% by weight of the abusable drug. In other preferred embodiments, said release rate is between 0% to about 1%, or 0% to about 3%, or 0% to about 5%, or 0% to about 10%, or 0% to about 15%, or 0% to about 20%, 0% to about 30%, or 0% to about 40%, or 0% to about 60%, or 0% to about 70%, or 0% to about 80%, or 0% to about 90%, 0% to about 100%.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release from the dosage form at one hour when measured by the USP Basket and Paddle Methods at 100 rpm in 900 mL aqueous buffer at a pH of between 1.6 and 7.2 at 37° C. of between 0% and about 60% at 1 hour, between about 0% and about 80% at 2 hours, between about 3% and about 95% at 4 hours and between about 10% and about 100% at 8 hours. In other preferred embodiments, said release rate is between 0% and about 10% at 1 hour, between about 0% and about 20% at 2 hours, between about 2% and about 80% at 4 hours and between about 5% and about 100% at 8 hours; or between 0% and about 20% at 1 hour, between about 0% and about 40% at 2 hours, between about 0% and about 80% at 4 hours and between about 2% and about 100% at 8 hours; or between 0% and about 40% at 1 hour, between about 0% and about 60% at 2 hours, between about 5% and about 85% at 4 hours and between about 5% and about 90% at 8 hours and greater than 20% at 12 hours; or between about 0% and about 50% at 1 hour, between about 0% and about 50% at 2 hours, between about 10% and about 90% at 4 hours and between about 15% and about 90% at 8 hours and greater than 30% at 12 hours; or between 0% and about 70% at 1 hour, between about 0% and about 70% at 2 hours, between about 10% and about 75% at 4 hours and between about 15% and about 90% at 8 hours and greater than 30% at 12 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release from the dosage form at one hour when measured by the USP Basket and Paddle Methods at 100 rpm in 900 mL aqueous buffer at a pH of between 1.6 and 7.2 at 37° C. of between 10% and about 65% at 1 hour, between about 20% and about 75% at 2 hours, between about 30% and about 95% at 4 hours and between about 40% and about 100% at 8 hours. In other preferred embodiments, said release rate is between 2% and about 70% at 1 hour, between about 5% and about 80% at 2 hours, between about 10% and about 90% at 4 hours and between about 20% and about 100% at 8 hours; or between 5% and about 60% at 1 hour, between about 10% and about 75% at 2 hours, between about 15% and about 85% at 4 hours and between about 30% and about 100% at 8 hours; or between 20% and about 70% at 1 hour, between about 20% and about 75% at 2 hours, between about 20% and about 90% at 4 hours and between about 40% and about 100% at 8 hours; or between 30% and about 80% at 1 hour, between about 40% and about 85% at 2 hours, between about 40% and about 90% at 4 hours and between about 60% and about 100% at 8 hours; or between 1% and about 20% at 1 hour, between about 5% and about 20% at 2 hours, between about 10% and about 40% at 4 hours and between about 20% and about 40% at 8 hours and greater than 40% at 12 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of the abusable drug, when measured by the USP Basket and Paddle Methods at 100 rpm in 900 mL aqueous buffer at a pH of between 1.6 and 7.2 at 37° C. of between 0% to about 47.5% at 1 hour, from about 10% to about 65% at 2 hours, from about 15% to about 70% at 4 hours, from about 25% to about 77.5% at 6 hours, from about 35% to about 87.5% at 9 hours, and greater than about 65% at 12 hours. In other preferred embodiments, said release rate is between 0% to about 30% at 1 hour, from about 5% to about 45% at 2 hours, from about 10% to about 60% at 4 hours, from about 15% to about 70% at 6 hours, from about 25% to about 80% at 9 hours, and greater than about 50% at 12 hours; or between 0% to about 20% at 1 hour, from about 2% to about 35% at 2 hours, from about 5% to about 50% at 4 hours, from about 10% to about 60% at 6 hours, from about 15% to about 70% at 9 hours, and greater than about 40% at 12 hours; or between 0% to about 10% at 1 hour, from about 1% to about 30% at 2 hours, from about 5% to about 40% at 4 hours, from about 10% to about 60% at 6 hours, from about 15% to about 70% at 9 hours, and greater than about 40% at 12 hours; or between 0% to about 5% at 1 hour, from about 0% to about 10% at 2 hours, from about 2% to about 20% at 4 hours, from about 5% to about 30% at 6 hours, from about 10% to about 40% at 9 hours, and greater than about 30% at 12 hours; or between 0% to about 50% at 1 hour, from about 15% to about 70% at 2 hours, from about 20% to about 75% at 4 hours, from about 30% to about 80% at 6 hours, from about 30% to about 90% at 9 hours, and greater than about 70% at 12 hours; or between 0% to about 60% at 1 hour, from about 15% to about 80% at 2 hours, from about 25% to about 85% at 4 hours, from about 35% to about 90% at 6 hours, from about 40% to about 90% at 9 hours, and greater than about 80% at 12 hours; or between 0% to about 70% at 1 hour, from about 20% to about 80% at 2 hours, from about 25% to about 80% at 4 hours, from about 35% to about 80% at 6 hours, from about 40% to about 80% at 9 hours, and greater than about 60% at 12 hours; or between 0% to about 75% at 1 hour, from about 30% to about 80% at 2 hours, from about 35% to about 90% at 4 hours, from about 50% to about 90% at 6 hours, from about 55% to about 95% at 9 hours, and greater than about 70% at 12 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of the abusable drug, when measured by the USP Basket and Paddle Methods at 100 rpm in 900 mL aqueous buffer at a pH of between 1.6 and 7.2 at 37° C. of between 5% and about 50% at 1 hour, between about 10% and about 75% at 2 hours, between about 20% and about 95% at 4 hours, between about 40% and about 100% at 8 hours, greater than about 50% at 12 hours, greater than about 70% at 18 hours, and greater than about 80% at 24 hours. In other preferred embodiments, said release rate is between 2% and about 50% at 1 hour, between about 5% and about 75% at 2 hours, between about 15% and about 75% at 4 hours, between about 30% and about 90% at 8 hours, greater than about 40% at 12 hours, greater than about 60% at 18 hours, and greater than about 70% at 24 hours; or between 1% and about 40% at 1 hour, between about 2% and about 60% at 2 hours, between about 10% and about 65% at 4 hours, between about 20% and about 80% at 8 hours, greater than about 30% at 12 hours, greater than about 40% at 18 hours, and greater than about 60% at 24 hours; or between 5% and about 60% at 1 hour, between about 15% and about 80% at 2 hours, between about 25% and about 95% at 4 hours, between about 45% and about 100% at 8 hours, greater than about 60% at 12 hours, greater than about 80% at 18 hours, and greater than about 90% at 24 hours; or between 10% and about 65% at 1 hour, between about 20% and about 85% at 2 hours, between about 30% and about 100% at 4 hours, between about 60% and about 100% at 8 hours, greater than about 70% at 12 hours, greater than about 90% at 18 hours, and greater than about 95% at 24 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of the abusable drug, when measured by the USP Basket and Paddle Methods at 100 rpm in 900 mL aqueous buffer at a pH of between 1.6 and 7.2 at 37° C. of between 0% to about 30% at 1 hour, from about 10% to about 65% at 4 hours, from about 20% to about 70% at 8 hours, from about 25% to about 80% at 12 hours, from about 35% to about 95% at 18 hours, and greater than about 65% at 24 hours. In other preferred embodiments, said release rate is between 0% to about 20% at 1 hour, from about 5% to about 50% at 4 hours, from about 10% to about 60% at 8 hours, from about 15% to about 70% at 12 hours, from about 25% to about 90% at 18 hours, and greater than about 55% at 24 hours; or between 0% to about 10% at 1 hour, from about 5% to about 40% at 4 hours, from about 8% to about 50% at 8 hours, from about 10% to about 60% at 12 hours, from about 22% to about 80% at 18 hours, and greater than about 45% at 24 hours; or between 0% to about 35% at 1 hour, from about 15% to about 70% at 4 hours, from about 25% to about 75% at 8 hours, from about 30% to about 85% at 12 hours, from about 40% to about 100% at 18 hours, and greater than about 75% at 24 hours; or between 0% to about 40% at 1 hour, from about 20% to about 70% at 4 hours, from about 30% to about 80% at 8 hours, from about 35% to about 90% at 12 hours, from about 45% to about 100% at 18 hours, and greater than about 80% at 24 hours; or between 0% to about 45% at 1 hour, from about 25% to about 75% at 4 hours, from about 35% to about 85% at 8 hours, from about 40% to about 90% at 12 hours, from about 50% to about 100% at 18 hours, and greater than about 90% at 24 hours; or between 0% to about 50% at 1 hour, from about 30% to about 80% at 4 hours, from about 40% to about 90% at 8 hours, from about 45% to about 95% at 12 hours, from about 60% to about 100% at 18 hours, and greater than about 95% at 24 hours; or between 0% to about 60% at 1 hour, from about 40% to about 80% at 4 hours, from about 45% to about 90% at 8 hours, from about 50% to about 100% at 12 hours, from about 70% to about 100% at 18 hours, and greater than about 80% at 24 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of the abusable drug, when measured by the USP Basket and Paddle Methods at 100 rpm in 900 mL aqueous buffer at a pH of between 1.6 and 7.2 at 37° C. of between 0% and about 50% at 1 hour, between about 0% and about 75% at 2 hours, between about 3% and about 95% at 4 hours, between about 10% and about 100% at 8 hours, between about 25% and about 100% at 12 hours, between about 30% and about 100% at 16 hours, between about 50% and about 100% at 24 hours, and greater than about 80% at 36 hours. In other preferred embodiments, said release rate is between 0% and about 40% at 1 hour, between about 0% and about 65% at 2 hours, between about 2% and about 85% at 4 hours, between about 8% and about 90% at 8 hours, between about 20% and about 95% at 12 hours, between about 25% and about 95% at 16 hours, between about 40% and about 90% at 24 hours, and greater than about 70% at 36 hours; or between 0% and about 30% at 1 hour, between about 0% and about 50% at 2 hours, between about 1% and about 75% at 4 hours, between about 5% and about 80% at 8 hours, between about 10% and about 85% at 12 hours, between about 15% and about 90% at 16 hours, between about 30% and about 80% at 24 hours, and greater than about 70% at 36 hours; or between 0% and about 60% at 1 hour, between about 0% and about 80% at 2 hours, between about 5% and about 100% at 4 hours, between about 15% and about 100% at 8 hours, between about 35% and about 100% at 12 hours, between about 40% and about 100% at 16 hours, between about 60% and about 100% at 24 hours, and greater than about 85% at 36 hours; or between 0% and about 65% at 1 hour, between about 0% and about 85% at 2 hours, between about 10% and about 100% at 4 hours, between about 20% and about 100% at 8 hours, between about 40% and about 100% at 12 hours, between about 50% and about 100% at 16 hours, between about 70% and about 100% at 24 hours, and greater than about 90% at 36 hours; or between 0% and about 70% at 1 hour, between about 0% and about 90% at 2 hours, between about 20% and about 100% at 4 hours, between about 30% and about 100% at 8 hours, between about 50% and about 100% at 12 hours, between about 60% and about 100% at 16 hours, between about 80% and about 100% at 24 hours, and greater than about 95% at 36 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of the abusable drug, when measured by the USP Basket and Paddle Methods at 100 rpm in 900 mL aqueous buffer at a pH of between 1.6 and 7.2 at 37° C. of between 20% and about 50% at 1 hour, between about 40% and about 75% at 2 hours, between about 60% and about 95% at 4 hours, between about 80% and about 100% at 8 hours and between about 90% and about 100% at 12 hours. In other preferred embodiments, said release rate is between 15% and about 45% at 1 hour, between about 35% and about 70% at 2 hours, between about 55% and about 90% at 4 hours, between about 75% and about 90% at 8 hours and between about 80% and about 95% at 12 hours; or between 10% and about 40% at 1 hour, between about 30% and about 65% at 2 hours, between about 50% and about 85% at 4 hours, between about 70% and about 85% at 8 hours and between about 75% and about 90% at 12 hours; or between 5% and about 35% at 1 hour, between about 25% and about 60% at 2 hours, between about 45% and about 80% at 4 hours, between about 65% and about 80% at 8 hours and between about 70% and about 85% at 12 hours; or between 25% and about 55% at 1 hour, between about 45% and about 80% at 2 hours, between about 65% and about 95% at 4 hours, between about 85% and about 100% at 8 hours and between about 95% and about 100% at 12 hours; or between 30% and about 60% at 1 hour, between about 50% and about 80% at 2 hours, between about 70% and about 95% at 4 hours, between about 90% and about 100% at 8 hours and between about 95% and about 100% at 12 hours; or between 35% and about 60% at 1 hour, between about 50% and about 80% at 2 hours, between about 80% and about 95% at 4 hours, between about 90% and about 100% at 8 hours and between about 95% and about 100% at 12 hours; or between 20% and about 40% at 1 hour, between about 40% and about 65% at 2 hours, between about 60% and about 85% at 4 hours, between about 70% and about 90% at 8 hours and between about 80% and about 100% at 12 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of the abusable drug, when measured by the USP Basket and Paddle Methods at 100 rpm in 900 mL aqueous buffer at a pH of between 1.6 and 7.2 at 37° C. of between 0% and about 50% at 1 hour, between about 0% and about 75% at 2 hours, between about 10% and about 95% at 4 hours, between about 35% and about 100% at 8 hours, between about 55% and about 100% at 12 hours, between about 70% to about 100% at 16 hours, and greater than about 90% at 24 hours. In other preferred embodiments, said release rate is between 0% and about 40% at 1 hour, between about 0% and about 65% at 2 hours, between about 8% and about 85% at 4 hours, between about 30% and about 90% at 8 hours, between about 45% and about 100% at 12 hours, between about 60% to about 100% at 16 hours, and greater than about 80% at 24 hours; or between 0% and about 30% at 1 hour, between about 0% and about 55% at 2 hours, between about 5% and about 75% at 4 hours, between about 20% and about 80% at 8 hours, between about 35% and about 100% at 12 hours, between about 50% to about 100% at 16 hours, and greater than about 70% at 24 hours; or between 0% and about 20% at 1 hour, between about 0% and about 45% at 2 hours, between about 5% and about 65% at 4 hours, between about 10% and about 70% at 8 hours, between about 25% and about 80% at 12 hours, between about 40% to about 100% at 16 hours, and greater than about 60% at 24 hours; or between 0% and about 60% at 1 hour, between about 0% and about 80% at 2 hours, between about 15% and about 95% at 4 hours, between about 40% and about 100% at 8 hours, between about 60% and about 100% at 12 hours, between about 75% to about 100% at 16 hours, and greater than about 90% at 24 hours; or between 0% and about 65% at 1 hour, between about 0% and about 85% at 2 hours, between about 20% and about 90% at 4 hours, between about 45% and about 100% at 8 hours, between about 65% and about 100% at 12 hours, between about 80% to about 100% at 16 hours, and greater than about 90% at 24 hours; or between 0% and about 40% at 1 hour, between about 0% and about 50% at 2 hours, between about 10% and about 80% at 4 hours, between about 25% and about 70% at 8 hours, between about 40% and about 80% at 12 hours, between about 60% to about 100% at 16 hours, and greater than about 90% at 24 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of the abusable drug, when measured by the USP Basket and Paddle Methods at 100 rpm in 900 mL aqueous buffer at a pH of between 1.6 and 7.2 at 37° C. of between 0% and about 30% at 1 hour, between about 0% and about 45% at 2 hours, between about 3% and about 55% at 4 hours, between about 10% and about 65% at 8 hours, between about 20% and about 75% at 12 hours, between about 30% to about 88% at 16 hours, between about 50% and about 100% hours at 24 hours and greater than 80% at 36 hours. In other preferred embodiments, said release rate is between 0% and about 25% at 1 hour, between about 0% and about 40% at 2 hours, between about 2% and about 50% at 4 hours, between about 8% and about 60% at 8 hours, between about 10% and about 70% at 12 hours, between about 25% to about 80% at 16 hours, between about 45% and about 100% hours at 24 hours and greater than 75% at 36 hours; or between 0% and about 20% at 1 hour, between about 0% and about 35% at 2 hours, between about 1% and about 45% at 4 hours, between about 5% and about 55% at 8 hours, between about 8% and about 65% at 12 hours, between about 20% to about 75% at 16 hours, between about 40% and about 100% hours at 24 hours and greater than 70% at 36 hours; or between 0% and about 15% at 1 hour, between about 0% and about 30% at 2 hours, between about 0% and about 40% at 4 hours, between about 5% and about 50% at 8 hours, between about 8% and about 60% at 12 hours, between about 15% to about 70% at 16 hours, between about 35% and about 100% hours at 24 hours and greater than 60% at 36 hours; or between 0% and about 10% at 1 hour, between about 0% and about 25% at 2 hours, between about 0% and about 35% at 4 hours, between about 5% and about 45% at 8 hours, between about 10% and about 50% at 12 hours, between about 10% to about 60% at 16 hours, between about 30% and about 90% hours at 24 hours and greater than 70% at 36 hours; or between 0% and about 35% at 1 hour, between about 0% and about 50% at 2 hours, between about 5% and about 60% at 4 hours, between about 15% and about 70% at 8 hours, between about 25% and about 80% at 12 hours, between about 35% to about 90% at 16 hours, between about 55% and about 100% hours at 24 hours and greater than 85% at 36 hours; or between 0% and about 40% at 1 hour, between about 0% and about 55% at 2 hours, between about 10% and about 65% at 4 hours, between about 20% and about 75% at 8 hours, between about 30% and about 85% at 12 hours, between about 40% to about 100% at 16 hours, between about 55% and about 100% hours at 24 hours and greater than 90% at 36 hours; or between 0% and about 45% at 1 hour, between about 0% and about 60% at 2 hours, between about 15% and about 70% at 4 hours, between about 25% and about 80% at 8 hours, between about 35% and about 90% at 12 hours, between about 45% to about 100% at 16 hours, between about 60% and about 100% hours at 24 hours and greater than 60% at 36 hours; or between 0% and about 50% at 1 hour, between about 5% and about 65% at 2 hours, between about 20% and about 75% at 4 hours, between about 30% and about 85% at 8 hours, between about 40% and about 95% at 12 hours, between about 50% to about 100% at 16 hours, between about 70% and about 100% hours at 24 hours and greater than 70% at 36 hours; or between 0% and about 30% at 1 hour, between about 5% and about 40% at 2 hours, between about 10% and about 60% at 4 hours, between about 20% and about 70% at 8 hours, between about 30% and about 100% at 12 hours, between about 40% to about 100% at 16 hours, between about 60% and about 100% hours at 24 hours and greater than 90% at 36 hours; or between 0% and about 30% at 1 hour, between about 0% and about 30% at 2 hours, between about 0% and about 30% at 4 hours, between about 5% and about 70% at 8 hours, between about 10% and about 80% at 12 hours, between about 20% to about 100% at 16 hours, between about 40% and about 100% hours at 24 hours and greater than 50% at 36 hours; or between 0% and about 20% at 1 hour, between about 0% and about 20% at 2 hours, between about 0% and about 20% at 4 hours, between about 0% and about 20% at 8 hours, between about 5% and about 40% at 12 hours, between about 10% to about 80% at 16 hours, between about 40% and about 100% hours at 24 hours and greater than 60% at 36 hours; or between 0% and about 10% at 1 hour, between about 0% and about 20% at 2 hours, between about 0% and about 40% at 4 hours, between about 5% and about 60% at 8 hours, between about 10% and about 80% at 12 hours, between about 20% to about 100% at 16 hours, between about 40% and about 100% hours at 24 hours and greater than 50% at 36 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of the abusable drug, when measured by the USP Basket and Paddle Methods at 100 rpm in 900 mL aqueous buffer at a pH of between 1.6 and 7.2 at 37° C. of between 0% and about 50% at 1 hour, between about 0% and about 75% at 2 hours, between about 3% and about 95% at 4 hours, between about 10% and about 100% at 8 hours, between about 20% and about 100% at 12 hours, between about 30% to about 100% at 16 hours, between about 50% and about 100% hours at 24 hours and greater than 80% at 36 hours. In other preferred embodiments, said release rate is between 0% and about 45% at 1 hour, between about 0% and about 70% at 2 hours, between about 3% and about 90% at 4 hours, between about 8% and about 100% at 8 hours, between about 15% and about 100% at 12 hours, between about 25% to about 100% at 16 hours, between about 45% and about 100% hours at 24 hours and greater than 80% at 36 hours; or between 0% and about 40% at 1 hour, between about 0% and about 65% at 2 hours, between about 0% and about 80% at 4 hours, between about 5% and about 80% at 8 hours, between about 10% and about 90% at 12 hours, between about 20% to about 100% at 16 hours, between about 40% and about 100% hours at 24 hours and greater than 70% at 36 hours; or between 0% and about 35% at 1 hour, between about 0% and about 60% at 2 hours, between about 0% and about 70% at 4 hours, between about 3% and about 70% at 8 hours, between about 5% and about 80% at 12 hours, between about 15% to about 100% at 16 hours, between about 30% and about 100% hours at 24 hours and greater than 40% at 36 hours; or between 0% and about 60% at 1 hour, between about 0% and about 80% at 2 hours, between about 5% and about 100% at 4 hours, between about 15% and about 100% at 8 hours, between about 30% and about 100% at 12 hours, between about 40% to about 100% at 16 hours, between about 60% and about 100% hours at 24 hours and greater than 70% at 36 hours; or between 0% and about 50% at 1 hour, between about 0% and about 75% at 2 hours, between about 5% and about 95% at 4 hours, between about 25% and about 80% at 8 hours, between about 30% and about 100% at 12 hours, between about 40% to about 100% at 16 hours, between about 60% and about 100% hours at 24 hours and greater than 60% at 36 hours; or between 0% and about 60% at 1 hour, between about 0% and about 85% at 2 hours, between about 5% and about 100% at 4 hours, between about 10% and about 100% at 8 hours, between about 20% and about 100% at 12 hours, between about 30% to about 100% at 16 hours, between about 50% and about 100% hours at 24 hours and greater than 80% at 36 hours.

In some preferred embodiments, the dosage form provides an oral pharmaceutical composition comprising a therapeutically effective amount of abusable drug or pharmaceutically acceptable salts thereof or mixtures thereof and ADER, said abusable drugs dosage form providing an in-vitro release rate by weight of the abusable drug, when measured by the USP Basket and Paddle Methods at 100 rpm in 900 mL aqueous buffer at a pH of between 1.6 and 7.2 at 37° C. of between 15% and about 25% at 1 hour, between about 25% and about 35% at 2 hours, between about 30% and about 45% at 4 hours, between about 40% and about 60% at 8 hours, between about 55% and about 70% at 12 hours and between about 60% to about 75% at 16 hours. In other preferred embodiments, said release rate is between 10% and about 20% at 1 hour, between about 20% and about 30% at 2 hours, between about 25% and about 40% at 4 hours, between about 30% and about 50% at 8 hours, between about 50% and about 65% at 12 hours and between about 55% to about 65% at 16 hours; or between 5% and about 15% at 1 hour, between about 15% and about 25% at 2 hours, between about 20% and about 35% at 4 hours, between about 25% and about 45% at 8 hours, between about 45% and about 60% at 12 hours and between about 50% to about 60% at 16 hours; or between 15% and about 30% at 1 hour, between about 20% and about 40% at 2 hours, between about 20% and about 50% at 4 hours, between about 30% and about 70% at 8 hours, between about 60% and about 80% at 12 hours and between about 70% to about 90% at 16 hours; or between 0% and about 50% at 1 hour, between about 5% and about 50% at 2 hours, between about 5% and about 70% at 4 hours, between about 10% and about 80% at 8 hours, between about 20% and about 100% at 12 hours and between about 40% to about 100% at 16 hours; or between 15% and about 40% at 1 hour, between about 15% and about 45% at 2 hours, between about 20% and about 60% at 4 hours, between about 20% and about 80% at 8 hours, between about 30% and about 90% at 12 hours and between about 40% to about 100% at 16 hours.

In some preferred embodiments, the dosage form provides an oral pharmaceutical composition comprising a therapeutically effective amount of abusable drug or pharmaceutically acceptable salts thereof or mixtures thereof and ADER, said in-vitro release rate being substantially independent of pH in that a difference, at any given time, between an amount of abusable drug released at one pH and an amount released at any other pH, when measured in-vitro using the USP Basket and Paddle Methods of USP Drug Release test of U.S. Pharmacopeia (2003) at 100 rpm in 900 ml aqueous buffer, is no greater than 30%. In other preferred embodiments, the difference, at any given time, between an amount of abusable drug released at one pH and an amount released at any other pH using the aforementioned methods is no greater than 50%, or no greater than 40%, or no greater than 35%, or no greater than 25%, or no greater than 20%, or no greater than 15%, or no greater than 10%, or no greater than 5%.

In some preferred embodiments, the dosage form provides an oral pharmaceutical composition comprising a therapeutically effective amount of abusable drug or pharmaceutically acceptable salts thereof or mixtures thereof and ADER, said dosage forms of abusable drug providing in-vitro release rates by weight of between 0% to about 50% by weight of the abusable drug from the dosage form at one hour when measured by the USP Basket and Paddle Methods at 100 rpm in 700 ml of Simulated Gastric Fluid (SGF) at 37° C. In other preferred embodiments, said release rate at one hour is between 0% to about 10% by weight, or 0% to about 20% by weight, or is between 0% to about 30% by weight, or 0% to about 40% by weight, or between 0% to about 60% by weight, or 0% to about 70% by weight, or 0% to about 80% by weight, or 0% to about 90% by weight, or 10% to about 50% by weight, or 10% to about 60% by weight, or 10% to about 70% by weight, or 10% to about 90% by weight, or 10% to about 100% by weight, or 30% to about 100% by weight, or 50% to about 100% by weight.

In some preferred embodiments, the dosage form provides an oral pharmaceutical composition comprising a therapeutically effective amount of abusable drug or pharmaceutically acceptable salts thereof or mixtures thereof and ADER, said dosage forms of abusable drug providing in-vitro release rates by weight of abusable drug, when measured by the USP Basket and Paddle Methods at 100 rpm in 900 mL aqueous buffer at a pH of between 1.6 and 7.2 at 37° C. of between 0% to about 80% at 0.5 hours, and greater than about 40% at 1 hour. In other preferred embodiments, said release rate is between 0% to about 40% at 0.5 hours, and greater than about 60% at 1 hour; or between 0% to about 20% at 0.5 hours, and greater than about 40% at 1 hour; or between 0% to about 20% at 0.5 hours, and greater than about 20% at 1 hour; or between 0% to about 90% at 0.5 hours, and greater than about 60% at 1 hour; or between 0% to about 100% at 0.5 hours, and greater than about 60% at 1 hour; or between 0% to about 90% at 1 hour, and greater than about 40% at 2 hours; or between 0% to about 100% at 1 hour, and greater than about 60% at 2 hours; or between 0% to about 60% at 1 hour, and greater than about 40% at 2 hours; or between 0% to about 40% at 1 hour, and greater than about 30% at 2 hours; or between 0% to about 50% at 1 hour, and greater than about 40% at 2 hours; or between 0% to about 30% at 1 hour, and greater than about 20% at 2 hours; or between 0% and about 50% at 1 hour, between about 0% and about 80% at 2 hours, between about 5% and about 100% at 4 hours and between about 10% and about 100% at 8 hours; or between 10% and about 60% at 1 hour, between about 15% and about 75% at 2 hours, between about 20% and about 95% at 4 hours and between about 30% and about 100% at 8 hours.

In some preferred embodiments, the oral dosage form of the present invention is directed to an oral dosage form comprising: (i) an abusable drug and (ii) ADER, such that the ratio of the mean $C_{max}$ of the abusable drug after single dose oral administration of the dosage form after tampering to the mean $C_{max}$ of abusable drug after single dose oral administration of an intact dosage form is not more than about 20:1. In other embodiments of the invention, the mean $C_{max}$ ratio using the aforementioned test method is not more than about 15:1, or about 10:1, or about 7.5:1, or about 6:1, or about 5:1, or about 4:1, or about 3:1, or about 2:1, or about 1.5:1, or about 1.25:1.

In some preferred embodiments, the oral dosage form of the present invention is directed to an oral dosage form comprising: (i) an abusable drug and (ii) ADER, such that the ratio of the mean $C_{max}$ of the abusable drug after single dose oral administration of an immediate release reference product containing an equivalent amount of abusable drug to the mean $C_{max}$ of abusable drug after single dose oral administration of an intact dosage form of the invention is at least about 1.25:1. In other embodiments of the invention, the mean $C_{max}$ ratio using the aforementioned test method is at least about 1.5:1, or about 2:1, or about 3:1, or about 4:1, or about 5:1, or about 6:1, or about 10:1, or about 15:1 or about 20:1.

In some preferred embodiments, the oral dosage form of the present invention is directed to an oral dosage form comprising: (i) an abusable drug and (ii) ADER, such that the ratio of the mean $AUC_{0-2}$ of the abusable drug after single dose oral administration of the dosage form after tampering to the mean $AUC_{0-2}$ of abusable drug after single dose oral administration of an intact dosage form is not more than about 20:1. In other embodiments, the mean AUC ratio using the aforementioned test method is measured from time 0 to up to 1, 2.5, 3, 4, 5 or 6 hours post dose (i.e., $AUC_{0-1}$, $AUC_{0-2.5}$, $AUC_{0-3}$, $AUC_{0-4}$, $AUC_{0-5}$ and $AUC_{0-6}$, respectively). In other embodiments of the invention, the mean $AUC_{0-1}$, $AUC_{0-2}$, $AUC_{0-2.5}$, $AUC_{0-3}$, $AUC_{0-4}$, $AUC_{0-5}$ and $AUC_{0-6}$ ratios using the aforementioned test method are not more than about 15:1, or about 10:1, or about 7.5:1, or about 6:1, or about 5:1, or about 4:1, or about 3:1, or about 2:1 or about 1.5:1.

In some preferred embodiments, the oral dosage form of the present invention is directed to an oral dosage form comprising: (i) an abusable drug and (ii) ADER, such that the ratio of the mean $AUC_{0-2}$ of the abusable drug after single dose oral administration of an immediate release reference product containing an equivalent amount of abusable drug to the mean $AUC_{0-2}$ of abusable drug after single dose oral administration of an intact dosage form of the invention is at least about 1.25:1. In other embodiments, the mean AUC ratio using the aforementioned test method is measured from time 0 to up to 1, 2.5, 3, 4, 5 or 6 hours post dose (i.e., $AUC_{0-1}$, $AUC_{0-2.5}$, $AUC_{0-3}$, $AUC_{0-4}$, $AUC_{0-5}$ and $AUC_{0-6}$, respectively). In other embodiments of the invention, the mean $AUC_{0-1}$, $AUC_{0-2}$, $AUC_{0-2.5}$, $AUC_{0-3}$, $AUC_{0-4}$, $AUC_{0-5}$ and $AUC_{0-6}$ ratios using the aforementioned test method are not more than about 15:1, or about 10:1, or about 7.5:1, or about 6:1, or about or about 5:1, or about 4:1, or about 3:1, or about 2:1 or about 1.5:1.

In some preferred embodiments, the oral dosage form of the present invention is directed to an oral dosage form comprising: (i) an abusable drug and (ii) ADER, such that the ratio of the mean $T_{max}$ of the abusable drug after single dose oral administration of the intact dosage form to the mean $T_{max}$ of abusable drug after single dose oral administration of an dosage form after tampering is not more than about 20:1. In other embodiments of the invention, the mean $T_{max}$ ratio using the aforementioned test method is not more than about 15:1, or not more than about 10:1, or not more than about 7.5:1, or not more than about 6:1, or not more than about 5:1, or not more than about 4:1, or not more than about 3:1, or not more than about 2:1, or not more than about 1.5:1, or not more than about 1.25:1.

In some preferred embodiments, the oral dosage form of the present invention is directed to an oral dosage form comprising: (i) an abusable drug and (ii) ADER, such that the ratio of the mean $T_{max}$ of the abusable drug after single dose oral administration of an immediate release reference product containing an equivalent amount of abusable drug to the mean $T_{max}$ of abusable drug after single dose oral administration of an intact dosage form of the invention is at least about 1.25:1. In other embodiments of the invention, the mean $T_{max}$ ratio using the aforementioned test method is at least about 1.5:1, or at least about 2:1, or at least about 3:1, or at least about 4:1, or at least about 5:1, or at least about 6:1, or at least about 10:1, or at least about 15:1 or at least about 20:1.

In some preferred embodiments, the invention is directed to an oral dosage form comprising (i) an abusable drug and (ii) ADER, such that less than 70% of the abusable drug is released from the intact dosage form after 1 hour based on the in-vitro dissolution of the dosage form in 900 mL of 40% ethanol in water using the USP Basket and Paddle Methods at 50 rpm and 37° C. In other embodiments of the invention, the release rate of the abusable drug from the intact dosage form by the aforementioned USP basket method at 1 hours is 60% or less, 50% or less, 45% or less, 40% or less, 35% or less, 33% or less, 30% or less, 25% or less, 20% or less or 15% or less.

In certain preferred embodiments of the invention, the mean ratio of the amount of abusable drug released from the dosage form after mechanical tampering (e.g., after crushing with a single crush of a spatula or in the case of a capsule containing a solid, cutting into two pieces) to the amount of abusable drug released from the intact dosage form based on the dissolution at 0.5 hours of the dosage form in 900 mL of Simulated Gastric Fluid using the USP Basket and Paddle Methods at 50 rpm at 37 degrees ° C. is less than 20:1. In other embodiments of the invention, the mean ratio by the aforementioned USP basket method at 0.5 hours is 15:1 or less, 10:1 or less, 7.5:1 or less, 5:1 or less. 3:1 or less, 2:1 or less, 1.5:1 or less.

In certain preferred embodiments of the invention, the mean ratio of the amount of abusable drug released from the dosage form after mechanical tampering (e.g., after crushing with a single crush of a spatula or in the case of a capsule containing a solid, cutting into two pieces) to the amount of abusable drug released from the intact dosage form based on the dissolution at 1 hour of the dosage form in 900 mL of Simulated Gastric Fluid using the USP Basket and Paddle Methods at 50 rpm at 37 degrees ° C. is less than 20:1. In other embodiments of the invention, the mean ratio by the aforementioned USP basket method at 1 hour is 15:1 or less, 10:1 or less, 7.5:1 or less, 5:1 or less. 3:1 or less, 2:1 or less, 1.5:1 or less.

In certain preferred embodiments of the invention, the mean ratio of the amount of abusable drug released from the dosage form after mechanical tampering (e.g., after crushing with a single crush of a spatula or in the case of a capsule containing a solid, cutting into two pieces) to the amount of abusable drug released from the intact dosage form based on the dissolution at 2 hours of the dosage form in 900 mL of Simulated Gastric Fluid using the USP Basket and Paddle Methods at 50 rpm at 37 degrees ° C. is less than 20:1. In other embodiments of the invention, the mean ratio by the aforementioned USP basket method at 2 hours is 15:1 or less, 10:1 or less, 7.5:1 or less, 5:1 or less. 3:1 or less, 2:1 or less, 1.5:1 or less.

In some preferred embodiments, the present invention is directed to an oral dosage form comprising (i) an abusable drug and (ii) ADER, such that the ratio of the mean $C_{max}$ of the abusable drug after single dose oral administration of the dosage form after tampering to the mean $C_{max}$ of abusable drug after single dose oral administration of an intact dosage form is less than about 20:1. In other embodiments of the invention, said mean ratio using the aforementioned test method is less than about 15:1 or less than about 10:1, or less than about 7:1, or less than about 5:1, or less than about 4:1, or less than about 3:1, or less than 2.5:1, or less than about 2:1, or less than about 1.75:1, or less than about 1.5:1, or less than about 1.25:1 or less than about 1.25:1

In some preferred embodiments, the present invention is directed to an oral dosage form comprising (i) an abusable drug and (ii) ADER, such that the ratio of the mean $AUC_{0-2}$ of the abusable drug after single dose oral administration of an immediate release dosage form containing an equivalent amount of abusable drug to the mean $AUC_{0-2}$ of abusable drug after single dose oral administration of an intact dosage form of the invention is at least 1.25:1. In other embodiments of the invention, the mean $AUC_{0-2}$ ratio using the aforementioned test method is at least about 1.5:1, or at least about 1.75:1, or at least about 2:1, or at least about 2.5:1, or at least about 3:1, or at least about 3.5:1, or at least about 4:1, or at least about 5:1, or at least about 6:1, or at least about 10:1 or at least about 15:1 or at least about 20:1.

The invention is also directed to methods of preventing abuse and misuse of an abusable drug utilizing the dosage forms disclosed herein. The method can comprise providing the abusable drug in an oral dosage form together with ADER, wherein the abusable drug is present in a form which is partially or substantially resistant to tampering (e.g., crushing, shear forces which break up the dosage form, solvent extraction, etc.).

In certain preferred embodiments of the invention, the release for the abusable drug component of the formulation is expressed in terms of a ratio of the release achieved after tampering, relative to the amount released from the intact formulation. The ratio is therefore expressed as [Crushed]/[Whole], and it is desired that this ratio have a numerical range of not more than 20:1 (crushed release in 1 hour/intact release in 1 hour), based on in-vitro dissolution of the dosage form in 900 ml of Simulated Gastric Fluid using the USP Basket and Paddle Methods at 50 rpm and 37° C. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1.

In some embodiments, the abusable drug dosage form of the invention is bioequivalent when taken under fed and fasted conditions.

In some embodiments, the abusable drug dosage form of the invention upon administration provides a mean fed to fasted abusable drug $AUC_{0-\infty}$ difference of less than about 50%, or less than about 45%, or less than about 40%, or less than about 35%, or less than about 30%, or less than about 27%, or less than about 25%, or less than about 22%, or less than about 20% or less than about 18%, or less than about 15%, or less than about 12%, or less than about 10%, or less than about 8%, or less than about 6%, or less than about 5%, or less than about 3%.

In some embodiments, the abusable drug dosage form of the invention upon administration provides a mean fed to fasted abusable drug $C_{max}$ difference of less than about 50%, or less than about 45%, or less than about 40%, or less than about 35%, or less than about 30%, or less than about 27%, or less than about 25%, or less than about 22%, or less than about 20% or less than about 18%, or less than about 15%, or less than about 12%, or less than about 10%, or less than about 8%, or less than about 6%, or less than about 5%, or less than about 3%.

In some embodiments, the abusable drug dosage form of the invention is bioequivalent when taken under with and without 30 mL, 60 mL, 90 mL, 120 mL, 180 mL, 240 mL, 270 mL, 300 mL of a 40% ethanol solution.

In some embodiments, the abusable drug dosage form of the invention upon administration provides a mean alcohol to no alcohol state abusable drug $AUC_{0-\infty}$ difference of less than about 50%, or less than about 45%, or less than about 40%, or less than about 35%, or less than about 30%, or less than about 27%, or less than about 25%, or less than about 22%, or less than about 20% or less than about 18%, or less than about 15%, or less than about 12%, or less than about 10%, or less than about 8%, or less than about 6%, or less than about 5%, or less than about 3%, said alcohol state induced by concurrent ingestion of the abusable drug with about 300 mL or about 270 mL, or about 240 mL, or about 210 mL, or about 180 mL or about 150 mL, or about 120 mL, or about 90 mL, or about 60 mL or about 30 mL of a 40% solution of ethanol.

In some embodiments, the abusable drug dosage form of the invention upon administration provides a mean alcohol to no alcohol state abusable drug $C_{max}$ difference of less than about 50%, or less than about 45%, or less than about 40%, or less than about 35%, or less than about 30%, or less than about 27%, or less than about 25%, or less than about 22%, or less than about 20% or less than about 18%, or less than about 15%, or less than about 12%, or less than about 10%, or less than about 8%, or less than about 6%, or less than about 5%, or less than about 3%, said alcohol state induced by concurrent ingestion of the abusable drug with about 300 mL or about 270 mL, or about 240 mL, or about 210 mL, or about 180 mL or about 150 mL, or about 120 mL, or about 90 mL, or about 60 mL or about 30 mL of a 40% solution of ethanol.

In some preferred embodiments, the dosage form provides an oral pharmaceutical composition comprising a therapeutically effective amount of abusable drug or pharmaceutically acceptable salts thereof or mixtures thereof, ADER material, and a pharmacologic antagonist to the abusable drug.

In some preferred embodiments, the dosage form provides an oral pharmaceutical composition comprising a therapeutically effective amount of abusable drug or pharmaceutically acceptable salts thereof or mixtures thereof, ADER material, and a pharmacologic antagonist to a co-abused abusable drug, said co-abused abusable drug not part of the dosage form.

In some preferred embodiments, the dosage form provides an oral pharmaceutical composition comprising a therapeutically effective amount of abusable drug or pharmaceutically acceptable salts thereof or mixtures thereof, ADER material, and a pharmacologic antagonist for both the abusable drug of the dosage form and a co-abused abusable drug, said co-abused abusable drug not part of the dosage form.

In some preferred embodiments, when the dosage form of the invention comprises a therapeutically effective amount of abusable drug or pharmaceutically acceptable salt thereof or mixture thereof, ADER material, and a pharmacologic antagonist to the abusable drug (and/or to a co-abused abusable drug, said co-abused abusable drug not part of the dosage form), some or all of the in vitro dissolution rates or in-vitro release rates (e.g., USP Basket and Paddle Methods) referred to in the embodiments and specifications herein and applicable to the abusable drug are also applicable to said antagonist. In the interest of brevity, such embodiments and specifications are not repeated here. In some preferred embodiments, the in vitro dissolution rates or in-vitro release rates for the abusable drug and the pharmacologic antagonists are the same. In other preferred embodiments, the in vitro dissolution rates or in-vitro release rates for the abusable drug and for the pharmacologic antagonists are from different.

In some preferred embodiments, when the dosage form of the invention comprises a therapeutically effective amount of abusable drug or pharmaceutically acceptable salt thereof or mixture thereof, ADER material, and an aversive agent, some or all of the in vitro dissolution rates or in-vitro release rates (e.g., USP Basket and Paddle Methods) referred to in the embodiments and specifications herein and applicable to the abusable drug are also applicable to said aversive agent. In the interest of brevity, such embodiments and specifications are not repeated here. In some preferred embodiments, the in vitro dissolution rates or in-vitro release rates for the abusable drug and the aversive agent are the same. In other preferred embodiments, the in vitro dissolution rates or in-vitro release rates for the abusable drug and for the aversive agent are different.

In some preferred embodiments, when the dosage form of the invention comprises a therapeutically effective amount of abusable drug or pharmaceutically acceptable salt thereof or mixture thereof, ADER material, and a pharmacologic antagonist to the abusable drug (and/or to a co-abused abusable drug, said co-abused abusable drug not part of the dosage form), some or all of the pharmacokinetic parameters (e.g., $AUC_{0-t}$, $AUC_{0-\infty}$, $AUC_{0-8}$, $AUC_{0-12}$, $AUC_{0-24}$, $C_{max}$, $C_8$, $C_{12}$, $C_{24}$, $t_{max}$ or $T_{max}$, $C_{min}$, HVD, $W_{50}$, steady state, percent fluctuation and AI) referred to in the embodiments and specifications herein and applicable to the abusable drug are also applicable to said antagonist. In the interest of brevity, such embodiments and specifications are not repeated here. In some preferred embodiments, the pharmacokinetic parameters for the abusable drug and the pharmacologic antagonists are the same. In other preferred embodiments, the pharmacokinetic parameters for the abusable drug and for the pharmacologic antagonists are different.

In some preferred embodiments, the ADER material provides extended release of the abusable drug and the pharmacologic antagonist for the abusable drug, thereby significantly reducing the risk precipitating signs and symptoms of abusable drug withdrawal or an abstinence syndrome in abusable drug dependent and tolerant individuals, and diminution of the intended therapeutic response from the abusable drug. When such a dosage form is tampered with, the ADER material provides one line of defense and the antagonist provides yet another line of defense against drug abuse.

The amount of pharmacologic antagonist to the abusable drug in the oral dosage form will vary for a variety of reasons, including the choice of abusable drug, the potency of the abusable drug, the potency of the antagonist, the oral bioavailability of the abusable drug and the antagonist, the safety and tolerability of the antagonist, the degree of blockade sought to the effects of the abusable drug, the patients prior exposure to the abusable drug, the nature of the formulation (e.g., immediate release or extended release), the pharmacokinetics, pharmacodynamics and physicochemical characteristics of the abusable drug and the antagonist.

In some embodiments, pharmacologic antagonist to the abusable drug is about 0.00001 mg to 1000 mg, or about 0.00001 mg to about 700 mg, or about 0.001 mg to about 500 mg, or about 0.01 mg to about 400 mg, or about 0.1 mg to about 200 mg, or about 1 mg to about 100 mg, or about 0.00001 to about 500 mg, or about 0.001 to about 300 mg, or about 0.01 to about 200 mg.

In certain preferred embodiments of the invention, wherein the abusable drug is an analgesic, the mean ratio of the time to confirmed perceptible pain relief after administration of the intact dosage form to the time to confirmed perceptible pain relief after administration of the tampered dosage form is less than 20:1. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1.

In certain preferred embodiments of the invention, wherein the abusable drug is an analgesic, the mean ratio of the time to meaningful pain relief after administration of the intact dosage form to the time to meaningful pain relief after administration of the tampered dosage form is less than 20:1. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1.

In certain preferred embodiments of the invention, wherein the abusable drug is an analgesic, the mean ratio of the peak pain intensity difference score after administration of the tampered dosage form to the peak pain intensity difference score after administration of the intact dosage form is less than 10:1. In other embodiments of the invention, the mean ratio using the aforementioned test method is less than about 8:1, or less than about 7:1, or less than about 5:1, or less than about 3:1, or less than about 2:1, or less than about 1.5:1, or less than about 1.25:1.

In certain preferred embodiments of the invention, wherein the abusable drug is an analgesic, the mean ratio of the peak pain relief score after administration of the tampered dosage form to the peak pain relief score after administration of the intact dosage form is less than 10:1. In other embodiments of the invention, the mean ratio using the aforementioned test method is less than about 8:1, or less than about 7:1, or less than about 5:1, or less than about 3:1, or less than about 2:1, or less than about 1.5:1, or less than about 1.25:1.

In certain preferred embodiments of the invention, wherein the abusable drug is an analgesic, the mean ratio of change from baseline to two hours post-dose in pain intensity score after administration of the tampered dosage form to the change from baseline to two hours post-dose in pain intensity score after administration of the intact dosage form is less than 20:1. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1.

In certain preferred embodiments of the invention, wherein the abusable drug is an analgesic, the mean ratio of the number of patients with pain who need to be treated to obtain ≥50% pain relief in one patient (i.e., number needed to treat or NNT) after administration of the tampered dosage form to the NNT after administration of the intact dosage form is less than 20:1. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1. Preferably, the aforementioned at NNT is measured at 0.5, 1, 1.5, 2, 3, 4, 5 or 6 hours post-dose.

In certain preferred embodiments of the invention, wherein the abusable drug is an analgesic, the mean ratio of the number needed to harm (referred to hereinafter as "NNH") due to moderate or severe nausea in healthy subjects (naïve to said analgesic) after administration of the tampered dosage form to the NNH after administration of the intact dosage form is less than 20:1. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1. Preferably, the aforementioned at NNH is measured at 0.5, 1, 1.5, 2, 3, 4, 5 or 6 hours post-dose.

In certain preferred embodiments of the invention, wherein the abusable drug is an analgesic, the mean ratio of the NNH due to moderate or severe sedation or drowsiness in healthy subjects (naïve to said analgesic) after administration of the tampered dosage form to the NNH after administration of the intact dosage form is less than 20:1. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1. Preferably, the aforementioned at NNH is measured at 0.5, 1, 1.5, 2, 3, 4, 5 or 6 hours post-dose.

In certain preferred embodiments of the invention, wherein the abusable drug is an analgesic, the mean ratio of the NNH due to moderate or severe sedation or drowsiness in healthy subjects who are naïve to said abusable drug and who are occasional or light consumers of alcohol after administration of the tampered dosage form to the NNH after administration of the intact dosage form is less than 20:1, said NNH measured 2.5 to 6 hours after administration of the dosage form, said dosage form administration followed about 1.5 hours later by alcohol (ethanol) administration sufficient to maintain a blood alcohol concentration of 0.04% to 0.08%. In other embodiments of the invention, the mean ratio using the aforementioned test method is less than about 15:1, or less than about 10:1, or less than about 7:1, or less than about 5:1, or less than about 3:1, or less than about 2:1, or less than about 1.5:1, or less than about 1.25:1.

In certain preferred embodiments of the invention, wherein patients have the medical condition for which the abusable drug is medically used, the mean ratio of the number of patients who need to be treated (NNT) to obtain ≥50% reduction in the cardinal sign or symptom of the medical condition after administration of the tampered dosage form to the NNT after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned at NNT is measured at 0.5, 1, 1.5, 2, 3, 4, 5 or 6 hours post-dose.

In certain preferred embodiments of the invention, wherein the abusable drug is produces sedation or drowsiness on administration to naïve (i.e., abusable drug naïve) healthy subjects, the mean ratio of the NNH due to moderate or severe sedation or drowsiness in naïve healthy subjects after administration of the tampered dosage form to the NNH after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned at NNH is measured at 0.5, 1, 1.5, 2, 3, 4, 5 or 6 hours post-dose.

In certain preferred embodiments of the invention, wherein the abusable drug is produces sedation or drowsiness on administration to naïve (i.e., abusable drug naïve) healthy subjects, the mean ratio of the NNH due to moderate or severe sedation or drowsiness in healthy subjects who are naïve to said abusable drug and who are occasional or light consumers of alcohol, after administration of the tampered dosage form to the NNH after administration of the intact dosage form is less than 20:1, said NNH measured 2.5 to 6 hours after administration of the dosage form, said dosage form administration followed about 1.5 hours later by alcohol (ethanol) administration sufficient to maintain a blood alcohol concentration of 0.04% to 0.08%. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1.

In certain preferred embodiments of the invention, wherein the abusable drug is produces nausea on administration to naïve (i.e., abusable drug naïve) healthy subjects, the mean ratio of the NNH due to moderate or severe nausea in naïve healthy subjects after administration of the tampered dosage form to the NNH after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned at NNH is measured at 0.5, 1, 1.5, 2, 3, 4, 5 or 6 hours post-dose.

In certain preferred embodiments of the invention, upon administration of abusable drug to naïve (i.e., abusable drug naïve) healthy subjects, the mean ratio of the NNH due to the incidence of dizziness in naïve healthy subjects after administration of the tampered dosage form to the NNH after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned at NNH is measured at 0.5, 1, 1.5, 2, 3, 4, 5 or 6 hours post-dose.

In certain preferred embodiments of the invention, upon administration of abusable drug to naïve (i.e., abusable drug naïve) healthy subjects, the mean ratio of the NNH due to the incidence of lightheadedness in naïve healthy subjects after administration of the tampered dosage form to the NNH after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned at NNH is measured at 0.5, 1, 1.5, 2, 3, 4, 5 or 6 hours post-dose.

In certain preferred embodiments of the invention, upon administration of abusable drug to naïve (i.e., abusable drug naïve) healthy subjects, the mean ratio of the NNH due to the incidence of dry mouth in naïve healthy subjects after administration of the tampered dosage form to the NNH after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, or less than about 3:1, or less than about 2.5:1, or less than about 2:1, less than about 1.75:1, or less than about 15:1, or less than about 1.25:1, or less than about 1.1:1. Preferably, the aforementioned at NNH is measured at 0.5, 1, 1.5, 2, 3, 4, 5 or 6 hours post-dose.

In certain preferred embodiments of the invention, upon administration of abusable drug to drug abusers and recreational drug users, the mean ratio of the drug liking score after administration of the tampered dosage form to the mean ratio of the drug liking score after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose In certain preferred embodiments of the invention, upon administration of abusable drug to drug abusers and recreational drug users, the mean ratio of the drug effect score after administration of the tampered dosage form to the mean ratio of the drug effect score after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose.

In certain preferred embodiments of the invention, upon administration of abusable drug to drug abusers and recreational drug users, the mean ratio of the score on the "take again" questionnaire after administration of the tampered dosage form to the mean ratio of the score on the "take again" questionnaire after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose.

In certain preferred embodiments of the invention, upon administration of abusable drug to drug abusers and recreational drug users, the mean ratio of the score on the "coasting" questionnaire after administration of the tampered dosage form to the mean ratio of the score on the "coasting" questionnaire after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose.

In certain preferred embodiments of the invention, wherein the abusable drug is produces sedation or drowsiness on administration to naïve (i.e., abusable drug naïve) healthy subjects, the mean ratio of impairment on the "critical tracking task" driving skills test in naïve healthy subjects after administration of the tampered dosage form to the impairment after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose.

In certain preferred embodiments of the invention, wherein the abusable drug is produces sedation or drowsiness on administration to healthy subjects who are naïve to said abusable drug and who are occasional or light consumers of alcohol, the mean ratio of impairment on the "critical tracking task" driving skills test score in naïve healthy subjects after administration of the tampered dosage form to the impairment after administration of the intact dosage form is less than 20:1, said "critical tracking task" driving skills test score measured 2.5 to 6 hours after administration of the dosage form, said dosage form administration followed about 1.5 hours later by alcohol (ethanol) administration sufficient to maintain a blood alcohol concentration of 0.04% to 0.08%. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1.

In certain preferred embodiments of the invention, wherein the abusable drug is produces sedation or drowsiness on administration to naïve (i.e., abusable drug naïve) healthy subjects, the mean ratio of impairment on the "stop signal task" driving skills test in naïve healthy subjects after administration of the tampered dosage form to the impairment after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose.

In certain preferred embodiments of the invention, wherein the abusable drug is produces sedation or drowsiness on administration to healthy subjects who are naïve to said abusable drug and who are occasional or light consumers of alcohol, the mean ratio of impairment on the "stop signal task" driving skills test score in naïve healthy subjects after administration of the tampered dosage form to the impairment after administration of the intact dosage form is less than 20:1, said "stop signal task" driving skills test score measured 2.5 to 6 hours after administration of the dosage form, said dosage form administration followed about 1.5 hours later by alcohol (ethanol) administration sufficient to maintain a blood alcohol concentration of 0.04% to 0.08%. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1.

In certain preferred embodiments of the invention, wherein the abusable drug is produces sedation or drowsiness on administration to naïve (i.e., abusable drug naïve) healthy subjects, the mean ratio of impairment on the "Tower of London" driving skills test score in naïve healthy subjects after administration of the tampered dosage form to the impairment after administration of the intact dosage form is less than 20:1. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1. Preferably, the aforementioned ratio is measured at 0.5, 1, 1.5, 2, 3, 4, 5 or 6 hours post-dose.

In certain preferred embodiments of the invention, wherein the abusable drug is produces sedation or drowsiness on administration to healthy subjects who are naïve to said abusable drug and who are occasional or light consumers of alcohol, the mean ratio of impairment on the "Tower of London" driving skills test score in naïve healthy subjects after administration of the tampered dosage form to the impairment after administration of the intact dosage form is less than 20:1 said "Tower of London" driving skills test score measured 2.5 to 6 hours after administration of the dosage form, said dosage form administration followed about 1.5 hours later by alcohol (ethanol) administration sufficient to maintain a blood alcohol concentration of 0.04% to 0.08%. In other embodiments of the invention, the mean ratio using the aforementioned test method is less than about 18:1, or less than about 16:1, or less than about 15:1, or less than about 14:1, or less than about 12:1, or less than about 11:1, or less than about 10:1, or less than about 9:1, or less than about 8:1, or less than about 7:1, or less than about 6:1, or less than about 5:1, or less than about 4:1, less than about 3:1, or less than about 2.5:1, or less than about 2:1, less than about 1.75:1, or less than about 15:1, or less than about 1.25:1, or less than about 1.1:1.

The invention is also directed to a method of treating or preventing diseases and disorders amenable to treatment with abusable drugs. The method can comprise providing an oral dosage form containing an abusable drug and ADER, said dosage form an immediate release formulation, an extended release formulation or a formulation comprising both immediate release and extended release.

The oral dosage form containing an abusable drug in combination with ADER includes, but is not limited to tablets or capsules. The dosage forms of the present invention may include any desired pharmaceutical excipients known to those skilled in the art. The oral dosage forms may further provide an immediate release of the abusable drug. In certain preferred embodiments, the oral dosage forms of the present invention provide a sustained release of the abusable drug contained therein. Oral dosage forms providing sustained release of the abusable drug may be prepared in accordance with formulations/methods of manufacture known to those skilled in the art of pharmaceutical formulation.

In some particularly preferred embodiments, the dosage form is capsule which is filled with the aid of heat as a liquid and which upon cooling becomes a solid within said capsule.

The benefits of the abuse-resistant dosage form are especially great in connection with oral dosage forms of potent abusable drug, which can provide valuable therapeutic benefits but are prone to being abused. This is particularly true for sustained release abusable drug products which have a large dose of a desirable abusable drug intended to be released over a period of time in each dosage unit. Drug abusers take such sustained-release product and crush, grind, extract or otherwise damage the product so that the full contents of the dosage form become available for immediate absorption. Since such tampering of the dosage form of the invention results in the abusable drug also becoming available for absorption, the present invention provides a means for deterring such abuse. In addition, the present invention addresses the risk of overdose to non-abusing patients from "dumping" effect of the full dose of the abusable drug if the product is accidentally chewed or crushed, co-ingested with a significant amount of alcohol or taken interchangeably in fasted and fed states.

In certain preferred embodiments, a combination of two abusable drug is included in the formulation with the ADER. In further embodiments, one or more abusable drug and ADER are included and a further non-abusable drug is also included for the treatment of the same medical condition as the abusable drug or for the treatment of a different medical condition.

Another embodiment of the invention is directed to a method of preventing or treating pain, addiction disorders, musculoskeletal disorders, and other medical maladies responsive to treatment with the abusable drugs with the disclosed dosage forms. In certain preferred embodiments, the method of treating the aforementioned disorders in patients with a dosage form having less abuse potential comprises providing an oral dosage form containing an abusable drug and ADER; and orally administering the dosage form to provide a plasma level of abusable drug greater than the minimum therapeutic or minimum effective concentration of the abusable drug.

The invention is also directed to methods of preparing the dosage forms disclosed herein.

The benefits of the abuse-resistant dosage form are especially great in connection potent abusable drugs, which would provide valuable therapeutic benefits but would be prone to being abused. This is particularly true for oral dosage forms, including, in some preferred embodiments, sustained release dosage forms of abusable drugs which would have a large dose of a desirable drug intended to be released over a period of time in each dosage unit. Drug abusers may tamper the dosage form of the invention so that the full contents of the dosage form become available for immediate and maximal mood altering effects. The dosage form of the present invention would reduce the mood altering effects of the abusable drugs upon tampering and as such the invention provides pharmaceutical compositions, dosage forms and methods of deterring misuse, abuse, tampering and diversion of the dosage form.

In some embodiments of the invention, when the dosage form of the invention is tampered, the amount of abusable drug released in immediate release form is reduced, which in turn reduces the euphoric, pleasurable, reinforcing, rewarding, mood altering and toxic effects of the abusable drugs of the dosage form.

When the dosage form of the present invention is orally administered as intended to humans, the abusable drugs is released into systemic circulation as intended and is therefore available for absorption into the body. However, if the dosage forms of the present invention is tampered (e.g., chemical, solvent, thermal or mechanical extraction, followed by administration into the body) the ADER of the invention would reduce the amount of abusable drugs available in immediate release form. Additionally, the dosage form of the invention substantially reduces the efficiency of drug aspiration into syringes, drug filtration after solvent extraction and drug extraction after attempts at chemical, mechanical or thermal extraction from both immediate and sustained release dosage form of the invention. These characteristic decrease the potential for abuse or diversion of the abusable drugs in the dosage form by blocking the mood altering, euphoric, pleasurable, reinforcing, rewarding or toxic effects of the abusable drug.

The term "tampering" or "tamper" means any manipulation by mechanical, thermal and/or chemical means which changes the physical or chemical properties of the dosage form, e.g., to liberate the abusable drugs for immediate release if it is in sustained release form, or to make the abusable drugs available for inappropriate use such as administration by an alternate route, e.g., parenterally. The tampering can be, e.g., by means of crushing, shearing, grinding, mechanical extraction, solvent extraction, solvent immersion, combustion, heating or any combination thereof.

The term "abuse", "drug abuse", "cannabinoid abuse", "stimulant abuse", "benzodiazepine abuse", or "sedative abuse", in the context of the present invention, when it refers to the effects of abusable drug in causing such, includes intermittent use, recreational use and chronic use of abusable drugs alone or in conjunction with other drugs means use: (i) in quantities or by methods and routes of administration that do not conform to standard medical practice; (ii) outside the scope of specific instructions for use provided by a qualified medical professional; (iii) outside the supervision of a qualified medical professional; (iv) outside the approved instructions on proper use provided by the drug's legal manufacturer; (v) which is not in specifically approved dosage forms for medical use as pharmaceutical agents; (vi) where there is an intense desire for and efforts to procure same; (vii) compulsive use; (viii) through acquisition by manipulation of the medical system, including falsification of medical history, symptom intensity, disease severity, patient identity, doctor shopping, prescription forgeries; (ix) where there is impaired control over use; (x) despite harm; (xi) by procurement from non-medical sources; (xii) by others through sale or diversion by the individual into the non-medical supply chain; (xiii) for medically unapproved or unintended mood altering purposes.

The term "mood altering" is defined for purposes of the present invention to mean that the "high", "liking", pleasurable, euphoric, alerting, calming, anxiolytic, auditory and visual perceptual alterations, relaxing, psychotomimetic, rewarding, reinforcing and toxic effects of the abusable drug.

The term "abuse resistant", "abuse deterrent", "tamper resistant", "deter abuse" and "deter abuse" (as well of the words "resist" or "deter" when applied to abusable drugs of the invention) are used interchangeably in the context of the present invention and include pharmaceutical compositions and methods that resist, deter, discourage, diminish, delay and/or frustrate: (i) the intentional, unintentional or accidental physical or chemical manipulation or tampering of the dosage form (e.g., crushing, shearing, grinding, chewing, dissolving, melting, needle aspiration, inhalation, insufflation, extraction by mechanical, thermal and chemical means, and/or filtration); (ii) the intentional, unintentional or accidental use or misuse of the dosage form outside the scope of specific instructions for use provided by a qualified medical professional, outside the supervision of a qualified medical professional and outside the approved instructions on proper use provided by the drug's legal manufacturer (e.g., intravenous use, intranasal use, inhalational use and oral ingestion to provide high peak concentrations); (iii) the intentional, unintentional or accidental conversion of an extended release dosage form of the invention into a more immediate release form; (iv) the intentional and iatrogenic increase in physical and psychic effects sought by recreational drug users, addicts, and patients with pain who have an addiction disorder; (v) attempts at surreptitious administration of the dosage form to a third party (e.g., in a beverage); (vi) attempts to procure the dosage form by manipulation of the medical system and from non-medical sources; (vii) the sale or diversion of the dosage form into the non-medical supply chain and for medically unapproved or unintended mood altering purposes; (viii) the intentional, unintentional or accidental attempts at otherwise changing the physical, pharmaceutical, pharmacological and/or medical properties of the dosage form from what was intended by the manufacturer.

As used herein, the term "aversive agents", "aversion producing agents" and "aversive compounds" means to compounds contained within the dosage form that produce an aversive, undesirable, repugnant, distasteful, unpleasant, unacceptable physiologic or unacceptable psychic effects, or that pharmacologically block or reduce one or more of the following effects: mood alterations; euphoria, pleasure; a feeling of high; a feeling of drug liking; anxiolysis; mental stimulation; increased mental arousal; sedation; calmness; a state of relaxation; psychotomimesis; hallucinations; alterations in perception, cognition and mental focus; insomnia; hypersomnia; increased wakefulness or alertness; memory improvement; increased sexual gratification; increased sexual arousal; increased sexual desire and sexual anticipation; increased socialization; reduced social anxiety; psychologically reinforcement; and psychologically rewarding.

In some embodiments, the intention of the aversive agent is deter or further deter the misuse, abuse, tampering or diversion of the drug for use by addicts, drug abusers and recreational drug users. Preferably the aversive agent produces aversive effects only when the dosage form of the abusable drug of the invention is abused. Preferably the aversive agent is contained within the dosage form at a dose or in a form that does not produce aversive effects when the dosage form of the abusable drug of the invention is taken as medically directed or in a manner that is consistent with the manufacturer's prescribing information, but which when abused or tampered with, produces an aversive effect. For example, in some embodiments, the dosage form of the abusable drug of the invention contains one or more aversive agents in a non-releasable form (i.e., sequestered) form, said aversive agent partially or substantially released upon tampering the dosage form (e.g., mechanical, thermal, chemical, solvent tampering, ingestion in ways not recommended, and the like). For example, in some other embodiments, the dosage form of the abusable drug of the invention contains one or more aversive agents in releasable or partially releasable form, said dosage form not aversive when taken at medically approved doses or at doses consistent with the manufacturers prescribing information, said dosage form producing an aversive effect when taken in excess of medically approved doses or the manufacturers prescribing information. For example, in yet other embodiments, the dosage form of the abusable drug of the invention contains one or more aversive agents in a non-releasable form (i.e., sequestered) form, said aversive agent partially or substantially released upon tampering the dosage form (e.g., mechanical, thermal, chemical, solvent tampering, ingestion in ways not recommended, and the like), and said aversive agent pharmacologically blocking the effects of the abusable drug and/or the effects of a co-abused drug, said co-abused drug not part of the dosage form of the invention.

As used herein, the term "ADER". "ADER material" and "ADER agent" refers to one or more compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof. In some preferred embodiments, ADER is a mixture of two or more compounds from the forgoing group [i.e., (a) to (d)]. In some preferred embodiments, to qualify as an "ADER" requires a mixture of two or more compounds from the form the foregoing group [i.e., (a) to (d)]. In some particularly preferred embodiments, to qualify as an "ADER" requires a mixture of two or more compounds selected from at least two categories [i.e., (a) to (d)].

As used herein, the term "ADER". "ADER material" and "ADER agent" also includes glyceryl behenate (e.g., Comptirol™ 888 ATO), glyceryl palmitostearate (e.g., Precirol™ ATO 5), stearoyl macrogolglycerides (Gelucire™ 50/13), lauroyl macrogolglycerides (Labrafil™ M 2130 CS).

In some preferred embodiments, references to the term "the invention", "the present invention", "the pharmaceutical composition of the invention", "the dosage form of the invention", "the current invention" and embodiments of the invention in the embodiments, claims and specifications refer to pharmaceutical compositions, dosage forms, methods, processes and other innovations that comprise (i) one or more abusable drugs, in unsalified form or their pharmaceutically acceptable salts, prodrugs, esters, analogs, derivatives, solvates, complexes, polymorphs, hydrates and metabolites, as racemates or an individual diastereoisomers or enantiomeric isomers thereof or mixtures thereof; (ii) one or more compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof, said compounds also referred to as ADER; and optionally [(iii) and/or (iv)], (iii) other abusable or non-abusable drugs for the treatment of the same or a different medical condition; and/or (iv) pharmaceutical excipients, adjuvants and auxiliary agents including binders, disintegrants, fillers, diluents, anti-adherents or glidants, lubricants, stabilizers, wetting agents, pharmaceutically compatible carriers and dissolution rate modifiers, and channel and pore formers.

In some preferred embodiments, references to the term "the invention", "the present invention", "the pharmaceutical composition of the invention", "the dosage form of the invention", "the current invention" and embodiments of the invention in the embodiments, claims and specifications refer to pharmaceutical compositions, dosage forms, methods, processes and other innovations that comprise (i) one or more abusable drugs, in unsalified form or their pharmaceutically acceptable salts, prodrugs, esters, analogs, derivatives, solvates, complexes, polymorphs, hydrates and metabolites, as racemates or an individual diastereoisomers or enantiomeric isomers thereof or mixtures thereof; (ii) two or more compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof, said compounds also referred to as ADER; and optionally [(iii) and/or (iv)], (iii) other abusable or non-abusable drugs for the treatment of the same or a different medical condition; and/or (iv) pharmaceutical excipients, adjuvants and auxiliary agents including binders, disintegrants, fillers, diluents, anti-adherents or glidants, lubricants, stabilizers, wetting agents, pharmaceutically compatible carriers and dissolution rate modifiers, and channel and pore formers.

In some preferred embodiments, the dosage form may optionally also contain hydrophobic polymers, hydrophilic polymers, gums, protein derived materials, other waxes, shellac, other oils and mixtures thereof.

In some preferred embodiments, the invention is directed at an abusable drug dosage form, said dosage form having flotation capabilities to deter surreptitious attempts at intoxication of another subject (e.g., in an alcoholic or non-alcoholic beverage).

In some preferred embodiments, the invention is directed at an abusable drug dosage form, said dosage form having flotation capabilities to deter surreptitious attempts at intoxication of another subject (e.g., in an alcoholic or non-alcoholic beverage), said dosage form staying substantially afloat (i.e., floatable or buoyant) on a liquid surface for at least about 3 minutes. In other preferred embodiments, said dosage form stays substantially afloat for at least about 5 minutes, or at least about 7 minutes, or at least about 10 minutes, or at least about 15 minutes, or at least about 20 minutes, or at least about 25 minutes, or at least about 30 minutes, or at least about 40 minutes, or at least about 50 minutes, or at least about 60 minutes, or at least about 90 minutes, or at least about 120 minutes, or at least about 150 minutes, or at least about 180 minutes, or at least about 210 minutes, or at least about 240 minutes, or at least about 270 minutes, or at least about 300 minutes, or at least about 330 minutes, or at least about 360 minutes, or at least about 400 minutes.

In some preferred embodiments, the invention is directed at an abusable drug dosage form, said dosage form having a non-toxic dye to deter surreptitious attempts at intoxication of another subject (e.g., in an alcoholic or non-alcoholic beverage).

In some preferred embodiments, the invention is directed at an abusable drug dosage form, said dosage form having a non-toxic bittering agent to deter surreptitious attempts at intoxication of another subject (e.g., in an alcoholic or non-alcoholic beverage).

In some preferred embodiments, the invention is directed at an abusable drug dosage form, said dosage form having a non-toxic bittering agent to deter oral or nasal ingestion of the dosage form.

In some preferred embodiments, the in vivo pharmacokinetic parameters of the specifications and claims are derived or determined from first administration. In other preferred embodiments, the in vivo pharmacokinetic parameters are derived or determined from steady state administration.

In some preferred embodiments, the in vivo pharmacokinetic parameters of the specifications and claims are derived or determined under fed conditions. In other preferred embodiments, the in vivo pharmacokinetic parameters are derived or determined under fasted conditions.

In some preferred embodiments, the in vivo pharmacokinetic parameters of the specifications and claims are derived or determined from an individual subject. In other preferred embodiments, the in vivo pharmacokinetic parameters are derived or determined from a population of subjects.

In some preferred embodiments, the in vivo pharmacokinetic parameters of the specifications and claims are derived or determined in subjects having a Body Mass Index (BMI) between 18 and 26 kg/m$^2$, inclusive (BMI=[weight in kg/height in m$^2$]×10,000). In some preferred embodiments, the in vivo pharmacokinetic parameters of the specifications and claims are derived or determined in subjects having a Body Mass Index (BMI)≥38 kg/m$^2$.

Also disclosed are methods for preventing and treating in pain, addiction disorders, musculoskeletal disorders, neurologic disorders, and other medical maladies responsive to treatment with the abusable drugs in a human patient suffering from same, comprising a therapeutically effective amount of oral abusable drugs or pharmaceutically acceptable salts thereof or mixtures thereof.

All pain states are contemplated by this invention, regardless of etiology, mechanisms, duration, prior treatment response and anatomic location, including acute pain, inflammatory pain, chronic pain, cancer pain, visceral pain and neuropathic pain.

Also disclosed are methods of providing relief in a human patient suffering from neuropathic and chronic pain comprising a therapeutically effective amount of oral abusable drug which possesses analgesic properties or pharmaceutically acceptable salts thereof or mixtures thereof. In some preferred embodiments, the dosage form of the invention is intended for the treatment of neuropathic pain, peripheral neuropathic pain, central neuropathic pain, chronic pain, osteoarthritis, back pain, cancer pain, fibromyalgia, and chronic inflammatory pain.

Also disclosed are methods of providing relief in a human patient suffering from acute pain comprising a therapeutically effective amount of oral abusable drug which possesses analgesic properties or pharmaceutically acceptable salts thereof or mixtures thereof.

All kinds of kits of the present invention are contemplated.

In some preferred embodiments, also provided are kits for use in treating or preventing the pain with the oral administration of an abusable drug or pharmaceutically acceptable salts thereof or mixtures thereof for a subject in need of such treatment, comprising: (i) a dosage form of the invention; (ii) a container for the dosage form; and optionally, any of (iii) to (vi): (iii) a container for individual units of the dosage form (e.g., individual tablets or capsules in blisters); (iv) educational instructions in any media about various medical conditions, including without limitation, pain, neurologic disorders and psychiatric disorders, their etiology, pathophysiology, consequences and treatment, including information on the potential for abuse and diversion and methods for prevention of same and information on the proper use and disposal of the medication; (v) containers or bags for the safe disposal of any used or remaining unused dosage form, preferably child proof and flushable; (vi) tamper evident and child proof packaging for the kit and its contents.

The amount of abusable drug in the oral dosage form will vary depending on variety of physiologic, pharmacologic, pharmacokinetic, pharmaceutical and physicochemical factors, including: (i) the choice of abusable drug as the unsalified form, pharmaceutically acceptable salt or mixtures therof; (ii) the nature of the oral dosage form (e.g, immediate release or extended release); (iii) the intensity and intractability of the medical condition; (iv) the absorption, metabolism, distribution and excretion of orally administered abusable drug in healthy subjects and in patients with various diseases and disorders, including renal and hepatic impairment; (v) the presence of comorbid pathology; (vi) the patient's risk of iatrogenic side effects; (vii) the tolerability of the dose, including the patient's propensity for abusable drug associated side effects; (viii) use of other drugs to treat the same medical condition; (ix) the efficiency of the dosage form; (x) the physicochemical properties of the abusable drug, including its solubility and hydrophilicity.

The invention is also directed to methods of preparing the dosage forms disclosed herein.

In certain preferred embodiments, the abusable drug in the dosage form is combined with one or more other drugs for the treatment of the same medical condition as the abusable drug or for the treatment of a different medical condition. All modes of co-administration are contemplated, including via an oral, subcutaneous, direct intravenous, slow intravenous infusion, continuous intravenous infusion, intravenous or epidural patient controlled analgesia (PCA and PCEA), intramuscular, intrathecal, epidural, intracisternal, intramuscular, intraperitoneal, transdermal, topical, transmucosal, buccal, sublingual, transmucosal, inhalation, intranasal, epidural, intra-atricular, intranasal, rectal or ocular routes.

The term "first administration" means administration of a dose of the present invention at the initiation of therapy to an individual patient or a patient population.

The term "steady state" means that the amount of the drug reaching the system is approximately the same as the amount of the drug leaving the system. Thus, at "steady-state", the patient's body eliminates the drug at approximately the same rate that the drug becomes available to the patient's system through absorption into the blood stream.

As used herein the terms: (i) "AUC$_{0-t}$" means area under the plasma drug concentration-time curve from time zero to the "t", where t is the time point of the maximum intended dosing frequency of the dosage form (e.g., 4 hours, 6 hours, 8 hours, 12 hours or 24 hours for dosage forms intended to be administered every 4 hours, every 6 hours, every 8 hours, every 12 hours and every 24 hours, respectively, thereby providing an $AUC_{0-t}$ time interval of 0 to 4 hours, 0 to 6 hours, 0 to 8 hours, 0 to 12 hours and 0 to 24 hours, respectively); (ii) "$AUC_{0-\infty}$" means area under the plasma drug concentration-time curve from time zero to infinity; (iii) "$AUC_{0-8}$" means area under the plasma drug concentration-time curve from time zero to 8 hours after dosing; (iv) "$AUC_{0-12}$" means area under the plasma drug concentration-time curve from time zero to 12 hours after dosing; (v) "$AUC_{0-24}$" means area under the plasma drug concentration-time curve from time zero to 24 hours after dosing; (vi) "$C_{max}$" means the maximum observed plasma drug concentration; (vii) "$C_8$" means the plasma drug concentration at 8 hours after dosing; (viii) "$C_{12}$" means the plasma drug concentration at 12 hours after dosing; (ix) "$C_{24}$" means the plasma drug concentration at 24 hours after dosing; (x) "$t_{max}$" or "$T_{max}$" means the time of the observed maximum drug concentration (also known as the time at which $C_{max}$ occurs); (xi) "$C_{min}$" means the minimum observed drug concentration following the maximum plasma concentration or the concentration at the end of the intended dosing interval; (xii) "time at which $C_{min}$ occurs" means the time at when the minimum observed drug concentration occurs; (xiii) "half value duration" or "HVD" means the duration over the dosing interval during which plasma concentration of drug are greater than or equal to one-half of $C_{max}$, obtained by calculating the time interval beginning when the interpolated concentration first equals or exceeds one-half of $C_{max}$ and ending at the first time point for which the interpolated concentration falls below one-half of $C_{max}$; (xiv) "$W_{50}$" means the duration of the dosing interval over which the plasma concentrations are equal to or greater than 50% of the peak concentration; (xv) "steady state" is a state of equilibrium wherein the amount of the drug reaching the system is approximately the same as the amount of the drug leaving the system or put another way, the patient's body eliminates the drug at approximately the same rate that the drug becomes available to the patient's system through absorption into the blood stream, said "time to steady state" measured by calculating the $C_{min}$ after each sequential dosing of drug administered at the intended dosing frequency until two consecutive $C_{min}$'s are not statistically different at a 10% significance level (p=0.10); (xvi) "percent fluctuation" means the variation in plasma concentrations of the drug computed as: (a) $(C_{max}-C_{min})/C_{min} \times 100$ (for an individual patient) and (mean $C_{max}$-mean $C_{min}$)/mean $C_{min} \times 100$ (for a population); or (b) $(C_{max}-C_{min})/C_{av} \times 100$ (for an individual patient) and (mean $C_{max}$-mean $C_{min}$)/mean $C_{av} \times 100$ (for a population); (xvii) "accumulation index" or "AI" means the ratio of the plasma concentration of the drug at the end of the intended dosing interval (i.e., 8 hours for a Q8H dosage form, 12 hours for a Q12H dosage form, and 24 hours for a Q24H dosage form) after administration, determined at steady-state ($C_{ssmin}$) to the plasma concentration of the drug at the end of the intended dosing interval determined at first administration (i.e., after the first dose).

Pharmacokinetic parameters of the invention are be computed from first administration and steady state pharmacokinetic studies conducted in an individual subject or in a population of subjects in the fasted or fed states. The AI and percent of steady state computations requires both single dose (i.e., first administration) and steady state pharmacokinetic assessment.

In certain preferred embodiments of the present invention, an effective amount of abusable drug in immediate release form is included in the controlled release unit dose abusable drug formulation to be administered. The immediate release form of the abusable drug is preferably included in an amount which is effective to shorten the time to $C_{max}$ or increase the magnitude of the $C_{max}$ of the abusable drug in the blood (e.g., plasma). In such embodiments, an effective amount of the abusable drug in immediate release form may be coated onto the substrates of the present invention. For example, where the extended release abusable drug from the formulation is due to a controlled release coating, the immediate release layer would be overcoated on top of the controlled release coating. On the other hand, the immediate release layer may be coated onto the surface of substrates wherein the abusable drug is incorporated in a controlled release matrix. Where a plurality of the sustained release substrates comprising an effective unit dose of the abusable drug are incorporated into a hard gelatin capsule, the immediate release portion of the abusable drug dose may be incorporated into the gelatin capsule via inclusion of the sufficient amount of immediate release abusable drug as a powder or granulate within the capsule. Alternatively, the gelatin capsule itself may be coated with an immediate release layer of the abusable drug. In some other embodiments, the immediate release abusable drug is in liquid form, for example as a capsule within a capsule or as a liquid in contact with an extended release dosage form within a capsule. One skilled in the art would recognize still other alternative manners of incorporating the immediate release abusable drug into the unit dose. Such alternatives are deemed to be encompassed by the appended claims. By including such an effective amount of immediate release abusable drug in the unit dose, they may experience of relatively higher levels of symptom relief or faster symptom relief.

In certain preferred embodiments, any one or all of the above in-vivo parameters are achieved after a first administration (often referred to as "single dose administration") of the dosage form to a human patient or a population of human patients.

In certain alternative embodiments, any one or all of the above in-vivo parameters are achieved after steady state administration of the dosage form to a human patient or a population of human patients.

Perceptible Pain Relief, Confirmed Perceptible Pain Relief and Meaningful Pain Relief are assessed and defined as follows: At the time of dosing with the study medication, a trained member of study staff starts two stopwatches for each patient. The patient is instructed to stop the first stopwatch at the time of perceptible pain relief and the second stopwatch at the time when they first experience meaningful pain relief. The usual definitions of the perceptible and meaningful pain relief are as follows: Perceptible Pain Relief is when the patient begins to feel any pain relieving effect from the drug. The patient is typically instructed as follows: "I would like you to stop the first stopwatch when you first feel any pain relief whatsoever. This does not mean you feel completely better, although you might, but when you first feel any difference in the pain that you have had". Meaningful Pain Relief is when the patient feels their pain relief is meaningful to them. The patient is typically instructed as follows: "I would like you to stop the second stopwatch when you have meaningful pain relief. That is, when the relief from the pain is meaningful to you". Confirmed Perceptible Pain Relief is Perceptible Pain Relief in those patients who go on to also have Meaningful Pain Relief.

As used herein, "NNT" or "the number needed to treat" is the number of patients who need to be treated in order for one patient to obtain ≥50% reduction in signs or symptoms (e.g., ≥50% reduction in pain intensity score).

The "NNH" or "number needed to harm" is a measure that indicates how many patients would require a specific treatment to cause harm in one patient. As used herein, the "NNH or "number needed to harm" is a measure that includes: (i) how many abusable drug naïve healthy subjects would require treatment to cause moderate or severe sedation (or drowsiness) in one subject, where moderate to severe sedation or drowsiness is defined as a VAS score of ≥50 mm on a 100 mm scale bounded on the left by "no sedation or drowsiness" and on the right by "extreme sedation or drowsiness"; (ii) how many abusable drug naïve healthy subjects would require treatment to cause moderate or severe nausea in one subject, where moderate to severe nausea is defined as a VAS score of ≥50 mm on a 100 mm scale bounded on the left by "no nausea" and on the right by "extreme nausea"; (iii) how many abusable drug naïve healthy subjects would require treatment to cause dizziness in one subject, where dizziness is defined as unsteadiness, imbalance, lightheadedness, spinning sensation or sensation that one is falling; (iv) how many abusable drug naïve healthy subjects would require treatment to cause a sensation of dry mouth in one subject, where dry mouth is defined as abnormal dryness of the mouth associated with decreased secretion of saliva.

The "drug effects" questionnaire assesses the extent to which subjects currently felt a drug effect, on a scale of 1 to 5 (1="I feel no effect from it at all"; 2="I think I feel a mild effect, but I'm not sure"; 3="I feel an effect, but it is not real strong"; 4="I feel a strong effect"; 5="I feel a very strong effect"). This questionnaire can be used to examine the overall drug effects of abusable drugs given intact and upon tampering, preferably in drug abusers and recreational drug users without the medical condition for which the drug is effective.

The "drug liking" questionnaire assesses the extent to which subjects currently like the effects of the drug on a 100-mm VAS, bounded on the left by "0=dislike a lot", bounded on the right by "100=like a lot". This questionnaire can be used to examine the overall drug liking of abusable drugs given intact and upon tampering, preferably in drug abusers and recreational drug users without the medical condition for which the drug is effective.

The "take again" questionnaire assesses whether subjects would take the abusable drug again if given the opportunity. The patient is asked "If given an opportunity, would you take this drug again? (circle one: YES or NO). This questionnaire can be used to examine the overall desirability of the drug experience with the abusable drugs taken intact and taken after tampering, preferably in drug abusers and recreational drug users without the medical condition for which the drug is effective.

On the "coasting" questionnaire the patient is asked to put a mark on a horizontal line that best describes their response to the question: "Do you feel like you are coasting or spaced out? The horizontal line is a visual analog scale (VAS) bounded on the left by "not at all" and on the right by "extremely". This questionnaire can be used to examine the degree to which subjects feel like they are coasting or spaced out with the abusable drugs taken intact and taken after tampering, preferably in drug abusers and recreational drug users without the medical condition for which the drug is effective.

Three performance tasks may be employed for measuring skills related to driving.

The "critical tracking task" measures the patient's ability to control a displayed error signal in a first-order compensatory tracking task. The error is displayed as a horizontal deviation of a cursor from the midpoint on a horizontal, linear scale. Compensatory joystick movements correct the error by returning the cursor to the midpoint. The frequency at which the patient loses the control is the critical frequency. The critical tracking task measures the psychomotor control during a closed loop operation. It is a laboratory analog to on-the-road tracking performance.

The "stop signal task" measures motor impulsivity, which is defined as the inability to inhibit an activated or pre-cued response leading to errors of commission. The task requires patients to make quick key responses to visual go signals, i.e. the letters ABCD presented one at a time in the middle of the screen, and to inhibit any response when a visual stop signal, i.e. "*" in one of the four corners of the screen, is presented at predefined delays. The main dependent variable is the stop reaction time on stop signal trials that represents the estimated mean time required to inhibit a response.

The Tower of London (TOL) is a decision-making task that measures executive function and planning. The task consists of computer generated images of begin- and end-arrangements of three colored balls on three sticks. The subject's task is to determine as quickly as possible, whether the end-arrangement can be accomplished by "moving" the balls in two to five steps from the beginning arrangement by pushing the corresponding number coded button. The total number of correct decisions is the main performance measure.

For the purposes of in vivo testing, unless specified otherwise, pain intensity is measured on a VAS or categorical scale. On the categorical scale, the patient is asked "My pain at this time is: None=0, Mild=1, Moderate=2, Severe=3. On the VAS, the patient is asked "My pain at this time is" (with VAS anchors: "No Pain" and "Extreme Pain").

For the purposes of in vivo testing, unless specified otherwise, pain relief is measured on a categorical scale. The patient is asked "My relief from starting pain is: None=0, A little=1, Some=2, A lot=3, Complete=4.

In certain preferred embodiments, the amount of abusable drug in the dosage form is about 0.01 µg to 1500 mg. In other more preferred embodiments, the amount of abusable drug in the dosage form is about 0.1 µg to 1000 mg or about 0.1 µg to 1500 mg. In most preferred embodiments, the amount of abusable drug in the dosage form is about 0.01 µg to 750 mg, or about 0.01 µg to about 500 mg, or about 0.01 µg to about 250 mg, or about 0.1 µg to about 500 mg, or 0.1 µg to about 250 mg, or about 0.1 µg to about 250 mg, or about 1 µg to about 1500 mg, or 1 µg to about 1000 mg, or about 1 µg to about 100 mg, or about 5 µg to about 1500 mg, or about 5 µg to about 1000 mg, or about 5 µg to about 500 mg, or about 10 µg to about 1000 mg, or about 10 µg to about 500 mg, or about 100 µg to about 1000 mg, or about 1 mg to about 1500 mg, or about 1 mg to about 1000 mg, or about 1 mg µg to about 800 mg, or about 1 mg to about 500 mg.

In certain embodiments, the amount of ADER in the claimed composition may be about 1 mg to 1500 mg. In a preferred embodiment, the amount of ADER in the claimed composition may be about 10 mg to 800 mg. In a most preferred embodiment, the amount of ADER in the claimed composition may be about 50 mg to 600 mg.

In certain preferred embodiments of the present invention, the ratio of the abusable drug and the ADER is about 1:10,000 to about 10,000:1 by weight, preferably about 1:1000 to about 1000:1 by weight, more preferably 1:250 to 250:1.

The term "USP Basket and Paddle Methods" is the Basket and Paddle Method described, e.g., in specified in the United States Pharmacopeia, USP-28 NF-23 (2005), published by the United States Pharmacopeial Convention, Inc, and herein incorporated by reference.

The term "pH-dependent" for purposes of the present invention is defined as having characteristics (e.g., dissolution) which vary according to environmental pH.

The term "pH-independent" for purposes of the present invention is defined as having characteristics (e.g., dissolution) which are substantially unaffected by pH.

The term "bioavailability" is defined for purposes of the present invention as the rate and extent to which the drug (e.g., the abusable drug) is absorbed from the unit dosage forms.

As used herein with respect to the abusable drug dosage forms of the invention, the term "oral", "oral dosage form", "oral pharmaceutical dosage form", "oral administration", and "oral route", refer to any method of administration involving contact with the mouth and oral mucosa, including the ingestion of intact drugs (e.g., capsules, tablets, liquids swallowed whole), lingual, sublingual administration, buccal administration and transmucosal administration. Particularly preferred embodiments involve oral ingestion of intact drugs (e.g., capsules, tablets, liquids swallowed whole).

All oral pharmaceutical dosage forms of the invention are contemplated, including oral suspensions, tablets, capsules, lozenges, effervescent tablets, effervescent powders, powders, solutions, powders for reconstitution, transmucosal films, buccal products, oral mucoretentive products, oral gastroretentive tablets and capsules, orally disintegrating tablets, fast dissolving tablets, fast dispersing tablets, fast disintegrating dosage forms, administered as immediate release, delayed release, modified release, enteric coated, sustained release, controlled release, pulsatile release and extended release dosage form.

As used herein, "controlled release" is interchangeable with "extended release", "sustained release", "modified release", "delayed release" and the like. Such products provide a longer duration of action than conventional immediate release formulations of the same drugs and are usually administered every 8, 12 or 24 hours.

Controlled release dosage forms of the present invention release abusable drug from the oral dosage form at slower rate than immediate release formulations. In some preferred embodiments, controlled release dosage forms release abusable drug at such a rate that blood (e.g., plasma) concentrations (levels) or therapeutic effects are maintained within the therapeutic range (above the minimum effective therapeutic concentration) but below toxic levels for intended duration (e.g., over a period of 1 to 24 hours, preferably over a period of time indicative of Q4, Q6, Q8, Q12 or Q24H administration). Notwithstanding the foregoing, in some preferred embodiments, the controlled release formulations of the present invention provide therapeutic effects for a duration that is longer or substantially longer than the duration of meaningful or detectable plasma concentrations of abusable drug. Controlled release dosage forms may be administered around the clock on a scheduled or time contingent basis, or on an as needed or PRN basis, e.g., Q3 PRN, Q4 PRN, Q6 PRN, Q8 PRN, Q12 PRN or Q24H PRN administration.

The term "immediate release abusable drug" for purposes of the present invention is abusable drug for oral administration in a dosage form which formulated to release the active drug from the dosage form immediately (i.e., without an attempt to delay or prolong the release of the active drug from the dosage form as is the case for extended release dosage forms). In the absence of a commercially available oral immediate release abusable drug product, an available parenteral formulation of abusable drug or a salt thereof may be used orally or a solution of abusable drug or a salt thereof may be prepared for the purpose of in vivo testing requiring immediate release abusable drug.

For purposes of the invention, the controlled release formulations disclosed herein and the immediate release control formulations are dose proportional. In such formulations, the pharmacokinetic parameters (e.g., AUC and $C_{max}$) increase linearly from one dosage strength to another. Therefore the pharmacokinetic parameters of a particular dose can be inferred from the parameters of a different dose of the same formulation.

The phrase "cardinal sign or symptom" and "cardinal sign or symptom of said medical condition" when referring to the use of the abusable drug of the present invention means the major sign or symptom of the medical condition for which the abusable drug is approved or commonly used, said sign or symptom commonly used as the primary endpoint in clinical trials published in peer-review journals and for approval of the drug by the U.S. FDA and other major drug regulatory authorities (e.g., the EMEA).

The term "agonist" means a ligand that binds to a receptor and alters the receptor state resulting in a biological response. Conventional agonists increase receptor activity, whereas inverse agonists reduce it (See Neubig et al, IUPHAR Committee on Receptor Nomenclature and Classification, Pharmacol Rev, 2003; Howlett et al., Mol Pharmacol, 1988).

The term "opioid agonist" means a molecule that causes a specific physiologic, pathophysiologic or pharmacologic effect after binding to an opioid receptor.

An "antagonist" is a drug or ligand that reduces the action of another drug or ligand, generally an agonist. Many antagonists act at the same receptor macromolecule as the agonist. (See Neubig et al, IUPHAR Committee on Receptor Nomenclature and Classification, Pharmacol Rev, 2003; Howlett et al., Mol Pharmacol, 1988).

The term "receptor" means a molecule within a cell, on a cell surface, on a membrane, in tissue, in fluid or otherwise found in humans that serve as a recognition or binding site to cause specific physiologic, pathophysiologic or pharmacologic effects. The term "receptor" also means a cellular macromolecule, or an assembly of macromolecules, that is concerned directly and specifically in chemical signaling between and within cells. Combination of a hormone, neurotransmitter, drug, ligand, or intracellular messenger with its receptor(s) initiates a change in cell function (Neubig et al, IUPHAR Committee on Receptor Nomenclature and Classification, Pharmacol Rev, 2003).

The term "abuse", "drug abuse", "opioid abuse", "opioid agonist abuse", "narcotic abuse", in the context of the present invention includes intermittent use, recreational use and chronic use of abusable drugs alone or in conjunction with other drugs: (i) in quantities or by methods and routes of administration that do not conform to standard medical practice; (ii) outside the scope of specific instructions for use provided by a qualified medical professional; (iii) outside the supervision of a qualified medical professional; (iv) outside the approved instructions on proper use provided by the drug's legal manufacturer; (v) which is not in specifically approved dosage forms for medical use as pharmaceutical agents; (vi) where there is an intense desire for and efforts to procure same; (vii) with evidence of compulsive use; (viii) through acquisition by manipulation of the medical system, including falsification of medical history, symptom intensity, disease severity, patient identity, doctor shopping, prescription forgeries; (ix) where there is impaired control over use; (x) despite harm; (xi) by procurement from non-medical sources; (xii) by others through sale or diversion by the individual into the non-medical supply chain; (xiii) for medically unapproved or unintended mood altering purposes.

As used herein, "abusable drugs", "abusable drug", "abusable pharmaceuticals", "abusable substances" and "abusable dosage forms" are: (i) opioid agonists for the prevention or treatment of diseases and disorders amenable to prevention or treatment with opioids.

In some preferred embodiments, abusable drugs of the invention may be in unsalified form as racemates or an individual diastereoisomers or enantiomeric isomers thereof or mixture thereof. In other preferred embodiment, abusable drugs of the invention may be pharmaceutically acceptable salts, prodrugs, esters, analogs, derivatives, solvates, complexes, polymorphs, hydrates and metabolites, as racemates or an individual diastereoisomers or enantiomeric isomers thereof or mixture thereof. In particularly preferred embodiment, abusable drugs of the invention may be in unsalified form, pharmaceutically acceptable salts, prodrugs, esters or with a covalently bound pharmaceutically active moiety or mixtures thereof, as racemates or an individual diastereoisomers or enantiomeric isomers thereof or mixture thereof.

The term "opioid receptor" includes mu ($\mu$), delta ($\delta$), kappa ($\kappa$) and/or nociceptin/orphanin FQ (N/OFQ) peptide (NOP) receptors, their subtypes and splice variants such as $\mu_1$, $\mu_2$, $\delta_1$, $\delta_2$, $\kappa_1$, $\kappa_2$ and $\kappa_3$, etc, regardless of whether they also bind to or influence other receptor systems (e.g., norepinephrine reuptake inhibition, serotonin reuptake inhibition, NMDA receptor antagonism).

For the purposes of this invention, the term "opioid" is interchangeable with the term "opioid agonist", except when there is a specific reference to an opioid antagonist.

For the purposes of the present invention and not withstanding anything to the contrary, the phrase "abusable drugs" in relation to the imparting the claimed properties of the invention are limited to one or more "opioid agonists" or "opioid receptor agonists", as further defined herein.

Opioid agonists include alfentanil, allylprodine, alphaprodine, anileridine, apomorphine, apocodeine, benzylmorphine, bezitramide, brifentanil, buprenorphine, butorphanol, carfentanil, clonitazene, codeine, cyclorphen, cyprenorphine, desomorphine, dextromoramide, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, mirfentanil, morphine, morphine-6-glucuronide, myrophine, nalbuphine, narceine, nicomorphine, norlevorphanol, normethadone, nalorphine, nociceptin/orphanin FQ (N/OFQ), normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, propheptazine, promedol, profadol, properidine, propiram, propoxyphene, remifentanil, sufentanil, tapentadol, tramadol, trefentanil, tilidine, nalbuphine, or any opioid having agonist activity at an opioid receptor belonging to the phenanthrene, morphinan, benzomorphan, methadone, phenylpiperidine, propionanilide 4-anilidopiperidine, 4-aryl piperidines, and 4-Heteroarylpiperidines class, any opioid having agonist activity at an opioid receptor having the same pentacyclic nucleus as nalmefene, naltrexone, buprenorphine, levorphanol, meptazinol, pentazocine and dezocine, any drug having agonist activity at an opioid receptor which is a fentanyl analog, or their pharmaceutically acceptable salts, prodrugs, esters, analogs, derivatives, solvates, complexes, polymorphs, hydrates and metabolites, as racemates or an individual diastereoisomers or enantiomeric isomers thereof or mixtures thereof. Opioid agonists also include drugs that bind to opioid receptors to exert agonist activity and are listed in the United States Controlled Substances Act of 1970, as amended, and regulations thereof, and drugs listed in the United States Psychotropic Substances Act of 1978, as amended, and regulations thereof.

In a preferred embodiment, the opioid agonist of the invention is selected from a group consisting of alfentanil, anileridine, buprenorphine, brifentanil, butorphanol, carfentanil, codeine, dextromoramide, dezocine, dihydrocodeine, dihydromorphine, fentanyl, heroin, hydrocodone, hydromorphone, hydroxypethidine, isomethadone, ketobemidone, levorphanol, levomethadone, lofentanil, meperidine, meptazinol, metazocine, methadone, 4-methoxymethylfentanyl, 3-methylfentanil, metopon, mirfentanil, morphine, morphine-6-glucuronide, nalbuphine, norlevorphanol, normethadone, ohmefentanyl, opium, oxycodone, oxymorphone, pentazocine, phenazocine, propiram, propoxyphene, remifentanil, sufentanil, tapentadol, trefentanil, tramadol, tilidine, any opioid having agonist activity at an opioid receptor belonging to the phenanthrene, morphinan, benzomorphan, methadone, phenylpiperidine, propionanilide 4-anilidopiperidine, 4-aryl piperidines, and 4-Heteroarylpiperidines class, any opioid having agonist activity at an opioid receptor having the same pentacyclic nucleus as nalmefene, naltrexone, buprenorphine, levorphanol, meptazinol, pentazocine and dezocine, any opioid having agonist activity at an opioid receptor which is a fentanyl analog, or their pharmaceutically acceptable salts, prodrugs, esters, analogs, derivatives, solvates, complexes, polymorphs, hydrates and metabolites, as racemates or an individual diastereoisomers or enantiomeric isomers thereof or mixtures thereof.

Opioid antagonists are known or readily determined by individuals who practice the art. Preferably, the opioid antagonists useful for the present invention may be selected from the group consisting of naltrexone, methylnaltrexone, naloxone, nalmefene, cyclazocine, cyclorphan, oxilorphan nalorphine, nalorphine dinicotinate, nalmefene, nadide and levallorphan.

The present invention anticipates the use of more than one abusable drug in some embodiments, given in the same formulation or in a different formulation, for use to treat, prevent or ameliorate the same disease or a different disease.

In certain preferred embodiments of the present invention, the invention allows for the use of lower doses of abusable drug by virtue of the inclusion or co-administration of an additional drug for the prevention or treatment of the same medical condition. By using lower amounts of either or both drugs, the side effects associated with treatment in humans are reduced.

The term "abusable drug" means an the abusable drug in unsalified form, a pharmaceutically acceptable salt, prodrugs, esters, analogs, derivatives, solvates, complexes, polymorphs, hydrates and metabolites, as racemates or an individual diastereoisomers or enantiomeric isomers thereof or mixture thereof.

The singular forms "a", "an" and "the" include plural referents unless the context clearly dictates otherwise. Thus, for example, reference to "ADER" includes an ADER compound as well as a mixture of two or more different ADER compounds, reference to "opioid agonists" includes an opioid agonist as well as two or more different opioid agonists in combination, and the like.

As used herein, the term "analgesic" includes pharmacologic agents intended for or effective in the prevention and/or treatment of pain.

In some embodiments, in addition to preventing or treating pain, analgesics provide salutary effects on signs and symptoms associated with pain. For example, analgesics, in addition to relieving pain in patients with osteoarthritis, relieve stiffness, improve physical function, sleep and quality of life. For example, analgesics, in addition to relieving pain in patients with neuropathic pain, reduce disability.

As used herein, the term "pain" includes: (i) peripheral neuropathic pain, e.g., acute and chronic inflammatory demeyelinating polyradiculopathy, alcoholic polyneuropathy, chemotherapy-induced polyneuropathy, complex regional pain syndrome (CRPS) Type I and Type II, entrapment neuropathies (e.g., carpal tunnel syndrome), HIV sensory neuropathy, iatrogenic neuralgias (e.g., postthoracotomy pain, postmastectomy pain), idiopathic sensory neuropathy, painful diabetic neuropathy, phantom limb pain, postherpetic neuralgia, trigeminal neuralgia, radiculopathy (e.g., cervical thoracic, lumbosacral), sciatica, acute herpes zoster pain, temporomandibular joint disorder pain and postradiation plexopathy; and (ii) central neuropathic pain, e.g., compressive myelopathy from spinal stenosis, HIV myelopathy, multiple sclerosis pain, Parkinson's disease pain, postischemic myelopathy, post postradiation myelopathy, poststroke pain, posttraumatic spinal cord injury and syringomyelia; and (iii) cancer associated neuropathic pain, e.g., chemotherapy induced polyneuropathy, neuropathy secondary to tumor infiltration or nerve compression, phantom breast pain, postmastectomy pain, postradiation plexopathy and myelopathy; (iv) chronic pain, e.g., back pain, rheumatoid arthritis, osteoarthritis, inflammatory pain, non-inflammatory pain, myofascial pain, fibromyalgia, cancer pain, visceral pain, somatic pain, pelvic pain, musculoskeletal pain, post-traumatic pain, bone pain and idiopathic pain; (v) acute pain, e.g, acute postsurgical pain (including laparoscopic, laparatomy, gynecologic, urologic, cardiothoracic, arthroscopic, gastrointestinal, neurologic, orthopedic, oncologic, maxillofacial, ophthalmic, otolaryngologic, soft tissue, plastic, cosmetic, vascular and podiatric surgery, including abdominal surgery, abdominoplasty, adenoidectomy, amputation, angioplasty, appendectomy, arthrodesis, arthroplasty, arthroscopy, bilateral cingulotomy, biopsy, brain surgery, breast biopsy, cauterization, cesarean section, cholecystectomy, circumcision, commissurotomy, cordotomy, corneal transplantation, cricothoracotomy, discectomy, diverticulectomy, episiotomy, endarterectomy, endoscopic thoracic sympathectomy, foreskin restoration, fistulotomy, frenectomy, frontalis lift, fundectomy, gastrectomy, grafting, heart transplantation, hemicorporectomy, hemorrhoidectomy, hepatectomy, hernia repair, hypnosurgery, hysterectomy, kidney transplantation, laminectomy, laparoscopy, laparotomy, laryngectomy, lithotripsy, lobotomy, lumpectomy, lung transplantation, mammectomy, mammoplasty, mastectomy, mastoidectomy, mentoplasty, myotomy, mryingotomy, nephrectomy, nissen fundoplication, oophorectomy, orchidectomy, parathyroidectomy, penectomy, phalloplasty, pneumotomy, pneumonectomy, prostatectomy, psychosurgery, radiosurgery, ritidoplasty, rotationplasty, sigmoidostomy, sphincterotomy, splenectomy, stapedectomy, thoracotomy, thrombectomy, thymectomy, thyroidectomy, tonsillectomy, tracheotomy, tracheostomy, tubal ligation, ulnar collateral ligament reconstruction, ureterosigmoidostomy, vaginectomy, vasectomy, vulvectomy; renal colic; incisional pain; inflammatory incisional pain; nociceptive incisional pain; acute neuropathic incisional pain following surgery), renal colic, trauma, acute back pain, burn pain, burn dressing change pain, migraine pain, tension headache pain, acute musculoskeletal pain, acute exacerbation or flare of chronic back pain, acute exacerbation or flare of osteoarthritis, acute exacerbation or flare of chronic pain, breakthrough chronic non-cancer pain, breakthrough cancer pain, acute exacerbation or flare of fibromylagia, acute exacerbation or flare of rheumatoid arthritis, acute exacerbation or flare of myofacsial pain, acute exacerbation or flare of chronic idiopathic pain, acute exacerbation or flare of neuropathic pain, procedure related pain (e.g., arthroscopy, laparoscopy, endoscopy, intubation, bone marrow biopsy, soft tissue biopsy, catheterization), and other self-limiting pain states.

As used herein, the term "acute pain" refers to self-limiting pain that subsides over time and usually lasting less that about 30 days and more preferably lasting less than about 21 days. Acute pain does not include chronic conditions such as chronic neuropathy, chronic neuropathic pain and chronic cancer and non-cancer pain.

As used herein, "neuropathic pain" is pain initiated or caused by a primary lesion or dysfunction of the nervous system and includes (i) peripheral neuropathic pain and (ii) central neuropathic pain.

As used herein, the term "chronic pain" includes all non-neuropathic pain lasting more than 30 days, including inflammatory pain, non-inflammatory pain, muscle pain, joint pain, fascia pain, visceral pain, bone pain and idiopathic pain.

As used herein, "neurologic disorders" are disorders that affect the central nervous system (brain and spinal cord), the peripheral nervous system (peripheral nerves-cranial nerves included), or the autonomic nervous system (parts of which are located in both central and peripheral nervous system). See Adams & Victor's Principles of Neurology (McGraw-Hill Professional; 7 edition, 2000); Merritt's *Textbook of Neurology* (9th ed. Edited by Lewis P. Rowland. Baltimore: Williams and Wilkins, 1995); and *Guide to Clinical Neurology* (Mohr and Gautier, eds, New York, Churchill Livingstone, 1995).

The term "psychiatric disorders" and "mental illness" are used interchangeably. A mental illness is an abnormal mental condition or disorder expressing symptoms that cause significant distress and/or dysfunction. This can involve cognitive, emotional, behavioral and interpersonal impairments. As used herein, psychiatric disorders are disorders described in the Diagnostic and Statistical Manual of Mental Disorders (DSM), 1994, as revised in 2000 (DSM-IV-TR).

The term "analgesic effectiveness" is defined for purposes of the present invention as a satisfactory prevention, reduction in or elimination of pain, along with a tolerable level of side effects, as determined by the human patient.

"Therapeutically effective amount", "therapeutic effectiveness" or "therapeutically-effective" refers to the amount of an active agent sufficient to induce a desired biological result. That result may be alleviation of the signs, symptoms, or causes of a disease, or any other desired alteration of a biological system.

The term "effective amount" means the quantity of a compound according to the invention necessary to prevent, to cure, or at least partially arrest a sign or symptom for which the compound (e.g., abusable drug) has been prescribed to a subject.

The term "abuse resistant" and "abuse deterrent" are used interchangeably and include pharmaceutical compositions and methods to resist intentional, unintentional or accidental physical, mechanical, chemical or thermal manipulation or tampering of the dosage form (e.g., crushing, shearing, grinding, pulverizing, chewing, dissolving, melting, needle aspiration, syringe aspiration, syringe injection, solvent extraction, inhalation, insufflation, extraction by mechanical, thermal and chemical means, and/or filtration). The term "abuse resistant" and "abuse deterrent" also includes pharmaceutical compositions and methods to resist intentional, unintentional or accidental use or misuse of the dosage form: (i) in quantities or by methods and routes of administration that do not conform to standard medical practice; (ii) outside the scope of specific instructions for use provided by a qualified medical professional; (iii) outside the supervision of a qualified medical professional; (iv) outside the approved instructions on proper use provided by the drug's legal manufacturer; (v) in unapproved dosage forms; (vi) for compulsive use; (vii) through acquisition by manipulation of the medical system; (viii) for medically unapproved or unintended mood altering purposes.

"Drug", "drug substance", "substance", "therapeutic agent", "pharmacological agent", "pharmaceutical agent", and "active agent" are used interchangeably and are intended to have their broadest interpretation as to any therapeutically active substance which is delivered to a living organism to produce a desired, usually beneficial effect. In general, this includes therapeutic agents in all of the major therapeutic areas.

The term "subject" for purposes of treatment is used interchangeably with "patient", "male", "female", and includes any human subject.

As used herein, "bioequivalent" and "bioequivalence" means that the 90% Confidence Interval (CI) of the relative mean $C_{max}$, $AUC_{(0-t)}$ and $AUC_{(0-\infty)}$ of the drug under test and reference conditions (e.g., generic vs. brand name, or fed versus fasted, or with and without concurrent alcohol) is within 80% to 125%, when tested in accordance with U.S. FDA guidelines (see "Guidance for Industry: Bioavailability and Bioequivalence Studies for Orally Administered Drug Products-General Considerations", Department of Health and Human Services, Food and Drug Administration, Center for Drug Evaluation and Research, July 2002 and "Guidance for Industry: Food-Effect Bioavailability and Fed Bioequivalence Studies: Study Design, Data Analysis and Labeling", Department of Health and Human Services, Food and Drug Administration, Center for Drug Evaluation and Research, October, 2001, which are hereby incorporated by reference).

"Pharmaceutically or therapeutically acceptable excipient or carrier" or "excipient" refers to a substance which does not interfere with the effectiveness or the biological activity of the active ingredients and which is not toxic to the subject. In some preferred embodiments of the present invention, pharmaceutically or therapeutically acceptable excipients or carriers may play a role in imparting or optimizing the rate and extent of absorption of the abusable drug or additional drugs in the pharmaceutical composition. In some preferred embodiments of the present invention, pharmaceutically or therapeutically acceptable excipients or carriers may play a role in stabilizing the abusable drug or additional drugs in the pharmaceutical composition.

In certain preferred embodiments of the present invention, the dosage form may include, in addition to abusable drug or a pharmaceutically acceptable salt thereof and ADER, other abuse deterrent or abuse resistant substances, process or technologies known in the art, including one or more aversive agents. All kinds of aversive agents are contemplated, including, without limitation, antagonists of abusable drugs, laxatives, cutaneous vasodilators, headache producing agents, emetics, emetogenic compound, nausea producing compounds, bittering agents, drugs that cause burning on irritation when in contact with tissue or mucous membranes (e.g., naso-mucosal irritants, oro-mucosal irritants, respiratory irritants), tissue irritants, gastrointestinal irritants, drugs that precipitate withdrawal effects, tissue dyes, lakes and colorants, beverage dyes, lakes and colorants, non-tissue staining beverage dyes, lakes and colorants (i.e, that do not stain or discolor the skin upon ingestion), fecal discolorants, urine discolorants, malodorous agents, opioid antagonists, benzodiazepine antagonists (e.g., flumazenil), cannabinoid antagonists and pharmacologic antagonists to co-abused drugs not contained in the dosage form. Such aversive agents may be in the dosage form in a releasable, partially releasable or a non-releasable form (i.e., sequestered), the latter being released on tampering the dosage form (e.g., mechanical, thermal, chemical, solvent tampering, ingestion in ways not recommended, and the like). Further, in some embodiments, such aversive agents may be in the dosage form in an amount that does not produce an aversive effect or aversion in any, many or substantially all patients when taken in accordance with the prescribing information or the manufacturer's instructions (for example, in small quantities), but which produce an aversive effect when taken in excess (e.g., higher dose or more frequently).

In some embodiments, one or more aversive agents may be added to the formulation in an aversive agent amount of less than about 80% by weight, preferably less than about 60% by weight, more preferably less than about 40% by weight of the dosage form, even more preferably less than about 20% by weight of the dosage form, and most preferably less than about 10 by weight of the dosage form (e.g., 0.000000000000001% to 1%, or 0.000000001% to 3%, or 0.0001% to 10%, or 0.001% to 5%, or 1% to 10%, or 0.001% to 2%, or 1% or 10%, or 2% to 7%) depending on the particular aversive agent used.

In some embodiments, the aversive agent in the dosage form may be about 0.00000000001 mg to about 2000 mg, or about 0.0000001 mg to about 1500 mg, or about 0.000001 mg to about 1000 mg, or about 0.0001 mg to about 1000 mg, or about 0.001 mg to about 1000 mg, or about 0.01 mg to about 1000 mg, or about 0.1 mg to about 1500 mg, or 1 mg to about 800 mg, or about 1 mg to about 500 mg, or about 1 mg to about 300 mg, or about 1 mg to about 150 mg, or about 5 mg to about 400 mg, or about 5 mg to about 200 mg, or about 0.00000000001 mg to about 200 mg, or about 0.00000000001 mg to about 100 mg, or about 0.00000000001 mg to about 50 mg, or about 0.0000001 mg to about 200 mg, or about 0.0000001 mg to about 100 mg, or about 0.00001 mg to about 400 mg, or about 0.0001 mg to about 300 mg.

As described above, the present invention can include one or more aversive agents, selected from the group including, without limitation antagonists of abusable drugs, laxatives, cutaneous vasodilators headache producing agents, emetics, emetogenic compound, nausea producing compounds, bittering agents, drugs that cause burning on irritation when in contact with tissue or mucous membranes (e.g., naso-mucosal irritants, oro-mucosal irritants, respiratory irritants), tissue irritants, gastrointestinal irritants, drugs that precipitate withdrawal effects, tissue dyes, lakes and colorants, beverage dyes, lakes and colorants, non-tissue staining beverage dyes, lakes and colorants, fecal discolorants, urine discolorants, malodorous agents, opioid antagonists, benzodiazepine antagonists, cannabinoid antagonists, and pharmacologic antagonists to co-abused drugs not contained in the dosage form. Preferably, the aversive agent is a pharmaceutically acceptable agent that produces an aversive effect only when the dosage form of the invention containing the aversive agent is abused, for example, when taken in excess of medically approved doses, taken in excess of approved doses in the manufacturer's prescribing information, taken after tampering of the dosage form (e.g., mechanical, thermal, chemical, solvent tampering), ingestion in ways not medically recommended, administration by routes not approved for the dosage form (e.g., intranasal, inhalation, intravenous) or in a manner inconsistent with the manufacturer's prescribing information.

In some embodiments, the amount of aversive agent in the dosage form of the present invention can be a fixed ratio in relation to the amount of abusable drug in the dosage form. By appropriately selecting the quantity of the aversive agent in the dosage form, aversive effects can be avoided under conditions of proper medical use (e.g., manufacturers prescribing directions). However, under some conditions of abuse, for example excessive intake of the dosage form of the invention, the quantity of aversive agent consumed will exceed the "no effect" or "minimum effect" threshold, thereby producing one or more aversive effects, for example, e.g., nausea, emesis, diarrhea, laxation, cutaneous vasodilation, headache, bitter taste, naso-mucosal irritation, oro-mucosal irritation, precipitation of abstinence from the abusable drug of the dosage form, precipitation of abstinence from a co-abused drug which is not part of the dosage form, reduction of the pleasurable, mood altering, rewarding, reinforcing, stimulant, depressant or other psychic and physiologic effects of the abusable drug or a co-abused drug, etc.).

In some embodiments, the "no effect" or "minimum effect" threshold amount of aversive agent can be exceeded when the dosage form of the invention is taken in excess of the manufacturer's recommendation by a factor of about 1.5, or about 2, or about 2.5, or about 3, or about 4, or about 5, or about 6, or about 7, or about 8, or about 10, or more than 10. In some embodiments, the production of an aversive effect can reduce or stop further abuse of the dosage form, thereby reducing the harm or toxicity of the drug in the subject who is tampering, misusing or abusing the dosage form, e.g., addicts, drug abusers and recreational drug users.

Various bittering agents can be employed including, for example and without limitation, T2R or TAS2R receptor agonists, phenylthiourea (phenylthiocarbamide), natural, artificial and synthetic flavor oils and flavoring aromatics and/or oils, oleoresins and extracts derived from plants, leaves, flowers, fruits, and so forth, and combinations thereof. Nonlimiting representative flavor oils include spearmint oil, peppermint oil, eucalyptus oil, oil of nutmeg, allspice, mace, oil of bitter almonds, menthol and the like. Also useful bittering agents are artificial, natural and synthetic fruit flavors such as citrus oils including lemon, orange, lime, grapefruit, and fruit essences and so forth. Additional bittering agents include sucrose derivatives (e.g., sucrose octaacetate), chlorosucrose derivatives, quinine and quinine salts, quinidine and quindine salts and the like. The preferred bittering agent for use in the present invention is denatonium, denatonium benzoate and denatonium saccharide. A dosage form including a bittering agent preferably discourages improper usage of the tampered dosage form by imparting a disagreeable taste to the tampered dosage form.

In some embodiments, the aversive agent in the dosage form may be denatonium, denatonium saccharide or denatonium benzoate, in a quantity expressed as mg of denatonium, of about 0.00000001 mg to about 100 mg, or about 0.000001 mg to about 100 mg, or about 0.0001 mg to about 100 mg, or about 0.0001 mg to about 20 mg, or about 0.0001 mg to about 10 mg, or about 0.0001 mg to about 5 mg, or about 0.0001 mg to about 2 mg, or about 0.0001 mg to about 1 mg, about 0.0001 mg to about 50 mg, or about 0.00000001 mg to about 50 mg, or about 0.00000001 mg to about 20 mg, or about 0.01 mg to about 20 mg, or about 0.01 mg to about 10 mg, or about 0.01 mg to about 5 mg, or about 0.01 mg to about 2 mg, or about 0.01 mg to about 1 mg, or about 0.01 mg to about 1 mg, or about 0.01 mg to about 0.5 mg, or about 0.1 mg to about 20 mg, or about 0.1 mg to about 10 mg, or about 0.1 mg to about 7 mg, or about 0.1 mg to about 5 mg, or about 0.1 mg to about 3 mg, or about 0.1 mg to about 2 mg.

In some embodiments, the aversive agent in the dosage form may be quinine or a pharmaceutically acceptable salt of quinine, in a quantity expressed as mg of quinine, of about 0.00001 mg to about 300 mg, or about 0.00001 mg to about 200 mg, or about 0.00001 mg to about 100 mg, or about 0.00001 mg to about 75 mg, or about 0.00001 mg to about 50 mg, or about 0.00001 mg to about 25 mg, or about 0.00001 mg to about 20 mg, or about 0.00001 mg to about 10 mg, or about 0.00001 mg to about 5 mg, or about 0.00001 mg to about 2.5 mg, or about 0.00001 mg to about 1 mg, or about 0.001 mg to about 300 mg, or about 0.001 mg to about 200 mg, or about 0.001 mg to about 100 mg, or about 0.001 mg to about 75 mg, or about 0.001 mg to about 50 mg, or about 0.001 mg to about 25 mg, or about 0.001 mg to about 20 mg, or about 0.001 mg to about 10 mg, or about 0.001 mg to about 5 mg, or about 0.001 mg to about 2.5 mg, or about 0.001 mg to about 1 mg, or about 1 mg to about 300 mg, or about 1 mg to about 200 mg, or about 1 mg to about 100 mg, or about 1 mg to about 75 mg, or about 1 mg to about 50 mg, or about 1 mg to about 25 mg, or about 1 mg to about 20 mg, or about 1 mg to about 10 mg, or about 1 mg to about 5 mg, or about 1 mg to about 2.5 mg.

Various emetic agents can be employed including, for example and without limitation, zinc and pharmaceutically acceptable salts thereof (e.g., zinc oxide, zinc gluconate, zinc acetate, zinc sulfate, zinc carbonate), dopamine agonists, apomorphine, ipecac, ipecacuanha, emetine, emetine (methylcephaeline), cephaeline, psychotrine, O-methylpsychotrine, ammonium chloride, potassium chloride, magnesium sulfate, ferrous gluconate, ferrous sulfate, aloin, algarot or antimonious oxychloride, antimony trichloride, folate, folic acid, niacin (niacin) and nicotinamide.

In some embodiments, the aversive agent in the dosage form may be zinc in the form of elemental zinc or a pharmaceutically acceptable salt of zinc, in a quantity expressed as mg of elemental zinc, of about 1 mg to about 400 mg, or about 1 mg to about 300 mg, or about 1 mg to about 200 mg, or about 1 mg to about 150 mg, or about 1 mg to about 100 mg, or about 1 mg to about 90 mg, or about 1 mg to about 80 mg, or about 1 mg to about 70 mg, or about 1 mg to about 60 mg, or about 1 mg to about 50 mg, or about 1 mg to about 45 mg, or about 1 mg to about 40 mg, or about 1 mg to about 40 mg, or about 1 mg to about 35 mg, or about 1 mg to about 30 mg, or about 1 mg to about 25 mg, or about 1 mg to about 20 mg, or about 1 mg to about 10 mg, or about 1 mg to about 5 mg, or about 5 mg to about 400 mg, or about 5 mg to about 300 mg, or about 5 mg to about 200 mg, or about 5 mg to about 150 mg, or about 5 mg to about 100 mg, or about 10 mg to about 150 mg, or about 10 mg to about 100 mg, or about 5 mg to about 80 mg, or about 5 mg to about 60 mg, or about 5 mg to about 50 mg, or about 5 mg to about 45 mg, or about 5 mg to about 40 mg, or about 5 mg to about 40 mg, or about 5 mg to about 35 mg, or about 5 mg to about 30 mg, or about 5 mg to about 25 mg, or about 5 mg to about 20 mg, or about 5 mg to about 10 mg, or about 10 mg to about 90 mg, or about 10 mg to about 80 mg, or about 10 mg to about 60 mg, or about 10 mg to about 50 mg, or about 10 mg to about 45 mg, or about 10 mg to about 40 mg, or about 10 mg to about 40 mg, or about 10 mg to about 35 mg, or about 10 mg to about 30 mg, or about 10 mg to about 25 mg, or about 10 mg to about 20 mg, or about 20 mg to about 100 mg, or about 20 mg to about 90 mg, or about 20 mg to about 80 mg, or about 20 mg to about 60 mg, or about 20 mg to about 50 mg, or about 20 mg to about 45 mg, or about 20 mg to about 40 mg, or about 20 mg to about 35 mg, or about 20 mg to about 30 mg, or about 15 mg to about 50 mg, or about 15 mg to about 40 mg, or about 15 mg to about 35 mg, or a quantity sufficient to be produce an aversive effect vasodilation when abused but not under conditions of medically appropriate use.

Various irritants can be employed including, for example and without limitation transient receptor potential vanilloid 1 (TRPV1 or VR1) agonists (including resiniferanoids, capsaicinoids, phorboid vanilloids, and terpenoid 1,4-unsaturated dialdehydes, capsaicin, capsaicin analogs and derivatives, resiniferatoxin, olvanil, piperine, zingerone, anandamide, 12- and 15-(S)-hydroperoxy-eicosatetraenoic acids, 5 and 15-(S)-hydroxyeicosatetraenoic acids, phorbol 12-phenylacetate 13-acetate 20-homovanillate, 2 phorbol 12,13-didecanoate 20-homovanillate, leukotriene B(4), tinyatoxin, heptanoyl-isobutylamide, N-(3-acyloxy-2-benzylpropyl)-N'-dihydroxytetrahydrobenzazepine, tetrahydroisoquinoline thiourea analogs, heptanoyl guaiacylamide, other isobutylamides or guaiacylamides, dihydrocapsaicin, homovanillyl octylester and nonanoyl vanillylamide), acids such as acids with one or more carboxyl moieties (e.g., formic acid, acetic acid, propionic acidy, butyric acid, valeric acid, caproic acid, caprillic acid, capric acid, oxalic acid, malonic acid, succicnic acid, glutaric acid, adipic acid, maleic acid, fumaric acid, and citric acid), sodium lauryl sulfate, poloxamer, sorbitan monoesters, glyceryl monooleates, niacin, mustard, allyl isothiocyaanate and p-hydroxybenzyl isothiocyanate, acetylsalicylic acid.

Various cutaneous vasodilators can be employed including, for example and without limitation, niacin acid, nicotinuric acid, beta-hydroxybutyrate and nicotinic receptor (e.g., HM74A or GPR109A) agonists.

In some embodiments, the aversive agent in the dosage form may be niacin, in a quantity of about 1 mg to about 400 mg, or about 1 mg to about 300 mg, or about 1 mg to about 200 mg, or about 1 mg to about 150 mg, or about 1 mg to about 100 mg, or about 1 mg to about 90 mg, or about 1 mg to about 80 mg, or about 1 mg to about 70 mg, or about 1 mg to about 60 mg, or about 1 mg to about 50 mg, or about 1 mg to about 45 mg, or about 1 mg to about 40 mg, or about 1 mg to about 40 mg, or about 1 mg to about 35 mg, or about 1 mg to about 30 mg, or about 1 mg to about 25 mg, or about 1 mg to about 20 mg, or about 1 mg to about 10 mg, or about 1 mg to about 5 mg, or about 5 mg to about 400 mg, or about 5 mg to about 300 mg, or about 5 mg to about 200 mg, or about 5 mg to about 150 mg, or about 5 mg to about 100 mg, or about 10 mg to about 150 mg, or about 10 mg to about 100 mg, or about 5 mg to about 80 mg, or about 5 mg to about 60 mg, or about 5 mg to about 50 mg, or about 5 mg to about 45 mg, or about 5 mg to about 40 mg, or about 5 mg to about 40 mg, or about 5 mg to about 35 mg, or about 5 mg to about 30 mg, or about 5 mg to about 25 mg, or about 5 mg to about 20 mg, or about 5 mg to about 10 mg, or or about 10 mg to about 90 mg, or about 10 mg to about 80 mg, or about 10 mg to about 60 mg, or about 10 mg to about 50 mg, or about 10 mg to about 45 mg, or about 10 mg to about 40 mg, or about 10 mg to about 40 mg, or about 10 mg to about 35 mg, or about 10 mg to about 30 mg, or about 10 mg to about 25 mg, or about 10 mg to about 20 mg, or about 20 mg to about 100 mg, or about 20 mg to about 90 mg, or about 20 mg to about 80 mg, or about 20 mg to about 60 mg, or about 20 mg to about 50 mg, or about 20 mg to about 45 mg, or about 20 mg to about 40 mg, or about 20 mg to about 35 mg, or about 20 mg to about 30 mg, or about 15 mg to about 50 mg, or about 15 mg to about 40 mg, or about 15 mg to about 35 mg, or a quantity sufficient to be produce an aversive effect when abused but not under conditions of medically appropriate use.

Various tissue dyes, lakes and colorants, beverage dyes, lakes and colorants, non-tissue staining beverage dyes, lakes and colorants, fecal discolorants, urine discolorants can be employed including, for example and without limitation, Curcumin, Riboflavin, Tartrazine, Quinoline yellow, Sunset yellow FCF, Carmine, Carmoisine, Amaranth, Ponceau 4R, Erythrosine, Allura red AC, Patent blue V, Indigo carmine, Brilliant blue FCF, Chlorophylls, Copper complexes of chlorophylls and chlorophyllins, Green S, Caramel, Brilliant black BN, Vegetable carbon, Carotenoids, Alpha-, beta-, gamma-carotene, Capsanthin, Capsorubin, Lycopene, Beta-apo-8' carotenal, Ethyl ester of beta-apo-8' carotenoic acid, Xanthophylls, Lutein, Canthaxanthin, Beetroot red, Anthocyanins, Cyanidin, Delphidin, Malvidin, Pelargonidin, Peonidin, Petunidin, Calcium carbonate, Titanium dioxide, Iron oxides and hydroxides, Aluminum, Brilliant blue FCF, Indigotine, Alphazurine FG, Indanthrene blue, Fast green FCF, Alizarin cyanine green F, Quinizarine green SS, Pyranine concentrated, Orange II, Dibromofluorescein, Diiodofluorescein, Erythrosine yellowish Na, Erythrosine, Ponceau SX, Lithol rubin B, Lithol rubin B Ca, Toney red, Tetrabromofluorescein, Eosine, Tetrachlorotetrabromofluorescein, Phloxine B, Helindone pink CN, Brilliant lake red R, Acid fuchsine, Lake bordeaux B, Flaming red, Alba red, Allura red AC, Allura Red AC, Alizurol purple SS, Tartrazine, Sunset yellow, FCF, Fluorescein, Naphthol yellow S, Uranine, Quinoline yellow WS, Quinoline yellow SS, Brilliant blue FCF, Indigotine, Alphazurine FG, Alizurol purple SS, Sunset yellow FCF, Alumina, Aluminum powder, Annatto extract, Beta-carotene, Bismuth oxychloride, Bronze powder, Calcium carbonate, Canthaxanthin, Caramel, Chromium-cobalt-aluminum oxide, Chromium hydroxide green, Chromium oxide green, Cochineal extract, carmine, Copper powder, Dihydroxyacetone, Ferric ammonium citrate, Ferric ammonium ferrocyanide, Ferric ferrocyanide, Guanine, Iron oxides synthetic, Logwood extract, Mica, Potassium sodium copper chlorophyllin, Pyrogallol, Pyrophyllite, Talc, Titanium dioxide, Zinc oxide, FD&C blue #1, FD&C blue #2, D&C blue #4, D&C blue #9, FD&C green #3, D&C green #5, D&C green #6, D&C green #8, D&C orange #4, D&C orange #5, D&C orange #10, D&C orange #11, FD&C red #3, FD&C red #4, D&C red #6, D&C red #7, D&C red #17, D&C red #21, D&C red #22, D&C red #27, D&C red #28, D&C red #30, D&C red #31, D&C red #33, D&C red #34, D&C red #36, D&C red #39, FD&C red #40, FD&C red #40 lake, D&C violet #2, FD&C yellow #5, FD&C yellow #6, D&C yellow #7, Ext. D&C yellow #7, D&C yellow #8, D&C yellow #10, D&C yellow #11, FD&C lakes, D&C lakes, Ext. D&C lakes, FD&C blue #1 lake, FD&C blue #2 lake, D&C blue #4 lake, FD&C green #3 lake, D&C green #5 lake, D&C green #6 lake, D&C orange #4 lake, D&C orange #5 lake, D&C orange #10 lake, D&C orange #11 lake, FD&C red #4 lake, D&C red #6 lake, D&C red #7 lake, D&C red #17 lake, D&C red #21 lake, D&C red #22 lake, D&C red #27 lake, D&C red #28 lake, D&C red #30 lake, D&C red #31 lake, D&C red #33 lake, D&C red #34 lake, D&C red #36 lake, D&C violet #2 lake, FD&C yellow #5 lake, FD&C yellow #6 lake, D&C yellow #7 lake, Ext. D&C yellow #7 lake, D&C yellow #8 lake, D&C yellow #10 lake, Turmeric, Lactoflavin, Cochineal, carminic acid, Indigotine, Magnesium chlorophyll, Brilliant green BS, Black PN, Carbo medicinalis vegetabilis, Paprika oleoresin, Paprika oleoresin, Betanin, Beta-carotene, indigo carmine, iron oxides, sunset yellow FCF, titanium dioxide, E100, E101, E102, E104, E110, E120, E122, E123, E124, E127, E129, E131, E132, E133, E140, E141, E142, E150, E151, E153, E160, E161, E162, E163, E170, E171, E172, E173 and phenazopyridine.

As used herein, "dyes", "lakes", "colorants" and "discolorants" are used interchangeably and refer to one or more pharmaceutically acceptable dyes, lakes or colorants which may be: (i) tissue staining; (ii) non-tissue staining; (iii) beverage staining; (iv) urine discolorant; and/or (v) fecal discolorant.

Various laxatives can be employed including, for example and without limitation, Bis(p-hydroxyphenyl)pyridyl-2-methane, Bisacodyl, bisoxatin, anthraquinone, anthraquinone analogs and derivatives (e.g., buckthorn, casanthranol, cascara, hydroxyanthracene, glucofrangulin), dantron, danthron, docusate (e.g., docusate sodium, docusate calcium, docusate potassium), gastrointestinal chloride channel activators (e.g., chloride channel subtype 2 activators), lubiprostone, magenesium salts (e.g., magnesium citrate, magnesium hydroxide, magnesium oxide), mannitol, oxyphenisatine, polyethylene glycol, poly(ethylene oxide) [PEO-1500], sodium phosphate, phenolphthalein, senna, senna constituents and derivatives (e.g., sennoside A, sennoside B) and sodium picosulfate.

In some embodiments, the aversive agent in the dosage form may be a laxative in the amount of about 0.001 mg to about 300 mg, or about 0.001 mg to about 200 mg, or about 0.001 mg to about 100 mg, or about 0.001 mg to about 75 mg, or about 0.001 mg to about 50 mg, or about 0.001 mg to about 25 mg, or about 0.001 mg to about 20 mg, or about 0.001 mg to about 10 mg, or about 0.001 mg to about 5 mg, or about 0.001 mg to about 2.5 mg, or about 0.001 mg to about 1 mg, or about 1 mg to about 300 mg, or about 1 mg to about 200 mg, or about 1 mg to about 100 mg, or about 1 mg to about 75 mg, or about 1 mg to about 50 mg, or about 1 mg to about 25 mg, or about 1 mg to about 20 mg, or about 1 mg to about 10 mg, or about 1 mg to about 5 mg, or about 1 mg to about 2.5 mg.

Aversive agents may include compounds found on the FDA EAFUS database (http://vm.cfsan.fda.gov/~dms/eafus.html); FDA Food Additives Status List (http://www.cfsan.fda.gov/~dms/opa-appa.html); FDAGRAS list and database; FDA Color Additive Status List (http://www.cfsan.fda.gov/~dms/opa-appc.html); FDA Inactive Ingredients Database (http://www.accessdata.fda.gov/scripts/cder/iig/index.cfm); Rowe, Sheskey and Owen, Handbook of Pharmaceutical Excipients, APhA Publications; 5th edition (2006); Goodman & Gilman's The Pharmacological Basis of Therapeutics (Brunton, Lazo and Parker, eds, 11th ed., McGraw Hill (2005); Remington: The Science and Practice of Pharmacy, 21st ed, Lippincott Williams & Wilkins (2005); Martindale: The Complete Drug Reference, 35th Edition, Pharmaceutical Press (2007); United States Pharmacopeia-National Formulary (USP-NF), (USP 30-NF 25, 2007), the International Programme on Chemical Safety (http://www.inchem.org/) and Health Canada's List of Acceptable Non-medicinal Ingredients (http://www.hc-sc.gc.ca/dhp-mps/prodnatur/legislation/docs/nmi-imn_list1_e.html), all hereby incorporated by reference in their entirety.

It should be noted that the above mentioned aversive agents may, in some embodiments be used in the dosage form of the invention for purposes other than as aversive agents, or for both aversive and non-aversive purposes. Such non-aversive uses can include, without limitation, pharmaceutical purposes and pharmacologic purposes. For example, in some embodiments, the laxative agent may be used to counteract the constipating effects of the abusable dosage form of the invention. In some embodiments, zinc and pharmaceutically acceptable salts of zinc and niacin may be used for pharmaceutical purposes (e.g., pharmaceutical optimization, drug release and drug stability).

In one preferred embodiment of the invention, the dosage form includes both an immediate release and extended release component.

In one preferred embodiment of the invention, the dosage form includes a capsule within a capsule, each capsule containing a different drug or the same drug intended for treating the same or a different medical condition. In some preferred embodiments, the outer capsule may be an enteric coated capsule or a capsule containing an immediate release formulation to provide rapid plasma concentrations or a rapid onset of effect or a loading dose and the inner capsule contains an extended release formulation. In some preferred embodiments, up to 3 capsules within a capsule are contemplated as part of the invention. In one preferred embodiment of the invention, the dosage form involves one or more tablets within a capsule, wherein the abusable drug is either in the tablet and/or in one of the capsules.

In one preferred embodiment of the invention, the formulation is ingested orally as a tablet or capsule, preferably as a capsule. In another preferred embodiment of the invention, the formulation is administered bucally. In yet another preferred embodiment of the invention, the formulation is administered sublingually.

The term "pharmaceutically acceptable salt" as used herein refers to a salt which is toxicologically safe for human and animal administration. Nonlimiting examples of salts include hydrochlorides, hydrobromides, hydroiodides, sulfates, bisulfates, nitrates, citrates, tartrates, bitartrates, phosphates, malates, maleates, napsylates, fumarates, succinates, acetates, terephlhalates, pamoates and pectinates.

In some embodiments, the abusable drug pharmaceutical composition is a salt or complex of inorganic cation salts, organic salts such primary, secondary, tertiary and quaternary amines include substituted amines In some embodiments, examples of suitable pharmaceutically acceptable salts of abusable drugs include any of the inorganic cation salts such as sodium, potassium, lithium, magnesium, calcium, cesium, ammonia, ferrous, zinc, manganous, aluminum, ferric, and manganic; organic salts with primary, secondary, tertiary and quaternary amines, or mixtures thereof. Examples of such primary, secondary, tertiary and quaternary amines include substituted amines including but not limited to naturally occurring substituted amines, cyclic amines, basic ion exchange resins, and mixtures thereof. More specifically, suitable amines include but are not limited to tromethamine, triethylamine, tripropylamine, dropopizine, 2-dimethylaminoethanol, 2-diethylaminoethanol, lysine, arginine, ornithine, histidine, caffeine, procaine, N-ethylpiperidine, hydrabamine, choline, betaine, ethylenediamine, glucosamine, tris-(hydroxymethyl)aminomethane, N-methylglucamine, methylglycamine, theobromine, piperazine, piperidine, polyamine resins and the like, and mixtures thereof.

In some embodiments, examples of suitable pharmaceutically acceptable salts of abusable drugs include aminoalcohols chosen from the group consisting of ethanolamine, 3-amino-1-propanol, (R)-1-amino-2-propanol, (S)-1-amino-2-propanol, 2-amino-1,3-propandiol, N-(2-hydroxyethyl)pyrrolidine, D-glucamine and L-prolinol, D-glucosamine, and N-methylglucosamine.

In some embodiments, examples of suitable pharmaceutically acceptable salts of abusable drugs include alkali and alkaline earth metals and salts of an organic nature, such as the salts of basic amino acids.

It is contemplated that the present invention may be used alone or in combination with other drugs to provide additive, complementary, or synergistic therapeutic effects or for the treatment of entirely different medical conditions.

Other pharmaceutically active ingredients from various therapeutic classes may also be used in combination with the present invention. They include, but are not limited to decongestants, analgesics, analgesic adjuvants, antidepressants, antipsychotics, anxiolytics, hypnotics, sedatives, anti-ADHD drugs, psychostimulants, drugs to treat urinary incontinence, antihistamines, expectorants, antitussives, diuretics, anti-inflammatory agents, antipyretics, antirheumatics, antioxidants, laxatives, local anesthetics, proton pump inhibitors, motility modifying agents, vasodilators, inotropes, beta blockers, beta adrenergic agonists, drugs to treat asthma and COPD, antiinfectives, anti-migraine agents, antihypertensives, antianginal agents, gastric acid reducing agents, anti-ulcer agents, anticoagulants, lipid and cholesterol lowering drugs, anti-diabetic drugs, anti-epileptics, hormones, smooth muscle relaxants, skeletal muscle relaxants, bronchodilators, vitamins, trace minerals, amino acids, biological peptides and drugs to treat various infectious, immunologic disorders, cardiovascular, pulmonary, gastrointestinal, hepatic, biliary, nutritional, metabolic, endocrine, hematologic, oncologic, musculoskeletal, neurologic, psychiatric, genitourinary, gynecologic, obstetric, pediatric, otolaryngogologic, ophthalmic, dermatologic, dental, oral, and genetic disorders, diseases and maladies. The drug being used in combination therapy with the present invention can be administered by any route, including parenterally, orally, topically, transdermally, sublingually, and the like.

The terms "medical condition", "malady", "disease", "disorder" and "pathological states" are used interchangeably and are intended to have their broadest interpretation to refer to any physiologic, pathologic or pathophysiologic state in a human that can be prevented, treated, managed or altered to produce a desired, usually beneficial effect.

In some preferred embodiments, the oral abusable drug is intended to prevent or treat pain. A co-administered drug (in the same or different dosage form, by any route of administration) may be used to provide additive, complementary, superadditive or synergistic therapeutic analgesic effects, including other NSAIDs, NO-NSAIDs, COX-2 selective inhibitors, acetaminophen, nitroparacetamol, nitric oxide donors, tramadol, beta adrenergic agonists, alpha-2 agonists, selective prostanoid receptor antagonists, NO-opioid receptor agonists, local anesthetics, purinergic P2 receptor antagonists, NMDA receptor antagonists, gabapentin, pregabalin, gabapentinoids, ligands of alpha(2)delta subunits of voltage-gated calcium channels, neuronal nicotinic receptor agonists, calcium channel antagonists, sodium channel blockers, superoxide dismutase mimetics, p38 MAP kinase inhibitors, TRPV1 agonists, dextromethorphan, dextrorphan, ketamine, glycine receptor antagonists, antidepressants, corticosteroids, and antiepileptics, and any other drugs that can be shown by a person proficient in the art to prevent or treat pain.

Compositions and methods of the present invention provide: (i) abuse deterrence; (ii) extended release; and/or (iii) protection against alcohol dose dumping; and/or (iv) protection against significant changes in bioavailability due to fed or fasted states; and/or (v) simultaneously providing more than one of foregoing (i) to (iv) abuse deterrence and extended release; wherein the dosage form is prepared using compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof.

In some preferred embodiments, the ADER agent of the invention is selected from among hydrogenated Type I or Type II vegetable oils.

In some preferred embodiments, the ADER agent of the invention is selected from among polyoxyethylene stearates.

In some preferred embodiments, the ADER agent of the invention is selected from among polyoxyethylene distearates.

In some preferred embodiments, the ADER agent of the invention is selected from among polyoxyethylene stearates or distearates.

In some preferred embodiments, the ADER agent of the invention is selected from among poorly water soluble, high melting point (mp=45 to 100° C.) waxes.

In some preferred embodiments, the ADER agent of the invention is selected from among hydrogenated Type I or Type II vegetable oils; said invention also including an aversive agent.

In some preferred embodiments, the ADER agent of the invention is selected from among polyoxyethylene stearates; said invention also including an aversive agent.

In some preferred embodiments, the ADER agent of the invention is selected from among polyoxyethylene distearates; said invention also including an aversive agent.

In some preferred embodiments, the ADER agent of the invention is selected from among polyoxyethylene stearates or distearates; said invention also including an aversive agent.

In some preferred embodiments, the ADER agent of the invention is selected from among poorly water soluble, high melting point (mp=45 to 100° C.) waxes; said invention also including an aversive agent.

In some preferred embodiments, the ADER agent of the invention excludes hydrogenated Type I vegetable oils.

In some preferred embodiments, the ADER agent of the invention excludes hydrogenated Type II vegetable oils.

In some preferred embodiments, the ADER agent of the invention excludes hydrogenated Type I or Type II vegetable oils.

In some preferred embodiments, the ADER agent of the invention excludes polyoxyethylene stearates.

In some preferred embodiments, the ADER agent of the invention excludes polyoxyethylene distearates.

In some preferred embodiments, the ADER agent of the invention excludes polyoxyethylene stearates or distearates.

In some preferred embodiments, the ADER agent of the invention excludes poorly water soluble, high melting point (mp=45 to 100° C.) waxes.

In some preferred embodiments, the ADER agent of the invention excludes poorly water soluble, high melting point (mp=50 to 100° C.) waxes.

In some preferred embodiments, the ADER agent of the invention excludes poorly water soluble, high melting point (mp=60 to 100° C.) waxes.

In some preferred embodiments, the ADER agent of the invention excludes poorly water soluble, high melting point (mp=70 to 85° C.) waxes.

In some preferred embodiments, the ADER agent of the invention excludes poorly water soluble, high melting point (mp=75 to 90° C.) waxes.

In some preferred embodiments, the ADER agent of the invention excludes poorly water soluble, high melting point (mp=70 to 100° C.) waxes.

In a particularly preferred embodiment of the invention, the dosage form includes two or more compounds selected from the categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes.

In a most preferred embodiment of the invention, the dosage form includes two or more compounds selected from at least two categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes.

In some preferred embodiments, the dosage form includes hydrogenated Type I or Type II vegetable oils in an amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

In some preferred embodiments, the dosage form includes polyoxyethylene stearates in an amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

In some preferred embodiments, the dosage form includes polyoxyethylene distearates in an amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

In some preferred embodiments, the dosage form includes glyceryl behenate, glyceryl palmitostearate, stearoyl macrogolglycerides and/or lauroyl macrogolglycerides in an amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

In some preferred embodiments, the dosage form includes glycerol monostearate in an amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

In some preferred embodiments, the dosage form includes poorly water soluble, high melting point (mp=45 to 100° C.) waxes in an amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

In some preferred embodiments, the dosage form includes two or more compounds selected from the categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes in total (i.e. cumulative) amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

In some preferred embodiments, the dosage form includes the dosage form includes two or more compounds selected from the categories [(i) to (iv)] from the group consisting of: (i) hydrogenated Type I or Type II vegetable oils; (ii) polyoxyethylene stearates and distearates; (iii) glycerol monostearate; (iv) poorly water soluble, high melting point (mp=45 to 100° C.) waxes in total (i.e. cumulative) amount that is less than about 1200 mg, or less than about 100 mg, or less than about 900 mg, or less than about 800 mg, or less than about 700 mg, or less than about 600 mg, or less than about 550 mg, or less than about 500 mg, or less than about 400 mg, or less than about 375 mg, or less than about 350 mg, or less than about 325 mg, or less than about 300 mg, or less than about 275 mg, or less than about 250 mg, or less than about 225 mg, or less than about 200 mg, or less than about 175 mg, or less than about 150 mg, or less than about 125 mg, or less than about 100 mg, or less than about 90 mg, or less than about 80 mg, or less than about 70 mg, or less than about 60 mg, or less than about 50 mg, or less than about 40 mg, or less than about 30 mg, or less than about 20 mg, or less than about 10 mg.

Representative examples of hydrogenated vegetable oils of the present invention include, without limitation, hydrogenated cottonseed oil (e.g., Akofine®; Lubritab®; Sterotex® NF), hydrogenated palm oil (Dynasan® P60; Softisan® 154), hydrogenated soybean oil (Hydrocote®; Lipovol HS-K®; Sterotex® HM) and hydrogenated palm kernel oil (e.g., Hydrokote® 112).

Representative examples of polyoxyethylene stearates and distearates of the present invention include, without limitation, Polyoxyl 2, 4, 6, 8, 12, 20, 30, 40, 50, 100 and 150 stearates (e.g., Hodag® DGS; PEG-2 stearate; Acconon® 200-MS; Hodag® 20-S; PEG-4 stearate; Cerasynt® 616; Kessco® PEG 300 Monostearate; Acconon® 400-MS; Cerasynt® 660; Cithrol® 4MS; Hodag® 60-S; Kessco® PEG 600 Monostearate; Cerasynt® 840; Hodag 100-S; Myrj® 51; PEG-30 stearate; polyoxyethylene (30) stearate; Crodet® S40; E431; Emerest® 2672; Atlas G-2153; Crodet® S50) and polyoxyl 4, 8, 12, 32 and 150 distearates (e.g., Lipo-PEG® 100-S; Myrj® 59; Hodag® 600-S; Ritox® 59; Hodag® 22-S; PEG-4 distearate; Hodag® 42-S; Kessco® PEG 400 DS; Hodag® 62-S; Kessco® PEG 600 Distearate; Hodag® 154-S; Kessco® PEG 1540 Distearate; Lipo-PEG® 6000-DS; Protamate® 6000-DS).

Representative examples of poorly water soluble, high melting point (mp=45 to 100° C.) waxes of the present invention include, without limitation: (i) animal waxes; (ii) insect waxes; (iii) vegetable waxes; (iv) mineral waxes; (v) petroleum waxes; (vi) synthetic waxes; (vi) nonionic emulsifying waxes or cetomacrogol emulsifying wax (e.g., Collone NI™; Crodex N™; Emulgade 1000NI™; Permulgin D™; Polawax™; Ritachol 2000; T-Wax™); (vii) anionic emulsifying wax (e.g., Collone HV™; Crodex A™; Cyclonette wax; Lanette wax SX™ BP); (viii) carnauba wax (also known as Brazil wax; caranda wax; E903); (ix) microcrystalline wax (also known as amorphous wax; E907; petroleum ceresin; petroleum wax (microcrystalline)); (x) yellow wax (e.g., yellow beeswax; Apifil™; E901; refined wax]; (xi) white wax (bleached wax; E901); (xii) cetyl esters wax (e.g., cera cetyla; Crodamol SS™; Cutina CP™; Liponate SPS™; Protachem MST™; Ritaceti™; Ritachol SS™; spermaceti wax replacement; Starfol wax CG™; Synaceti 116™; synthetic spermaceti); (xiii) hydrogenated castor oil (e.g., Castorwax™; Castorwax MP 70™; Castorwax MP 80™; Croduret™; Cutina HR™; Fancol™; Simulsol 1293™); (xiv) lanolin alcohols (e.g., Cholesterol; lanolin; lanolin, hydrous; petrolatum and lanolin alcohols; mineral oils); (xv) lanolin (e.g., cera lanae; E913; lanolina; lanolin anhydrous; Protalan anhydrous; purified lanolin; refined wool fat); (xvi) glyceryl palmitostearate; (xvii) cetostearyl alcohol (e.g., cetearyl alcohol; Crodacol CS90™; Lanette O™; Tego Alkanol 1618™; Tego Alkanol 6855™); (xviii) beeswax.

In some embodiments, the dosage form is devoid of animal waxes. In other embodiments, the dosage form is devoid of insect waxes. In other embodiments, the dosage form is devoid of vegetable waxes. In other embodiments, the dosage form is devoid of mineral waxes. In other embodiments, the dosage form is devoid of petroleum waxes. In other embodiments, the dosage form is devoid of synthetic waxes. In other embodiments, the dosage form is devoid of nonionic emulsifying waxes or cetomacrogol emulsifying wax. In other embodiments, the dosage form is devoid of anionic emulsifying wax. In other embodiments, the dosage form is devoid of carnauba wax. In other embodiments, the dosage form is devoid of microcrystalline wax. In other embodiments, the dosage form is devoid of yellow wax. In other embodiments, the dosage form is devoid of white wax. In other embodiments, the dosage form is devoid of cetyl esters wax. In other embodiments, the dosage form is devoid of hydrogenated castor oil. In other embodiments, the dosage form is devoid of lanolin alcohols. In other embodiments, the dosage form is devoid of lanolin. In other embodiments, the dosage form is devoid of glyceryl palmitostearate. In other embodiments, the dosage form is devoid of cetostearyl alcohol. In other embodiments, the dosage form is devoid of beeswax.

In one preferred embodiment of the present invention, the abusable drug is combined with beeswax, hydroxypropyl methyl cellulose (e.g, HPMC K15M), silicon dioxide (alone or in combination with $Al_2O_3$; e.g, Aerosil®, Aerosil® 200, Aerosil® COK84).

In one preferred embodiment of the present invention, the abusable drug is combined with hydrogenated cottonseed oil (e.g., Sterotex® NF), hydroxypropyl methyl cellulose (e.g, HPMC K15M), fractionated coconut oil and silicon dioxide (alone or in combination with $Al_2O_3$; e.g, Aerosil®, Aerosil® 200, Aerosil® COK84).

In another preferred embodiment of the present invention, the abusable drug is combined with glycerol monostearate (e.g., Cithrol® GMS), hydroxypropyl methyl cellulose (e.g, HPMC K100M) and silicon dioxide (alone or in combination with $Al_2O_3$; e.g, Aerosil®, Aerosil® 200, Aerosil® COK84).

In yet another preferred embodiment of the present invention, the abusable drug is combined with hydrogenated palm kernel oil (e.g., Hydrokote® 112), hydroxypropyl methyl cellulose (e.g, HPMC K15M) and silicon dioxide (alone or in combination with $Al_2O_3$; e.g, Aerosil®, Aerosil® 200, Aerosil® COK84).

In one preferred embodiment of the present invention, release rate modifiers may be incorporated. Release rate modifiers can also have additional useful properties that optimize the formulation.

In one preferred embodiment of the present invention, also included are cellulose and cellulose derivatives including, without limitation cellulose acetate, microcrystalline cellulose, powdered cellulose, cellulose acetate phthalate, hydroxyethyl cellulose, silicified microcrystalline cellulose, hydroxypropyl cellulose, hydroxyethylmethyl cellulose, low-substituted hydroxypropyl cellulose, carboxymethylcellulose, carboxymethylcellulose calcium, hypromellose acetate succinate, hypromellose phthalate and ethylcellulose.

In one preferred embodiment of the present invention, also included are coconut oil products, including without limitation, coconut oil, fractionated coconut oil, cetyl alcohol, lauric acid and medium chain triglycerides (e.g., Bergabest; caprylic/capric triglyceride; Captex 300; Captex 355; Crodamol GTC/C; glyceryl tricaprylate/caprate; Labrafac CC; MCT oil; Miglyol 810™; Miglyol 812™; Myritol; Neobee M5™; Nesatol™; oleum neutrale; oleum vegetable tenue; thin vegetable oil; Waglinol 3/9280™). In a most preferred embodiment, the coconut oil is fractionated coconut oil.

In one preferred embodiment of the present invention, hydroxypropyl methyl cellulose (e.g, HPMC K15M) may be incorporated.

A variety of agents may be incorporated into the ADER invention as thixotropes (e.g., fumed silicon dioxides, Aerosil®, Aerosil® COK84, Aerosil® 200, etc.). Thixotropes enhance the pharmaceutical formulations of the invention by increasing the viscosity of solutions during attempted extraction, complementing the action of HPMCs. They may also provide a tamper resistance by helping to retain the structure of dosage units that have been heated to temperatures greater than the melting point of the base excipient (Aerosils are unaffected by heat).

As described above, the present invention can include one or more ADER agents. Any amount of ADER may be used. In some embodiments, the total amount of ADER agent is about 5 to about 98 percent, preferably 7 to 90 percent and more preferably 10 to 85 percent on a dry weight basis of the composition.

In one preferred embodiment, the ADER can prevent less than or equal to about 98%, 90%, 80% 75%, 60%, 50%, 45%, 40%, 33%, 30%, 25%, 15%, 10%, 8%, 5%, or 2% of the total amount of drug in a dosage form from being recovered from a solvent in contact with a dosage form of the present invention.

In some preferred embodiments, the dosage form is devoid of hydrogenated Type I vegetable oils. In other embodiments, the dosage form is devoid of hydrogenated Type II vegetable oils. In other embodiments, the dosage form is devoid of polyoxyethylene stearates. In other embodiments, the dosage form is substantially of polyoxyethylene distearates; in other embodiments, the dosage form is substantially of glycerol monostearate. In other embodiments, the dosage form is substantially of poorly water soluble, high melting point (mp=45 to 100° C.) waxes.

In preferred embodiments, the abuse deterrent, extended release, alcohol dose dumping protective and/or abuse deterrent plus extended release dosage form of the invention comprises at least two ADER agents, each a hydrogenated Type I vegetable oil. In other embodiments, the abuse deterrent, extended release and/or abuse deterrent plus extended release dosage form of the invention comprises at least two ADER agents, each a hydrogenated Type II vegetable oil. In other embodiments, the abuse deterrent, extended release and/or abuse deterrent plus extended release dosage form of the invention comprises at least two ADER agents, each a hydrogenated Type I or Type II vegetable oil. In other embodiments, the abuse deterrent, extended release and/or abuse deterrent plus extended release dosage form of the invention comprises at least two ADER agents, each a polyoxyethylene stearate. In other embodiments, the abuse deterrent, extended release and/or abuse deterrent plus extended release dosage form of the invention comprises at least two ADER agents, each a polyoxyethylene distearate. In other embodiments, the abuse deterrent, extended release and/or abuse deterrent plus extended release dosage form of the invention comprises at least two ADER agents, each a glycerol monostearate. In other embodiments, the abuse deterrent, extended release and/or abuse deterrent plus extended release dosage form of the invention comprises at least two ADER agents, each a wax.

In some particularly preferred embodiments, the abuse deterrent, extended release, resistance against alcohol dose dumping when formulated as extended release, and/or abuse deterrent plus extended release dosage form of the invention comprises at least two ADER agents, selected from at least two groups, comprising: (i) a hydrogenated Type I vegetable oil; (ii) a hydrogenated Type II vegetable oil; (iii) a polyoxyethylene stearate; (iv) a polyoxyethylene distearate; (v) a glycerol monostearate; and (vi) a wax.

In some particularly preferred embodiments, the abuse deterrent, extended release, resistance against alcohol dose dumping when formulated as extended release, and/or abuse deterrent plus extended release dosage form of the invention comprises at least two ADER agents, selected from at least two groups, comprising: (i) a hydrogenated Type I vegetable oil; (ii) a hydrogenated Type II vegetable oil; (iii) a polyoxyethylene stearate; (iv) a polyoxyethylene distearate; (v) a glycerol monostearate; and (vi) a wax, said dosage form having a melting point >50° C., or >55° C., or >60° C., or >65° C., or >70° C., or >75° C., or >80° C., or >85° C., or >90° C., or between 50 and 60° C., or between 55 and 65° C., or between 60 and 70° C., or between 65 and 75° C., or between 70 and 80° C., or between 75 and 85° C., or between 80 and 90° C., or between 90 and 100° C., or between 50 and 100° C., or between 60 and 100° C., or between 70 and 100° C., or between 80 and 100° C., or between 60 and 80° C., or between 60 and 90° C., or between 65 and 85° C., or between 70 and 90° C.

In other particularly preferred embodiments, the abuse deterrent, extended release, resistance against alcohol dose dumping when formulated as extended release, and/or abuse deterrent plus extended release dosage form of the invention comprises at least two ADER agents, selected from at least two groups, comprising: (i) hydrogenated Type I or Type II vegetable oil; (ii) polyoxyethylene stearate or distearate; (iii) a glycerol monostearate; and (iv) a wax.

In other particularly preferred embodiments, the abuse deterrent, extended release, resistance against alcohol dose dumping when formulated as extended release, and/or abuse deterrent plus extended release dosage form of the invention comprises at least two ADER agents, selected from at least two groups, comprising: (i) hydrogenated Type I or Type II vegetable oil; (ii) polyoxyethylene stearate or distearate; (iii) a glycerol monostearate; and (iv) a wax, said dosage form having a melting point >50° C., or >55° C., or >60° C., or >65° C., or >70° C., or >75° C., or >80° C., or >85° C., or >90° C., or between 50 and 60° C., or between 55 and 65° C., or between 60 and 70° C., or between 65 and 75° C., or between 70 and 80° C., or between 75 and 85° C., or between 80 and 90° C., or between 90 and 100° C., or between 50 and 100° C., or between 60 and 100° C., or between 70 and 100° C., or between 80 and 100° C., or between 60 and 80° C., or between 60 and 90° C., or between 65 and 85° C., or between 70 and 90° C.

The present invention can also optionally include other ingredients to enhance dosage form manufacture from a pharmaceutical composition of the present invention and/or alter the release profile of a dosage form including a pharmaceutical composition of the present invention.

Some embodiments of the present invention include one or more pharmaceutically acceptable fillers, diluents, glidants and lubricants of various particle sizes and molecular weights.

The dosage form according to the invention may also comprise a coating which is resistant to gastric juices and dissolves as a function of the pH value of the release environment. By means of this coating, it is possible to ensure that, when correctly administered, the dosage form according to the invention passes through the stomach undissolved and the active ingredient is only released in the intestines.

In some preferred embodiments, the dosage form may include a surfactant ingredient to impart suitable formulation characteristics to the composition. Surfactants may be hydrophilic preferably selected from the group consisting of non-ionic hydrophilic surfactants and anionic hydrophilic surfactants or the surfactant may have hydrophobic properties. Examples of non-ionic hydrophilic surfactants are polyoxyethylene sorbitan esters, cremophores and poloxamers. Examples of anionic surfactants are sodium lauryl sarcosinate, docusate and pharmaceutically acceptable docusate salts. Also a mixture of these surfactants can be used.

The formulation optionally comprises auxiliary materials. Examples of these auxiliary materials (or pharmaceutically acceptable excipients) are (i) Binders such as acacia, alginic acid and salts thereof, cellulose derivatives, methylcellulose, hydroxyethyl cellulose, hydroxypropyl cellulose, magnesium aluminum silicate, polyethylene glycol, gums, polysaccharide acids, bentonites, hydroxypropyl methylcellulose, gelatin, polyvinylpyrrolidone, polyvinylpyrrolidone/vinyl acetate copolymer, crospovidone, povidone, polymethacrylates, hydroxypropylmethylcellulose, hydroxypropylcellulose, starch, pregelatinized starch, ethylcellulose, tragacanth, dextrin, microcrystalline cellulose, sucrose, or glucose, and the like; (ii) Disintegrants such as starches, pregelatinized corn starch, pregelatinized starch, celluloses, cross-linked carboxymethylcellulose, crospovidone, cross-linked polyvinylpyrrolidone, a calcium or a sodium alginate complex, clays, alginates, gums, or sodium starch glycolate, and any disintegration agents used in tablet preparations; (iii) Filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like; (iv) Stabilizers such as any antioxidation agents, reducing agents, buffers, or acids, sodium citrate, ascorbyl palmitate, propyl gallate, ascorbic acid, vitamin E, sodium bisulfite, butylhydroxyl toluene, BHA, acetylcysteine, monothioglycerol, phenyl-alpha-nathylamine, lecithin, EDTA, and the like; (v) Lubricants such as magnesium stearate, calcium hydroxide, talc, colloidal silicon dioxide, sodium stearyl fumarate, hydrogenated vegetable oil, stearic acid, glyceryl behenate, magnesium, calcium and sodium stearates, stearic acid, talc, waxes, Stearowet, boric acid, sodium benzoate, sodium acetate, sodium chloride, DL-leucine, polyethylene glycols, sodium oleate, or sodium lauryl sulfate, and the like; (vi) Wetting agents such as oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, or sodium lauryl sulfate, and the like; (vii) Diluents such lactose, starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, or bentonite, and the like; (viii) Anti-adherents or glidants such as talc, corn starch, DL-leucine, sodium lauryl sulfate, and magnesium, calcium, or sodium stearates, and the like; (ix) Pharmaceutically compatible carriers such as acacia, gelatin, colloidal silicon dioxide, calcium glycerophosphate, calcium lactate, maltodextrin, glycerin, magnesium silicate, sodium caseinate, soy lecithin, sodium chloride, tricalcium phosphate, dipotassium phosphate, sodium stearoyl lactylate, carrageenan, monoglyceride, diglyceride, or pregelatinized starch, and the like; (x) Other pharmaceutical excipients including polymers, hydrogels, silicon dioxide, ion exchange resins, cellulose acetate butyrate, carbohydrate polymers, organic acids of carbohydrate polymers caprylic/capric triglyceride, isopropyl myristate, ethyl oleate, triethyl citrate, dimethyl phthalate, and benzyl benzoate.

The pharmaceutical compositions and dosage form of the invention may further contain one or more pharmaceutically acceptable excipients. When used in the present invention, pharmaceutically acceptable excipients can play a small or significant role in the behavior of the dosage form, depending on the choice of excipient, quantity of excipient and interaction with other constituents of the dosage form and the gastrointestinal tract. Pharmaceutically acceptable excipients are well known in the art and include, without limitation, excipients referenced in the FDA EAFUS database (http://vm.cfsan.fda.gov/~dms/eafus.html); FDA Food Additives Status List (http://www.cfsan.fda.gov/~dms/opa-appa.html); FDA-GRAS list and database; FDA Color Additive Status List (http://www.cfsan.fda.gov/~dms/opa-appc.html); FDA Inactive Ingredients Database (http://www.accessdata.fda.gov/scripts/cder/iig/index.cfm); Rowe, Sheskey and Owen, Handbook of Pharmaceutical Excipients, APhA Publications; 5th edition (2006); Remington: The Science and Practice of Pharmacy, 21st ed, Lippincott Williams & Wilkins (2005); United States Pharmacopeia-National Formulary (USP-NF), (USP 30-NF 25, 2007), the International Programme on Chemical Safety (http://www.inchem.org/) and Health Canada's List of Acceptable Non-medicinal Ingredients (http://www.hc-sc.gc.ca/dhp-mps/prodnatur/legislation/docs/nmi-imn_list1_e.html), all hereby incorporated by reference in their entirety.

The dosage form according to the invention may also comprise a coating which is resistant to gastric juices and dissolves as a function of the pH value of the release environment.

By means of this coating, it is possible to ensure that, when correctly administered, the dosage form according to the invention passes through the stomach undissolved and the active ingredient is only released in the intestines.

In one preferred embodiment of the invention, the formulation is ingested orally as a tablet or capsule, preferably as a capsule. In another preferred embodiment of the invention, the formulation is administered bucally. In yet another preferred embodiment of the invention, the formulation is administered sublingually.

In one preferred embodiment, the invention provides for methods and pharmaceutical compositions to prevent or minimizing excessive peak concentrations (dose dumping) of therapeutic doses of extended release abusable drugs for medical purposes, when they are co-ingested with alcohol.

In one preferred embodiment, the invention provides for methods and pharmaceutical compositions to achieve an extended release formulation of abusable drugs.

In one preferred embodiment, the invention provides for methods and pharmaceutical compositions to achieve an abuse deterrent formulation of abusable drugs.

In one preferred embodiment, the invention provides for methods and pharmaceutical compositions to simultaneously achieve an extended release and abuse deterrence for abusable drugs.

In one preferred embodiment, the invention provides for methods and pharmaceutical compositions to simultaneously achieve an extended release and abuse deterrence for abusable drugs, using substantially the same excipients.

In one preferred embodiment, the invention provides for methods and pharmaceutical compositions to achieve abuse deterrence, without the use of aversive agents.

In one preferred embodiment, the invention provides for methods and pharmaceutical compositions to simultaneously achieve extended release and abuse deterrence, without the use of aversive agents.

In one preferred embodiment, the invention provides for methods and pharmaceutical compositions to simultaneously achieve an extended release formulation and an abuse deterrence formulation, using substantially the same ADER agents.

In one preferred embodiment, the invention provides for methods and pharmaceutical compositions to achieve one or more of the following properties: (a) abuse resistance; (b) extended release; (c) resistant to dose dumping due to alcohol; (d) resistant to significant changes in oral bioavailability due to changes in food intake; (e) resistant to intentional or surreptitious adulteration of beverages.

In one preferred embodiment, the invention provides for methods and pharmaceutical compositions to achieve two ore more of the following properties: (a) abuse resistance; (b) extended release; (c) resistant to dose dumping due to alcohol; (d) resistant to significant changes in oral bioavailability due to changes in food intake; (e) resistant to intentional or surreptitious adulteration of beverages.

In one preferred embodiment, the invention provides for methods and pharmaceutical compositions to achieve three or more of the following properties: (a) abuse resistance; (b) extended release; (c) resistant to dose dumping due to alcohol; (d) resistant to significant changes in oral bioavailability due to changes in food intake; (e) resistant to intentional or surreptitious adulteration of beverages.

In one preferred embodiment, the invention provides for methods and pharmaceutical compositions to achieve four or more of the following properties: (a) abuse resistance; (b) extended release; (c) resistant to dose dumping due to alcohol; (d) resistant to significant changes in oral bioavailability due to changes in food intake; (e) resistant to intentional or surreptitious adulteration of beverages.

In one preferred embodiment, the invention provides for methods and pharmaceutical compositions to achieve the following properties: (a) abuse resistance; (b) extended release; (c) resistant to dose dumping due to alcohol; (d) resistant to significant changes in oral bioavailability due to changes in food intake; (e) resistant to intentional or surreptitious adulteration of beverages.

In one preferred embodiment, the invention provides for methods and pharmaceutical compositions to achieve the following properties: (i) abuse deterrence; and/or (ii) extended release; and/or (iii) resistance against alcohol dose dumping; and/or (iv) resistance against alcohol dose dumping when formulated as extended release; and/or (v) more than one of the foregoing [(i) to (iv)] properties; said invention comprising one or more abusable drugs and one or more ADER agents.

In one preferred embodiment, the invention provides for methods and pharmaceutical compositions to achieve the following properties: (i) abuse deterrence; and/or (ii) extended release; and/or (iii) resistance against alcohol dose dumping; and/or (iv) resistance against alcohol dose dumping when formulated as extended release; and/or (v) more than one of the foregoing [(i) to (iv)] properties; said invention comprising one or more abusable drugs and one or more ADER agents; said invention providing abuse deterrence without the use of aversive agents.

In one preferred embodiment, the invention provides for methods and pharmaceutical compositions to achieve the following properties: (i) abuse deterrence; and/or (ii) extended release; and/or (iii) resistance against alcohol dose dumping; and/or (iv) resistance against alcohol dose dumping when formulated as extended release; and/or (v) more than one of the foregoing [(i) to (iv)] properties; said invention comprising one or more abusable drugs and one or more ADER agents; said invention using substantially the same ADER agents to achieve the foregoing (i) to (v).

In one preferred embodiment, the invention provides for methods and pharmaceutical compositions to achieve the following properties: (i) abuse deterrence; and/or (ii) extended release; and/or (iii) resistance against alcohol dose dumping; and/or (iv) resistance against alcohol dose dumping when formulated as extended release; and/or (v) more than one of the foregoing [(i) to (iv)] properties; said invention comprising one or more abusable drugs and one or more ADER agents; said invention using substantially the same ADER agents to achieve the foregoing (i) to (v); said invention providing abuse deterrence without the use of aversive agents.

In one preferred embodiment, the invention provides for methods and pharmaceutical compositions to achieve the following properties: (i) abuse deterrence; and/or (ii) extended release; and/or (iii) resistance against alcohol dose dumping; and/or (iv) resistance against alcohol dose dumping when formulated as extended release; and/or (v) more than one of the foregoing [(i) to (iv)] properties; said invention comprising one or more abusable drugs and at least two ADER agents.

In one preferred embodiment, the invention provides for methods and pharmaceutical compositions to achieve the following properties: (i) abuse deterrence; and/or (ii) extended release; and/or (iii) resistance against alcohol dose dumping; and/or (iv) resistance against alcohol dose dumping when formulated as extended release; and/or (v) more than one of the foregoing [(i) to (iv)] properties; said invention comprising one or more abusable drugs and at least two ADER agents; said invention providing abuse deterrence without the use of aversive agents.

In one preferred embodiment, the invention provides for methods and pharmaceutical compositions to achieve the following properties: (i) abuse deterrence; and/or (ii) extended release; and/or (iii) resistance against alcohol dose dumping; and/or (iv) resistance against alcohol dose dumping when formulated as extended release; and/or (v) more than one of the foregoing [(i) to (iv)] properties; said invention comprising one or more abusable drugs and at least two ADER agents; said invention using substantially the same ADER agents to achieve the foregoing (i) to (v).

In one preferred embodiment, the invention provides for methods and pharmaceutical compositions to simultaneously achieve an extended release formulation and an abuse deterrence formulation, using substantially the same ADER agents without the use of aversive agents.

It is understood that each of the various embodiments of methods and pharmaceutical compositions described herein may be used alone or in conjunction with one or more or all of the various embodiments described herein.

Additionally, it is understood that each of the various embodiments of the pharmaceutical compositions described herein may be used with each of the various embodiments of the described method of the present invention as described herein.

Determination of Biologic Effects in Humans

The pharmacologic effects of the pharmaceutical compositions of the present invention can be evaluated using methods well established in the art. The choice of method will depend, among other things, on: (i) the abusable drug and (ii) the therapeutic use to which the abusable drug is applied (i.e., the disease, disorder, or symptom(s) being treated with the abusable drug). Opioid analgesics, while primarily used for the treatment of pain have multiple therapeutic applications. Additionally, certain evaluations may be conducted in healthy subjects, recreational drug users or drug addicts. A wide variety of clinical states and study designs may be used to evaluate the therapeutic effects of intact and tampered dosage forms of the invention. This invention therefore contemplates the use of test methods other than those specifically disclosed herein, including those which may hereafter become known to the art to be capable of performing the necessary functions. Sample sizes in the studies are sufficient to demonstrate the objectives of the testing. A non-limiting list of methods to evaluate the analgesic and other effects of the invention is provided below:

Third Molar Extraction Model

Male and female patients with acute postsurgical pain following the removal of one or more bony impacted third molars are participants. Within 4 to 6 hours after completion of surgery, patients who are experiencing moderate or severe pain, as measured by a visual analog pain intensity scale (VAS≥50 mm) and by a categorical pain intensity scale (moderate or severe pain descriptor), and who meet all other inclusion/exclusion criteria are admitted to the study. Patients are randomly assigned to receive the dosage form of the invention given intact or placebo, in some preferred embodiments, and the dosage form of the invention given intact or dosage form of the invention given in tampered form in other embodiments. Both single and multiple (repeated) dose studies may be conducted. Pain intensity (VAS and categorical), pain relief (categorical) and whether pain is half-gone is recorded by the patient under the supervision of the investigator study coordinator at the various time points: Baseline (0 hour—pain intensity only), 15, 30 and 45 minutes, and at 1, 1.5, 2, 3, 4, 5, 6, 7, 8 and 12 hours after administration of study medication, and immediately prior to the first rescue dose. Sedation and nausea may be evaluated using VAS or categorical scales. Time to onset of perceptible and meaningful pain relief is evaluated using the two stopwatch method. Patients record their global evaluation of study medication at the completion of the 8-hour assessment or at the time of first rescue medication use. Efficacy endpoints include Total Pain Relief (TOTPAR), Sum of Pain Intensity Difference (SPID) and Sum of Pain Relief Intensity Difference (SPRID) at various time points, Time to First Rescue, Time Specific Pain Intensity Difference (PID), Time Specific Pain Relief (PR), Peak Pain Intensity Difference (PPID), Peak Pain Relief (PPR), Time to Confirmed Perceptible Pain Relief (stopwatch), Time to Meaningful Pain Relief (stopwatch), Patient Global Evaluation, Time to Change in Categorical PID≥1, Percent Change in Pain Intensity Score from Baseline, Mean Change in Pain Intensity Score From Baseline, Percent Change in Pain Relief Score from Baseline, Mean Change in Pain Relief Score From Baseline, Percent of Responders, Number of Patients Needed to Treat to Obtain One Patient with ≥50% Response (NNT).

Bunionectomy Surgery

Male or female patients requiring primary unilateral first metatarsal bunionectomy surgery alone or with ipsilateral hammertoe repair (without additional collateral procedures) under regional anesthesia (Mayo block) are participants.

Patients who experience moderate or severe pain on a categorical scale (moderate or severe descriptor) and on a visual analog pain intensity scale (VAS; ≥50 mm) within 6 hours following completion of bunionectomy surgery are randomly assigned to receive the dosage form of the invention given intact or placebo In some preferred embodiments, and the dosage form of the invention given intact or dosage form of the invention given in tampered form in other embodiments. Both single and multiple (repeated) dose studies may be conducted. Patients are encouraged to wait at least 60 minutes before requesting remediation for pain. At the completion of the single-dose phase (8 hours) or at first request for remediation (whichever is earlier), patients enter into a multiple-dose phase lasting approximately 72 hours. During the multiple dose phase patients receive study medication or placebo at a fixed dose interval (e.g., every 8, 12 or 24 hours). Once the multiple dose phase of the study has begun, patients experiencing pain between scheduled doses of study medication are provided access to supplemental open-label (rescue) analgesia. Patients whose pain cannot be adequately managed on a combination of study medication and rescue medication or who develop unacceptable side effects during the study are discontinued from further study participation and their pain managed conventionally.

Pain intensity (VAS and categorical), pain relief (categorical) and whether pain is half-gone is recorded by the patient under the supervision of the investigator study coordinator at representative time points, e.g., Baseline (pain intensity only), 15, 30 and 45 minutes and 1, 1.5, 2, 3, 4, 5, 6, 7 and 8 hours after administration of study medication and immediately prior to the first remediation. Sedation and nausea may be evaluated using VAS or categorical scales. Time to onset of perceptible and meaningful pain relief is evaluated using the double-stopwatch method. Patients complete a global evaluation of study medication at the completion of the 8-hour assessment or just prior to the first remediation. Following completion of the single-dose phase (8 hours or just prior to first remediation, if ≤8 hours), patients begin the multiple dose phase of the study. During the multiple dose phase, patients record their overall pain intensity since the previous scheduled dose, their current pain intensity and a patient global, immediately prior to each scheduled dose of study medication and at early termination.

Measures of efficacy in the single-dose phase include Sum of Pain Intensity Difference (SPID), Total Pain Relief (TOTPAR), Sum of Pain Relief Intensity Difference (SPRID), Time to First Remediation, Time Specific Pain Intensity Difference (PID), Time Specific Pain Relief (PR), Peak Pain Intensity Difference (PPID), Peak Pain Relief (PPR), Time to Confirmed Perceptible Pain Relief (stopwatch), Time to Meaningful Pain Relief (stopwatch), Patient Global Evaluation, Time to Change in Categorical PID≥1, Percent Change in Pain Intensity Score from Baseline, Mean Change in Pain Intensity Score From Baseline, Percent Change in Pain Relief Score from Baseline, Mean Change in Pain Relief Score From Baseline, Percent of Responders, Number of Patients Needed to Treat to Obtain One Patient with ≥50% Response (NNT).

Measures of efficacy in the multiple-dose phase include the time specific overall pain intensity, current pain intensity and patient global at the time of scheduled remediation, the average of overall pain intensity, current pain intensity and patient global over 0-24, 24-48 and 48-72 and number of doses of rescue analgesic over 0-24, 24-48 and 48-72 and 0-72 hours.

Chronic Pain of Osteoarthritis

The analgesic efficacy of the invention may be demonstrated in single or repeated dose randomized double-blind, controlled studies. Patients are randomized to receive the dosage form of the invention given intact or placebo, in some preferred embodiments, and the dosage form of the invention given intact or dosage form of the invention given in tampered form in other embodiments. In repeated dose studies, typically, patients who meet the American College of Rheumatology criteria for knee and/or hip OA are washed off their analgesics for 2 to 7 days to allow for pain of moderate to severe intensity to return. Once a stable baseline pain score is established, patients are randomized to treatment, usually for a period of 1 to 12 weeks. Pain, joint stiffness and physical function can be measured with a multidimensional instrument, such as the WOMAC, quality of life with the SF-12 or SF-36 and adverse events with a non-directed questionnaire at baseline and at post-baseline return visits. Response to pain, stiffness, physical function, quality of life and adverse events are calculated as change from baseline and compared between treatments. Sedation and nausea may be evaluated using VAS or categorical scales.

Migraine

The analgesic efficacy of the invention may be demonstrated in single or repeated dose randomized double-blind, controlled studies. Patients are randomized to receive the dosage form of the invention given intact or placebo, in some preferred embodiments, and the dosage form of the invention given intact or dosage form of the invention given in tampered form in other embodiments. Patients with migraine headaches are typically evaluated in prospective, randomized, double-blind, parallel group, single-dose studies. Crossover studies are also possible. The study population consists of male and non-pregnant female subjects, 18 to 65 years of age with a primary headache diagnosis of either migraine attack without aura or migraine attack with aura, as diagnosed according to the International Classification of Headache Disorders-2 criteria. To qualify, the subject must typically have a history, on average, of at least one migraine attack per month, but an average of no more than 6 migraine attacks each month during the past year. Using a headache diary subjects are instructed to treat and evaluate the headache pain and symptoms associated with one eligible migraine attack, with or without aura, with at least moderate headache pain intensity. Eligible subjects are randomly assigned to receive the drug to treat one migraine attack, with or without aura, with headache pain of at least moderate pain intensity as determined by them migraine questionnaire they are asked to take a single dose of study drug, according to their randomized treatment assignment. Headache pain intensity, nausea, photophobia, phonophobia, vomiting, and ability to function are assessed at baseline, 0.25, 0.5, 0.75, 1, 1.5, 2, 2.5, 3, 4, 8, 16 and 24 hours post-dose. In addition, the recurrence of pain and use of any rescue mediation is documented. Primary efficacy variables typically consist of the percent of subjects who are without: (i) pain; (ii) nausea; (iii) photophobia and, (iv) phonophobia, each at 2 hours post-dosing. Secondary efficacy variables typically consist of headache pain intensity and associated symptoms at each evaluation time point, incidence of vomiting, patient function, sum of pain intensity difference at each evaluation time (SPID), percent of subjects who experience headache recurrence up to 24 hours, and the median time to recurrence. Sedation may be evaluated using VAS or categorical scales. Recurrence is defined as the reduction in pain from moderate or severe pain to none at 2 hours after taking study drug, followed by: (i) an increase to mild, moderate or severe pain within 24 hours after taking the study drug, or (ii) consuming a rescue medication within 24 hours after taking the study drug.

Postherpetic Neuralgia

The analgesic efficacy of the invention may be demonstrated in repeated dose randomized double-blind, controlled studies. Patients are randomized to receive the dosage form of the invention given intact or placebo, in some preferred embodiments, and the dosage form of the invention given intact or dosage form of the invention given in tampered form in other embodiments. Patients with a history of postherpetic neuralgia ≥3 months and pain of at least moderate intensity are enrolled in the study. Patients with hypersensitivity to study medications, a history of drug or alcohol abuse and significant pain of alternate etiology are generally excluded. Patients meeting study eligibility criteria are "washed off" their analgesics in some embodiments, generally for 2 to 7 days to allow for pain of moderate to severe intensity to return. Once a stable baseline pain score is established, patients are randomized to treatment, usually for a period of 4 to 12 weeks. Pain intensity is assessed one to several times a day and in some cases only once weekly using VAS, categorical or numerical rating scales. Various dimensions of neuropathic pain may be assessed, including steady pain (ongoing pain), brief pain (paroxysmal pain) and skin pain (allodynia). Pain may also be assessed at scheduled clinic study visits. Pain may also be assessed using standardized pain scales such as the Neuropathic Pain Scale (Galer et al., Neurology 1997; 48:332-8), the Neuropathic Pain Symptom Inventory (Bouhassira et al., Pain 2004; 108:248-57), interference measures of the Brief Pain Inventory (Cleeland, CRC Press, 1991: 293-305 and Ann Acad Med Singapore 1994; 23:129-38) or the McGill Pain Questionnaire Short-Form (Melzack, Pain 1987; 30:191-7). Patient global assessment may be measured using a number of available tools, for example Patient Global Impression of Change (Farrar et al., Pain 2001; 94:149-580). Quality of life may similarly be assessed using number of available tools, for example the SF-36, SF-12 or SF-8. Examples of randomized, placebo or active studies conducted in postherpetic neuralgia are known in the art (e.g., Watson and Babul, Neurology 1998; 50:1837-41; Sabatowski et al., Pain. 2004; 109:26-35; Rowbotham et al., JAMA. 1998; 280: 1837-42). Adverse events may be assessed using a non-directed questionnaire, a symptom checklist or specific queries on adverse signs and symptoms. Response to pain, function, quality of life and adverse events are calculated as change from baseline and compared between treatments. Sedation and nausea may be evaluated using VAS or categorical scales.

Evaluating Effects Fed and Fasted State on Oral Bioavailability

The effects of fed and fasted state of the invention, and in particular, their effects on $C_{max}$, $AUC_{0-t}$ and $AUC_{0-\infty}$, can be evaluated using methods well know in the art. More specifically, the invention relies on the methods contained in the document entitled: "Guidance for Industry: Food-Effect Bioavailability and Fed Bioequivalence Studies: Study Design, Data Analysis and Labeling", Department of Health and Human Services, Food and Drug Administration, Center for Drug Evaluation and Research, October, 2001, which is here incorporated by reference. Additional guidance on the conduct of bioavailability studies is found in "Guidance for Industry: Bioavailability and Bioequivalence Studies for Orally Administered Drug Products-General Considerations", Department of Health and Human Services, Food and Drug Administration, Center for Drug Evaluation and Research, July 2002, which is here incorporated by reference.

Alcohol induced dose dumping may be evaluated using the above methods, where the test drug is co-administered with and without a specified amount of ethanol.

Tamper Resistance and Tamper Deterrence Testing

The popularity of immediate release formulations of abusable drugs among drug addicts and recreational drug users is in part due to the mood altering and reinforcing effects of the drug. The popularity of extended release formulations of abusable drugs among drug addicts and recreational drug users is in part due to the pharmacologic properties of the drug therein (e.g., mood altering and reinforcing effects) and in part due to the large amount of drug per tablet or capsule (e.g., a 12 or 24 hour supply). For example commercially available immediate release abusable drugs tablets and capsules are usually administered every 4 to 6 hours and they release their dose into the systemic circulation over one to two hours. New, extended release formulations are designed to gradually release their much larger abusable drugs content over a 12 or 24-hour period. Most recreational drug users and addicts have a unit of use which is one tablet or capsule. The 12 or 24-hour supply of an abusable drugs typically contained in one extended release tablet or capsule, instead of in 4 to 6 tablets or capsules means that there is a greater risk that such formulations may be highly sought by drug addicts and recreational drug users alike, for non-medical use. Intentional or inadvertent tampering from extended release formulations will rapidly deliver a massive dose and produce profound pharmacologic effects.

Addicts and recreational drug users commonly use abusable drugs by a variety of routes of administration. Commonly used methods include 1) parenteral (e.g., intravenous injection, where the drug is crushed and extracted or melted and the contents of a dosage unit then injected), 2) intranasal (e.g., snorting, where the drug is inhaled as powdered dosage unit), and 3) episodic or repeated oral ingestion of crushed product, where the drug is chewed to increase the surface area and permit rapid release of drug substance. All of these strategies are intended to more efficiently get the abusable drug into the CNS, both in terms of total amount of drug, peak concentration of drug and time to peak concentration of drug.

One mode of abuse involves the extraction of the drug component from the dosage form by first mixing the tablet or capsule with a suitable solvent (e.g., water or alcohol), and then filtering and/or extracting the drug component from the mixture for intravenous injection. Another mode of abuse of extended release drugs involves dissolving the drug in water, alcohol or another "recreational solvent" to hasten its release and to ingest the contents orally, in order to provide high peak concentrations and maximum euphoriant effects.

It is necessary to be able to measure resistance or deterrence to the likely routes of abuse in a meaningful and relevant way. The in vitro tests below are provided for illustration of some testing methods and are intended to be non-limiting examples. This invention therefore contemplates the use of test methods other than those specifically disclosed herein, including those which may hereafter become known to the art to be capable of performing the necessary functions.

Extraction With Alcohol on Whole Dosage Unit
Method: Place a whole dosage unit in 18 mL of 0.1N HCl in a 60 mL amber bottle and shake at 240 rpm on an orbital shaker for 30 min. After 30 min add 12 mL of ethanol (95-96%) to each bottle. Swirl by hand and remove a 1 mL sample from each bottle ($T_0$). Place the solutions back in the orbital shaker for further shaking at 240 rpm. Take 1 mL samples after 10, 20, 30, 40, 60 and 180 min of further shaking for each bottle. Analyze and graph the results on a linear scale of cumulative release (%) vs. time (min).

Extraction with Alcohol on a Crushed or Cut Dosage Unit
Extension of the above test. Method: Place a tablet (after crushing with a single crush with a spatula) or a capsule (cut in half) in 18 mL of 0.1N HCl in a 60 mL amber bottle and shake at 240 rpm on an orbital shaker for 30 min. Continue the test as in 1) above.

Extraction into Water
Method: Crush with a mortar and pestle and grind in 5 mL of water for 5 minutes. The resulting suspension is filtered through a 0.45 micron filter into a flask and diluted to 50 mL with water. Quantify drug concentration by HPLC.

Freeze and Crush
Method: Freeze the dosage unit in a domestic freezer for 24 hr, then grind with a mortar and pestle for five minutes. Sieve through a suitable sieve (ca 600 micron) and, by weighing, measure the percentage passing the sieve.

Taste of Base Excipient Mix (Organoleptic Test)
Method: Chew a placebo mix for five minutes and rate the taste on a 0-10 scale with 0 as bland to repulsive at 10. This method is relevant only to dosage units containing taste modifiers.

Extraction into Acid
Method: Crush with a mortar and pestle and heat to boiling in 5 mL of vinegar. The resulting suspension is filtered through a 0.45 micron filter into a flask and diluted to 50 mL with water. Quantify drug concentration by HPLC.

Application of Heat (Melting Temperature >50° C. Or 55° C.)
Method: Heat the squashed contents of a dosage unit on a hot plate until melted. Determine the temperature of melting and test whether the mix becomes sufficiently fluid to be drawn up into a syringe via a 1.2 mm needle then expelled.

EXAMPLES

Non-limiting examples for preparing the dosage form are set forth below.

Detailed Description of the Preferred Embodiments

The following examples illustrate various aspects of the present invention. They are not to be construed to limit the claims in any manner whatsoever.

A wide variety of methods known in the art for the preparation of immediate release and controlled release dosage forms may be incorporated into the invention.

Other suitable abusable drugs as defined in this invention may also be prepared by modification of the examples herein and by use of material other than those specifically disclosed herein, including those which may hereafter become known to the art to be capable of performing the necessary functions. Other suitable modifications and adaptations of the variety of conditions and parameters normally encountered and obvious to those skilled in the art are within the spirit and scope of the invention.

More than abusable drug may be included in the dosage form either in an immediate release or extended release form The ingredients used for the preparation of the dosage form may be modified depending on the selection of dose and desired duration of effect of the abusable drug and any included aversive agent, pharmacologic antagonist or other non-abusable therapeutic agent. In some embodiments, a change in the dose or amount of abusable drug does not require a change in amount of other ingredients. In other embodiments, a proportional change in the amount of other ingredients is required to maintain the desired properties. In yet other embodiments, a change in the dose or amount of abusable drug necessitates a change in the nature and/or amount of ingredients to provide the required characteristics of the abusable drug (e.g., immediate release, sustained release, duration of effect, rate and extent of absorption, therapeutic concentrations and effect, abuse deterrence properties, protection against alcohol dose dumping; and/or protection against significant changes in bioavailability due to fed or fasted states etc.)

Optionally, aversive agents may be included selected from the group comprising (i) laxatives; (ii) cutaneous vasodilators; (iii) headache producing agents; (iv) emetics, emetogenic and nausea producing compounds; (iv) bittering agents (v) mucosal, naso-mucosal, oro-mucosal, respiratory, tissue and gastrointestinal irritants; (vi) tissue staining, non-tissue staining and beverage staining dyes, lakes and colorants; (vii) fecal and urine discolorants; (viii) malodorous agents; (ix) opioid antagonists; and (x) and (x) benzodiazepine antagonists (e.g., flumazenil), and mixtures thereof.

The preparation of oral immediate release dosage forms is well known in the art—see Remington: the science of Pharmacy Practice, 21$^{st}$ Edition, 2006, Lippincott, Williams & Wilkins, Baltimore, Md.; Pharmaceutical Preformulation and Formulation: A Practical Guide from Candidate Drug Selection to Commercial Dosage Form. Gibson, M (ed). CRC Press, 2001; Niazi, S. Handbook of Pharmaceutical Manufacturing Formulations: Uncompressed Solid Products (Volume 2 of 6), CRC Press, 2004; Niazi, S. Handbook of Pharmaceutical Manufacturing Formulations: Compressed Solid Products (Volume 1 of 6), CRC Press, 2004; Mollet, H, Grubenmann A, Payne H. Formulation Technology: Emulsions, Suspensions, Solid Forms, Wiley-VCH, 2001; Niazi S and Niazi S K, Pharmaceutical Capsules, 2$^{nd}$ Ed., Podczeck, F and Jones B E (eds), Pharmaceutical Press, 2004, London (all of which are hereby incorporated by reference). A majority of oral dosage forms commercially available world wide are formulated as immediate release products.

Manufacturing methods described herein are utilized for the preparation of the abusable drugs as shown in the examples below. Variations to the methods may be employed, in some embodiments, depending on the specific chemical, physicochemical, pharmaceutical and pharmacologic properties of the abusable drug, excipients and their interaction and other factors. Compositions and methods of the present invention provide: (i) abuse deterrence; (ii) extended release; and/or (iii) protection against alcohol dose dumping; and/or (iv) protection against significant changes in bioavailability due to fed or fasted states; and/or (v) simultaneously providing more than one of foregoing (i) to (iv); wherein the dosage form is prepared using compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof.

As shown in further examples below, any abusable drug of the invention may be prepared to provide (i) abuse deterrence; or (ii) extended release; or (iii) resistance against alcohol dose dumping; or (iv) resistance against alcohol dose dumping when formulated as extended release; or (v) protection against significant changes in bioavailability due to fed or fasted states; or (vi) more than one of the foregoing [(i) to (v)] properties; said invention comprising one or more abusable drugs and one or more ADER agents; said invention, in some embodiments, providing further abuse deterrence through the use of aversive agents; said invention, in some embodiments, using substantially the same ADER agents to achieve the foregoing (i) to (v); said invention, in some embodiments, providing more than one of the foregoing [(i) to (v)] properties; said invention, in some embodiments, comprising one or more abusable drugs and at least two ADER agents; said invention, in some embodiments, comprising at least two ADER agents selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes; said invention, in some embodiments, comprising at least two ADER agents selected from at least two categories [(a) to (d)] from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes; said invention, in some embodiments, further comprising an immediate release form of the abusable drug; said invention, in some embodiments, further comprising an immediate release form of the abusable drug in solution; said invention, in some embodiments, simultaneously providing more than one of foregoing (i) to (v); said invention, in some embodiments, simultaneously providing more than one of foregoing (i) to (v) using substantially the same ADER agents.

In some embodiments, the ADER material does not include compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof. Instead, other ADER material of the invention described herein is utilized to achieve some or all of the objectives of the invention.

Example 1 to 33 may be prepared as follows: (i) Dispense the hydrogenated Type I vegetable oil, hydrogenated Type II vegetable oil, polyoxyethylene stearates, polyoxyethylene distearates, glycerol monostearate, poorly water soluble, high melting point (mp=45 to 100° C.) waxes and/or other ADER material of the invention (e.g., glyceryl behenate, glyceryl palmitostearate, stearoyl macrogolglycerides or lauroyl macrogolglycerides) into a mixer; (ii) Heat until fully melted; (iii) dispense the hydroxypropyl methyl cellulose (HPMC) into the mixer; (iv) Mix until dispersed; (v) Dispense the Aerosil into the same vessel; (vi) Mix until dispersed; (vii) Dispense the desired abusable drug or mixture of abusable drugs into the same vessel; (viii) Stir thoroughly with a high shear mixer; (ix) Transfer the mix into a liquid filling machine; (x) Fill into hard gelatin (or HPMC) capsule; (xi) Optionally, transfer the capsules to a banding machine and band the capsules.

Example 1

| Ingredients | Quantity (mg)/Dose |
| --- | --- |
| Sterotex ® NF | 200 |
| Fractionated coconut oil | 70 |
| Methocel ® K 15M | 81 |
| Aerosil ® COK 84 | 4 |
| Oxycodone | 20 |
| Capsule fill weight | 375 |

Example 2

| Ingredients | Quantity (mg)/Dose |
| --- | --- |
| Sterotex ® NF | 135 |
| Fractionated coconut oil | 50 |
| Methocel ® K 15M | 60 |
| Aerosil ® COK 84 | 3 |
| Levorphanol | 2 |
| Capsule fill weight | 250 |

Example 3

| Ingredients | Quantity (mg)/Dose |
|---|---|
| Sterotex ® NF | 170 |
| Fractionated coconut oil | 100 |
| Methocel ® K 15M | 70 |
| Aerosil ® COK 84 | 4.5 |
| Hydromorphone | 5.5 mg |
| Capsule fill weight | 350 |

Example 4

| Ingredients | Quantity (mg)/Dose |
|---|---|
| Sterotex ® NF | 200 |
| Fractionated coconut oil | 90 |
| Methocel ® K 15M | 80 |
| Aerosil ® COK 84 | 5 |
| Morphine HCl | 25 |
| Capsule fill weight | 400 mg |

Example 5

| Ingredients | Quantity (mg)/Dose |
|---|---|
| Beeswax | 200 |
| HPMC, K15M | 80 |
| Aerosil COK 84 | 8 |
| Levorphanol | 12 |
| Capsule fill weight | 300 |

Example 6

| Ingredients | Quantity (mg)/Dose |
|---|---|
| Sterotex NF | 150 |
| HPMC, K15M | 75 |
| Coconut oil | 75 |
| Aerosil COK 84 | 5 |
| Hydrocodone bitartrate | 20 |
| Capsule fill weight | 325 |

Example 7

| Ingredients | Quantity (mg)/Dose |
|---|---|
| Cithrol GMS | 275 |
| HPMC, K100M | 40 |
| Aerosil COK 84 | 10 |
| Morphine Sulfate | 25 |
| Capsule fill weight | 350 |

Example 8

| Ingredients | Quantity (mg)/Dose |
|---|---|
| Hydrokote 112 | 250 |
| HPMC, K15M | 60 |
| Aerosil COK 84 | 10 |
| Oxycodone HCl | 30 |
| Capsule fill weight | 350 |

Example 9

| Ingredients | Quantity (mg)/Dose |
|---|---|
| Beeswax | 200 |
| HPMC, Pharmacoat 606 | 62.5 |
| Aerosil COK 84 | 7.5 |
| Oxymorphone HCl | 30 |
| Capsule fill weight | 300 |

Example 10

| Ingredients | Quantity (mg)/Dose |
|---|---|
| Gelucire 50/02 | 190 |
| Methocel K 100M | 35 |
| Aerosil COK 84 | 10 |
| Hydromorphone HCl | 15 |
| Capsule fill weight | 250 |

Example 11

| Ingredients | Quantity (mg)/Dose |
|---|---|
| Cetyl alcohol | 280 |
| Methocel K 100M | 50 |
| Aerosil COK 84 | 10 |
| Morphine HCl | 10 |
| Capsule fill weight | 350 |

Example 12

| Ingredients | Quantity (mg)/Dose |
|---|---|
| Sterotex NF | 320 |
| Methocel K 15M | 60 |
| Aerosil COK 84 | 10 |
| Hydromorphone HCl | 10 |
| Capsule fill weight | 400 |

Example 13

| Ingredients | Quantity (mg)/Dose |
|---|---|
| Cithrol GMS | 320 |
| Methocel K 100M | 55 |
| Aerosil COK 84 | 15 |
| Levorphanol Tartrate | 10 |
| Capsule fill weight | 400 |

Example 14

| Ingredients | Quantity (mg)/Dose |
|---|---|
| Sterotex ® NF | 100 |
| Fractionated coconut oil | 70 |
| Beeswax | 100 |
| Methocel ® K 15M | 81 |
| Aerosil ® COK 84 | 4 |
| Oxycodone HCl | 20 |
| Capsule fill weight | 375 |

Example 15

| Ingredients | Quantity (mg)/Dose |
|---|---|
| Sterotex ® NF | 135 |
| Fractionated coconut oil | 50 |
| Beeswax | 52 |
| Methocel ® K 15M | 60 |
| Aerosil ® COK 84 | 3 |
| Morphine Sulfate | 50 |
| Capsule fill weight | 350 |

Example 16

| Ingredients | Quantity (mg)/Dose |
|---|---|
| Sterotex ® NF | 130 |
| Fractionated coconut oil | 100 |
| Beeswax | 70 |
| HPMC, K15M | 20.5 |
| Methocel ® K 15M | 70 |
| Aerosil ® COK 84 | 4.5 |
| Hydrocodone bitartrate | 15 |
| Capsule fill weight | 410 |

Example 17

| Ingredients | Quantity (mg)/Dose |
|---|---|
| Sterotex ® NF | 150 |
| Fractionated coconut oil | 80 |
| Cithrol GMS | 120 |
| HPMC, K100M | 20 |
| Methocel ® K 15M | 80 |
| Aerosil ® COK 84 | 5 |
| Morphine Sulfate | 60 |
| Capsule fill weight | 515 mg |

Example 18

| Ingredients | Quantity (mg)/Dose |
|---|---|
| Beeswax | 150 |
| HPMC, K15M | 80 |
| Aerosil COK 84 | 10 |
| Cithrol | 150 |
| Oxymorphone HCl | 20 |
| Capsule fill weight | 410 |

Example 19

| Ingredients | Quantity (mg)/Dose |
|---|---|
| Beeswax | 150 |
| HPMC, K15M | 80 |
| Aerosil COK 84 | 15 |
| Hydrokote 112 | 75 |
| Codeine Sulfate | 60 |
| Capsule fill weight | 380 |

Example 20

| Ingredients | Quantity (mg)/Dose |
|---|---|
| Sterotex NF | 150 |
| HPMC, K15M | 75 |
| Coconut oil | 75 |
| Aerosil COK 84 | 5 |
| Oxymorphone HCl | 20 |
| Hydrokote 112 | 75 |
| Capsule fill weight | 400 |

Example 21

| Ingredients | Quantity (mg)/Dose |
|---|---|
| Cithrol GMS | 275 |
| HPMC, K100M | 50 |
| Aerosil COK 84 | 15 |
| Hydrokote 112 | 100 |
| Methadone HCl | 60 |
| Capsule fill weight | 500 |

Example 22

| Ingredients | Quantity (mg)/Dose |
|---|---|
| Cithrol GMS | 275 |
| HPMC, K100M | 60 |
| Aerosil COK 84 | 15 |
| Gelucire 50/02 | 100 |
| Methadone HCl | 25 |
| Capsule fill weight | 475 |

Example 23

| Ingredients | Quantity (mg)/Dose |
|---|---|
| Gelucire 50/02 | 140 |
| Methocel K 100M | 35 |
| Aerosil COK 84 | 15 |
| Sterotex ® NF | 75 |
| Fractionated coconut oil | 45 |
| Methadone HCl | 15 |
| Capsule fill weight | 325 |

Example 24

| Ingredients | Quantity (mg)/Dose |
|---|---|
| Gelucire 50/02 | 100 |
| Methocel K 100M | 28 |
| Aerosil COK 84 | 12 |
| Beeswax | 125 |
| HPMC, K15M | 65 |
| Propiram HCl | 30 |
| Capsule fill weight | 370 |

Example 25

| Ingredients | Quantity (mg)/Dose |
|---|---|
| Gelucire 50/02 | 200 |
| Methocel K 100M | 60 |
| Aerosil COK 84 | 20 |
| Cithrol GMS | 140 |
| Propiram HCl | 80 |
| Capsule fill weight | 500 |

Example 26

| Ingredients | Quantity (mg)/Dose |
|---|---|
| Sterotex ® NF | 200 |
| Fractionated coconut oil | 70 |
| Methocel ® K 15M | 81 |
| Aerosil ® COK 84 | 4 |
| Dihydrocodeine | 20 |
| Capsule fill weight | 375 |

Example 27

| Ingredients | Quantity (mg)/Dose |
|---|---|
| glyceryl behenate | 135 |
| Fractionated coconut oil | 50 |
| Methocel ® K 15M | 60 |
| Aerosil ® COK 84 | 3 |
| Levorphanol | 2 |
| Capsule fill weight | 250 |

Example 28

| Ingredients | Quantity (mg)/Dose |
|---|---|
| Sterotex ® NF | 170 |
| glyceryl behenate | 100 |
| Methocel ® K 15M | 70 |
| Aerosil ® COK 84 | 4.5 |
| Levorphanol Tartrate | 5.5 mg |
| Capsule fill weight | 350 |

Example 29

| Ingredients | Quantity (mg)/Dose |
|---|---|
| glyceryl behenate | 200 |
| Fractionated coconut oil | 90 |
| Methocel ® K 15M | 80 |
| Aerosil ® COK 84 | 5 |
| Oxycodone HCl | 25 |
| Capsule fill weight | 400 mg |

Example 30

| Ingredients | Quantity (mg)/Dose |
|---|---|
| glyceryl behenate | 200 |
| HPMC, K15M | 80 |
| Aerosil COK 84 | 8 |
| Hydromorphone HCl | 12 |
| Capsule fill weight | 300 |

Example 31

| Ingredients | Quantity (mg)/Dose |
|---|---|
| Glyceryl palmitostearate | 150 |
| HPMC, K15M | 75 |
| Coconut oil | 75 |
| Aerosil COK 84 | 5 |
| Morphine Sulfate | 20 |
| Capsule fill weight | 325 |

Example 32

| Ingredients | Quantity (mg)/Dose |
| --- | --- |
| Glyceryl palmitostearate | 275 |
| HPMC, K100M | 40 |
| Aerosil COK 84 | 10 |
| Methadone HCl | 25 |
| Capsule fill weight | 350 |

Example 33

| Ingredients | Quantity (mg)/Dose |
| --- | --- |
| Glyceryl palmitostearate | 250 |
| HPMC, K15M | 60 |
| Aerosil COK 84 | 10 |
| Oxymorphone HCl | 30 |
| Capsule fill weight | 350 |

Example 34 to 66 may be prepared as using the formula of Examples 1 to 33, respectively with the following modification: (i) Dispense the hydrogenated Type I vegetable oil, hydrogenated Type II vegetable oil, polyoxyethylene stearates, polyoxyethylene distearates, glycerol monostearate, poorly water soluble, high melting point (mp=45 to 100° C.) waxes and/or and/or other ADER material of the invention (e.g., glyceryl behenate, glyceryl palmitostearate, stearoyl macrogolglycerides or lauroyl macrogolglycerides) into a mixer; (ii) Heat until fully melted; (iii) dispense the hydroxypropyl methyl cellulose (HPMC) into the mixer; (iv) Mix until dispersed; (v) Dispense the Aerosil into the same vessel; (vi) Mix until dispersed; (vii) Dispense the desired abusable drug or mixture of abusable drugs into the same vessel; (viii) Stir thoroughly with a high shear mixer; (ix) Feed the blended material continuously into a twin screw extruder and collect the resultant strands on a conveyor and allow to cool (the conveyor is set to provide extrudate diameter of 0.5 mm or 1 mm and the pelletizer is set to provide pellets of approximately 0.5 or 1 mm length); (x) Screen the pellets so formed through a sieve and collect the desired particle size (sieve portion); (xi) Fill pellets into capsules or blend the pellets with talc and magnesium stearate and compress into tablets.

These and other embodiments of the present invention will readily occur to those of ordinary skill in the art in view of the disclosure herein.

The included examples are illustrative but not limiting of the methods and composition of the present invention. Other suitable modifications and adaptations of the variety of conditions and parameters normally encountered and obvious to those skilled in the art are within the spirit and scope of the invention.

A wide variety of materials can be used for preparing the dosage form according to this invention. This invention therefore contemplates the use of materials other than those specifically disclosed herein, including those which may hereafter become known to the art to be capable of performing the necessary functions.

Materials in the series of experiments below included the following: Aerosil® 200, Lot 1412033, ex Degussa Huls, Aerosil® COK84, Lot 2258, ex Degussa Huls, Beeswax, Lot A018035701, ex Acros Organics, Cetyl alcohol (1-hexadecanol), Lot A019258301, ex Acros Organics, Cithrol® GMS 0400, Lot 6483-0103, ex Croda, Fractionated coconut oil, Lot 165544, ex A E Connock Gelucire® 44/14, Lot 22009, ex Gattefosse, Gelucire® 50/02, Lot 19255, ex Gattefosse, Gelucire® 50/13, Lot 20529, ex Gattefosse, Hydrokote 112 Lot 048M3, ex Abitech Corp, Hydrokote APS, Lot 340J1, ex Abitech Corp, Hydrokote M, Lot 126J2, ex Abitech Corp, Methocel® AM4, Lot Q101012N01, ex Colorcon, Methocel® K100M, Lot QA15012N01, ex Colorcon, Methocel® Kl5M, Lot QK02012N11, ex Colorcon, Paraffin wax, Lot P/0680/90, ex Fisher Scientific, PEG 400, Lot 310354, ex NOF Corp, Pluriol E6005 (PEG 6000), Lot 97193, ex BASF, Pharmacoat 606 (hypromellose USP), Lot 308522, ex Shin-Etsu Chemical Co Ltd., Poloxamer 124 (Pluronic L44), Lot WPWV-645B, ex BASF, Poloxamer 188 (Lutrol F68), Lot 0306043523, ex BASF, Propoylene glycol, Lot 09521HO, ex Aldrich, Propranolol HCl, Lot 044K1219, ex Sigma, Shellac, Lot 4010 2465 2056, ex Syntapharm, Size 1 clear/clear gelatin capsules, Lot C14893, ex Capsugel, Starch 1500, Lot IN 500578, ex Colorcon, Sterotex® N F, Lot 324M2, ex Abitech Corp., Tramadol HCl, Lot 3TRMDN0D105 & 3TRMDN0E056, ex Chemagis Ltd, Zein (Paroxite), Lot 5041C, ex Variati & Co.

Equipment in the series of experiments below included the following: Caleva 9ST dissolution apparatus with ERWEKA P thermostatically controlled water heater, Copley ZT54 disintegration apparatus, Haake DC5 water bath, Heidolph bench mixer, HiBar bench filling machine, Qualiseal bench banding machine, Silverson SL2 bench high shear mixer, Thermo Electron Vision uv/visible spectrometry data acquisition program with Vision Security, Unicam UV2-400 spectrophotometer, Watson Marlow 205U peristaltic pump 650µ nominal s/s Laboratory test sieve, 600µ s/s certified Laboratory test sieve from Endecotts Ltd, London, Whatman 25 mm 45µ filters used in combination with a 5 ml Luer lock syringe.

Example 1

Binary Mix Compatibility Trials

Binary mixes were prepared of tramadol HCL in potential excipients (in some instances a third material, fractionated coconut oil was used to bring two non melting materials into intimate contact). The mixes were stored in sealed amber glass bottles under conditions of 40° C./75% RH for four weeks then examined by HPLC for signs of interaction or degradation. Excipients were chosen from materials considered to potentially cover the range of material properties that were likely to be required by this project. Materials were chosen for properties such as dissolution rate i.e. from materials that are relatively soluble in aqueous media to totally insoluble materials; their potential as viscosity/release rate modifiers, including such materials as different HPMC (viscosity) grades and Aerosils for contributing thixotropic properties. Mixes containing 25% w/w tramadol HCL were prepared for each excipient. Samples were prepared by mixing tramadol HCl with the melted excipient or for non melting excipients materials were placed in contact by blending with a 50/50 mix of excipient and fractionated coconut oil. Samples of each excipient were also stored in sealed amber glass bottles at 40° C./75% RH as control samples. The project objective describes a target of 15 binary mixes; however, 25 different mixes were made during this trial to maximize the range of excipients available for formulation.

Dissolution Testing

Initially two test formulations were prepared as noted below. The capsules for this and all other small scale capsule preparations were manufactured by the melting and mixing of the ingredients in a water bath or on a hot plate then hand filling capsules to the target weight. All capsules used were size 1 gelatin capsules.

| | | Formulation 052/014 |
|---|---|---|
| Material | % w/w | Quantity per cap mg |
| Poloxamer 188 | 62.8 | 282.7 |
| HPMC K100M | 17.9 | 80.3 |
| Aerosol COK 84 | 2.7 | 12.0 |
| Tramadol HCl | 16.6 | 74.9 |
| Capsule fill weight | | 450 |

| | | Formulation 052/015 |
|---|---|---|
| Material | % w/w | Quantity per cap mg |
| Gelucire 50/02 | 58.3 | 233.3 |
| HPMC Pharmacoat 606 | 19.9 | 79.8 |
| Aerosil ® COK 84 | 3.0 | 12.0 |
| Tramadol HCl | 18.7 | 74.9 |
| Capsule fill weight | | 400 |

The target fill weight was set as 400 mg for a size 1 capsule. Formulation 052/014 was initially targeted on a 400 mg fill, however, the mix proved too viscous to fill. Additional poloxamer 188 had to be added to reduce the mix viscosity to a level that could be encapsulated. The addition of extra poloxamer 188 required that the fill weight be increased to 450 mg. This quantity could be hand filled into a capsule and would meet the requirements of this preliminary trial; however, such a quantity would be excessive for machine filling into a size 1 capsule.

The tramadol HCl dissolution release profile was determined, for each formulation. Full dissolution testing is carried out using six individual capsule sets. Preliminary screening trials used between two and six capsules per test. This permitted several candidate formulations to be screened at once and clearly unsuitable formulations eliminated quickly. Potentially useful formulations could be modified further first before going on to six capsule sample dissolution testing.

Tramadol HCl in aqueous solution shows an absorbance maximum between 240 nm and 290 nm with the maximum at 271 nm. It starts to show increasingly strong absorbance below the minimum at 240 nm to 200 nm (the limit of the instrument) however absorbance in this area is shown by many compounds so observation in the more definitive region of 240 nm to 290 was selected with 270-272 nm chosen as the preferential wavelength of observation. A plot of the UV spectrum of tramadol HCl in water is shown in FIG. 1.

Dissolution testing was carried out using the USP paddle method on a Caleva 9ST dissolution apparatus with an ERWEKA P, thermostatically controlled, water heater. Each solution was continuously cycled through a Unicam UV2-400 spectrophotometer using a Watson Marlow 205U peristaltic pump and the solution absorbance in a 1 cm silica cell, at 271 nm, recorded against the absorbance of a placebo or SIF blank with the data captured by Thermo Electron Vision UV/visible spectrometry data acquisition software protected by Vision Security. The spectrophotometer was fitted with a six cell autochanger permitting continuous automatic recording of cell solution absorbances. The capsules were weighed down with 316 stainless steel sinking wire, wrapped round each capsule. Each solution passed through a filter as it was pumped from the dissolution bath. Except where otherwise specified, the dissolution medium was 600 ml of Simulated Intestinal Fluid (SIF) USP without the inclusion of enzyme. This dissolution set up was selected to give a final absorbance value, with full release of tramadol HCl, of not more than 1.5 absorbance units (au). Typically, the final absorbance of a test solution did not exceed 1.0 au. A placebo blank was used in the reference cell. This comprised of a capsule containing the same proportion and quantity of each material used in the active test capsules but without the tramadol HCl. This ensured that the reference solution contained the same quantity (and thus gave the same background absorbance) as the excipients in the active capsules.

Binary Mix Compatibility Study

25 Different materials were tested for compatibility with Tramadol HCl. The results of storage in sealed amber glass bottles under conditions of 40° C./75% RH for four weeks then subsequent analysis by HPLC for degradants or impurities are as below.

| | Material | Assay % | Peaks from stressed excipient | Impurities/Degradants % area normalized | Comments |
|---|---|---|---|---|---|
| 1 | Gelucire 44/14 | 127.9 | none | none | |
| 1 | Gelucire 44/14 REPEAT SAMPLE | 71.2 | none | none | Mean 2 samples 99.5% |
| 2 | Gelucire 50/13 | 106.3 | none | none | |
| 3 | Gelucire 43/01 | | | | Not available |
| 4 | Poloxamer 188 | 101.9 | none | none | |
| 5 | Poloxamer 124 (Pluronic L44) | 98.6 | none | none | Separated suspension re-mixed before sampling |
| 6 | PEG 6000 | 96.6 | none | none | |
| 7 | PEG 400 | 100.7 | none | none | |
| 8 | Propylene glycol | 96.5 | none | none | |
| 9 | Beeswax (refined yellow) | 2.1 | none | none | Material insoluble in sample diluent |
| 10 | Starch 1500 (+ Miglyol) | 97.3 | none | none | Separated suspension re-mixed before sampling |
| 11 | Cetyl alcohol 1-hexadecanol | 4.5 | none | none | Solution produced was a thick slime. Very hard to take HPLC sample |
| 12 | Paraffin wax | 15.0 | none | none | Material insoluble in sample diluent |

-continued

| | Material | Assay % | Peaks from stressed excipient | Impurities/ Degradants % area normalized | Comments |
|---|---|---|---|---|---|
| 13 | Miglyol (fractionated coconut oil) | 102.3 | none | none | Separated suspension re-mixed before sampling |
| 14 | HPMC Methocel ® K15MP (+ Miglyol) | 104.0 | none | none | |
| 15 | HPMC Methocel ® K100MP (+ Miglyol) | 98.9 | none | none | Separated of components re-mixed before sampling |
| 16 | Methocel ® A (+ Miglyol) | 101.1 | none | none | |
| 17 | Hydrokote 112 | 104.2 | None | None | |
| 18 | Hydrokote AP5 | 101.2 | None | None | |
| 19 | Hydrokote M | 102.8 | None | none | |
| 20 | Shellac (+ Miglyol) | 99.8 | Peaks at 5.065, 10.702 and 12.491 minutes | RT 5.057 = 0.1% – excipient RT 10.436 = 0.1% RT 10.704 = 0.5% – excipient RT 12.488 = 0.3% – excipient RT 15.043 = 0.1% RT 15.402 = 0.1% | Yellow semisolid Excipient insoluble in diluent |
| 20 | Shellac UNSTRESSED | N/A | Main peaks: 5.035, 10.393, 10.656, 12.455 Several small peaks in time zone 14 to 18 minutes | N/A | Conclude: peaks present in stressed Shellac were present before stress test |
| 21 | Zein (+ Miglyol) | 100.5 | Peak at 7.083 minutes | RT 7.080 = 0.1% – excipient | Yellow semisolid |
| 22 | Aerosil ® COK 84 (+ Miglyol) | 100.2 | none | None | |
| 23 | Aerosil ® 200 (+ Miglyol) | 101.9 | none | none | |
| 24 | Cithrol ® GMS | 99.3 | Not available Control sample 96.4% assay | none | Solution produced a viscous mix |
| 25 | Sterotex ® | 62.9 | none | none | Solution produced a viscous mix |
| 25 | Sterotex ® REPEAT SAMPLE | 32.7 | none | none | Mean 2 samples 47.8% |
| 26 | Gelucire 50/02 | 104.1 | none | none | Solution produced a viscous mix |

The results above show that none of the excipients tested show any detectable signs of degradation or interaction after one month storage under conditions of 40° C./75% RH. It was therefore possible to use any of these materials as formulation ingredients.

Initial Test Formulation Dissolution Testing

Preliminary test formulations were prepared based on poloxamer 188 and Gelucire 50/02. The formulation compositions are as below.

| | Formulation 052/014 | |
|---|---|---|
| Material | % w/w | Quantity per cap mg |
| Poloxamer 188 | 62.8 | 282.7 |
| HPMC K100M | 17.9 | 80.3 |
| Aerosol ® COK 84 | 2.7 | 12.0 |
| Tramadol HCl | 16.6 | 74.9 |
| Capsule fill weight | | 450 |

| | Formulation 052/015 | |
|---|---|---|
| Material | % w/w | Quantity per cap mg |
| Gelucire 50/02 | 58.3 | 233.3 |
| HPMC Pharmacoat 606 | 19.9 | 79.8 |
| Aerosol ® COK 84 | 3.0 | 12.0 |
| Tramadol HCl | 18.7 | 74.9 |
| Capsule fill weight | | 400 |

| | Placebo for 052/014 | |
|---|---|---|
| Material | % w/w | Quantity per cap mg |
| Poloxamer 188 | 75.4 | 282.4 |
| HPMC K100M | 21.4 | 80.0 |
| Aerosol COK 84 | 3.2 | 12.0 |
| Capsule fill weight | | 374.4 |

| | Placebo for 052/015 | |
|---|---|---|
| Material | % w/w | Quantity per cap mg |
| Gelucire 50/02 | 71.5 | 232.2 |
| HPMC Pharmacoat 606 | 24.8 | 80.6 |
| Aerosil ® COK 84 | 3.7 | 12.1 |
| Capsule fill weight | | 325 |

The release profiles, determined from dissolution testing in SIF are shown in FIGS. 2 and 3. Some HPMC gel remained at the end of the trial in sample 052/014 (poloxamer 188 based) but all poloxamer 188 and tramadol HCl had dissolved very quickly. Plot 2 shows that release took place over a 2-5 hr time span. This release rate is too fast to be useable in this project so the use of poloxamer 188 as a base excipient was discarded. The material of formulation 052/015 remained as a plug at the end of dissolution testing. It appears that the tramadol HCl and HPMC dissolved and migrates out through the Gelucire 50/02 over a period of 10-12 hr. This is shorter than the project targeted release time of 18-24 hr but Gelucire 50/02 was retained as a material worth testing further.

Example 2

Dissolution Testing of a Modified Gelucire 50/02 Formulation

Methocel® Ki OOM, a very high viscosity HPMC, was substituted for Pharmacoat 606, a very low viscosity HPMC, to investigate whether this substitution using a much higher viscosity HPMC would significantly slow the release rate of tramadol HCl from the formulation. The active and reference placebo capsules' formulations are shown in FIG. 4. It should be noted that the relative viscosity of HPMC is based on the viscosity of a 2% aqueous solution at 20° C. measured in mPas (millipascal Seconds). The numbers and letters in the HPMC's designation indicate (different manufacturers use slightly different conventions) the HPMC's 2% viscosity in mPas (1 mPas=1 centipoise (cps)), e.g. Pharmacoat 606 (Pharmacoat 6 is the HPMC type with the final 6 referring to the 2% viscosity) has a viscosity of 6 mPas (6 centipoise) as a 2% solution while Methocel® K100M (Methocel® K is the HPMC type and 100M is the 2% viscosity using the letter M as the convention for a multiplication factor of 1000) has a viscosity of 100,000 mPas (100 Pascal Seconds) as a 2% solution.

| | Formulation 052/019 | |
|---|---|---|
| Material | % w/w | Quantity per cap mg |
| Gelucire 50/02 | 58.2 | 232.9 |
| Methocel ® K100M | 19.9 | 79.4 |
| Aerosil ® COK 84 | 3.0 | 12.0 |
| Tramadol HCl | 18.7 | 75.0 |
| Capsule fill weight | | 400 |

| | Placebo for 052/019 | |
|---|---|---|
| Material | % w/w | Quantity per cap mg |
| Gelucire 50/02 | 71.6 | 232.8 |
| HPMC Pharmacoat 606 | 24.6 | 79.8 |
| Aerosil ® COK 84 | 3.8 | 12.4 |
| Capsule fill weight | | 325 |

The dissolution rate had been slowed down slightly compared with 052/015 from 10-12 hr to approximately 15-18 hr; however, this mix was a thick cream and was probably too viscous to machine fill as this exact formulation.

Example 3

Dissolution Testing of Tramadol HCl in Gelucire 50/02 without Additional Excipients Initial dissolution trials on formulations were performed as 'sighting' trials to give some idea of the range of profiles possible for 75 mg of tramadol HCl in a matrix made up to 400 mg. The two major excipients used poloxamer 188 and Gelucire 50/02 are at opposite ends of the water solubility/dispersibility scale so would give a good indication of the range of release rates potentially available. Poloxamer 188 is readily water soluble while Gelucire 50/02 is highly lipophilic and only very slowly dispersible in water. The Gelucire 50/02 formulation 052/019 dissolution release rate, shown in FIG. 5, is close to that desired for this project. This formulation does incorporate materials which would modify (increase) the release rate so samples were prepared containing only tramadol HCl and Gelucire 50/02 to determine the slowest release rate that could be achieved with Gelucire 50/02. Samples were prepared according to the formulation below and their release rate determined.

| | Formulation 052/024 | |
|---|---|---|
| Material | % w/w | Quantity per cap mg |
| Gelucire 50/02 | 81.2 | 325.0 |
| Tramadol HCl | 18.8 | 75.0 |
| Capsule fill weight | | 400 |

| | Placebo for 052/024 | |
|---|---|---|
| Material | % w/w | Quantity per cap mg |
| Gelucire 50/02 | 100 | 325 |

A single capsule was initially tested then a further five capsules were also tested. All the data has been incorporated into the single plot shown below. The profile with the extended time scale is that of the first capsule tested.

These experiments indicate that full release takes place in the order of 30 hr. The outlying profiles was considered to be potentially due to uneven distribution of tramadol HCl in these hand mixed preparations but it was not deemed worthwhile to investigate this further at this stage. Gelucire 50/02 melts over a range centered on 50° C. and is hard enough to be crumbled into a powder. This makes formulations susceptible to abuse (by powdering, extraction, dose dumping, snorting etc) and it would be essential to include abuse deterrent materials such as HPMC and Aerosils in the final formulation. The release rate indicated by these profiles fall within the acceptable range of release rates worthy of further consideration at this stage of the project, however, as only two materials had been examined (with one rejected) by this stage it was decided to investigate other materials before narrowing the selection of potential formulations.

Example 4

Dissolution Testing of Tramadol HCl in Gelucire 50/02 in SIF Containing Pancreatin The Gelucire range of materials is described as polyglycolized glycerides consisting of mono-, di- and triglycerides and of mono- and di-fatty acid esters of polyethylene glycol (PEG) with a range of HLB (hydrophilic lipophilic balance) values from 1 to 14. A material with a value of 14 is at the hydrophilic end of the scale where the material is easily water dispersible; 1 or 2 is at the other end of the scale and the material is extremely slowly water dispersible, at best.

Gelucire 50/02 (the 02 suffix shows the HLB value to be 2) is highly lipophilic and only disperses very slowly in aqueous media. These materials are potentially digestible so it is possible that a formulation that shows very slow release in vitro, in purely aqueous media such as SIF, could show dramatically faster release due to digestion, as opposed to dispersion, in vivo in the presence of enzymes.

An experiment was performed to look for any indications that the presence of an enzyme, pancreatin, modified the release rate of tramadol HCl in Gelucire 50/02. This experiment encountered difficulties as pancreatin in solution absorbs strongly over a range exceeding that of tramadol HCl's 240 nm to 290 nm band and pancreatin in suspension tended to block the solution filters.

The dissolution profile of capsules containing formulation 052/024 was recorded using UV absorbance determination. The pancreatin level was reduced to one fifth of that specified in the USP method so that solution absorbance values did not significantly exceed 1 au. The results shown below were very erratic, however, as this was intended as no more than a check on whether this family of materials (atypical of future excipients) was susceptible to acceleration of release rate by digestion it was decided not to divert the project into the development of an HPLC assay for tramadol HCL in the presence of pancreatin at this stage.

The profile (FIG. 6) shows an initial dip due to suspended/dissolved pancreatin affecting the reference cell. The absorbance of the mix appears to stop increasing after approximately 30 hr which does indicate that the tramadol HCl is fully released after this time. This corresponds well with the release time of tramadol HCl in this excipient tested in SIF in the absence of pancreatin (FIG. 5). This suggests that, at the level of pancreatin used, no major variation in dissolution release rate is observed in the presence of pancreatin. The Gelucire 50/02 units were allowed to be stirred in this medium for a further two days. The units maintained their shape and size for the entire period adding some confirmatory evidence that the Gelucire 50/02 content remained substantially unchanged (undigested).

Example 5

Dissolution Testing of Propranolol HCl in Gelucire 50/02 in SIF Containing Pancreatin The above trial using Gelucire 50/02, as the base excipient, in SIF containing pancreatin suffered from the pancreatin UV absorbance overlapping and being of greater intensity than the tramadol HCl absorbance in the monitored 290 nm region. An alternative model compound was found in propranolol HCl, as a substitute for the tramadol HCl. Propranolol HCl has similar solubility and similar UV specific absorbance to tramadol HCl but has its UV absorbance maximum at 319 nm, just outside the absorbance window of pancreatin. This allowed the testing of the propranolol HCl analogue of the above formulation, 052/024, to be tested in the presence of pancreatin with reduced interference.

The propranolol HCl analogue was subjected to dissolution testing in 600 ml of SIF, with and without (full strength) pancreatin. Six capsule samples were tested in each case. FIGS. 7 and 8 shows data for dissolution with and without pancreatin while FIG. 9 shows the combined averaged data of dissolution in the absence and presence of pancreatin.

The pancreatin in suspension caused difficulties with filter blockage in both test and reference vessels leading to irregularities appearing in the data for propranolol HCl in SIF in the presence of pancreatin. Overall, despite the irregularities in the data, it is concluded that there is no difference detected in the overall rate of release for Gelucire 50/02 between dissolution in SIF in the absence or presence of pancreatin. This supports the conclusion reached for the similar experiment carried out using tramadol HCl in Gelucire 50/02.

Example 6

Dissolution Testing of Current Tramadol HCl Extended Release Products

Tramadol HCl is available in commercial extended release products. These products contain different doses of tramadol HCl, typically 150 mg, from the dosage unit under development in this project but it was considered useful to broaden our knowledge of such products and to obtain a dissolution release profile using our current conditions. It was also intended that proprietary products such as these were used later in this project as comparators during product tampering and extraction tests.

Zydol® XL 150 from Pfizer for once a day administration and Dromadol® SR by IVAX for twice a day administration are two proprietary products which both contain 150 mg of tramadol HCl in an extended release formulation. Two tablets of each product had their dissolution profile determined in 600 ml of SIF without added enzyme with UV monitoring at 271 nm according to the standard method used in this development project. The combined release profiles are shown in FIG. 10. All tablets were substantially whole at the end of the test period. The release profiles match so closely that it is not possible to distinguish visually one tablet type from the other. Under the above conditions full release takes of the order of 40 hr and, as the tablets contain double the dose of the experimental formulations, the final absorbance is approximately double that shown in earlier plots. The slight dip in the plot about 17 hr is considered to be an artifact of the method.

Example 7

Indicative Dissolution Testing of Potential Dosage Unit Base Excipients

Previous trials demonstrated that the hard fats and slowly dissolving materials were the best choice of base material (a base excipient is the predominant excipient in a dosage unit) for a 75 mg tramadol HCl extended release dosage unit. This identified seven other materials, from those tested in the compatibility trial, as potential base excipients. Six of these were formulated as binary mixtures with tramadol HCl and filled into capsules to a fill weight of 400 mg containing 75 mg tramadol HCl as had been carried out previously. The final material, beeswax, was formulated with the additional presence of HPMC as an unmodified formulation was unlikely to show any significant release due to the known insolubility of beeswax in aqueous media. All formulations had their dissolution profiles determined using single capsule samples for initial screening. The materials and formulations used are as below. The reference cell contained 600 mL of SIF.

| Formulation 052/034-1 | | |
|---|---|---|
| Material | % w/w | Quantity per cap mg |
| Cetyl alcohol | 81.2 | 325.0 |
| Tramadol HCl | 18.8 | 75.0 |
| Capsule fill weight | | 400 |

| Formulation 052/035-2 | | |
|---|---|---|
| Material | % w/w | Quantity per cap mg |
| Hydrokote 112 | 81.2 | 324.8 |
| Tramadol HCl | 18.8 | 75.2 |
| Capsule fill weight | | 400 |

| Formulation 052/035-3 | | |
|---|---|---|
| Material | % w/w | Quantity per cap mg |
| Hydrokote AP5 | 81.3 | 325.2 |
| Tramadol HCl | 18.7 | 74.8 |
| Capsule fill weight | | 400 |

| Formulation 052/035-4 | | |
|---|---|---|
| Material | % w/w | Quantity per cap mg |
| Hydrokote M | 81.3 | 325.4 |
| Tramadol HCl | 18.7 | 74.6 |
| Capsule fill weight | | 400 |

| Formulation 052/035-5 | | |
|---|---|---|
| Material | % w/w | Quantity per cap mg |
| Cithrol ® GMS | 81.6 | 326.2 |
| Tramadol HCl | 18.4 | 73.8 |
| Capsule fill weight | | 400 |

| Formulation 052/035-6 | | |
|---|---|---|
| Material | % w/w | Quantity per cap mg |
| Sterotex ® NF | 81.2 | 324.9 |
| Tramadol HCl | 18.8 | 75.1 |
| Capsule fill weight | | 400 |

| Formulation 052/035-7 | | |
|---|---|---|
| Material | % w/w | Quantity per cap mg |
| Beeswax | 61.2 | 244.8 |
| Methocel ® K 100M | 20.1 | 80.5 |
| Tramadol HCl | 18.7 | 74.7 |
| Capsule fill weight | | 400 |

The above tests were carried out using only filtered SIF in the reference cell. Absorbance values obtained may be composed of two components, namely, absorbance due to tramadol HCl and absorbance due to dissolved excipient. 75 mg of Tramadol HCl in SIF gives an absorbance of 0.74 au therefore the absorbance must reach 0.7 au (allowing for inter capsule variation) before it is possible for all the tramadol HCl to have been dissolved. Absorbances significantly in excess of 0.7 au will have some contribution from excipient dissolution.

FIGS. 11 and 12 show that Hydrokote and Hydrokote AP5 dissolve rapidly and release their tramadol HCl in approximately 2 hours. This is too fast a release rate for the requirements of this project so these excipients were not able to be used as base excipients.

The other excipients were in two groups. Cithrol® GMS, Cetyl alcohol and the beeswax/HPMC combination showed release rates that were slightly slower than the target of total release in 18-24 hr while the Hydrokote 112 and Sterotex® NF were significantly slower. One of the requirements of this project is to develop dosage units with demonstrable deterrence to physical or solvent based tampering. Materials were to be incorporated into formulations to enhance abuse resistance. As it was likely that these materials would accelerate release then all of the materials mentioned in this paragraph were suitable for further consideration.

Example 8

Dissolution Testing of Modified Tramadol HCl Formulations

The base excipients Cithrol® GMS, Hydrokote 112, Cetyl alcohol, Sterotex® NF and beeswax showed potential as formulation base excipients in the trial above. These materials, in binary combination (beeswax as a ternary combination), gave dissolution release rates slower than the 18-24 hr target.

In this trial HPMCs were incorporated into the formulations to accelerate release and provide a level of tamper deterrence. Up to this point formulations contained tramadol HCl, a water soluble material, with a water insoluble base excipient which could make separation by extraction relatively easy. HPMC has been chosen as a material which might enhance tamper resistance as it has the property of being water soluble and thus would 'follow' tramadol HCl during attempted aqueous extraction, making separation of the tramadol HCl more difficult. HPMC comes in high viscosity grades which can impart a viscous nature to aqueous extracts of dosage units i.e. if anyone tries to extract the tramadol HCl with a small amount of water in a small spoon then, at best, they will produce an unpleasant mixture with a 'gummy' appearance which will tend to block attempts at filtration. Additionally, HPMC behaves in an unusual manner in aqueous solution. Most water soluble materials increase in solubility as the water temperature rises. HPMC is most soluble in cold water, becoming less soluble with temperature increase until, at about 40° C., it becomes totally insoluble. Solutions of HPMC that are heated to 40° C. or above turn into solid gels.

This means that although an HPMC may be added to increase release rates from a dosage unit, it can actively deter abuse by extraction. If an individual tries to extract tramadol HCl with warm or hot water then the HPMC will become completely insoluble and actively resist the diffusion of tramadol HCl through the relatively impermeable base excipient.

Several formulations were produced incorporating a high viscosity HPMC, Methocel® K 100M, into the matrix. The formulations tested and the release profiles obtained are shown below.

| | Formulation 052/039-1 | |
|---|---|---|
| Material | % w/w | Quantity per cap mg |
| Cetyl alcohol | 71.2 | 284.9 |
| Methocel ® K 100M | 10.0 | 40.0 |
| Tramadol HCl | 18.8 | 75.1 |
| Capsule fill weight | | 400 |

| | Formulation 052/039-2 | |
|---|---|---|
| Material | % w/w | Quantity per cap mg |
| Hydrokote 112 | 57.0 | 227.9 |
| Methocel ® K 100M | 24.5 | 97.9 |
| Tramadol HCl | 18.6 | 74.2 |
| Capsule fill weight | | 400 |

| | Formulation 052/040-5 | |
|---|---|---|
| Material | %w/w | Quantity per cap mg |
| Hydrokote 112 | 66.1 | 264.4 |
| Methocel ® K 100M | 15.1 | 60.3 |
| Tramadol HCl | 18.8 | 75.3 |
| Capsule fill weight | | 400 |

| | Formulation 052/039-3 | |
|---|---|---|
| Material | % w/w | Quantity per cap mg |
| Cithrol ® GMS | 71.0 | 284.0 |
| Methocel ® K 100M | 10.2 | 40.8 |
| Tramadol HCl | 18.8 | 75.2 |
| Capsule fill weight | | 400 |

| | Formulation 052/040-4 | |
|---|---|---|
| Material | % w/w | Quantity per cap mg |
| Sterotex ® NF | 56.5 | 225.8 |
| Methocel ® K 100M | 25.1 | 100.4 |
| Tramadol HCl | 18.4 | 73.8 |
| Capsule fill weight | | 400 |

FIG. 13 is based on using only SIF in the reference cell. As described previously, the flattening of the curve, having reached an absorbance of at least 0.7 au, indicates full release of tramadol HCl from the dosage unit. Materials dissolving or suspending in the dissolution media may increase the recorded absorbance significantly above 0.7 as is clearly seen above for the Sterotex® NF plot. FIG. 13 shows that all formulations release all/almost all tramadol HCl within approximately 17-27 hr. This is satisfactory at this stage in the project. An example of the data and scatter for a five capsule dissolution set of results produced using one of the formulations used in the combined plot above (cetyl alcohol 052/039-1) is shown in FIG. 14.

Example 9

Dissolution Testing of Modified Tramadol HCl in Sterotex® NF Formulations

The future processing of formulations at manufacturing scale required to be considered at this stage. Some formulations had too low a viscosity, as a melt, to maintain insoluble excipients in suspension and others were so viscous that, although they could be hand filled for the purposes of these trials, they were so viscous that they would cause great difficulty during manufacture on full scale machinery. Formulations, unstable due to low viscosity, could have their viscosity increased using low levels of thixotrope but formulations of excessive viscosity required that excipients were reduced or substituted.

An Aerosil® was chosen as both a thixotrope and contributor to abuse deterrence. Aerosil® is the commercial name for fumed silicon dioxide manufactured by Degussa Hüls. They produce a range of Aerosils with differing properties. These include different particle size, hydrophobic or hydrophilic characteristics or blended with additional materials such as aluminum oxide for specific purposes. Aerosil® COK84 was chosen as the Aerosil® of choice for this project. Aerosil® COK 84 is a mixture of fumed silicon dioxide and highly dispersed aluminum oxide in a 5:1 ratio. This material effectively thickens aqueous systems and other polar liquids. In this project Aerosil® COK 84 will increase viscosity in a formulation, however, if attempts are made to add a small quantity of water to produce a solution (e.g. for injection) the Aerosil® COK 84 will contribute to increase the viscosity of any solution produced as it is specifically designed to thicken aqueous systems. Silicon dioxide and aluminum oxide, additionally, do not melt below 100° C. (or even 1000° C.) and are insoluble. The thickening effect of this Aerosil® is unaffected by heat thus an abuser attempting to melt a dosage unit will find that the structure and shape of the dosage unit tends to remain unchanged when sufficient Aerosil® is incorporated even though the melting point of all other excipients has been exceeded Formulations were modified by having Aerosil® COK 84 added in some instances to improve process characteristics and enhance abuse resistance while others had the HPMC grade substituted to bring the dissolution release rate towards the target range or to adjust the formulation properties to that required for commercial production.

The Sterotex® NF formulation above, 052/040-4, contained 25% of a very high viscosity HPMC which produced a mix that could be hand filled but was excessively viscous for machine encapsulation. This formulation was modified with a lower quantity of a lower viscosity grade HPMC with the aim of producing a machine fillable formulation of similar release rate

| | Formulation 052/058 | |
|---|---|---|
| Material | % w/w | Quantity per cap mg |
| Sterotex ® NF | 66.2 | 264.9 |
| Methocel ® K 15M | 15.0 | 60.0 |
| Tramadol HCl | 18.8 | 75.0 |
| Capsule fill weight | | 400 |

| | Placebo for 052/058 | |
|---|---|---|
| Material | % w/w | Quantity per cap mg |
| Sterotex ® NF | 81.5 | 265 |
| Methocel ® K 15M | 18.5 | 60.0 |
| Capsule fill weight | | 325 |

The dissolution profile of a four capsule sample is shown in FIGS. 15 and 16. The above profiles indicate release in 25-30 hr. (Later data will demonstrate that full release of 75 mg tramadol HCl from Sterotex® NF results in an absorbance of approximately 0.8 au under the above conditions). This formulation was quite thin with fast separation of the insoluble ingredients and required an increase in viscosity. This undoubtedly contributed to the variation between individual profiles. The dosage unit was swollen after dissolution testing but retained its original shape and was tough to break up. This demonstrated that the tramadol HCl has diffused out from the dosage unit rather than released after dosage unit dissolution or disintegration.

Example 10

Dissolution Testing of Further Modified Tramadol HCl in Sterotex® NF Formulations Aerosil® COK 84 was added to the tramadol HCl in Sterotex® NF formulations. Formulations containing quantities of Aerosil® COK 84 in excess of 2% w/w were too viscous for machine filling so formulation 052/058 was modified to contain 2% Aerosil® COK 84 and subjected to dissolution testing against a placebo without tramadol HCl but which contained the same quantities of all other ingredients.

| | Formulation 052/060 | |
|---|---|---|
| Material | % w/w | Quantity per cap mg |
| Sterotex ® NF | 63.9 | 255.4 |
| Methocel ® K 15M | 15.2 | 61.0 |
| Aerosil ® COK 84 | 2.1 | 8.6 |
| Tramadol HCl | 18.9 | 75.5 |
| Capsule fill weight | | 400 |

The dosage units had expanded and were soft and easily broken up after dissolution testing. The average release profile was not significantly different from that of formulation 052/058, with release in approximately 25-30 hr, however, there was less variation between individual samples indicating that low viscosity of 052/058 was a major contributor to individual sample variation (FIGS. 17 and 18).

Example 11

Dissolution Testing of Tramadol HCl in Hydrokote 112 with HPMC and Aerosil® COK 84

FIG. 13 shows the plot for a formulation based on Hydrokote 112 containing 15% Methocel® K 100M, formulation 052/040-5. Trials indicated that Aerosil® COK 84 could be incorporated at 1.5% w/w to produce a flowing light cream. The above formulation was modified to contain 1.5% Aerosil® COK 84 and to compare release profiles for formulations containing equal quantities of Methocel® K 15M or the much higher viscosity grade Methocel® K 100M. Formulations were prepared as below.

| | Formulation 052/062-1 | |
|---|---|---|
| Material | % w/w | Quantity per cap mg |
| Hydrokote 112 | 64.7 | 258.7 |
| Methocel ® K 100M | 15.0 | 60.1 |
| Aerosil ® COK 84 | 2.1 | 8.6 |
| Tramadol HCl | 1.6 | 6.3 |
| Capsule fill weight | | 400 |

| | Formulation 052/062-2 | |
|---|---|---|
| Material | % w/w | Quantity per cap mg |
| Hydrokote 112 | 64.7 | 258.6 |
| Methocel ® K 15M | 15.0 | 60.2 |
| Aerosil ® COK 84 | 2.1 | 8.6 |
| Tramadol HCl | 1.5 | 6.2 |
| Capsule fill weight | | 400 |

Three capsule samples of each formulation had their dissolution absorbance profiles measured in 600 mL of SIF, without enzyme at 271 nm, using the USP paddle apparatus, at 75 rpm, as carried out previously. The combined individual and averaged profiles are shown in FIGS. 19 and 20. Both dosage units were soft and crumbling at the end of dissolution testing. Both gave acceptable release times for the tramadol HCl of 25-30 hr. As would be expected, the lower viscosity grade dissolution was slightly faster than that of the formulation containing the higher viscosity grade.

Example 12

Dissolution Testing of a Formulation Containing 250 mg Tramadol HCl in Sterotex® NF A dosage unit containing 250 mg of tramadol HCl was considered as a future possibility for this type of slow release dosage form so a preliminary investigation was carried out to estimate the likelihood of this being achievable.

Tramadol HCl is highly water soluble. This can lead to difficulty in producing a slow release formulation as, with the preferred largest capsule size as a size 0, the largest quantity of formulated material that can be filled as a liquid fill is approximately 550 mg. This means that the formulation will contain approximately 45% as the very soluble tramadol HCl.

The objective of this exercise was to determine whether 250 mg tramadol HCl could be formulated to 500-550 mg in a mix, with the properties to enable machine filling, and having a release rate that delivered the tramadol HCl into solution over at least 18-24 hr. If the formulation released tramadol at a much slower rate then this was completely acceptable as the release rate could be accelerated by the incorporation of materials such as HPMC. Difficulties would arise if the release rate could not achieve 18-24 hr release with only the base excipient.

Sterotex® NF was chosen as the base excipient for this trial as, at the 18.8% w/w tramadol HCl level (FIG. 12), it was the 'slowest' of the excipients under examination and able to deliver extremely slow release. A formulation targeted on 500 mg dosage was too viscous to be filled. Diluting to a total mass of 550 mg and the addition of a small quantity of Aerosil® COK 84 gave a flowing cream that could be machine filled.

| | Formulation 052/066 | |
|---|---|---|
| Material | % w/w | Quantity per cap mg |
| Sterotex ® NF | 52.8 | 290.5 |
| Aerosil ® COK 84 | 1.8 | 10.0 |
| Tramadol HCl | 45.4 | 249.6 |
| Capsule fill weight | | 550 |

The dissolution profile of a six capsule set was obtained in the previous manner. The only difference from previous conditions was that the dissolution medium volume had been increased to 1 liter. At this level, total release of the 250 mg of tramadol HCl would give an absorbance of at least 1.5 au. A placebo containing all materials in identical quantities without tramadol HCl was used as the reference.

The individual plots (FIGS. 21 and 22) showed some atypical behavior due to bubble generation in the flow through cells. Despite this, the clear observation is that this formulation released less than a quarter of its tramadol HCl content over the 38 hr period of the dissolution trial. This release time and the percentage released comfortably exceeds the minimum requirement of release of all tramadol HCl in not less than 18-24 hr. This trial demonstrates that it should be feasible to produce a similar slow release, liquid filled dosage unit to the objective of this project, containing up to 250 mg tramadol HCl in a total formulated mass of up to 550 mg.

Example 13

Dissolution Testing of Tramadol HCl in Beeswax Based Formulations

Previous beeswax based formulations (052/035-7), containing 20% Methocel® K 100M released in a period of approximately 40 hr. This exceeded the 18-24 hr target range of the study, however, it was considered useful to include a slightly slower, in vitro, formulation to broaden the range of formulations that would eventually be subject to an in vivo trial.

Two other beeswax formulations were prepared to compare the quantity and type of HPMC that should be incorporated and the effect of Aerosil® COK 84 inclusion. It was found that up to 2% Aerosil® COK 84 could be included and the material remained as a potentially machine fillable mix. 25% HPMC was found to produce an excessively viscous mix. Two formulas were tested containing 20 and 23% w/w of the lower viscosity Methocel® K 15M HPMC. The formulations subjected to dissolution testing were as below.

| | Formulation 052/068 | |
|---|---|---|
| Material | % w/w | Quantity per cap mg |
| Beeswax | 59.4 | 237.6 |
| Methocel ® K 15M | 19.9 | 79.5 |
| Aerosil ® COK 84 | 2.0 | 8.2 |
| Tramadol HCl | 18.7 | 74.7 |
| Capsule fill weight | | 400 |

| | Formulation 052/070 | |
|---|---|---|
| Material | % w/w | Quantity per cap mg |
| Beeswax | 56.3 | 225.0 |
| Methocel ® K 15M | 23.0 | 92.0 |
| Aerosil ® COK 84 | 2.0 | 8.0 |
| Tramadol HCl | 18.7 | 75.0 |
| Capsule fill weight | | 400 |

The dissolution profiles of both formulations were obtained using 600 mL of SIF and the USP paddle method with monitoring at 271 nm, unchanged from previous dissolution trials. Placebos containing all materials in identical quantities without tramadol HCl were used as the reference in each case. The dissolution profiles obtained shown in FIGS. 23, 24, 25, 26 and 27.

Tramadol HCl was released over approximately 40 hr in both cases. The dissolution of 052/070, containing 23% Methocel® K 15M, was allowed to continue running for 95 hr to confirm the final absorbance achieved. It would have been expected that formulation 052/070, containing slightly more soluble matter, would have shown the faster release. It appears that there is little real difference in release rates at this level of HPMC content so the formulation containing 20% Methocel® K 15M was selected for use.

Example 14

HPLC Analysis of Tramadol HCl During Dissolution Testing

Tramadol HCl release during dissolution testing had been monitored to this point using the absorbance of the dissolution media at 271 nm (absorbance maximum for tramadol HCl at longest wavelength) as a function of the quantity of tramadol HCl released into solution. This approach was reasonable as the excipients used in formulations were either almost insoluble or had negligible absorbance at this wavelength. It was considered that tramadol HCl was fully released when the absorbance of the solution became constant. For 75 mg tramadol formulations and the system used, this meant that the absorbance would be in excess of 0.7 au. The absorbance profile would be composed of absorbance from tramadol HCl plus a small contribution from absorbance/scattering from the other excipients.

This trial subjected all of the formulations under consideration, at this point, to dissolution testing of two capsule samples (or twox two) with concurrent sampling and HPLC analysis for tramadol HCL. Sufficient samples for HPLC analysis were taken over the course of a dissolution run to allow a plot of absorbance profile versus quantity of tramadol HCl released to be constructed. This permitted the assumptions on absorbance profile versus release profile to be tested. The formulations tested are detailed below. FIG. 28 shows the combined absorbance profiles for three formulation followed by individual plots combining the percentage (of 75 mg) released into solution as determined by HPLC with the initial absorbance plot overlaid and normalized on the first or nearest position to 100% tramadol HCl release by HPLC (FIGS. 29, 30, 31, 32, 33, 34, 35, 36, 37, 38, 39, 40 and 41). This allows comparison of the quantity of tramadol HCl released and the quantity that would have been estimated from the absorbance plot as having been released. Note: The formulation reference details the exact quantities used in a particular set of samples. The same basic formula e.g. 55% of X plus 20% of Y plus 18% of Z, may appear as different formulation references as the quantities in a particular set vary slightly due to weighing variations.

| Formulation 052/072-1 | | |
|---|---|---|
| Material | % w/w | Quantity per cap mg |
| Beeswax | 59.3 | 237.0 |
| HPMC Pharmacoat 606 | 20.0 | 79.8 |
| Aerosil ® COK 84 | 2.0 | 8.0 |
| Tramadol HCl | 18.8 | 75.1 |
| Capsule fill weight | | 400 |

| Formulation 052/072-2 (Same as 052/019) | | |
|---|---|---|
| Material | % w/w | Quantity per cap mg |
| Gelucire 50/02 | 68.2 | 272.6 |
| Methocel ® K 100M | 10.0 | 40.1 |
| Aerosil ® COK 84 | 3.0 | 12.1 |
| Tramadol HCl | 18.7 | 74.8 |
| Capsule fill weight | | 400 |

| Formulation 052/073-3 | | |
|---|---|---|
| Material | % w/w | Quantity per cap mg |
| Cetyl alcohol | 67.9 | 271.5 |
| Methocel ® K 100M | 9.8 | 39.2 |
| Aerosil ® COK 84 | 3.9 | 15.8 |
| Tramadol HCl | 18.4 | 73.6 |
| Capsule fill weight | | 400 |

| Formulation 052/073-4 (Similar to 052/060) | | |
|---|---|---|
| Material | % w/w | Quantity per cap mg |
| Sterotex ® NF | 64.2 | 256.8 |
| Methocel ® K 15M | 15.0 | 60.1 |
| Aerosil ® COK 84 | 2.0 | 7.9 |
| Tramadol HCl | 18.8 | 75.2 |
| Capsule fill weight | | 400 |

| Formulation 052/073-5 | | |
|---|---|---|
| Material | % w/w | Quantity per cap mg |
| Cithrol ® GMS | 68.3 | 273.0 |
| Methocel ® K 100M | 10.0 | 40.1 |
| Aerosil ® COK 84 | 3.0 | 12.0 |
| Tramadol HCl | 18.7 | 74.9 |
| Capsule fill weight | | 400 |

| Formulation 052/074-6 | | |
|---|---|---|
| Material | % w/w | Quantity per cap mg |
| Hydrokote 112 | 63.2 | 252.7 |
| Methocel ® K 15M | 15.1 | 60.2 |
| Aerosil ® COK 84 | 3.0 | 12.2 |
| Tramadol HCl | 18.7 | 74.9 |
| Capsule fill weight | | 400 |

| Formulation 052/074-7 | | |
|---|---|---|
| Material | % w/w | Quantity per cap mg |
| Beeswax | 59.2 | 236.9 |
| Methocel ® K 15M | 20.0 | 80.1 |
| Aerosil ® COK 84 | 2.0 | 8.1 |
| Tramadol HCl | 18.7 | 74.9 |
| Capsule fill weight | | 400 |

TABLE 2

Formulation Release Data Summary from HPLC

| Formula | Base excipient | HPMC and % w/w | 100% release after approx (ex HPLC data) |
|---|---|---|---|
| 052/072-1 | Beeswax | 20% Pharmacoat 606 | 70-75% in 45 hr |
| 052/072-2 | Gelucire 50/02 | 10% Methocel ® K 100M | 15 hr |
| 052/073-3 | Cetyl alcohol | 10% Methocel ® K 100M | 15 hr |
| 052/073-4 | Sterotex ® NF | 15% Methocel ® K 15M | 38 hr |
| 052/073-5 | Cithrol ® GMS | 10% Methocel ® K 100M | 20 hr |
| 052/074-6 | Hydrokote 112 | 15% Methocel ® K 15M | 40 hr |
| 052/074-7 | Beeswax | 20% Methocel ® K 15M | 25 hr |

Overall the HPLC data correlated well with absorbance data confirming that the modification of formulations based on their absorbance profiles, minimizing delays that HPLC analysis would cause if applied to every sample, was a viable and acceptable approach. The above formulations cover a broad range of release profiles exceeding the 18-24 hr guide value for this project. At the present stage only the first beeswax formulation (52/072-1) is to be discontinued. Further modifications may arise during tamper resistance testing.

Example 15

Formulations 052/074-7, 052/093-3, 052/073-5 and 052/074-6 were remanufactured with Aerosil® COK 84 replaced in each with Aerosil® 200. The change in Aerosil® did not modify the dissolution profile or the tamper deterrence of the drug.

Tamper Resistance Testing

The popularity of extended release oxycodone among addicts and recreational drug users is due to a large amount of drug per tablet (12 hour supply). Commercially available immediate release opioid tablets and capsules are usually administered every 4 to 6 hours and they release their dose into the systemic circulation over one to two hours. New, extended release formulations are designed to gradually release their much larger opioid content over a 12 or 24-hour period.

Most recreational drug users and addicts have a unit of use which is one tablet or capsule. The 12 or 24-hour supply of opioid contained in one tablet or capsule, instead of 4 to 6 tablets or capsules means that there is a greater risk that such formulations may be highly sought by drug addicts and recreational drug users alike, for non-medical use. Intentional or inadvertent tampering from extended release formulations will rapidly deliver a massive dose and produce profound a variety of serious and life threatening side effects, including respiratory depression and failure, sedation, cardiovascular collapse, coma and death.

Addicts and recreational drug users commonly use extended release opioids by a variety of routes of administration. Commonly used methods include 1) parenteral (e.g., intravenous injection, where the drug is crushed and extracted or melted and the contents of a dosage unit then injected), 2) intranasal (e.g., snorting, where the drug is inhaled as powdered dosage unit), and 3) episodic or repeated oral ingestion of crushed product, where the drug is chewed to increase the surface area and permit rapid release of drug substance. All of these strategies are intended to more efficiently get the opioid into the CNS, both in terms of total amount of drug, peak concentration of drug and time to peak concentration of drug.

One mode of abuse involves the extraction of the opioid component from the dosage form by first mixing the table or capsule with a suitable solvent (e.g., water or alcohol), and then filtering and/or extracting the opioid component from the mixture for intravenous injection. Another mode of abuse of extended release opioids involves dissolving the drug in water, alcohol or another "recreational solvent" to hasten its release and to ingest the contents orally, in order to provide high peak concentrations and maximum euphoriant effects.

It is necessary to be able to measure resistance to the likely routes of abuse in a meaningful and relevant way. No standard set of tests exist with companies, interested in abuse resistance, generating their own particular set of tests. The series of tests chosen to evaluate abuse resistance and the source of the test were:

Extraction with Alcohol on Whole Dosage Unit

This method is based on US patent application 2004/0161382 A1 (P 11, [0122]). Method: Place a whole dosage unit in 18 mL of 0.1 N HCl in a 60 mL amber bottle and shake at 240 rpm on an orbital shaker for 30 min. After 30 min add 12 mL of ethanol (95-96%) to each bottle. Swirl by hand and remove a 1 mL sample from each bottle ($T_0$). Place the solutions back in the orbital shaker for further shaking at 240 rpm. Take 1 mL samples after 10, 20, 30, 40, 60 and 180 min of further shaking for each bottle. Analyze and graph the results on a linear scale of cumulative release (%) vs. time (min).

Extraction with Alcohol on a Crushed or Cut Dosage Unit

Extension of test in above patent. Method: Place a tablet (after crushing with a single crush with a spatula) or a capsule (cut in half) in 18 mL of 0.1N HCl in a 60 mL amber bottle and shake at 240 rpm on an orbital shaker for 30 min. Continue the test as in 1) above.

Extraction into Water

This method is based on US patent application 2004/0161382 A1 (P12, [0130]). Method: Crush with a mortar and pestle and grind in 5 mL of water for 5 minutes. The resulting suspension is filtered through a 0.45 micron filter into a flask and diluted to 50 mL with water. Quantify Tramadol HCl concentration by HPLC.

Freeze and Crush

Method: Freeze the dosage unit in a domestic freezer for 24 hr, then grind with a mortar and pestle for five minutes. Sieve through a suitable sieve (ca 600 micron) and, by weighing, measure the percentage passing the sieve.

Taste of Base Excipient Mix (Organoleptic Test)

Method: Chew a placebo mix for five minutes and rate the taste on a 0-10 scale with 0 as bland to repulsive at 10. This method is relevant only to dosage units containing taste modifiers.

Extraction into Acid

Method: Crush with a mortar and pestle and heat to boiling in 5 mL of vinegar. The resulting suspension is filtered through a 0.45 micron filter into a flask and diluted to 50 mL with water. Quantify tramadol HCl concentration by HPLC.

Application of Heat

Melting Temperature >50° C. or 55° C.

Method: Heat the squashed contents of a dosage unit on a hot plate until melted. Determine the temperature of melting and test whether the mix becomes sufficiently fluid to be drawn up into a syringe via a 1.2 mm needle then expelled. The formulations tested were the last six of those listed in Table 2 (omits the first sample 052/072-1). Dromadol® SR tablets were included into the testing for to allow comparison of the liquid filled dosage units with a commercial tramadol HCl prolonged release preparation. The results of testing are presented below.

Example 16

Extraction with Alcohol on Whole Dosage Unit

The results of this test are shown in FIG. 42.

Example 17

Extraction with Alcohol on Cut or Crushed Dosage Unit

The samples under test were reduced to four formulations plus the Dromadol® SR comparator at this point. The Cetyl alcohol based formulation (052/073-3) and Gelucire 50/02 (052/072-2) were deselected due to their dissolution release time of approx 15 hr to 100% release and their high extractable fraction, as seen in FIG. 42. Formulations showing a slower than target in vitro release profile may possibly show more rapid release in vivo due to the presence of digestion materials but is seems unlikely that formulations showing a faster than desirable in vitro dissolution rate will show a retarded rate in vivo.

The above two tests demonstrate that whole dosage units release their contents into alcohol relatively slowly but once crushed or cut the waxy liquid fill dosage unit is much harder to extract than the tablet. One single crush turns the Dromadol® tablet into an easily extractable powder. This feature would apply to any tablet. It should be noted that the apparent high quantity released at $T_0$ is due to the conditions specified in the method. The method requires an initial 30 min of shaking in 18 mL of 0.1N HCl before the addition of ethanol.

The time is defined in the method as starting from the addition of ethanol. The tramadol HCl, shown as released at $T_0$, has dissolved during the 30 min pre ethanol addition sample preparation. This test demonstrates that the liquid fill formulations are clearly superior in abuse resistance by ethanol extraction to an extended release tablet (FIG. 43).

Example 18

Extraction into Water Via Crushing and Grinding in Water

The four formulations continuing under test plus Dromadol® SR tablets were crushed and ground for 5 minutes in 5 mL of water to simulate extraction in preparation for swallowing or injection. The material was then filtered (by pressurizing a 45µ filter using an attached syringe) and diluted before quantifying by HPLC. The results are presented in Table 3 and 4 below with comments on the mix produced after grinding given below.

TABLE 3

| Product | Observations |
|---|---|
| Dromadol® SR tablet | Ground easily and formed a mobile easily filtered solution. |
| Sterotex® NF formulation 052/073-4 | Difficult to grind, forms a light paste that filtered slowly. |
| Cithrol® GMS formulation 052/073-5 | Difficult to grind, forms a light paste that filtered very slowly. |
| Hydrokote 112 formulation 052/074-6 | Difficult to grind, forms a light paste that filtered very slowly. |
| Beeswax formulation 052/074-7 | Difficult to grind, forms a light paste that filtered relatively easily |

The Dromadol® SR tablet crushed easily and produced a solution that filtered in a matter of seconds while the beeswax formed a light paste, with difficulty, which took approximately five minutes to filter. This difficulty of preparation was common to the other capsule samples with filtration time graduating from the five minutes of the beeswax sample to over 60 minutes for the Cithrol® GMS sample. All liquid fill samples gave much greater difficulty in grinding and filtering than the tablet sample.

TABLE 4

Percentage release on extraction into water.

| Base excipient | Formulation | % released on extraction |
|---|---|---|
| Dromadol® SR tablets | n/a | 84.0 |
| Sterotex® NF | 052/073-4 | 38.7 |
| Cithrol® GMS | 052/073-5 | 17.1 |
| Hydrokote 112 | 052/074-6 | 24.5 |
| Beeswax | 052/074-7 | 30.1 |

The HPLC data shows that tramadol HCl was easily extracted from the tablet, as would be expected as a tablet crushes easily to give a large surface area from which extraction can take place. Extraction from the liquid fill formulation was reduced considerably due to the waxy nature of the base excipients and the inclusion of HPMC which caused the liquid extracts to turn into a filtration resistant light paste.

Example 19

Extraction into Acid Water Via Crushing and Grinding in Dilute Acetic Acid

Dilute acetic acid (6% w/w glacial acetic in water) was used to simulate the vinegar that drug abusers may use when extracting dosage units for injection. Dosage units were crushed forcibly 2-3 times in a mortar and pestle then transferred to a small beaker where 5 mL of the above dilute acetic acid was added. The mix was heated to boiling on a hotplate and held boiling for 5-10 s. The mix was allowed to cool to room temperature, the resulting solution filtered through a 45µ filter, as above, the solution diluted to volume and the content of tramadol HCl determined by HPLC. The assay results are shown below expressed as a percentage of the contents released into solution.

TABLE 5

Percentage release on extraction into dilute acid.

| Base excipient | Formulation | % released on extraction |
|---|---|---|
| Dromadol® SR tablets | n/a | 83.9 |
| Sterotex® NF | 052/073-4 | 29.3 |
| Cithrol® GMS | 052/073-5 | 41.7 |
| Hydrokote 112 | 052/074-6 | 30.2 |
| Beeswax | 052/074-7 | 17.6 |

Tramadol HCl was easily extracted from the tablet. All liquid fill formulations showed appreciably better resistance to extraction. The waxy mass of the four test formulations coalesced on melting and floated as a mass on the surface. The HPMC content of the mass is insoluble above 40° C. so, instead of its normal property of assisting release at room temperature, it actively prevents release at this temperature by helping to hold the molten mass together. The tramadol HCl migrates relatively slowly to the surface when boiling agitates the mass while the powdered tablet releases most of its content instantly. It is easily understood why the formulated capsule dosages give superior extraction resistance to that of tablets.

Example 20

Effect of Heat on Dosage Units

Tablets can be crushed and extracted easily while soft gel contents have been known to be liquefied by slight warming (to about 40° C.) and the contents injected directly. This test records the temperature at which the meltable excipients in a formulation have liquefied and tests whether this material can be sucked into a syringe and ejected as would take place during an injection. Formulated material was placed in a beaker then slowly warmed in a water bath. The mix temperature was recorded with a calibrated thermocouple. The results are listed in Table 5 below.

TABLE 6

Melting point range and potential for direct injection

| Base excipient | Excipient mp | Formulation | Formulation melted | Comment |
|---|---|---|---|---|
| Sterotex® NF | 61-66° C. | 052/073-4 | 65° C. | Light cream, can't suck into syringe, sets instantly in needle tip |

TABLE 6-continued

Melting point range and potential for direct injection

| Base excipient | Excipient mp | Formulation | Formulation melted | Comment |
|---|---|---|---|---|
| Cithrol ® GMS | 55-60° C. | 052/073-5 | 58° C. | Light cream, can't suck into syringe, sets instantly in needle tip |
| Hydrokote 112 | 43-46° C. | 052/074-6 | 45° C. | Viscous paste, can suck and eject about 5 mm of material from needle |
| Beeswax | 61-66° C. | 052/074-7 | 66° C. | Viscous paste, can't suck into syringe, sets instantly in needle tip |

All of the mixes melted around the melting points of the base excipients and, due to this elevated melting point, none could be effectively introduced into a syringe nor could be ejected (or injected).

Example 21

Modification to Increase Resistance to Powdering

It was observed during this trial that the Sterotex NF formulation can be powdered with careful crushing. This occurs to a lesser extent with the Cithrol® GMS and Hydrokote 112 formulations. It was desirable to decrease the ease with which this formulation could be powdered. Both the Sterotex® NF and Hydrokote 112 formulations gave full release of tramadol HCl in 38-40 hr during dissolution testing. It would therefore be acceptable to add modifiers that decrease the ease of crumbling formulated material into a powder even if these accelerated release. Several materials were tested including small levels of beeswax, adding hydrophilic liquids such as maltitol or glucose syrup or adding surfactants such as Crillet 4. The addition of hydrophilic liquids or surfactants immediately turned the mix into a lumpy unfillable mass by binding the powder content together. The use of these liquids was discontinued.

Formulations containing Sterotex® NF with increased level of HPMC to accelerate dissolution plus 0, 5% and 10% beeswax were produced for examination of any change in resistance to powdering. The dissolution profiles of each formulation were recorded as the absorbance curve via UV monitoring at 271 nm as previously. The formulas used are show below. The dissolution results are show in FIG. 44.

| Formulation 052/087-1 | | |
|---|---|---|
| Material | % w/w | Quantity per cap mg |
| Sterotex ® NF | 60.3 | 241.0 |
| Methocel ® K 15 M | 20.0 | 80.0 |
| Aerosil ® COK 84 | 1.0 | 4.0 |
| Beeswax | 0.0 | 0.0 |
| Tramadol HCl | 18.8 | 75.0 |
| Capsule fill weight | | 400 |

| Formulation 052/087-2 | | |
|---|---|---|
| Material | % w/w | Quantity per cap mg |
| Sterotex ® NF | 55.3 | 221.0 |
| Methocel ® K 15 M | 20.0 | 80.0 |
| Aerosil ® COK 84 | 1.0 | 4.0 |
| Beeswax | 5.0 | 20.0 |
| Tramadol HCl | 18.8 | 75.0 |
| Capsule fill weight | | 400 |

| Formulation 052/087-3 | | |
|---|---|---|
| Material | % w/w | Quantity per cap mg |
| Sterotex ® NF | 50.3 | 201.2 |
| Methocel ® K 15 M | 20.0 | 79.9 |
| Aerosil ® COK 84 | 1.0 | 4.0 |
| Beeswax | 10.0 | 40.0 |
| Tramadol HCl | 18.8 | 74.9 |
| Capsule fill weight | | 400 |

The Sterotex® formulation without beeswax showed considerable variability. The addition of 5% or 10% beeswax significantly increased the rate of release to an approximate time for full release of 25 hr. There was no meaningful difference in release rate between either formulation containing added beeswax so the formulation containing 10% beeswax (052/087-3) was selected for inclusion in subsequent trials.

Example 22

Ease of Powdering and Percentage of Resultant Particles of 650 Micron or Less

Capsules were initially powdered at room temperature as an indicative guide and for comparison with subsequent frozen samples. The contents were removed from the capsules and ground until the finest powder achievable had been formed. The stated period of five minutes was not normally required and it was observed that excessive grinding could cause the particles to start to coalesce. The data obtained is shown in Table 7.

TABLE 7

Powder generation by grinding of formulated material at RT

| Base Excipient | Formulation | Comment | % as 650 µ or less |
|---|---|---|---|
| Dromadol ® SR tablet | | | 64.2% |
| Dromadol ® SR tablet | | Repeat sample | 79.9% |
| Sterotex ® NF | 052/087-1 | 0% beeswax | 84.7% |
| Sterotex ® NF | 052/087-3 | Plus 10% beeswax | 84.8% |
| Cithrol ® GMS | 052/073-5 | | 86.9% |
| Hydrokote 112 | 052/074-6 | | 2.1% |
| Beeswax | 052/074-7 | | 1.9% |

The test was repeated using capsules that had been cooled in a domestic freezer. The results of this trial are shown in Table 8.

TABLE 8

Powder generation by grinding of formulated material cooled to domestic freezer temperatures

| Base Excipient | Formulation | Comment | % as 650 µ or less |
|---|---|---|---|
| Dromadol ® SR tablet | | | 70.6% |
| Sterotex ® NF | 052/073-4 | | 78.8% |
| Sterotex ® NF | 052/087-3 | Plus 10% beeswax | 82.1% |
| Cithrol ® GMS | 052/073-5 | | 85.7% |
| Hydrokote 112 | 052/074-6 | | 5.5% |
| Beeswax | 052/074-7 | | 1.5% |

There was little significant difference, within experimental variation, between the results obtained at room temperature and that obtained from dosage units frozen to domestic freezer temperature (−20° C.). The Dromadol® SR tablet ground to a fine powder relatively easily. The Sterotex® NF and Cithrol® GMS formulations also produced similar amounts of fine powder. The incorporation of 10% beeswax in one of the Sterotex® NF formulations made to detectable difference. The beeswax and Hydrokote 112 formulations provided excellent resistance against powdering.

Example 23

Sterotex® NF Formulation Modification to Enhance Resistance to Powdering

Further modifications were made to the Sterotex® NF based formulation, using fractionated coconut oil, to improve resistance to powdering. Samples were prepared substituting 15, 20 and 25% of Sterotex® NF for fractionated coconut oil. The formulations used were as listed below.

| | Formulation 052/093-1 | |
|---|---|---|
| Material | % w/w | Quantity per cap mg |
| Sterotex ® NF | 45.2 | 180.8 |
| Fractionated coconut oil | 15.0 | 59.9 |
| Methocel ® K 15 M | 20.0 | 80.1 |
| Aerosil ® COK 84 | 1.0 | 4.1 |
| Tramadol HCl | 18.8 | 75.1 |
| Capsule fill weight | | 400 |

| | Formulation 052/093-2 | |
|---|---|---|
| Material | % w/w | Quantity per cap mg |
| Sterotex ® NF | 40.2 | 160.8 |
| Fractionated coconut oil | 20.0 | 79.9 |
| Methocel ® K 15 M | 20.0 | 79.9 |
| Aerosil ® COK 84 | 1.0 | 4.2 |
| Tramadol HCl | 18.8 | 75.1 |
| Capsule fill weight | | 400 |

| | Formulation 052/094-3 | |
|---|---|---|
| Material | %w/w | Quantity per cap mg |
| Sterotex ® NF | 35.3 | 141.0 |
| Fractionated coconut oil | 25.0 | 100.0 |
| Methocel ® K 15 M | 19.9 | 79.8 |
| Aerosil ® COK 84 | 1.0 | 4.1 |
| Tramadol HCl | 18.8 | 75.0 |
| Capsule fill weight | | 400 |

Example 24

The test to quantify the ease of powdering, Test 3, was repeated using capsules that had been cooled in a domestic freezer. The results of this trial are shown in table 8 below.

TABLE 9

Powder generation from Sterotex ® NF formulations containing fractionated coconut oil by grinding of formulated material cooled to domestic freezer temperatures

| Base Excipient | Formulation | Comment | % as 650µ or less |
|---|---|---|---|
| Sterotex ® NF | 052/073-4 | Data from Table 6 | 78.8% |
| Sterotex ® NF | 052/093-1 | Plus 15% fractionated coconut oil | 49.7% |
| Sterotex ® NF | 052/093-2 | Plus 20% fractionated coconut oil | 33.7% |
| Sterotex ® NF | 052/094-4 | Plus 25% fractionated coconut oil | 8.3% |

The addition of fractionated coconut oil produced the desired effect in decreasing the ability to grind cooled formulated mix into a powder. The hot mix remained a machine fillable light cream. The melting point of the 25% mix had decreased from the 65° C. melting point of a Sterotex® NF mix with zero added fractionated coconut oil to an acceptable 62° C. for the mix containing 25%.

Example 25

Abuse Resistance Testing

Re-Evaluation of Modified Sterotex® NF Combinations

Further testing was required, after revising the Sterotex® NF formulation by substituting part of the Sterotex® NF for fractionated coconut oil, to determine how this change had affected the other parameters.

Dissolution testing was carried out, in the same manner as previously; using the USP paddle method to obtain the dissolution profiles of the Sterotex® NF formulations with and without additional fractionated coconut oil. This plot is shown below in FIG. 45

Example 26

Tests for ethanol extraction of whole and crushed or cut dosage units were also repeated. Sterotex® NF with 25% fractionated coconut oil (052/094-3) was tested alongside the fractionated coconut oil free analogue (052/087-1). The opportunity was taken to test some additional relevant samples. The three previously tested formulations based on Cithrol® GMS (052/073-5), Hydrokote 112 (052/074-6) and the beeswax formulation (052/074-7) were retested. Zydol® XL 150 tablets were substituted for the previously used Dromadol® SR tablets. Both of these are slow release formulations containing 150 mg of tramadol HCl. OxyContin® extended release 80 mg tablets were included for comparison purposes as oxycodone extended release tablets are the subject of current concerns over tablet abuse and they provide another tablet comparator containing a similar quantity of water soluble active in a slow release formula. The results of ethanol extraction of whole dosage units and cut/crushed dosage units are shown below in FIGS. 46 and 47, respectively.

The Sterotex® NF formulation containing 25% fractionated coconut oil did show increased susceptibility to ethanol extraction compared with the formulation without fractionated coconut oil however this was demonstrably much better than the tablets or the Cithrol® GMS formulation so was considered as acceptable. The quantities extracted were broadly in line with that determined in the earlier ethanol extraction tests, shown in FIGS. 42 and 43. The Zydol® XL 150 tablets showed comparable release to the Dromadol® SR tablets in the earlier test. The OxyContin® tablets showed much greater and faster release than any of the dosage units in either of these sets of tests.

Example 27

The abuse resistance test involving extraction into water by grinding a dosage unit in a mortar and pestle with subsequent filtration was repeated. All of the samples included in the above ethanol extraction tests were included. Table 10 shows the results of HPLC analysis of the filtrate expressed as the percentage of drug substance released. The results are also depicted in Left Panel of FIG. 58 (the bars from left to right are Formulation 052/094-3, Formulation 052/073-5, Formulation 052/074-7, Formulation 052/074-6, Zydol XL® 150 mg and OxyContin® 80 mg, respectively).

TABLE 10

Percentage release on extraction into water.

| Base excipient | Formulation | % released on extraction |
|---|---|---|
| Zydol ® XL 150 | n/a | 87.4 |
| OxyContin ® 80 mg | n/a | 90.0 |
| Sterotex ® NF | 052/087-1 | 28.1 |
| Sterotex ® NF with 25% fr. coconut oil | 052/094-3 | 11.6 |
| Cithrol ® GMS | 052/073-5 | 15.3 |
| Hydrokote 112 | 052/074-6 | 23.1 |
| Beeswax | 052/074-7 | 18.6 |

Example 28

The abuse resistance test involving extraction into dilute acetic acid by heating to boiling was repeated. The same samples as immediately above were tested and the results of HPLC analysis of the resulting filtrates are shown in Table 11. The results are also depicted in Right Panel of FIG. 58 (the bars from left to right are Formulation 052/094-3, Formulation 052/074-6, Formulation 052/074-7, Formulation 052/073-5, Zydol XL® 150 mg and OxyContin® 80 mg, respectively)

TABLE 11

Percentage release on extraction into dilute acid.

| Base excipient | Formulation | % released on extraction |
|---|---|---|
| Zydol ® XL 150 | n/a | 87.4 |
| OxyContin ® 80 mg | n/a | 82.2 |
| Sterotex ® NF | 052/087-1 | 10.8 |
| Sterotex ® NF with 25% fr. coconut oil | 052/094-3 | 7.0 |
| Cithrol ® GMS | 052/073-5 | 34.9 |
| Hydrokote 112 | 052/074-6 | 11.1 |
| Beeswax | 052/074-7 | 14.5 |

Both sets of results gave similar results for comparable formulations in this and the earlier set of tests. All liquid fill formulations were significantly superior to any of the three commercial tablets formulations.

Example 29

Ease of Powdering and Percentage of Resultant Particles of 600 Micron or Less

Initial powdering tests were carried out using a laboratory stainless steel sieve of nominal 650 micron size. The sieve size used had been qualitatively determined as a size that could differentiate between the powders generated. Initially much finer sieves had been tested but were found to be too fine e.g. a 45 micron sieve was tested but this was too fine resulting in almost zero powder passing through the sieve from any samples. As result of the initial tests, a certified sieve was obtained of 600 micron size for further trials. All of the above samples were subjected to the powdering test. The results are shown in Table 12.

TABLE 12

Powder generation of formulations and comparator tablets by grinding of dosage units cooled to domestic freezer temperatures

| Base Excipient | Formulation | Comment | % as 600µ or less. Sample 1 | % as 600µ or less. Sample 2 |
|---|---|---|---|---|
| Dromadol ® SR | n/a | | 48.1% | 51.9% |
| Zydol ® XL 150 | n/a | | 52.6% | 41.2% |
| OxyContin ® 80 mg | n/a | | 66.6% | Not tested |
| Sterotex ® NF with 25% fr. coconut oil | 052/094-3 | With 25% fractionated coconut oil | 2.2% | 0.6% |
| Cithrol ® GMS | 052/073-5 | | 40.3% | 72.4% |
| Hydrokote 112 | 052/074-6 | | 7.3% | 2.6% |
| Beeswax | 052/074-7 | | 0.7% | 0.6% |

It should be noted that the lower results found in this trial than those reported previously are due to a slightly finer sieve size being used. The tablets all powdered relatively easily while the Sterotex® NF, Hydrokote 112 and beeswax were very resistant to powdering. The Cithrol® GMS gave a high quantity of powder. The same approach of adding a room temperature oil could be used on the Cithrol® GMS as used on Sterotex® NF however, with the Cithrol® GMS formulation showing a release rate of approximately 20 hr, on the fast size of the target 24 hr, it was decided not to amend it at this stage.

Example 30

Dissolution Testing of Stored Samples

Samples of the above formulations were stored for a period of at least four weeks at room temperature (in some cases much longer) after which their dissolution release profile was redetermined. This was carried out to find out if there were any short term changes in the release rate. The tested formulations are shown in Table 13 and FIGS. 48 to 57.

TABLE 13

Formulations used for dissolution testing after a minimum of 4 weeks storage.

| Base Excipient | Formulation | Storage period days | Comment |
|---|---|---|---|
| Sterotex ® N | 052/087-1 | 75 | 20% HPMC |
| Sterotex ® NF with 25% fr. coconut oil | 052/094-3 | 71 | |
| Cithrol ® GMS | 052/073-5 | 95 | |
| Hydrokote 112 | 052/074-6 | 98 | |
| Beeswax | 052/074-7 | 83 | |

Manufacturing methods described above and others are utilized for the preparation of other abusable drugs as shown in the prophetic examples below. Variations to the methods may be employed, in some embodiments, depending on the specific chemical, physicochemical, pharmaceutical and pharmacologic properties of the abusable drug, excipients and their interaction and other factors. Compositions and methods of the present invention provide: (i) abuse deterrence; (ii) extended release; and/or (iii) protection against alcohol dose dumping; and/or (iv) protection against significant changes in bioavailability due to fed or fasted states; and/or (v) simultaneously providing more than one of foregoing (i) to (iv); wherein the dosage form is prepared using compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof.

As shown in further examples below, any abusable drug of the invention may be prepared to provide (i) abuse deterrence; or (ii) extended release; or (iii) resistance against alcohol dose dumping; or (iv) resistance against alcohol dose dumping when formulated as extended release; or (v) protection against significant changes in bioavailability due to fed or fasted states; or (vi) more than one of the foregoing properties; said invention comprising one or more abusable drugs and one or more ADER agents; said invention, in some embodiments, providing further abuse deterrence through the use of aversive agents; said invention, in some embodiments, using substantially the same ADER agents to achieve the foregoing (i) to (v); said invention, in some embodiments, providing more than one of the foregoing properties; said invention, in some embodiments, comprising one or more abusable drugs and at least two ADER agents; said invention, in some embodiments, comprising at least two ADER agents selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes; said invention, in some embodiments, comprising at least two ADER agents selected from at least two categories from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes; said invention, in some embodiments, further comprising an immediate release form of the abusable drug; said invention, in some embodiments, further comprising an immediate release form of the abusable drug in solution; said invention, in some embodiments, simultaneously providing more than one of foregoing (i) to (v); said invention, in some embodiments, simultaneously providing more than one of foregoing (i) to (v) using substantially the same ADER agents.

Example 31

| Ingredients | Quantity (mg)/Dose |
|---|---|
| Sterotex ® NF | 200 |
| Fractionated coconut oil | 70 |
| Methocel ® K 15M | 81 |
| Aerosil ® COK 84 | 4 |
| Hydromorphone HCl | 20 |
| Capsule fill weight | 375 |

Example 32

| Ingredients | Quantity (mg)/Dose |
|---|---|
| Sterotex ® NF | 135 |
| Fractionated coconut oil | 50 |
| Methocel ® K 15M | 60 |
| Aerosil ® COK 84 | 3 |
| Fentanyl HCl | 2 |
| Capsule fill weight | 250 |

Example 33

| Ingredients | Quantity (mg)/Dose |
|---|---|
| Sterotex ® NF | 170 |
| Fractionated coconut oil | 100 |
| Methocel ® K 15M | 70 |
| Aerosil ® COK 84 | 4.5 |
| Levorphanol | 5.5 mg |
| Capsule fill weight | 350 |

Example 34

| Ingredients | Quantity (mg)/Dose |
|---|---|
| Sterotex ® NF | 200 |
| Fractionated coconut oil | 90 |
| Methocel ® K 15M | 80 |
| Aerosil ® COK 84 | 5 |
| Hydrocodone | 25 |
| Capsule fill weight | 400 mg |

Example 35

| Ingredients | Quantity (mg)/Dose |
|---|---|
| Beeswax | 200 |
| HPMC, K15M | 80 |
| Aerosil COK 84 | 8 |
| Levorphanol Tartrate | 12 |
| Capsule fill weight | 300 |

Example 36

| Ingredients | Quantity (mg)/Dose |
|---|---|
| Sterotex NF | 150 |
| HPMC, K15M | 75 |
| Coconut oil | 75 |
| Aerosil COK 84 | 5 |
| Oxymorphone | 20 |
| Capsule fill weight | 325 |

Example 37

| Ingredients | Quantity (mg)/Dose |
|---|---|
| Cithrol GMS | 275 |
| HPMC, K100M | 40 |
| Aerosil COK 84 | 10 |
| Methadone | 25 |
| Capsule fill weight | 350 |

Example 38

| Ingredients | Quantity (mg)/Dose |
|---|---|
| Hydrokote 112 | 250 |
| HPMC, K15M | 60 |
| Aerosil COK 84 | 10 |
| Morphine | 30 |
| Capsule fill weight | 350 |

Example 39

| Ingredients | Quantity (mg)/Dose |
|---|---|
| Beeswax | 200 |
| HPMC, Pharmacoat 606 | 62.5 |
| Aerosil COK 84 | 7.5 |
| Hydrocodone | 30 |
| Capsule fill weight | 300 |

Example 40

| Ingredients | Quantity (mg)/Dose |
|---|---|
| Gelucire 50/02 | 190 |
| Methocel K 100M | 35 |
| Aerosil COK 84 | 10 |
| Hydromorphone HCl | 15 |
| Capsule fill weight | 250 |

Example 41

| Ingredients | Quantity (mg)/Dose |
|---|---|
| Cetyl alcohol | 280 |
| Methocel K 100M | 50 |
| Aerosil COK 84 | 10 |
| Levorphanol | 10 |
| Capsule fill weight | 350 |

Example 42

| Ingredients | Quantity (mg)/Dose |
|---|---|
| Sterotex NF | 320 |
| Methocel K 15M | 60 |
| Aerosil COK 84 | 10 |
| Oxycodone | 10 |
| Capsule fill weight | 400 |

Example 43

| Ingredients | Quantity (mg)/Dose |
|---|---|
| Cithrol GMS | 320 |
| Methocel K 100M | 55 |
| Aerosil COK 84 | 15 |
| Oxymorphone | 10 |
| Capsule fill weight | 400 |

Example 44

| Ingredients | Quantity (mg)/Dose |
|---|---|
| Hydrokote 112 | 225 |
| Methocel K 15M | 50 |
| Aerosil COK 84 | 10 |
| Hydrocodone | 15 |
| Capsule fill weight | 300 |

Example 45

| Ingredients | Quantity (mg)/Dose |
|---|---|
| Beeswax | 225 |
| Methocel K 15M | 75 |
| Aerosil COK 84 | 10 |
| Dihydrocodeine | 15 |
| Capsule fill weight | 325 |

Example 46

| Ingredients | Quantity (mg)/Dose |
|---|---|
| Beeswax | 10 |
| HPMC, K15M | 80 |
| Aerosil COK 84 | 8 |
| Remifentanil | 2 |
| Capsule fill weight | 300 |

Example 47

| Ingredients | Quantity (mg)/Dose |
|---|---|
| Sterotex NF | 166 |
| HPMC, K15M | 75 |
| Coconut oil | 75 |
| Aerosil COK 84 | 5 |
| Sufentanil | 4 |
| Capsule fill weight | 325 |

Example 48

| Ingredients | Quantity (mg)/Dose |
|---|---|
| Cithrol GMS | 285 |
| HPMC, K100M | 49 |
| Aerosil COK 84 | 10 |
| Alfentanil | 6 |
| Capsule fill weight | 350 |

Example 49

| Ingredients | Quantity (mg)/Dose |
|---|---|
| Hydrokote 112 | 240 |
| HPMC, K15M | 50 |
| Aerosil COK 84 | 10 |
| Propiram HCl | 100 |
| Capsule fill weight | 400 |

Example 50

| Ingredients | Quantity (mg)/Dose |
|---|---|
| Beeswax | 195 |
| HPMC, Pharmacoat 606 | 45 |
| Aerosil COK 84 | 10 |
| Propiram | 150 |
| Capsule fill weight | 400 |

Example 51

| Ingredients | Quantity (mg)/Dose |
|---|---|
| Gelucire 50/02 | 190 |
| Methocel K 100M | 30 |
| Aerosil COK 84 | 10 |
| Hydromorphone HCl | 20 |
| Capsule fill weight | 250 |

Example 52

| Ingredients | Quantity (mg)/Dose |
|---|---|
| Cetyl alcohol | 290 |
| Methocel K 100M | 50 |
| Aerosil COK 84 | 10 |
| Hydrocodone | 50 |
| Capsule fill weight | 400 |

Example 53

| Ingredients | Quantity (mg)/Dose |
|---|---|
| Sterotex NF | 320 |
| Methocel K 15M | 60 |
| Aerosil COK 84 | 10 |
| Oxymorphone | 40 |
| Capsule fill weight | 430 |

Example 54

| Ingredients | Quantity (mg)/Dose |
|---|---|
| Cithrol GMS | 320 |
| Methocel K 100M | 68 |
| Aerosil COK 84 | 12 |
| Oxycodone | 60 |
| Capsule fill weight | 460 |

Example 55

| Ingredients | Quantity (mg)/Dose |
|---|---|
| Hydrokote 112 | 225 |
| Methocel K 15M | 50 |
| Aerosil COK 84 | 10 |
| Methadone | 40 |
| Capsule fill weight | 325 |

Example 56

| Ingredients | Quantity (mg)/Dose |
|---|---|
| Beeswax | 235 |
| Methocel K 15M | 75 |
| Aerosil COK 84 | 14 |
| Codeine $SO_4$ | 150 |
| Capsule fill weight | 474 |

Example 57

| Ingredients | Quantity (mg)/Dose |
|---|---|
| Beeswax | 200 |
| HPMC, K15M | 90 |
| Aerosil COK 84 | 10 |
| Pentazocine | 100 |
| Capsule fill weight | 40 |

Example 58

| Ingredients | Quantity (mg)/Dose |
| --- | --- |
| Sterotex NF | 150 |
| HPMC, K15M | 75 |
| Coconut oil | 80 |
| Aerosil COK 84 | 10 |
| Anleridine | 100 |
| Capsule fill weight | 415 |

Example 59

| Ingredients | Quantity (mg)/Dose |
| --- | --- |
| Cithrol GMS | 290 |
| HPMC, K100M | 48 |
| Aerosil COK 84 | 12 |
| Lofentanil | 0.1 |
| Capsule fill weight | 350.1 |

Example 60

| Ingredients | Quantity (mg)/Dose |
| --- | --- |
| Hydrokote 112 | 270 |
| HPMC, K15M | 65 |
| Aerosil COK 84 | 15 |
| Carfentanil | 0.2 |
| Capsule fill weight | 350.2 |

Example 61

| Ingredients | Quantity (mg)/Dose |
| --- | --- |
| Beeswax | 177 |
| HPMC, Pharmacoat 606 | 60 |
| Aerosil COK 84 | 10 |
| Fentanyl | 3 |
| Capsule fill weight | 250 |

Example 62

| Ingredients | Quantity (mg)/Dose |
| --- | --- |
| Gelucire 50/02 | 190 |
| Methocel K 100M | 40 |
| Aerosil COK 84 | 10 |
| Alfentanil | 10 |
| Capsule fill weight | 250 |

Example 63

| Ingredients | Quantity (mg)/Dose |
| --- | --- |
| Cetyl alcohol | 270 |
| Methocel K 100M | 50 |
| Aerosil COK 84 | 10 |
| Buprenorphine | 20 |
| Capsule fill weight | 350 |

Example 64

| Ingredients | Quantity (mg)/Dose |
| --- | --- |
| Sterotex NF | 293 |
| Methocel K 15M | 45 |
| Aerosil COK 84 | 10 |
| Sufentanil | 2 |
| Capsule fill weight | 350 |

Example 65

| Ingredients | Quantity (mg)/Dose |
| --- | --- |
| Cithrol GMS | 325 |
| Methocel K 100M | 55 |
| Aerosil COK 84 | 15 |
| Fentanyl | 5 |
| Capsule fill weight | 400 |

Example 66

| Ingredients | Quantity (mg)/Dose |
| --- | --- |
| Hydrokote 112 | 225 |
| Methocel K 15M | 50 |
| Aerosil COK 84 | 10 |
| Hydrocodone | 15 |
| Capsule fill weight | 300 |

Example 67

| Ingredients | Quantity (mg)/Dose |
| --- | --- |
| Beeswax | 225 |
| Methocel K 15M | 75 |
| Aerosil COK 84 | 10 |
| Racemorphan | 20 |
| Capsule fill weight | 330 |

Example 68

| Ingredients | Quantity (mg)/Dose |
| --- | --- |
| Sterotex ® NF | 100 |
| Fractionated coconut oil | 70 |

-continued

| Ingredients | Quantity (mg)/Dose |
|---|---|
| Beeswax | 100 |
| Methocel ® K 15M | 81 |
| Aerosil ® COK 84 | 4 |
| Hydromorphone HCl | 20 |
| Capsule fill weight | 375 |

Example 69

| Ingredients | Quantity (mg)/Dose |
|---|---|
| Sterotex ® NF | 135 |
| Fractionated coconut oil | 50 |
| Beeswax | 50 |
| Methocel ® K 15M | 60 |
| Aerosil ® COK 84 | 3 |
| Fentanyl HCl | 2 |
| Capsule fill weight | 300 |

Example 70

| Ingredients | Quantity (mg)/Dose |
|---|---|
| Sterotex ® NF | 130 |
| Fractionated coconut oil | 100 |
| Beeswax | 70 |
| HPMC, K15M | 20 |
| Methocel ® K 15M | 70 |
| Aerosil ® COK 84 | 4.5 |
| Levorphanol | 5.5 mg |
| Capsule fill weight | 400 |

Example 71

| Ingredients | Quantity (mg)/Dose |
|---|---|
| Sterotex ® NF | 150 |
| Fractionated coconut oil | 80 |
| Cithrol GMS | 120 |
| HPMC, K100M | 20 |
| Methocel ® K 15M | 80 |
| Aerosil ® COK 84 | 5 |
| Methadone | 60 |
| Capsule fill weight | 515 mg |

Example 72

| Ingredients | Quantity (mg)/Dose |
|---|---|
| Beeswax | 150 |
| HPMC, K15M | 80 |
| Aerosil COK 84 | 10 |
| Cithrol | 150 |
| Levorphanol Tartrate | 20 |
| Capsule fill weight | 410 |

Example 73

| Ingredients | Quantity (mg)/Dose |
|---|---|
| Beeswax | 150 |
| HPMC, K15M | 80 |
| Aerosil COK 84 | 15 |
| Hydrokote 112 | 75 |
| Morphine Sulfate | 60 |
| Capsule fill weight | 380 |

Example 74

| Ingredients | Quantity (mg)/Dose |
|---|---|
| Sterotex NF | 150 |
| HPMC, K15M | 75 |
| Coconut oil | 75 |
| Aerosil COK 84 | 5 |
| Oxymorphone | 20 |
| Hydrokote 112 | 75 |
| Capsule fill weight | 400 |

Example 75

| Ingredients | Quantity (mg)/Dose |
|---|---|
| Cithrol GMS | 275 |
| HPMC, K100M | 50 |
| Aerosil COK 84 | 15 |
| Hydrokote 112 | 100 |
| Methadone | 60 |
| Capsule fill weight | 500 |

Example 76

| Ingredients | Quantity (mg)/Dose |
|---|---|
| Cithrol GMS | 275 |
| HPMC, K100M | 60 |
| Aerosil COK 84 | 15 |
| Gelucire 50/02 | 100 |
| Methadone | 25 |
| Capsule fill weight | 475 |

Example 77

| Ingredients | Quantity (mg)/Dose |
|---|---|
| Gelucire 50/02 | 140 |
| Methocel K 100M | 35 |
| Aerosil COK 84 | 15 |
| Sterotex ® NF | 75 |
| Fractionated coconut oil | 45 |
| Hydromorphone HCl | 15 |
| Capsule fill weight | 325 |

Example 78

| Ingredients | Quantity (mg)/Dose |
|---|---|
| Gelucire 50/02 | 100 |
| Methocel K 100M | 28 |
| Aerosil COK 84 | 12 |
| Beeswax | 125 |
| HPMC, K15M | 65 |
| Levorphanol Tartrate | 30 |
| Capsule fill weight | 370 |

Example 79

| Ingredients | Quantity (mg)/Dose |
|---|---|
| Gelucire 50/02 | 200 |
| Methocel K 100M | 60 |
| Aerosil COK 84 | 20 |
| Cithrol GMS | 140 |
| Oxycodone HCl | 80 |
| Capsule fill weight | 500 |

Example 80

| Ingredients | Quantity (mg)/Dose |
|---|---|
| Sterotex ® NF | 200 |
| Fractionated coconut oil | 70 |
| Methocel ® K 15M | 81 |
| Aerosil ® COK 84 | 4 |
| Dronabinol | 20 |
| Capsule fill weight | 375 |

Example 81

| Ingredients | Quantity (mg)/Dose |
|---|---|
| Sterotex ® NF | 135 |
| Fractionated coconut oil | 50 |
| Methocel ® K 15M | 60 |
| Aerosil ® COK 84 | 3 |
| Nabilone | 2 |
| Capsule fill weight | 250 |

Example 82

| Ingredients | Quantity (mg)/Dose |
|---|---|
| Sterotex ® NF | 170 |
| Fractionated coconut oil | 100 |
| Methocel ® K 15M | 70 |
| Aerosil ® COK 84 | 4.5 |
| THC | 5.5 mg |
| Capsule fill weight | 350 |

Example 83

| Ingredients | Quantity (mg)/Dose |
|---|---|
| Sterotex ® NF | 200 |
| Fractionated coconut oil | 90 |
| Methocel ® K 15M | 80 |
| Aerosil ® COK 84 | 5 |
| Cannabinoid Agonist | 25 |
| Capsule fill weight | 400 mg |

Example 84

| Ingredients | Quantity (mg)/Dose |
|---|---|
| Beeswax | 200 |
| HPMC, K15M | 80 |
| Aerosil COK 84 | 8 |
| Dronabinol | 12 |
| Capsule fill weight | 300 |

Example 85

| Ingredients | Quantity (mg)/Dose |
|---|---|
| Sterotex NF | 150 |
| HPMC, K15M | 75 |
| Coconut oil | 75 |
| Aerosil COK 84 | 5 |
| Dronabinol | 20 |
| Capsule fill weight | 325 |

Example 86

| Ingredients | Quantity (mg)/Dose |
|---|---|
| Cithrol GMS | 275 |
| HPMC, K100M | 40 |
| Aerosil COK 84 | 10 |
| Dronabinol | 25 |
| Capsule fill weight | 350 |

Example 87

| Ingredients | Quantity (mg)/Dose |
|---|---|
| Hydrokote 112 | 250 |
| HPMC, K15M | 60 |
| Aerosil COK 84 | 10 |
| Dronabinol | 30 |
| Capsule fill weight | 350 |

Example 88

| Ingredients | Quantity (mg)/Dose |
|---|---|
| Beeswax | 200 |
| HPMC, Pharmacoat 606 | 62.5 |
| Aerosil COK 84 | 7.5 |
| Dronabinol | 30 |
| Capsule fill weight | 300 |

Example 89

| Ingredients | Quantity (mg)/Dose |
|---|---|
| Gelucire 50/02 | 190 |
| Methocel K 100M | 35 |
| Aerosil COK 84 | 10 |
| Dronabinol | 15 |
| Capsule fill weight | 250 |

Example 90

| Ingredients | Quantity (mg)/Dose |
|---|---|
| Cetyl alcohol | 280 |
| Methocel K 100M | 50 |
| Aerosil COK 84 | 10 |
| Dronabinol | 10 |
| Capsule fill weight | 350 |

Example 91

| Ingredients | Quantity (mg)/Dose |
|---|---|
| Sterotex NF | 320 |
| Methocel K 15M | 60 |
| Aerosil COK 84 | 10 |
| Dronabinol | 10 |
| Capsule fill weight | 400 |

Example 92

| Ingredients | Quantity (mg)/Dose |
|---|---|
| Cithrol GMS | 320 |
| Methocel K 100M | 55 |
| Aerosil COK 84 | 15 |
| Dronabinol | 10 |
| Capsule fill weight | 400 |

Example 93

| Ingredients | Quantity (mg)/Dose |
|---|---|
| Hydrokote 112 | 225 |
| Methocel K 15M | 50 |
| Aerosil COK 84 | 10 |
| Dronabinol | 15 |
| Capsule fill weight | 300 |

Example 94

| Ingredients | Quantity (mg)/Dose |
|---|---|
| Beeswax | 225 |
| Methocel K 15M | 75 |
| Aerosil COK 84 | 10 |
| Dronabinol | 15 |
| Capsule fill weight | 325 |

Example 95

| Ingredients | Quantity (mg)/Dose |
|---|---|
| Beeswax | 210 |
| HPMC, K15M | 80 |
| Aerosil COK 84 | 8 |
| Nabilone | 2 |
| Capsule fill weight | 300 |

Example 96

| Ingredients | Quantity (mg)/Dose |
|---|---|
| Sterotex NF | 166 |
| HPMC, K15M | 75 |
| Coconut oil | 75 |
| Aerosil COK 84 | 5 |
| Nabilone | 4 |
| Capsule fill weight | 325 |

Example 97

| Ingredients | Quantity (mg)/Dose |
|---|---|
| Cithrol GMS | 285 |
| HPMC, K100M | 49 |
| Aerosil COK 84 | 10 |
| Nabilone | 6 |
| Capsule fill weight | 350 |

Example 98

| Ingredients | Quantity (mg)/Dose |
|---|---|
| Hydrokote 112 | 239 |
| HPMC, K15M | 50 |
| Aerosil COK 84 | 10 |
| Nabilone | 1 |
| Capsule fill weight | 300 |

Example 99

| Ingredients | Quantity (mg)/Dose |
|---|---|
| Beeswax | 195 |
| HPMC, Pharmacoat 606 | 45 |
| Aerosil COK 84 | 7.5 |
| Nabilone | 2.5 |
| Capsule fill weight | 250 |

Example 100

| Ingredients | Quantity (mg)/Dose |
|---|---|
| Gelucire 50/02 | 190 |
| Methocel K 100M | 30 |
| Aerosil COK 84 | 10 |
| Nabilone | 20 |
| Capsule fill weight | 250 |

Example 101

| Ingredients | Quantity (mg)/Dose |
|---|---|
| Cetyl alcohol | 280 |
| Methocel K 100M | 50 |
| Aerosil COK 84 | 10 |
| Nabilone | 10 |
| Capsule fill weight | 350 |

Example 102

| Ingredients | Quantity (mg)/Dose |
|---|---|
| Sterotex NF | 320 |
| Methocel K 15M | 60 |
| Aerosil COK 84 | 10 |
| Nabilone | 10 |
| Capsule fill weight | 400 |

Example 103

| Ingredients | Quantity (mg)/Dose |
|---|---|
| Cithrol GMS | 320 |
| Methocel K 100M | 63 |
| Aerosil COK 84 | 12 |
| Nabilone | 5 |
| Capsule fill weight | 400 |

Example 104

| Ingredients | Quantity (mg)/Dose |
|---|---|
| Hydrokote 112 | 225 |
| Methocel K 15M | 50 |
| Aerosil COK 84 | 10 |
| Nabilone | 15 |
| Capsule fill weight | 300 |

Example 105

| Ingredients | Quantity (mg)/Dose |
|---|---|
| Beeswax | 235 |
| Methocel K 15M | 75 |
| Aerosil COK 84 | 14 |
| Nabilone | 1 |
| Capsule fill weight | 325 |

Example 106

| Ingredients | Quantity (mg)/Dose |
|---|---|
| Beeswax | 200 |
| HPMC, K15M | 80 |
| Aerosil COK 84 | 10 |
| THC | 10 |
| Capsule fill weight | 300 |

Example 107

| Ingredients | Quantity (mg)/Dose |
|---|---|
| Sterotex NF | 150 |
| HPMC, K15M | 75 |
| Coconut oil | 80 |
| Aerosil COK 84 | 10 |
| THC | 5 |
| Capsule fill weight | 325 |

Example 108

| Ingredients | Quantity (mg)/Dose |
| --- | --- |
| Cithrol GMS | 275 |
| HPMC, K100M | 48 |
| Aerosil COK 84 | 12 |
| THC | 15 |
| Capsule fill weight | 350 |

Example 109

| Ingredients | Quantity (mg)/Dose |
| --- | --- |
| Hydrokote 112 | 265 |
| HPMC, K15M | 65 |
| Aerosil COK 84 | 15 |
| THC | 5 |
| Capsule fill weight | 350 |

Example 110

| Ingredients | Quantity (mg)/Dose |
| --- | --- |
| Beeswax | 177 |
| HPMC, Pharmacoat 606 | 60 |
| Aerosil COK 84 | 10 |
| THC | 3 |
| Capsule fill weight | 250 |

Example 111

| Ingredients | Quantity (mg)/Dose |
| --- | --- |
| Gelucire 50/02 | 190 |
| Methocel K 100M | 35 |
| Aerosil COK 84 | 10 |
| THC | 15 |
| Capsule fill weight | 250 |

Example 112

| Ingredients | Quantity (mg)/Dose |
| --- | --- |
| Cetyl alcohol | 280 |
| Methocel K 100M | 50 |
| Aerosil COK 84 | 10 |
| THC | 10 |
| Capsule fill weight | 350 |

Example 113

| Ingredients | Quantity (mg)/Dose |
| --- | --- |
| Sterotex NF | 293 |
| Methocel K 15M | 45 |
| Aerosil COK 84 | 10 |
| THC | 2 |
| Capsule fill weight | 350 |

Example 114

| Ingredients | Quantity (mg)/Dose |
| --- | --- |
| Cithrol GMS | 325 |
| Methocel K 100M | 55 |
| Aerosil COK 84 | 15 |
| THC | 5 |
| Capsule fill weight | 400 |

Example 115

| Ingredients | Quantity (mg)/Dose |
| --- | --- |
| Hydrokote 112 | 225 |
| Methocel K 15M | 50 |
| Aerosil COK 84 | 10 |
| THC | 15 |
| Capsule fill weight | 300 |

Example 116

| Ingredients | Quantity (mg)/Dose |
| --- | --- |
| Beeswax | 225 |
| Methocel K 15M | 75 |
| Aerosil COK 84 | 10 |
| THC | 5 |
| Capsule fill weight | 315 |

Example 117

This formulation of the strong opioid levorphanol was prepared in accordance with the procedure described in the above similar examples for Tramadol. The formulation provided robust dissolution characteristics consistent with an extended release formulation (see FIG. 59).

| Ingredients | Quantity (mg)/Dose |
| --- | --- |
| Beeswax | 237 |
| HPMC, K15M | 80 |
| Aerosil COK 84 | 8 |
| Levorphanol Tartrate | 10 |
| Capsule fill weight | 335 |

Example 118

This formulation of the strong opioid levorphanol was prepared in accordance with the procedure described in the above similar examples for Tramadol. The formulation provided robust dissolution characteristics consistent with an extended release formulation (see FIG. 60).

| Ingredients | Quantity (mg)/Dose |
| --- | --- |
| Cithrol GMS | 273 |
| HPMC, K100M | 40 |
| Aerosil COK 84 | 12 |
| Levorphanol Tartrate | 10 |
| Capsule fill weight | 335 |

Example 119

This formulation of the strong opioid levorphanol was prepared in accordance with the procedure described in the above similar examples for Tramadol. The formulation provided robust dissolution characteristics consistent with an extended release formulation (see FIG. 61).

| Ingredients | Quantity (mg)/Dose |
| --- | --- |
| Sterotex NF | 141 |
| Methocel K 15M | 80 |
| Fractionated Coconut oil | 100 |
| Aerosil 200 | 4 |
| Levorphanol Tartrate | 10 |
| Capsule fill weight | 335 |

Example 120

This formulation of the strong opioid levorphanol was prepared in accordance with the procedure described in the above similar examples for Tramadol. The formulation provided robust dissolution characteristics consistent with an extended release formulation (see FIG. 62).

| Ingredients | Quantity (mg)/Dose |
| --- | --- |
| Hydrokote 112 | 253 |
| HPMC, K15M | 60 |
| Aerosil COK 84 | 12 |
| Levorphanol Tartrate | 10 |
| Capsule fill weight | 335 |

Example 121

Compositions and methods of the present invention can be prepared in accordance with the present invention to provide: (i) abuse deterrence; or (ii) extended release; or (iii) protection against alcohol dose dumping; or (iv) protection against significant changes in bio availability due to fed or fasted states; or (v) protection against significant changes in bio-availability due to fed or fasted states; or (vi) more than one of the foregoing properties; wherein the dosage form is prepared: (I) using compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof; and (II) benzodiazepine agonist selected from the group consisting of alprazolam, bromazepam, brotizolam, camazepam, chlordiazepoxide, cinolazepam, clobazam, clonazepam, clorazepate, desalkylflurazepam, diazepam, estazolam, flunitrazepam, flurazepam, halazepam, ketazolam, loprazolam, lorazepam, lormetazepam, medazepam, metaclazepam, midazolam, nitrazepam, nordazepam, oxazepam, phenazepam, pinazepam, prazepam, quazepam, temazepam, tetrazepam, triazolam, zaleplone, zolpidem and zopiclone; said inventions comprising one or more abusable drugs and one or more ADER agents; said invention, in some embodiments, providing further abuse deterrence through the use of aversive agents; said invention, in some embodiments, using substantially the same ADER agents to achieve the foregoing (i) to (v); said invention, in some embodiments, providing more than one of the foregoing properties; said invention, in some embodiments, comprising one or more abusable drugs and at least two ADER agents; said invention, in some embodiments, comprising at least two ADER agents selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes; said invention, in some embodiments, comprising at least two ADER agents selected from at least two categories from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes; said invention, in some embodiments, further comprising an immediate release form of the abusable drug; said invention, in some embodiments, further comprising an immediate release form of the abusable drug in solution; said invention, in some embodiments, simultaneously providing more than one of foregoing (i) to (v); said invention, in some embodiments, simultaneously providing more than one of foregoing (i) to (v) using substantially the same ADER agents.

Example 122

Compositions and methods of the present invention can be prepared in accordance with the present invention to provide: (i) abuse deterrence; or (ii) extended release; or (iii) protection against alcohol dose dumping; or (iv) protection against significant changes in bio availability due to fed or fasted states; or (v) protection against significant changes in bioavailability due to fed or fasted states; or (vi) more than one of the foregoing properties; wherein the dosage form is prepared: (I) using compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof; and (II) non-benzodiazepine hypnotics and CNS depressants selected from the group comprising sodium oxybate, diphenhydramine, chlorpheniramine, trazadone, amitriptyline, cyclobenzaprine, methocarbamol, carisoprodol and rameltteon; said inventions comprising one or more abusable drugs and one or more ADER agents; said invention, in some embodiments, providing further abuse deterrence through the use of aversive agents; said invention, in some embodiments, using substantially the same ADER agents to achieve the foregoing (i) to (v); said invention, in some embodiments, providing more than one of the foregoing properties; said invention, in some embodiments, comprising one or more abusable drugs and at least two ADER agents; said invention, in some embodiments, comprising at least two ADER agents selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes; said invention, in some embodiments, comprising at least two ADER agents selected from at least two categories from the group consisting of: (a) hydrogenated Type I or Type II vegetable oils; (b) polyoxyethylene stearates and distearates; (c)

glycerol monostearate; (d) poorly water soluble, high melting point (mp=45 to 100° C.) waxes; said invention, in some embodiments, further comprising an immediate release form of the abusable drug; said invention, in some embodiments, further comprising an immediate release form of the abusable drug in solution; said invention, in some embodiments, simultaneously providing more than one of foregoing (i) to (v); said invention, in some embodiments, simultaneously providing more than one of foregoing (i) to (v) using substantially the same ADER agents.

Example 123

Compositions and methods of the present invention can be prepared in accordance with the present invention to provide: (i) abuse deterrence; or (ii) extended release; or (iii) protection against alcohol dose dumping; or (iv) protection against significant changes in bio availability due to fed or fasted states; or (v) protection against significant changes in bio-availability due to fed or fasted states; or (vi) more than one of the foregoing properties; wherein the dosage form is prepared: (I) using compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof; and (II) cannabinoid agonists selected from the group comprising THC, nabilone, dronabinol, cannabidiol, 9-THC propyl analog, cannabidiol, cannabidiol propyl analog, cannabinol, cannabichromene, cannabichromene propyl analog, cannabigerol, cannabinoid terpenoids, cannabinoid flavonoids, endocannabinoids, anandamide and 2-arachidonoylglycerol, THC-like ABC tricyclic cannabinoid analogues, exemplified by HU210 and desacetyllevonantradol; synthetic AC bicyclic and ACD tricyclic cannabinoid analogues, exemplified by CP55940, and CP55244 and aminoalkylindole compounds, exemplified by WIN55212-2; said inventions comprising one or more abusable drugs and one or more ADER agents; said invention, in some embodiments, providing further abuse deterrence through the use of aversive agents; said invention, in some embodiments, using substantially the same ADER agents to achieve the foregoing (i) to (v); said invention, in some embodiments, providing more than one of the foregoing properties; said invention, in some embodiments, comprising one or more abusable drugs and at least two ADER agents; said invention, in some embodiments, comprising at least two ADER agents selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes; said invention, in some embodiments, comprising at least two ADER agents selected from at least two categories from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes; said invention, in some embodiments, further comprising an immediate release form of the abusable drug; said invention, in some embodiments, further comprising an immediate release form of the abusable drug in solution; said invention, in some embodiments, simultaneously providing more than one of foregoing (i) to (v); said invention, in some embodiments, simultaneously providing more than one of foregoing (i) to (v) using substantially the same ADER agents.

Example 124

Compositions and methods of the present invention can be prepared in accordance with the present invention to provide: (i) abuse deterrence; or (ii) extended release; or (iii) protection against alcohol dose dumping; or (iv) protection against significant changes in bio availability due to fed or fasted states; or (v) protection against significant changes in bio-availability due to fed or fasted states; or (vi) more than one of the foregoing properties; wherein the dosage form is prepared: (I) using compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof; and (II) CNS-stimulants, psychostimulants, alkylxanthine, and anorectic compounds selected from the group comprising adrafanil, alkyxanthine derivatives, almitrine, amfetaminil, aminophylline, amiphenazole, ammonium camphocarbonate, amphetamine, bamifylline, benzfetamine, brolamfetamine, caffeine, cathine [(+)-norpseudoephedrine], cathinone, celastrin, chlorphentermine, clonobenzorex, cropropamide, crotetamide, deanol, dextroamphetamine, diethylaminoethanol, diethylpropion, dimfline, doxapram, doxofylline, diprophylline, dyphylline, etamivan, etofylline, enprophylline, etamiphylline, methylphenidate, dexmethylphenidate, fencamfamin, fenetylline, fenozolone, fenproporex, lisdexamfetamine, lisdexamfetamine dimesylate, lisofylline, lobeline, mazindol, mefenorex, mepixanox, methamphetamine, methylenedioxymethamphetamine, modafinil, nicotine, nikethamide, oxtriphylline, pemoline, pentetrazol, phedimetrazine, phenmetrazine, phentermine, pentoxifylline, phenylpropanolamine, pipradrol, prethcamide, prolintane, propylhexedrine, propentofylline, pentifylline, pseudoephedrine, pyridophylline, proxyphylline, sibutramine, tenamfetamine (methylenedioxeamphetamine), theophylline, theobromine; said inventions comprising one or more abusable drugs and one or more ADER agents; said invention, in some embodiments, providing further abuse deterrence through the use of aversive agents; said invention, in some embodiments, using substantially the same ADER agents to achieve the foregoing (i) to (v); said invention, in some embodiments, providing more than one of the foregoing properties; said invention, in some embodiments, comprising one or more abusable drugs and at least two ADER agents; said invention, in some embodiments, comprising at least two ADER agents selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes; said invention, in some embodiments, comprising at least two ADER agents selected from at least two categories from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes; said invention, in some embodiments, further comprising an immediate release form of the abusable drug; said invention, in some embodiments, further comprising an immediate release form of the abusable drug in solution; said invention, in some embodiments, simultaneously providing more than one of foregoing (i) to (v); said invention, in some embodiments, simultaneously providing more than one of foregoing (i) to (v) using substantially the same ADER agents.

Example 125

Compositions and methods of the present invention can be prepared in accordance with the present invention to provide: (i) abuse deterrence; or (ii) extended release; or (iii) protection against alcohol dose dumping; or (iv) protection against significant changes in bioavailability due to fed or fasted states; or (v) protection against significant changes in bioavailability due to fed or fasted states; or (vi) more than one of the foregoing properties; wherein the dosage form is prepared: (I) using compounds selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes, and mixtures thereof; and (II) opioid agonists selected from the group comprising alfentanil, allylprodine, alphaprodine, anileridine, apomorphine, apocodeine, benzylmorphine, bezitramide, brifentanil, buprenorphine, butorphanol, carfentanil, clonitazene, codeine, cyclorphen, cyprenorphine, desomorphine, dextromoramide, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, mirfentanil, morphine, morphine-6-glucuronide, myrophine, nalbuphine, narceine, nicomorphine, norlevorphanol, normethadone, nalorphine, nociceptin/orphanin FQ (N/OFQ), normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, propheptazine, promedol, profadol, properidine, propiram, propoxyphene, remifentanil, sufentanil, tapentadol, tramadol, trefentanil, tilidine, nalbuphine, or any opioid having agonist activity at an opioid receptor belonging to the phenanthrene, morphinan, benzomorphan, methadone, phenylpiperidine, propionanilide 4-anilidopiperidine, 4-aryl piperidines, and 4-Heteroarylpiperidines class, any opioid having agonist activity at an opioid receptor having the same pentacyclic nucleus as nalmefene, naltrexone, buprenorphine, levorphanol, meptazinol, pentazocine and dezocine, any drug having agonist activity at an opioid receptor which is a fentanyl analog; said inventions comprising one or more abusable drugs and one or more ADER agents; said invention, in some embodiments, providing further abuse deterrence through the use of aversive agents; said invention, in some embodiments, using substantially the same ADER agents to achieve the foregoing (i) to (v); said invention, in some embodiments, providing more than one of the foregoing properties; said invention, in some embodiments, comprising one or more abusable drugs and at least two ADER agents; said invention, in some embodiments, comprising at least two ADER agents selected from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes; said invention, in some embodiments, comprising at least two ADER agents selected from at least two categories from the group consisting of: (a) hydrogenated Type I or Type II vegetable oils; (b) polyoxyethylene stearates and distearates; (c) glycerol monostearate; (d) poorly water soluble, high melting point (mp=45 to 100° C.) waxes; said invention, in some embodiments, further comprising an immediate release form of the abusable drug; said invention, in some embodiments, further comprising an immediate release form of the abusable drug in solution; said invention, in some embodiments, simultaneously providing more than one of foregoing (i) to (v); said invention, in some embodiments, simultaneously providing more than one of foregoing (i) to (v) using substantially the same ADER agents.

Having now fully described the invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A dosage form for administration via the oral cavity, the dosage form comprising
   a) a drug, being an opioid agonist, combined with
   b) at least two abuse deterrent extended release (ADER) ingredients including a hydrogenated vegetable oil and a fractionated coconut oil,
   wherein the ADER ingredients are selected and are present in amounts sufficient to reduce the amount of drug released from the dosage form at one hour in the USP Basket and Paddle Method at 100 revolutions per minute in 700 milliliters of simulated gastric fluid at 37 degrees Celsius, relative to the same dosage form lacking the ADER ingredients, and
   wherein the fractionated coconut oil is present in an amount sufficient to enhance by at least a third resistance to powdering of the dosage form to particle sizes of 650 micrometers or less, relative to an otherwise identical dosage form having the hydrogenated vegetable oil substituted in place of the fractionated coconut oil.

2. The dosage form of claim 1, wherein the drug is in a form selected from the group consisting of a pharmaceutically acceptable salt of the drug, an ester of the drug, and combinations of these.

3. The dosage form of claim 1, wherein the hydrogenated vegetable oil is hydrogenated cottonseed oil.

4. The dosage form of claim 1, wherein the ADER ingredients are present in an amount effective to reduce the rate of release of the drug, relative to the dosage form lacking the ADER ingredients, when administered to a human.

5. The dosage form of claim 1, wherein the drug is an opioid agonist selected from the group consisting of alfentanil, allylprodine, alphaprodine, anileridine, apomorphine, apocodeine, benzylmorphine, bezitramide, brifentanil, buprenorphine, butorphanol, carfentanil, clonitazene, codeine, cyclorphen, cyprenorphine, desomorphine, dextromoramide, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, lofentanil, meperidine, meptazinol, metazocine, methadone, methylmorphine, metopon, mirfentanil, morphine, morphine-6-glucuronide, myrophine, nalbuphine, narceine, nicomorphine, norlevorphanol, normethadone, nalorphine, nociceptin/orphanin FQ (N/OFQ), normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, propheptazine, promedol, profadol, properidine, propiram, propoxyphene, remifentanil, sufentanil, tapentadol, tramadol, trefentanil, tilidine, nalbuphine, pharmaceutically acceptable salts thereof and mixtures thereof.

6. The dosage form of claim 1, further comprising an aversive agent.

7. A method of treating a medical condition amenable to treatment with an opioid agonist, the method comprising administering to the oral cavity of a human patient afflicted with the condition an effective amount of the dosage form of claim 1.

8. The dosage form of claim 1, further comprising a third ADER ingredient selected from the group consisting of hydroxypropyl methyl celluloses and thixotropes.

9. The dosage form of claim 8, comprising both a hydroxypropyl methyl cellulose and a thixotrope.

10. The dosage form of claim 9, wherein the thixotrope is a fumed silicon dioxide.

11. The dosage form of claim 1, wherein the opioid agonist is levorphanol.

12. The dosage form of claim 11, wherein the levorphanol is present in the form of levorphanol tartrate.

13. The dosage form of claim 12, comprising four ADER ingredients, being hydrogenated cottonseed oil, fractionated coconut oil, hydroxypropyl methyl cellulose, and fumed silicon dioxide.

14. The dosage form of claim 1, wherein the drug is an opioid agonist selected from the group consisting of opioids having agonist activity at an opioid receptor belonging to the phenanthrene, morphinan, benzomorphan, methadone, phenylpiperidine, propionanilide 4-anilidopiperidine, 4-aryl piperidines, and 4-Heteroarylpiperidines classes.

15. The dosage form of claim 1, wherein the drug is an opioid agonist selected from the group consisting of opioids having agonist activity at an opioid receptor having the same pentacyclic nucleus as any of nalmefene, naltrexone, buprenorphine, levorphanol, meptazinol, pentazocine and dezocine.

16. The dosage form of claim 1, wherein the dosage form comprises the fractionated coconut oil in an amount from 15 to 30% w/w.

17. The dosage form of claim 1, wherein the dosage form is a capsule and comprises the fractionated coconut oil in an amount from 15 to 30% w/w of the capsule contents.

18. The dosage form of claim 1, wherein the weight ratio of hydrogenated vegetable oil:fractionated coconut oil is from 7:5 to 3.

19. The dosage form of claim 1, wherein the opioid agonist is butorphanol.

20. The dosage form of claim 1, wherein the opioid agonist is buprenorphine.

\* \* \* \* \*